(12) United States Patent
Malek et al.

(10) Patent No.: US 11,850,390 B2
(45) Date of Patent: Dec. 26, 2023

(54) SYSTEMS AND METHODS FOR MINIMALLY INVASIVE DRUG DELIVERY TO A SUBARACHNOID SPACE

(71) Applicant: CEREVASC, INC., Auburndale, MA (US)

(72) Inventors: Adel M. Malek, Weston, MA (US); Carl B. Heilman, Wayland, MA (US); David A. Rezac, Westborough, MA (US); Jack B. Sattell, Boston, MA (US); Alexander Bonin, Franklin, MA (US)

(73) Assignee: Cerevasc, Inc., Auburndale, MA (US)

( * ) Notice: Subject to any disclaimer, the term of this patent is extended or adjusted under 35 U.S.C. 154(b) by 261 days.

(21) Appl. No.: 17/317,027

(22) Filed: May 11, 2021

(65) Prior Publication Data
US 2021/0268252 A1 Sep. 2, 2021

Related U.S. Application Data

(63) Continuation of application No. 16/976,057, filed as application No. PCT/US2019/021471 on Mar. 8, 2019, now Pat. No. 11,013,900.
(Continued)

(51) Int. Cl.
*A61M 39/02* (2006.01)
*A61M 25/00* (2006.01)
(Continued)

(52) U.S. Cl.
CPC ........ *A61M 39/0208* (2013.01); *A61M 25/00* (2013.01); *A61M 39/0247* (2013.01);
(Continued)

(58) Field of Classification Search
CPC ...... A61M 39/0208; A61M 2039/0223; A61M 2039/0232; A61M 2039/0238;
(Continued)

(56) References Cited

U.S. PATENT DOCUMENTS

| 575,997 | A | 1/1897 | Spencer |
|---|---|---|---|
| 3,492,996 | A | 2/1970 | Fountain |

(Continued)

FOREIGN PATENT DOCUMENTS

| CN | 189564 | 1/2007 |
|---|---|---|
| CN | 1895694 | 1/2007 |

(Continued)

OTHER PUBLICATIONS

Final Office Action for U.S. Appl. No. 16/337,346 dated Oct. 3, 2022.

(Continued)

*Primary Examiner* — Theodore J Stigell
(74) *Attorney, Agent, or Firm* — Vista IP Law Group, LLP

(57) ABSTRACT

Endovascular drug delivery systems and methods are disclosed herein for delivering a therapeutic agent to the intracranial subarachnoid space of a patient, and/or deploying an endovascular drug delivery device distal portion in the intracranial subarachnoid space and a portion of the drug delivery device body in a dural venous sinus such that a therapeutic agent is delivered from the deployed drug delivery device into the intracranial subarachnoid space.

15 Claims, 94 Drawing Sheets

Related U.S. Application Data

(60) Provisional application No. 62/805,091, filed on Feb. 13, 2019, provisional application No. 62/768,296, filed on Nov. 16, 2018, provisional application No. 62/755,078, filed on Nov. 2, 2018, provisional application No. 62/727,401, filed on Sep. 5, 2018, provisional application No. 62/667,852, filed on May 7, 2018, provisional application No. 62/640,471, filed on Mar. 8, 2018.

(51) Int. Cl.
*A61B 34/10* (2016.01)
*A61B 90/00* (2016.01)

(52) U.S. Cl.
CPC ... *A61B 2034/105* (2016.02); *A61B 2034/107* (2016.02); *A61B 2090/365* (2016.02); *A61M 2039/0223* (2013.01); *A61M 2039/0232* (2013.01); *A61M 2039/0238* (2013.01); *A61M 2205/32* (2013.01); *A61M 2210/0687* (2013.01)

(58) Field of Classification Search
CPC .............. A61M 25/00; A61M 39/0247; A61M 2205/32; A61M 2210/0687; A61M 2039/0291; A61M 25/0662; A61M 25/0074; A61M 25/0075; A61M 25/0102; A61B 2034/107; A61B 2090/365; A61B 2034/105; A61B 2090/08021; A61B 17/3401; A61B 17/3478
See application file for complete search history.

(56) References Cited

U.S. PATENT DOCUMENTS

| | | |
|---|---|---|
| 3,894,541 A | 7/1975 | El-Shafei |
| 4,413,985 A | 11/1983 | Wellner et al. |
| 4,474,569 A | 10/1984 | Newkirk |
| 4,475,898 A | 10/1984 | Brodner et al. |
| 4,631,051 A | 12/1986 | Harris |
| 4,737,153 A | 4/1988 | Shimamura et al. |
| 4,950,232 A | 8/1990 | Ruzicka et al. |
| 5,000,731 A | 3/1991 | Wong et al. |
| 5,137,288 A | 8/1992 | Starkey et al. |
| 5,160,325 A | 11/1992 | Nichols et al. |
| 5,193,546 A | 3/1993 | Shaknovich |
| 5,221,261 A | 6/1993 | Termin et al. |
| 5,385,541 A | 1/1995 | Kirsch et al. |
| 5,405,316 A | 4/1995 | Magram |
| 5,496,329 A | 3/1996 | Reisinger |
| 5,562,641 A | 10/1996 | Flomenblit et al. |
| 5,634,475 A | 6/1997 | Wolvek |
| 5,725,571 A | 3/1998 | Imbert et al. |
| 5,725,572 A | 3/1998 | Lam et al. |
| 5,746,725 A | 5/1998 | Shalon et al. |
| 5,792,157 A | 8/1998 | Mische et al. |
| 5,800,520 A | 9/1998 | Fogarty et al. |
| 5,830,222 A | 11/1998 | Makower |
| 5,851,199 A | 12/1998 | Peerless et al. |
| 5,885,258 A | 3/1999 | Sachdeva et al. |
| 5,976,131 A | 11/1999 | Guglielmi et al. |
| 5,984,929 A | 11/1999 | Bashiri et al. |
| 6,015,405 A | 1/2000 | Schwartz et al. |
| 6,066,158 A | 5/2000 | Engelson et al. |
| 6,068,638 A | 5/2000 | Makower |
| 6,071,292 A | 6/2000 | Makower et al. |
| 6,093,199 A | 7/2000 | Brown et al. |
| 6,096,053 A | 8/2000 | Bates |
| 6,126,628 A | 10/2000 | Nissels |
| 6,126,649 A | 10/2000 | VanTassel et al. |
| 6,126,672 A | 10/2000 | Berryman et al. |
| 6,159,225 A | 12/2000 | Makower |
| 6,186,972 B1 | 2/2001 | Nelson et al. |
| 6,190,353 B1 | 2/2001 | Makower et al. |
| 6,231,587 B1 | 5/2001 | Makower |
| 6,283,934 B1 | 9/2001 | Borgeson |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,350,271 B1 | 2/2002 | Kurz et al. |
| 6,375,615 B1 | 4/2002 | Flaherty et al. |
| 6,379,319 B1 | 4/2002 | Garibotto et al. |
| 6,402,771 B1 | 6/2002 | Palmer et al. |
| 6,425,909 B1 | 7/2002 | Dieck et al. |
| 6,432,127 B1 | 8/2002 | Kim et al. |
| 6,491,707 B2 | 12/2002 | Makower et al. |
| 6,508,824 B1 | 1/2003 | Flaherty et al. |
| 6,527,790 B2 | 3/2003 | Chien et al. |
| 6,530,935 B2 | 3/2003 | Wensel |
| 6,544,230 B1 | 4/2003 | Flaherty et al. |
| 6,561,998 B1 | 5/2003 | Roth et al. |
| 6,569,145 B1 | 5/2003 | Shmulewitz et al. |
| 6,575,997 B1 | 6/2003 | Palmer et al. |
| 6,579,302 B2 | 6/2003 | Duerig et al. |
| 6,579,311 B1 | 6/2003 | Makower |
| 6,589,164 B1 | 7/2003 | Flaherty |
| 6,602,241 B2 | 8/2003 | Makower et al. |
| 6,613,081 B2 | 9/2003 | Kim et al. |
| 6,616,675 B1 | 9/2003 | Evard et al. |
| 6,638,293 B1 | 10/2003 | Makower et al. |
| 6,655,386 B1 | 12/2003 | Makower et al. |
| 6,660,021 B1 | 12/2003 | Palmer et al. |
| 6,660,024 B1 | 12/2003 | Flaherty et al. |
| 6,663,650 B2 | 12/2003 | Sepetka et al. |
| 6,685,648 B2 | 2/2004 | Flaherty et al. |
| 6,685,716 B1 | 2/2004 | Flaherty et al. |
| 6,709,444 B1 | 3/2004 | Makower |
| 6,716,238 B2 | 4/2004 | Elliott |
| 6,719,750 B2 | 4/2004 | Varner et al. |
| 6,726,677 B1 | 4/2004 | Flaherty et al. |
| 6,730,104 B1 | 5/2004 | Sepetka et al. |
| 6,746,426 B1 | 6/2004 | Flaherty et al. |
| 6,746,464 B1 | 6/2004 | Makower |
| 6,863,684 B2 | 3/2005 | Kim et al. |
| 7,056,325 B1 | 6/2006 | Makower et al. |
| 7,083,588 B1 | 8/2006 | Shmulewitz et al. |
| 7,094,230 B2 | 8/2006 | Flaherty et al. |
| 7,134,438 B2 | 11/2006 | Makower et al. |
| 7,172,571 B2 | 2/2007 | Moskowitz et al. |
| 7,179,270 B2 | 2/2007 | Makower |
| 7,191,015 B2 | 3/2007 | Lamson et al. |
| 7,300,458 B2 | 11/2007 | Henkes et al. |
| 7,303,571 B2 | 12/2007 | Makower et al. |
| 7,316,655 B2 | 1/2008 | Garibotto et al. |
| 7,316,692 B2 | 1/2008 | Huffmaster |
| 7,357,794 B2 | 4/2008 | Makower et al. |
| 7,407,506 B2 | 8/2008 | Makower |
| 7,606,615 B2 | 10/2009 | Makower et al. |
| 7,621,950 B1 | 11/2009 | Globernnan |
| 7,637,870 B2 | 12/2009 | Flaherty et al. |
| 7,648,517 B2 | 1/2010 | Makower et al. |
| 7,670,329 B2 | 3/2010 | Flaherty et al. |
| 7,729,738 B2 | 6/2010 | Flaherty et al. |
| 7,797,053 B2 | 9/2010 | Atkinson et al. |
| 7,846,172 B2 | 12/2010 | Makower |
| 7,955,343 B2 | 6/2011 | Makower et al. |
| 7,966,057 B2 | 6/2011 | Macaulay et al. |
| 7,989,042 B2 | 8/2011 | Obara et al. |
| 8,075,580 B2 | 12/2011 | Makower |
| 8,083,708 B2 | 12/2011 | Flaherty et al. |
| 8,088,140 B2 | 1/2012 | Ferrera et al. |
| 8,090,430 B2 | 1/2012 | Makower et al. |
| 8,118,827 B2 | 2/2012 | Duerig |
| 8,214,015 B2 | 7/2012 | Macaulay et al. |
| 8,292,950 B2 | 10/2012 | Dorn et al. |
| 8,295,947 B2 | 10/2012 | Lamson et al. |
| 8,317,748 B2 | 11/2012 | Fiorella et al. |
| 8,486,104 B2 | 7/2013 | Samson et al. |
| 8,494,243 B2 * | 7/2013 | Sundar ...................... G06T 7/33 382/128 |

(56) References Cited

U.S. PATENT DOCUMENTS

| | | |
|---|---|---|
| 8,540,759 B2 | 9/2013 | Porter |
| 8,585,596 B1 | 11/2013 | Flaherty et al. |
| 8,672,871 B2 | 3/2014 | Heilman et al. |
| 8,672,920 B2 | 3/2014 | Makower et al. |
| 8,715,314 B1 | 5/2014 | Janardhan et al. |
| 8,727,988 B2 | 5/2014 | Flaherty et al. |
| 8,740,833 B2 | 6/2014 | Moskowitz et al. |
| 8,753,366 B2 | 6/2014 | Makower et al. |
| 8,795,317 B2 | 8/2014 | Grandfield et al. |
| 8,852,205 B2 | 10/2014 | Brady et al. |
| 8,876,792 B2 | 11/2014 | Holmin et al. |
| 8,926,680 B2 | 1/2015 | Ferrera et al. |
| 8,974,513 B2 | 3/2015 | Ford et al. |
| 8,992,456 B1 | 3/2015 | Powell |
| 9,039,749 B2 | 5/2015 | Shrivastava et al. |
| 9,113,936 B2 | 8/2015 | Palmer et al. |
| 9,119,656 B2 | 9/2015 | Bose et al. |
| 9,387,311 B1 | 7/2016 | Heilman et al. |
| 9,387,331 B2 | 7/2016 | Zhao et al. |
| 9,402,982 B2 | 8/2016 | Baert et al. |
| 9,433,429 B2 | 9/2016 | Vale et al. |
| 9,545,505 B2 | 1/2017 | Heilman et al. |
| 9,669,195 B2 | 6/2017 | Heilman et al. |
| 9,682,216 B2 | 6/2017 | Teitelbaum |
| 9,724,501 B2 | 8/2017 | Heilman et al. |
| 10,004,621 B2 | 6/2018 | Kelly |
| 10,022,251 B2 | 7/2018 | Teitelbaum |
| 10,058,686 B2 | 8/2018 | Heilman et al. |
| 10,258,284 B1 | 4/2019 | Malek et al. |
| 10,272,230 B2 | 4/2019 | Malek et al. |
| 10,279,154 B2 | 5/2019 | Heilman et al. |
| 10,307,576 B2 | 6/2019 | Heilman et al. |
| 10,307,577 B2 | 6/2019 | Malek et al. |
| 10,625,061 B2 | 4/2020 | Borgesen |
| 2001/0041899 A1 | 11/2001 | Foster |
| 2002/0183786 A1 | 12/2002 | Girton |
| 2002/188308 A1 | 12/2002 | Tu et al. |
| 2003/0040754 A1 | 2/2003 | Mitchell |
| 2003/0135147 A1 | 7/2003 | Rosenberg et al. |
| 2003/0181938 A1 | 9/2003 | Roth et al. |
| 2003/0187495 A1 | 10/2003 | Cully et al. |
| 2003/0191520 A1 | 10/2003 | Pelton |
| 2003/0220604 A1 | 11/2003 | Al-Anazi |
| 2003/0225395 A1 | 12/2003 | Griffis et al. |
| 2003/0229366 A1 | 12/2003 | Reggie et al. |
| 2004/0059280 A1 | 3/2004 | Makower et al. |
| 2004/0073242 A1 | 4/2004 | Chanduszko |
| 2004/0087887 A1 | 5/2004 | Nilsson |
| 2004/0147871 A1 | 7/2004 | Burnett |
| 2004/0153110 A1 | 8/2004 | Kurz et al. |
| 2004/0176743 A1 | 9/2004 | Morris et al. |
| 2004/0186368 A1 | 9/2004 | Ramzipoor et al. |
| 2004/0236309 A1 | 11/2004 | Yang |
| 2004/0236409 A1 | 11/2004 | Pelton et al. |
| 2004/0254517 A1 | 12/2004 | Quiroz-Mercado et al. |
| 2004/0260384 A1 | 12/2004 | Allen |
| 2005/0033334 A1 | 2/2005 | Santra et al. |
| 2005/0119668 A1 | 6/2005 | Teague |
| 2005/0137646 A1 | 6/2005 | Wallace et al. |
| 2005/0234509 A1 | 10/2005 | Widomski et al. |
| 2005/0245906 A1 | 11/2005 | Makower et al. |
| 2005/0251151 A1 | 11/2005 | Teague |
| 2005/0256510 A1 | 11/2005 | Moskowitz et al. |
| 2006/0015089 A1 | 1/2006 | Meglin et al. |
| 2006/0015152 A1 | 1/2006 | Wallace |
| 2006/0079915 A1 | 4/2006 | Chin et al. |
| 2006/0089704 A1 | 4/2006 | Douglas |
| 2006/0173440 A1 | 8/2006 | Lamson et al. |
| 2006/0217755 A1 | 9/2006 | Eversull et al. |
| 2006/0224101 A1 | 10/2006 | Glenn |
| 2006/0241687 A1 | 10/2006 | Glaser et al. |
| 2006/0259063 A1 | 11/2006 | Bates et al. |
| 2007/0005125 A1 | 1/2007 | Berenstein et al. |
| 2007/0073337 A1 | 3/2007 | Abbott et al. |
| 2007/0112291 A1 | 5/2007 | Borgesen |
| 2007/0129746 A1 | 6/2007 | Mische |
| 2007/0156230 A1 | 7/2007 | Dugan et al. |
| 2007/0179426 A1 | 8/2007 | Selden |
| 2007/0179428 A1 | 8/2007 | Kralick et al. |
| 2007/0208376 A1 | 9/2007 | Meng |
| 2007/0225794 A1 | 9/2007 | Thramann et al. |
| 2007/0276316 A1 | 11/2007 | Haffner et al. |
| 2008/0045863 A1 | 2/2008 | Bakos |
| 2008/0057106 A1 | 3/2008 | Erickson et al. |
| 2008/0058759 A1 | 3/2008 | Makower et al. |
| 2008/0097398 A1 | 4/2008 | Mitelberg et al. |
| 2008/0125805 A1 | 5/2008 | Mische |
| 2008/0249458 A1 | 10/2008 | Yamasaki |
| 2009/0005645 A1 | 1/2009 | Frassica et al. |
| 2009/0017098 A1 | 1/2009 | Bartolomeo |
| 2009/0069828 A1 | 3/2009 | Martin et al. |
| 2009/0076357 A1 | 3/2009 | Purdy |
| 2009/0171293 A1 | 7/2009 | Yang et al. |
| 2009/0287291 A1 | 11/2009 | Becking et al. |
| 2010/0010476 A1 | 1/2010 | Galdonik et al. |
| 2010/0016887 A1 | 1/2010 | Inderbitzi |
| 2010/0063531 A1 | 3/2010 | Rudakov et al. |
| 2010/0076404 A1 | 3/2010 | Ring |
| 2010/0121357 A1 | 5/2010 | Flaherty et al. |
| 2010/0191168 A1 | 7/2010 | Heilman |
| 2010/0222732 A1 | 9/2010 | Sevrain |
| 2011/0082385 A1 | 4/2011 | Diaz et al. |
| 2011/0319917 A1 | 12/2011 | Ferrera et al. |
| 2012/0130467 A1 | 5/2012 | Selden et al. |
| 2012/0130468 A1 | 5/2012 | Khosravi et al. |
| 2012/0172844 A1 | 7/2012 | Mullen |
| 2013/0035628 A1 | 2/2013 | Garrison et al. |
| 2013/0144328 A1 | 6/2013 | Weber et al. |
| 2013/0178828 A1 | 7/2013 | Takagi et al. |
| 2014/0005586 A1 | 1/2014 | Feinstein |
| 2014/0052047 A1 | 2/2014 | Wilson |
| 2014/0052160 A1 | 2/2014 | Singh et al. |
| 2014/0128905 A1 | 5/2014 | Molaei |
| 2014/0180098 A1 | 6/2014 | Flaherty et al. |
| 2014/0180222 A1 | 6/2014 | Flaherty et al. |
| 2014/0236207 A1 | 8/2014 | Makower et al. |
| 2014/0276342 A1 | 9/2014 | Stone et al. |
| 2014/0277079 A1 | 9/2014 | Vale et al. |
| 2014/0288414 A1 | 9/2014 | Makower et al. |
| 2014/0336559 A1 | 11/2014 | Heilman et al. |
| 2015/0196741 A1 | 7/2015 | Heilman et al. |
| 2015/0201303 A1 | 7/2015 | Ji et al. |
| 2015/0209058 A1 | 7/2015 | Ferrera et al. |
| 2015/0223908 A1 | 8/2015 | Westerfeld et al. |
| 2015/0258260 A1 | 9/2015 | Tuseth |
| 2015/0305756 A1 | 10/2015 | Rosenbluth et al. |
| 2016/0136398 A1* | 5/2016 | Heilman ........... A61M 25/0108 604/9 |
| 2016/0143756 A1 | 5/2016 | Rezac et al. |
| 2016/0287276 A1 | 10/2016 | Cox et al. |
| 2017/0050000 A1 | 2/2017 | Randall |
| 2018/0015267 A1 | 1/2018 | Heilman et al. |
| 2018/0126132 A1 | 5/2018 | Heilman et al. |
| 2019/0021750 A1 | 1/2019 | Heilman et al. |
| 2019/0307403 A1 | 10/2019 | Malek et al. |
| 2021/0220135 A1 | 7/2021 | Kovalsky et al. |

FOREIGN PATENT DOCUMENTS

| | | |
|---|---|---|
| EP | 1082070 | 5/1999 |
| EP | 0964636 | 12/1999 |
| EP | 1047341 | 11/2000 |
| EP | 1067869 | 1/2001 |
| EP | 1067874 | 1/2001 |
| EP | 1082070 | 3/2001 |
| EP | 1171183 | 1/2002 |
| EP | 1253859 | 11/2002 |
| EP | 1359967 | 11/2003 |
| EP | 1377335 | 1/2004 |
| EP | 1496956 | 1/2005 |
| EP | 1854499 | 12/2009 |
| EP | 2589344 | 5/2013 |
| EP | 1981413 | 11/2014 |
| GB | 2089215 | 6/1982 |

(56) References Cited

FOREIGN PATENT DOCUMENTS

| | | |
|---|---|---|
| JP | 2006-289086 | 8/2011 |
| WO | WO1998016161 | 4/1998 |
| WO | WO2002/022028 | 3/2002 |
| WO | WO2006/080113 | 8/2006 |
| WO | WO2007115314 | 10/2007 |
| WO | WO2009/014723 | 1/2009 |
| WO | WO2009014723 | 1/2009 |
| WO | WO2009036039 | 3/2009 |
| WO | WO2009/088783 | 7/2009 |
| WO | WO2009126935 | 10/2009 |
| WO | WO2011011787 | 1/2011 |
| WO | WO2012/009518 | 1/2012 |
| WO | WO2012009518 | 1/2012 |
| WO | WO2012158152 | 11/2012 |
| WO | WO2013034602 | 3/2013 |
| WO | WO2014165754 | 10/2014 |
| WO | WO 2015/108917 | 7/2015 |
| WO | WO2015108917 | 7/2015 |
| WO | WO2016070147 | 5/2016 |
| WO | WO 2016070147 A1 | 5/2016 |
| WO | WO2017/075544 | 5/2017 |
| WO | WO201707554 | 5/2017 |
| WO | WO 2017075544 A1 | 5/2017 |
| WO | WO2017117427 | 7/2017 |
| WO | WO2018/005621 | 1/2018 |
| WO | WO2018005621 | 1/2018 |
| WO | WO2018071600 | 4/2018 |
| WO | WO2018160966 | 9/2018 |

OTHER PUBLICATIONS

Foreign OA for JP Patent Appln. No. 2019-116178 dated Jun. 30, 2021 (with attached machine translation).

Non-Final Office Action for U.S. Appl. No. 16/337,346 dated Mar. 15, 2022.

PCT International Search Report and Written Opinion for International Application No. PCT/2015/011317, Applicant Tufts Medical Center, Inc., Forms PCT/ISA/210, 220, and 237, dated Mar. 26, 2015 (15 pages).

Non-Final Office Action for U.S. Appl. No. 14/179,622, dated May 13, 2015 (13 pages).

PCT Notification of Transmittal of the International Search Report and Written Opinion, dated Feb. 17, 2016, for PCT/US2015/058505, Applicant CereVasc, LLC., international filing date Oct. 30, 2015 (16 pages).

Non-Final Office Action for U.S. Appl. No. 14/596,335, dated Jul. 7, 2016 (16 pages).

PCT International Search Report and Written Opinion for International Appln. No. PCTIUS2016/069280, applicant CereVasc, LLC, dated Mar. 27, 2017 (80 pages).

Non-Final Office Action for U.S. Appl. No. 15/294,000, dated Feb. 16, 2017 (26 pages).

Final Office Action for U.S. Appl. No. 14/596,335, dated Oct. 26, 2016 (19 pages).

Interview Summary for U.S. Appl. No. 14/596,335, dated Oct. 11, 2016 (3 pages).

PCT Notification of Transmittal of the International Search Report and Written Opinion of the I.S.A. for PCT/US2016/0595952, dated Jan. 20, 2017, 14 pages.

PCT International Search Report and Written Opinion for International Appln. No. PCT/US2017/056227, Applicant Cerevasc, LLC, Forms PCT/ISA/210, 220, and 237, dated Mar. 29, 2018 (24 pages).

Non-Final Office Action for U.S. Appl. No. 15/862,120, dated Apr. 19, 2018.

Amendment Response to Office Action for U.S. Appl. No. 15/862,120 dated May 1, 2018.

Supplemental Amendment for U.S. Appl. No. 15/862,120 dated May 7, 2018.

PCT Invitation to Pay Additional Fees for International Appln. No. PCT/US2018/020667, dated May 29, 2018 (17 pages).

PCT International Search Report and Written Opinion for International Appln. No. PCT/US2018/020667, dated Aug. 1, 2018 (21 pages).

Examination Report dated Jan. 25, 2019 for EP Appln. No. 15791220.5.

Non-Final Office Action dated Nov. 6, 2018 for U.S. Appl. No. 15/668,657.

Response to Non Final Office Action filed Nov. 14, 2018 for U.S. Appl. No. 15/668,657.

Notice of Allowance dated Dec. 14, 2018 for U.S. Appl. No. 15/668,657.

Notice of Allowance dated Dec. 14, 2018 for U.S. Appl. No. 15/745,961.

Non-final office action dated Mar. 21, 2019 for U.S. Appl. No. 16/212,511.

Amendment Response to Office Action for U.S. Appl. No. 16/212,547 dated Mar. 4, 2019.

Notice of Allowance dated Apr. 17, 2019 for U.S. Appl. No. 16/212,511.

Notice of Rejection for JP International Patent Appln. No. 2017-542811 dated Nov. 13, 2018.

Office Action dated Mar. 5, 2019 for Japanese Patent Appln. No. 2017-542811, with English translation provided by Foreign Associate.

Notice of Allowance dated Apr. 9, 2019 for U.S. Appl. No. 16/212,547.

PCT Invitation to Pay Additional Fees for International Appln. No. PCT/US2019/021471, dated Jun. 28, 2019 (10 pages).

PCT International Search Report and Written Opinion dated Aug. 20, 2019 for PCT Appln. No. PCT/US2019/021471, 17 pages.

Office action and search report dated Jul. 29, 2019 for Chinese Application No. 2015800588073, in Chinese with English translation provided by foreign associate.

Response to Examination Report filed Jun. 4, 2019 for EP Appln. No. 15791220.5.

Response to Foreign Office Action filed Jun. 24, 2019 for JP Patent Appln. No. 2017-542811.

PCT Invitation to Pay Additional Fees dated Jan. 5, 2018 for PCT/US2017/056227, Applicant CereVasc, LLC, 17 pages.

Response to Office action filed Oct. 29, 2019 for Chinese Application No. 2015800588073.

EPO communication Rule 71(3) allowance dated Nov. 7, 2019 for European patent application No. 15791220.5.

PCT Notification of Transmittal of the International Search Report and Written Opinion for PCT/US2019/021471, dated Aug. 20, 2019, 17 pages.

PCT International Preliminary Report on Patentability (Chapter I of the Patent Cooperation Treaty) for PCT/US2019/021471, dated Sep. 17, 2020, 11 pages.

Extended European Search Report fot EP Patent Appln. No. 20189096.9 dated Sep. 11, 2020.

Foreign Office Action for Japanese Patent Application No. 2019-116178 dated Sep. 28, 2020 (translated).

\* cited by examiner

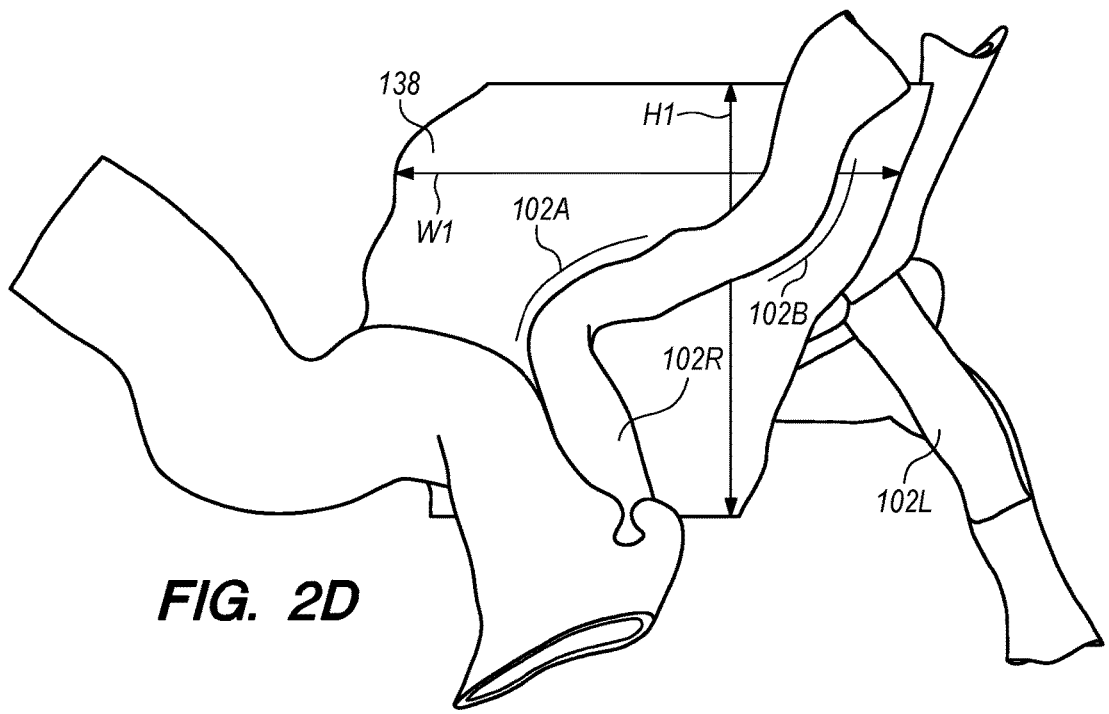
FIG. 2D
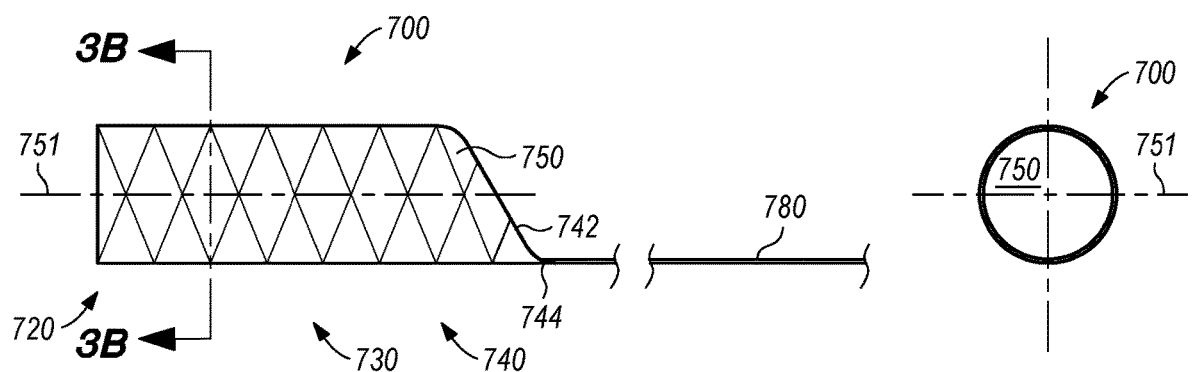
FIG. 3A
FIG. 3B
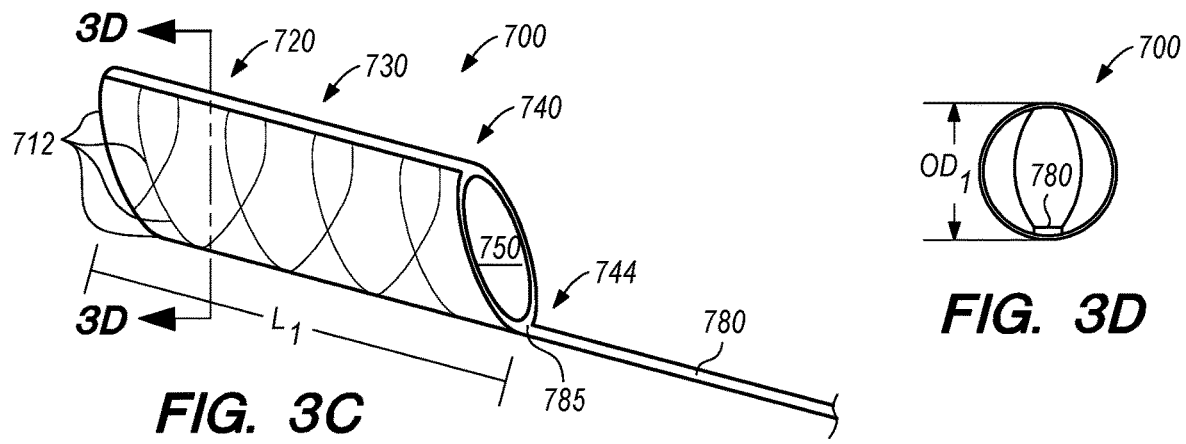
FIG. 3C
FIG. 3D

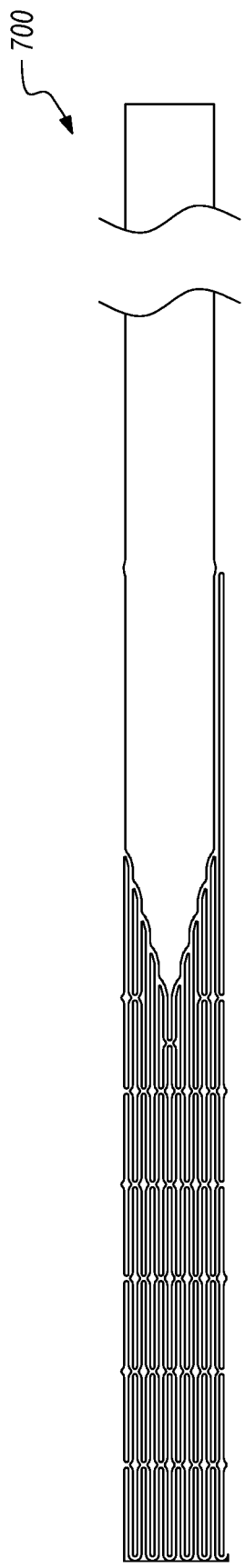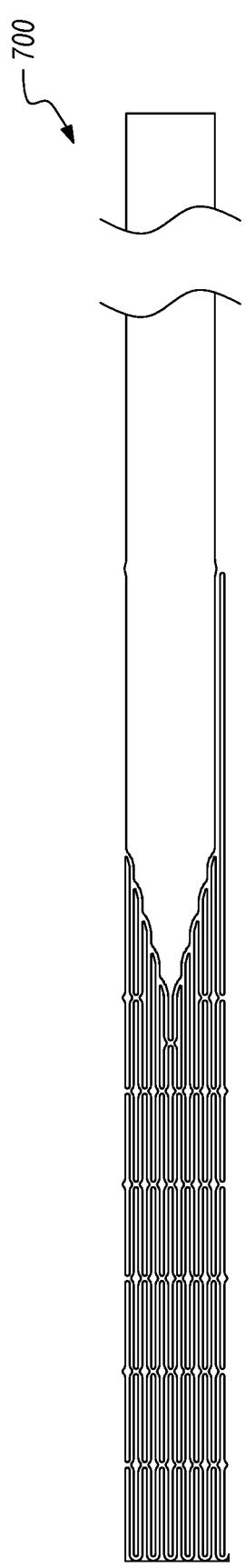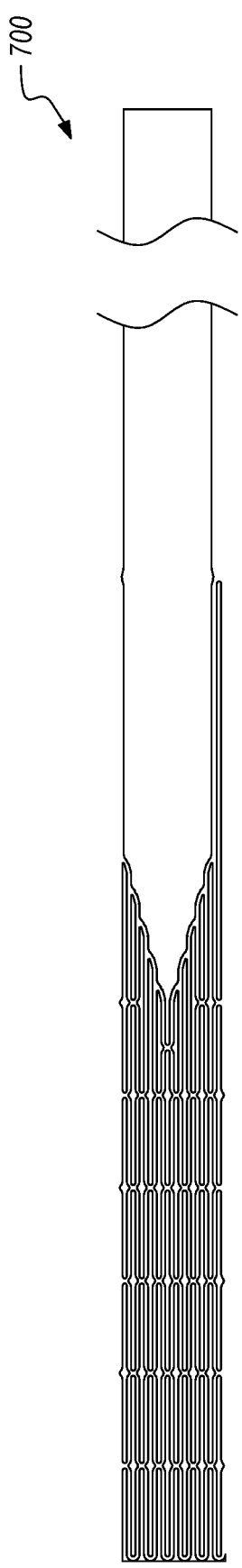

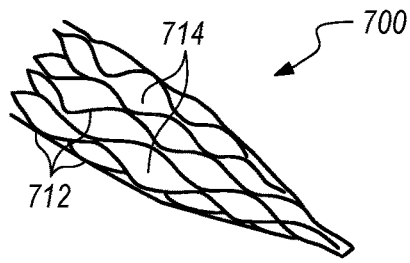
FIG. 5O
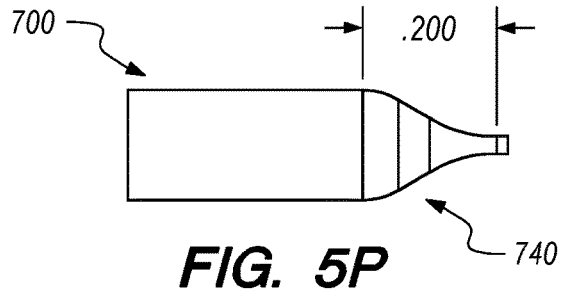
FIG. 5P
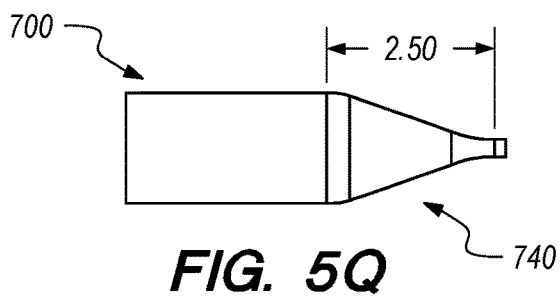
FIG. 5Q
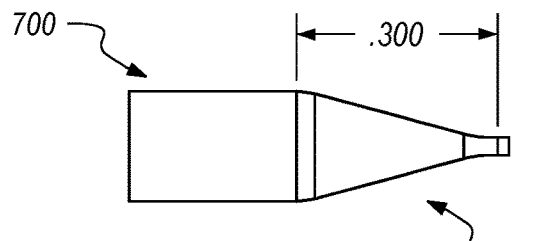
FIG. 5R
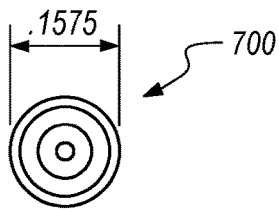
FIG. 5S
| DASH NO. | TRANSITION LENGTH |
|---|---|
| -01 | 0.200 |
| -02 | 0.250 |
| -03 | 0.300 |
FIG. 5T

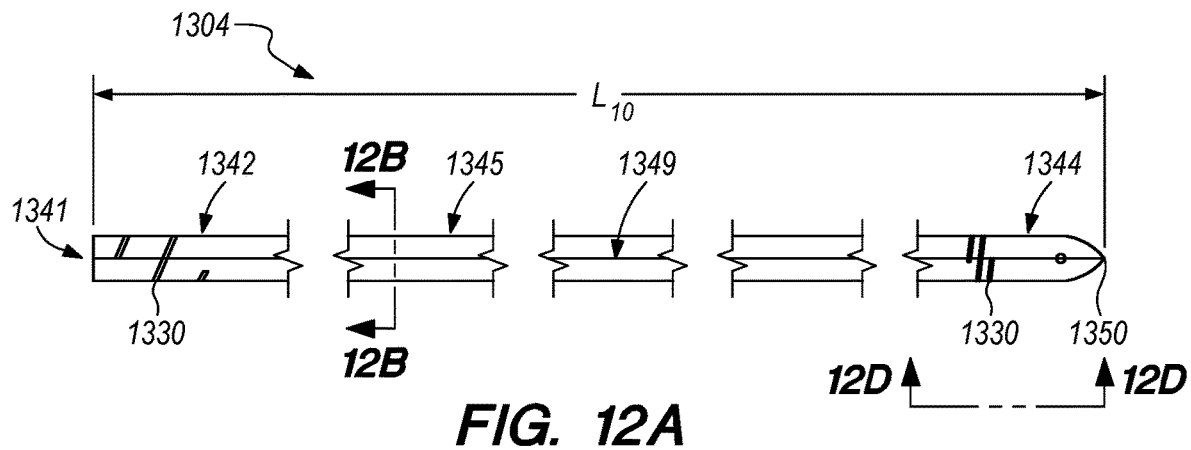
FIG. 12A
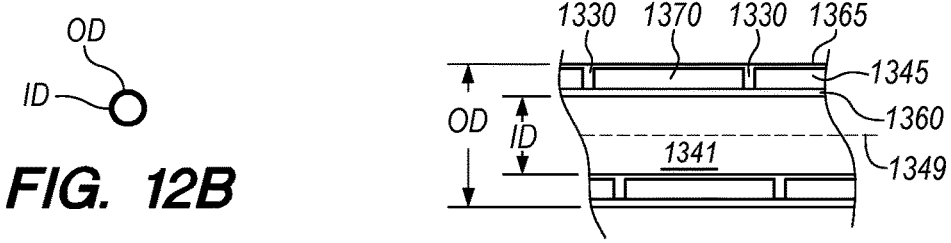
FIG. 12B
FIG. 12C
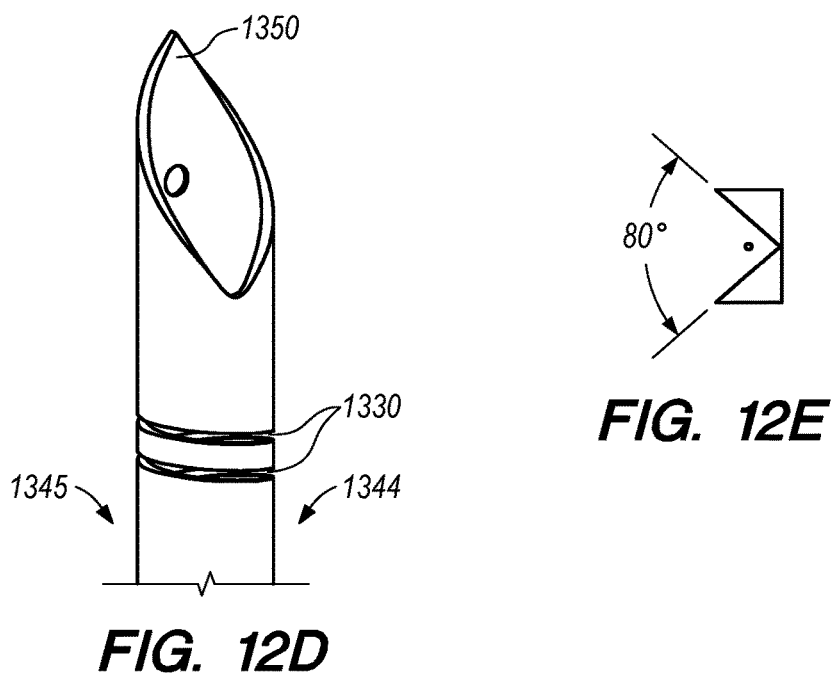
FIG. 12D
FIG. 12E

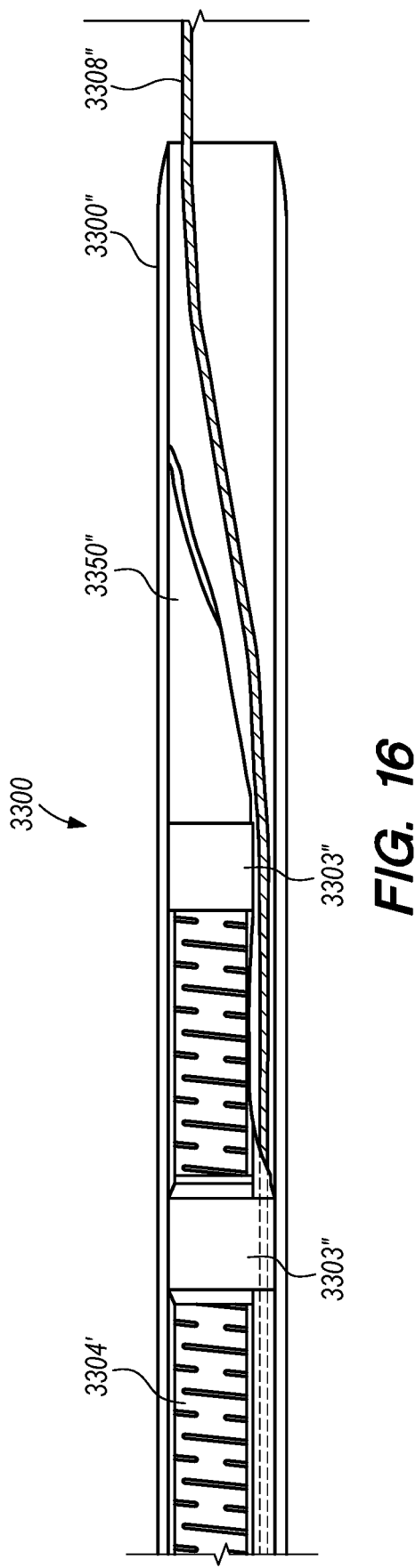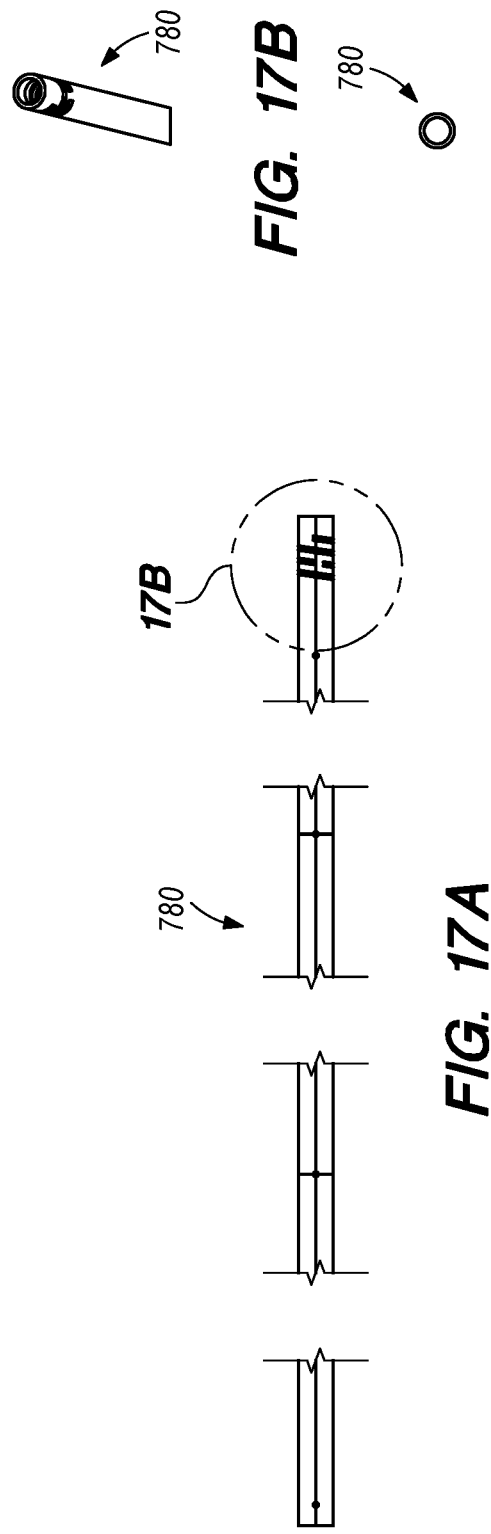

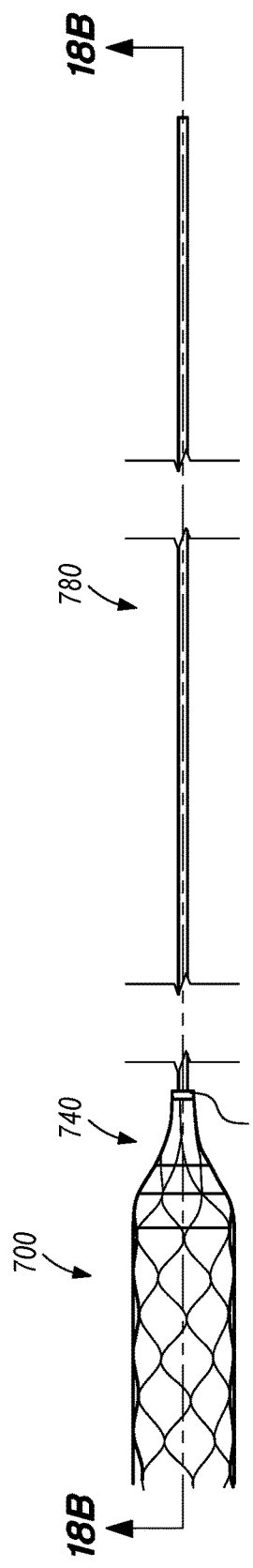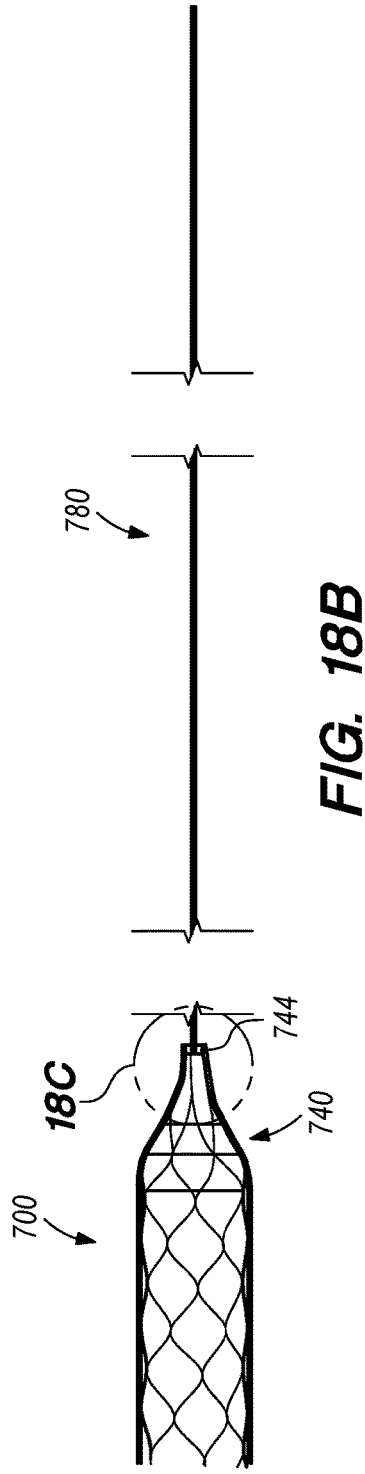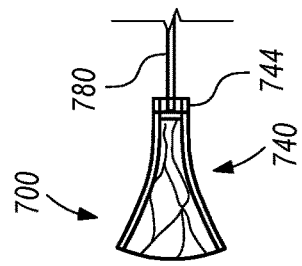
FIG. 18A
FIG. 18B
FIG. 18C

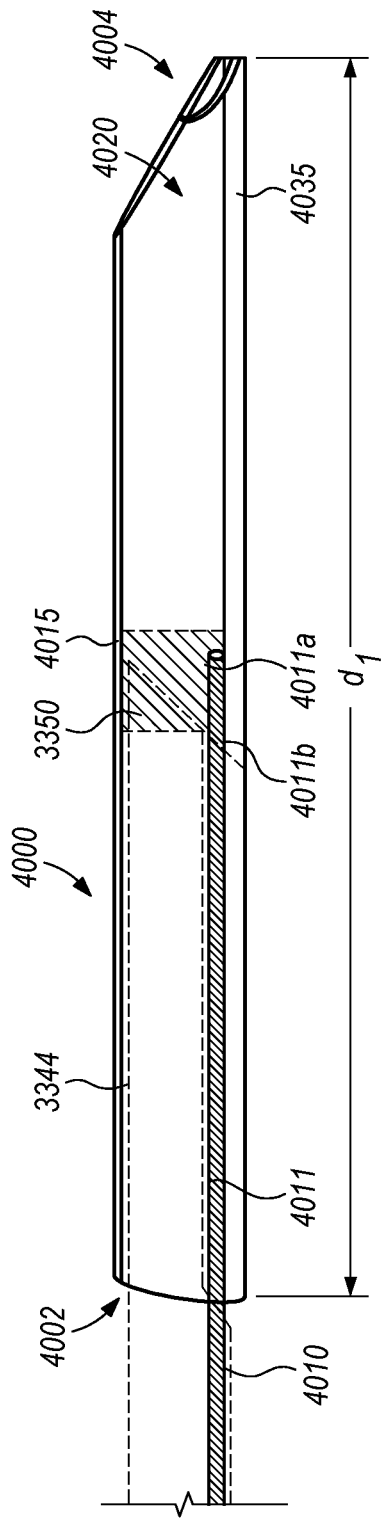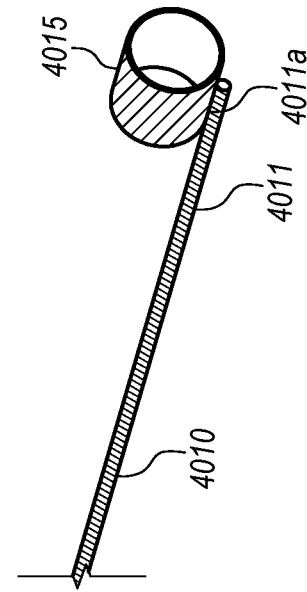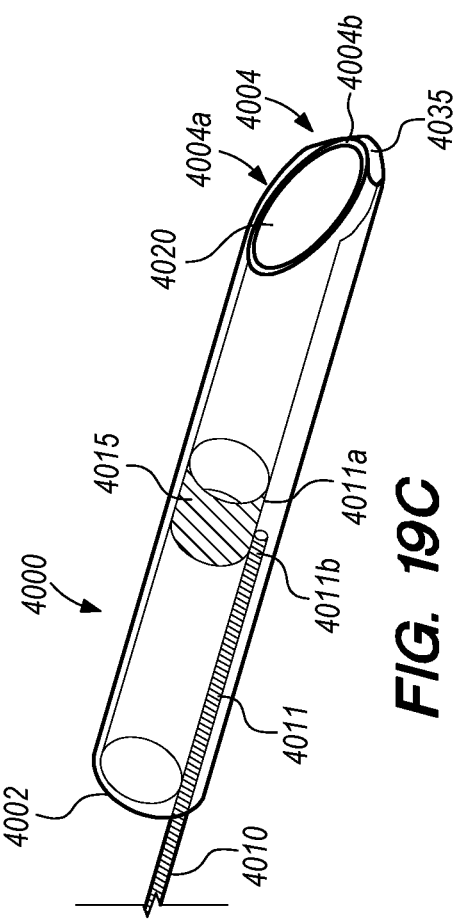

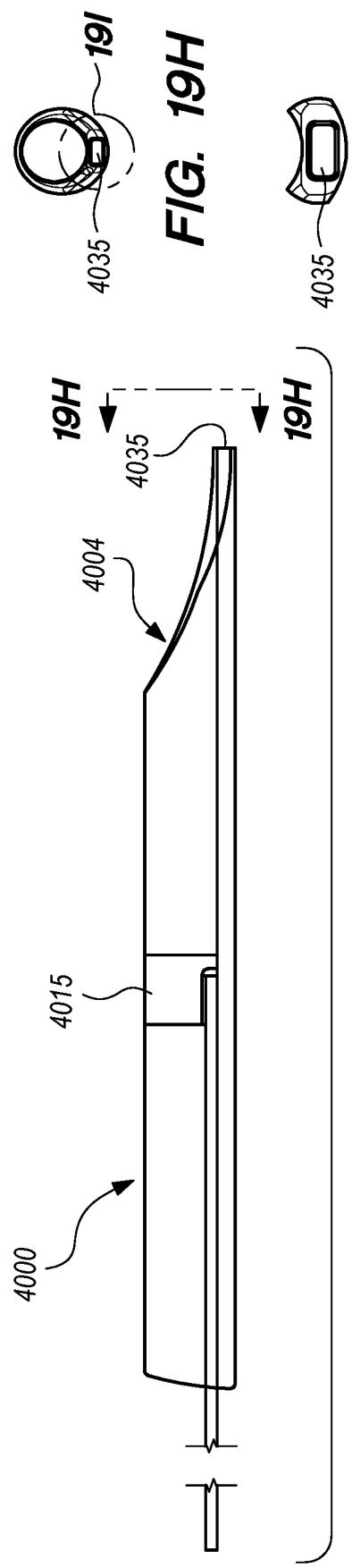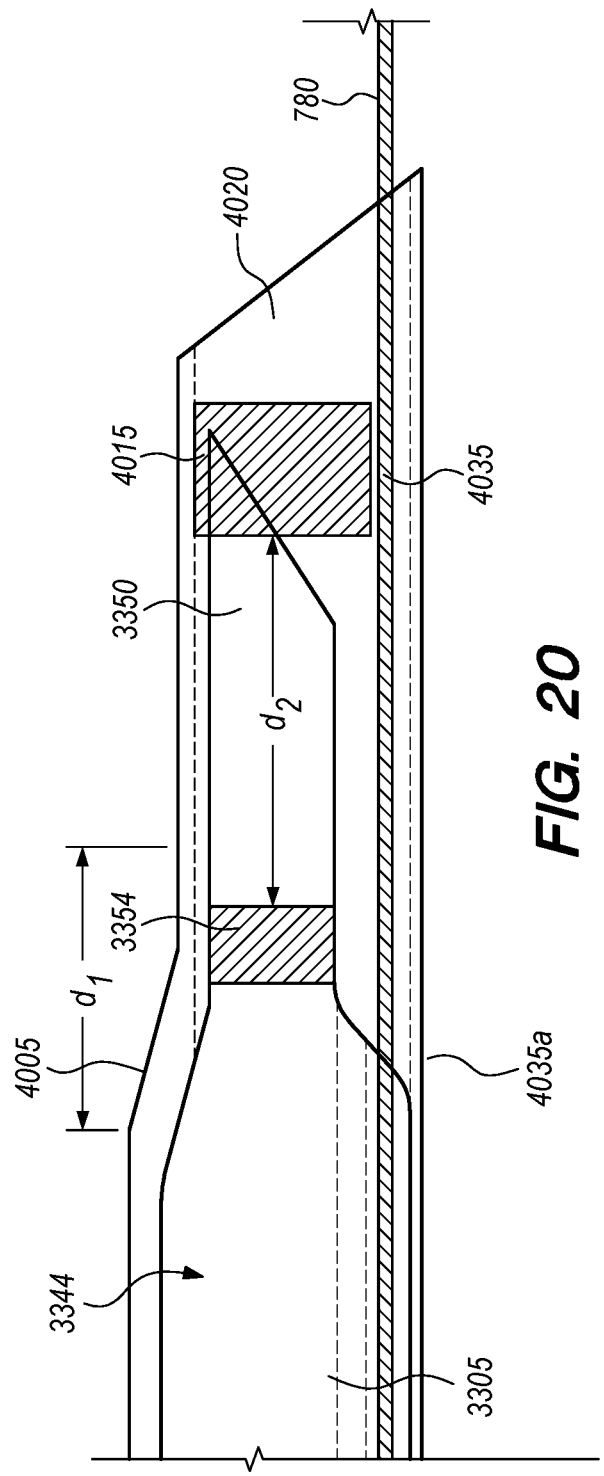

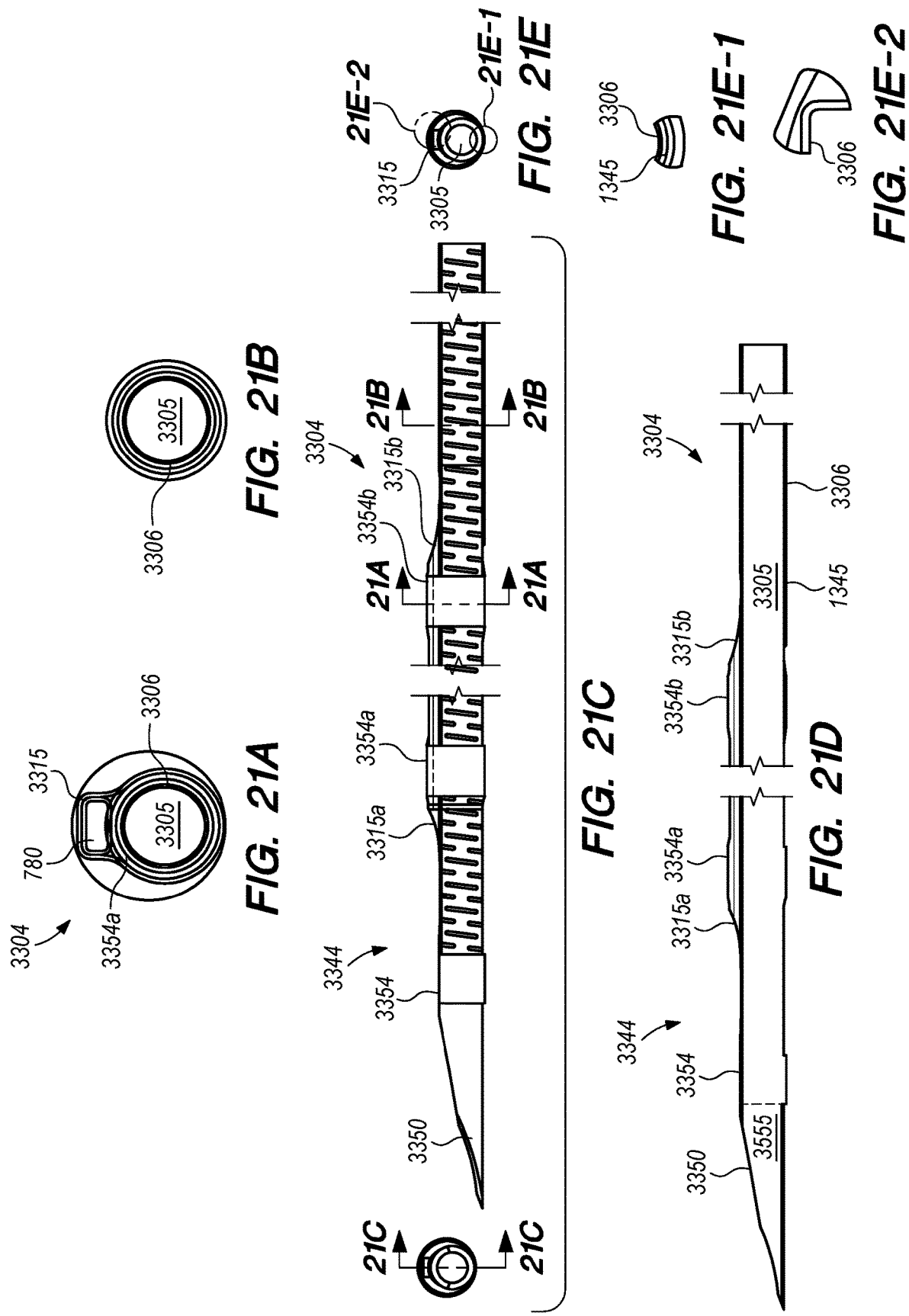

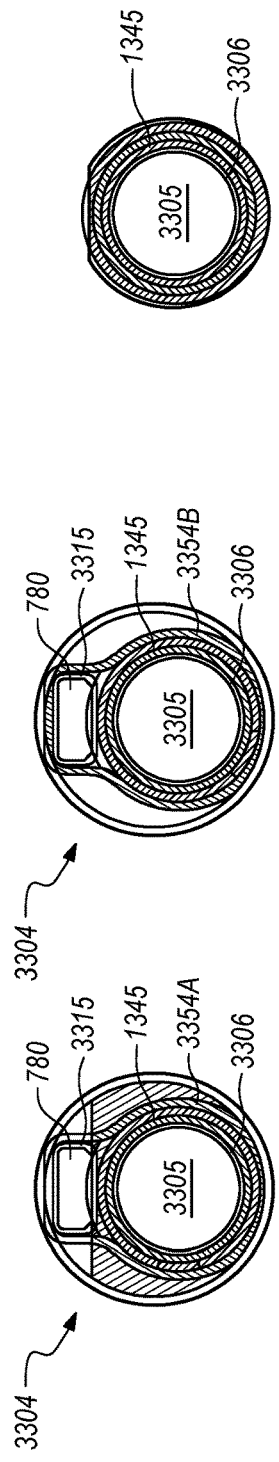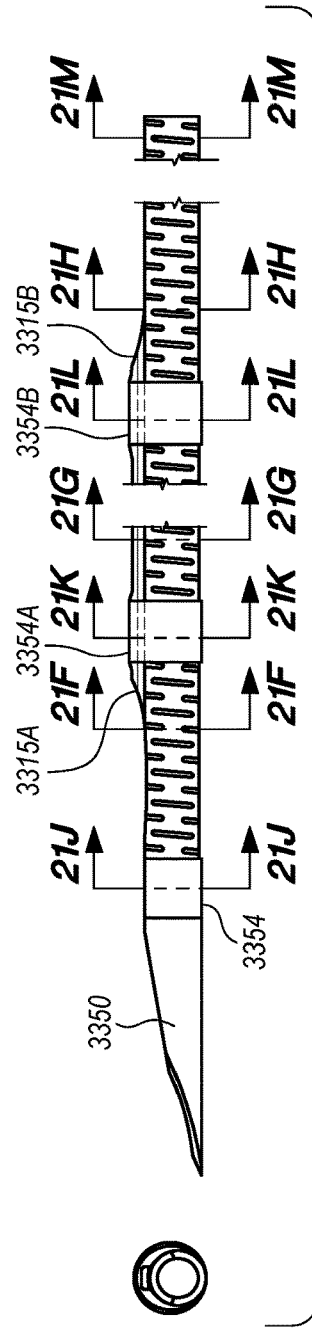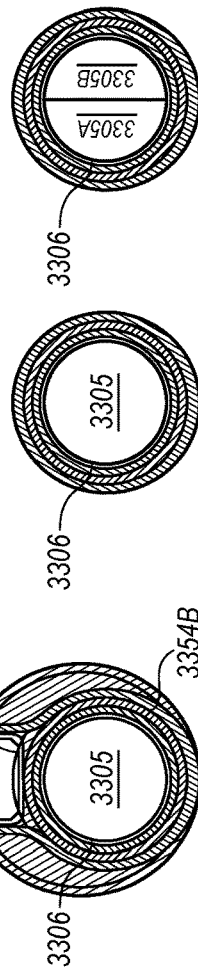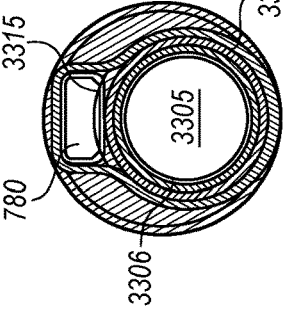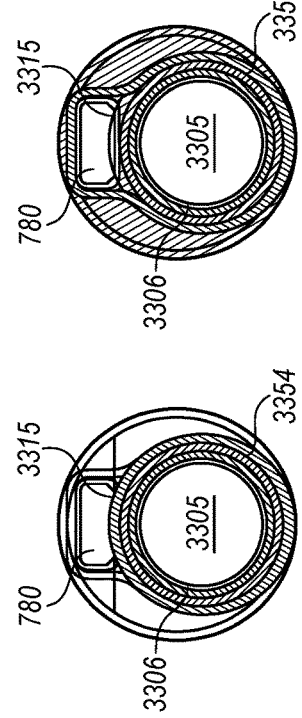

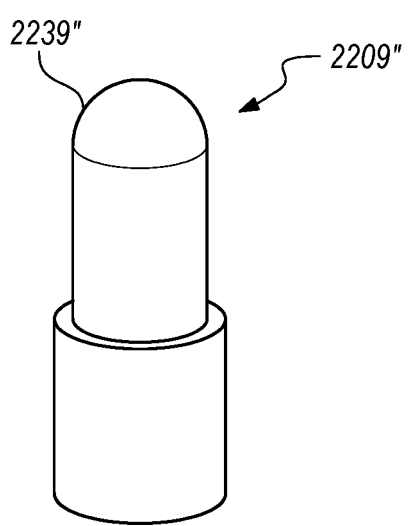
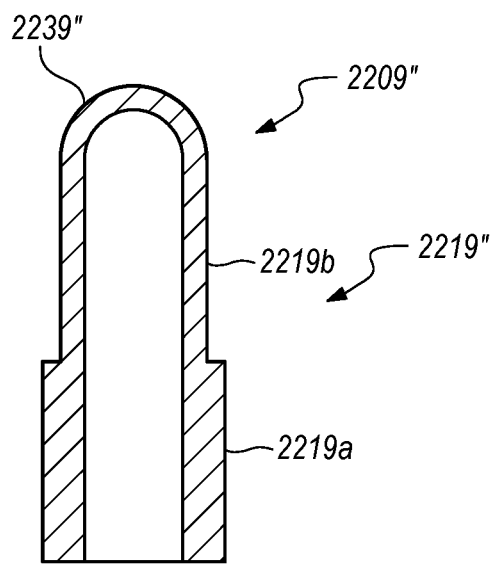
FIG. 25A  FIG. 25B
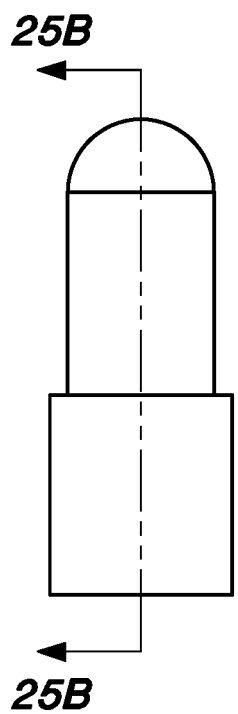
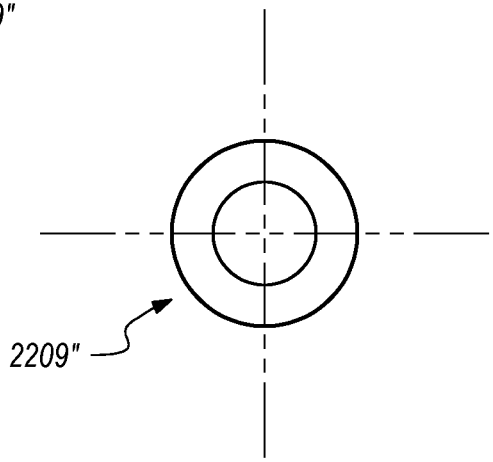
FIG. 25C  FIG. 25D

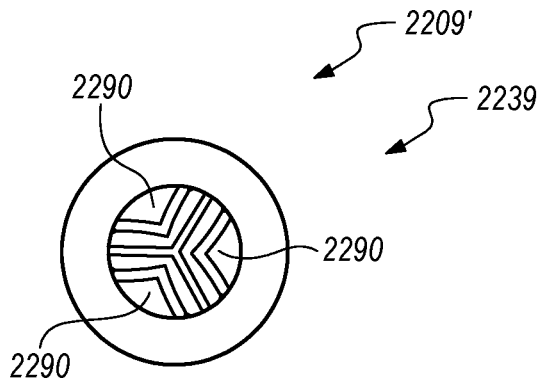
FIG. 25H
| DESIGN TABLE | | |
|---|---|---|
| DASH NO. | DOME THICKNESS | MIN THICKNESS |
| -01 | 0.005 | 0.001 |
| -02 | 0.007 | 0.002 |
| -03 | 0.009 | 0.003 |
FIG. 25I
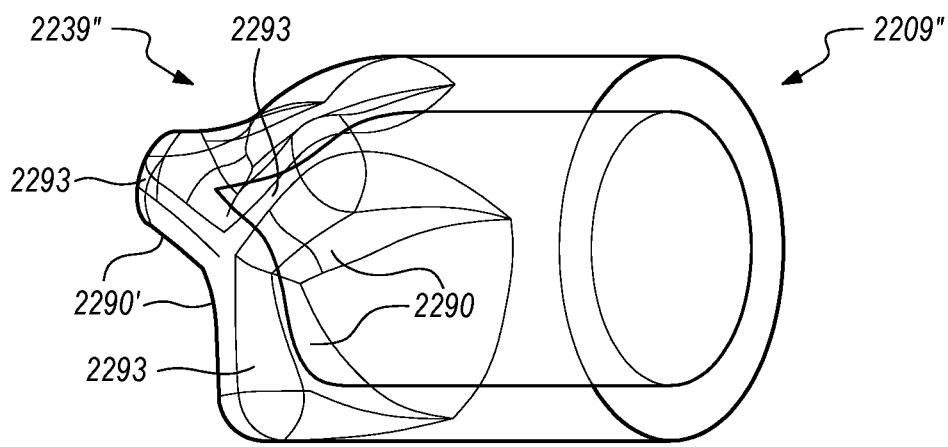
FIG. 25J

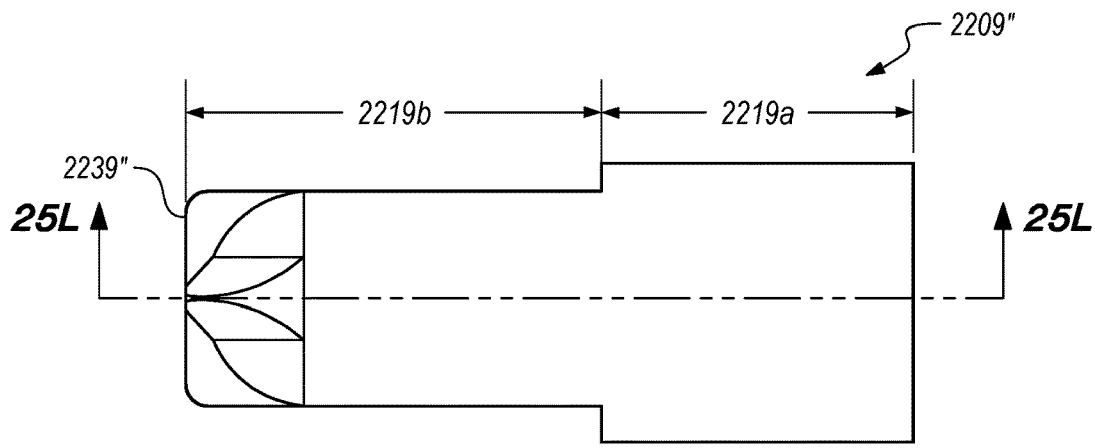
FIG. 25K
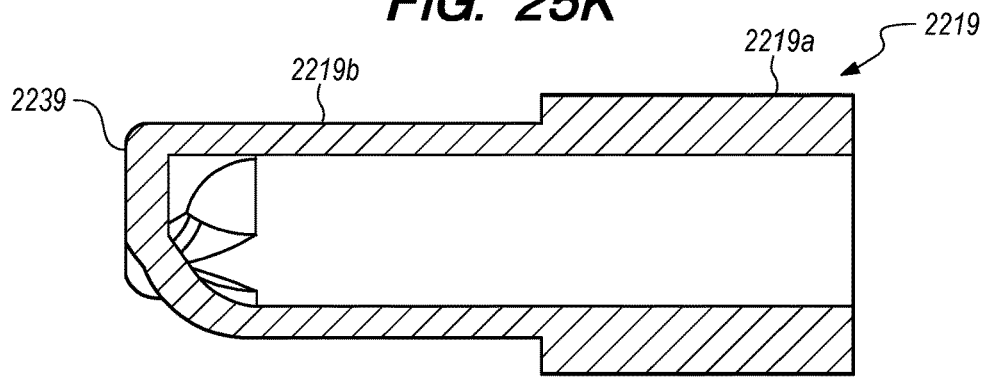
FIG. 25L
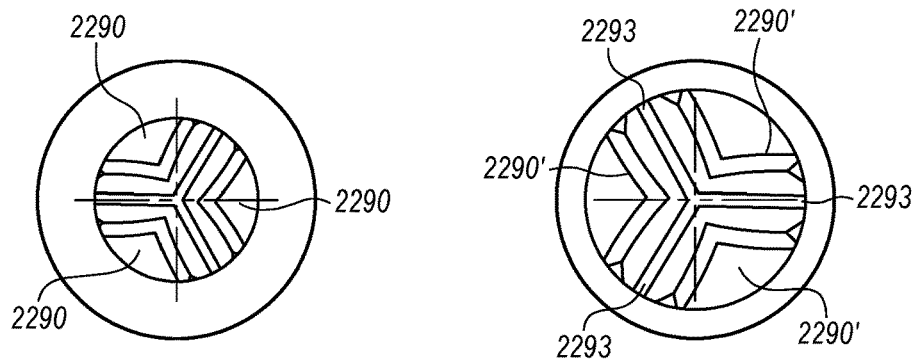
FIG. 25M     FIG. 25N
| DESIGN TABLE ||
| DASH NO. | DOME THICKNESS |
| --- | --- |
| -01 | 0.002 |
| -02 | 0.003 |
| -03 | 0.004 |
FIG. 25O

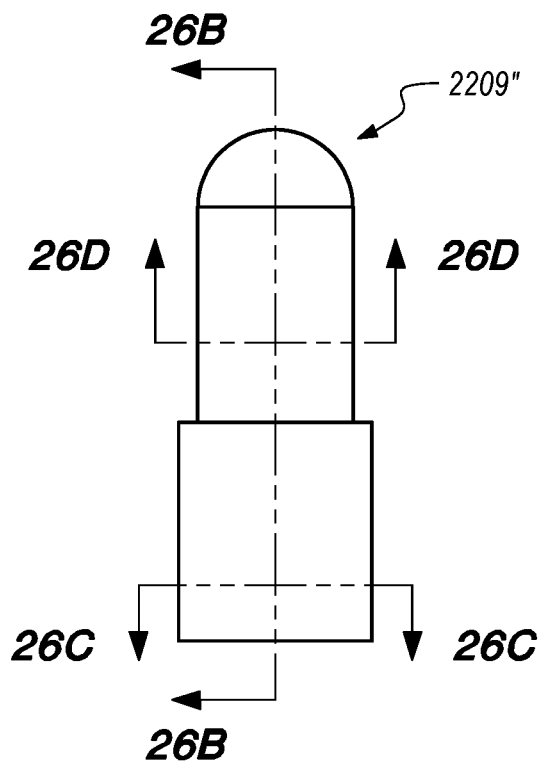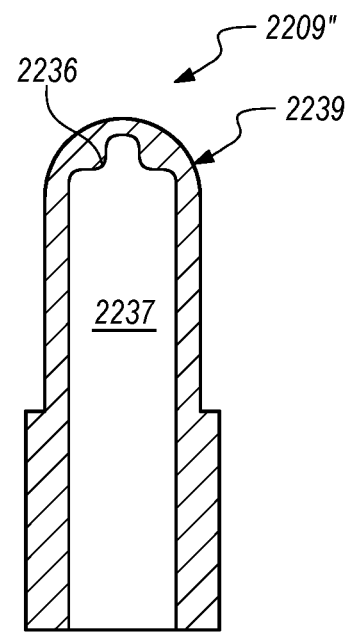
FIG. 26A
FIG. 26B
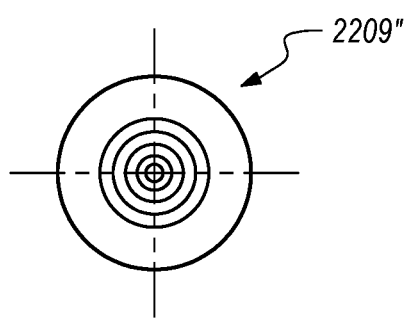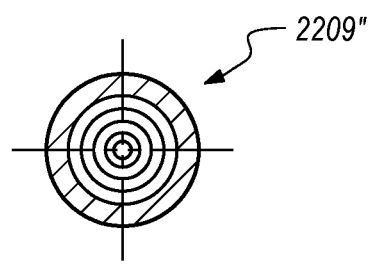
FIG. 26C
FIG. 26D

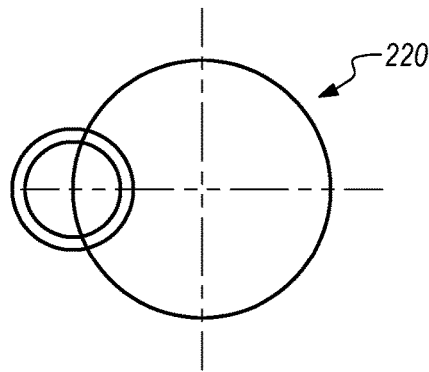
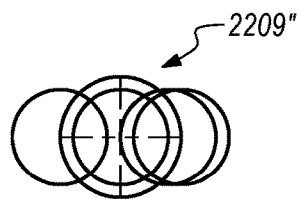
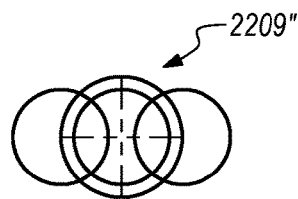
FIG. 28J     FIG. 28K     FIG. 28L
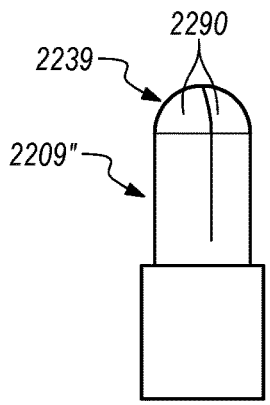
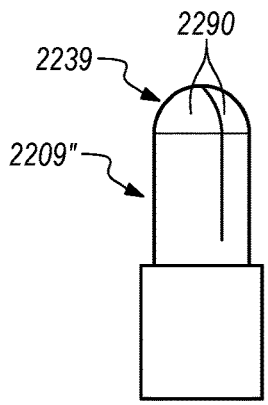
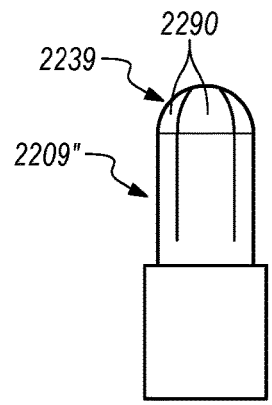
FIG. 28M     FIG. 28N     FIG. 28O
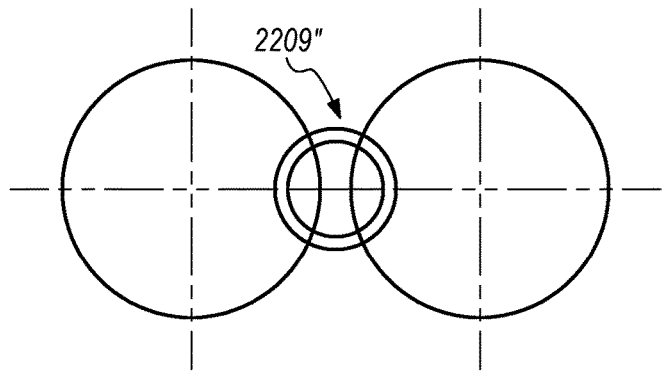
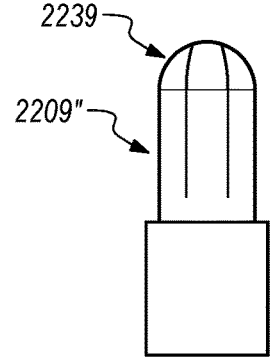
FIG. 28P     FIG. 28Q

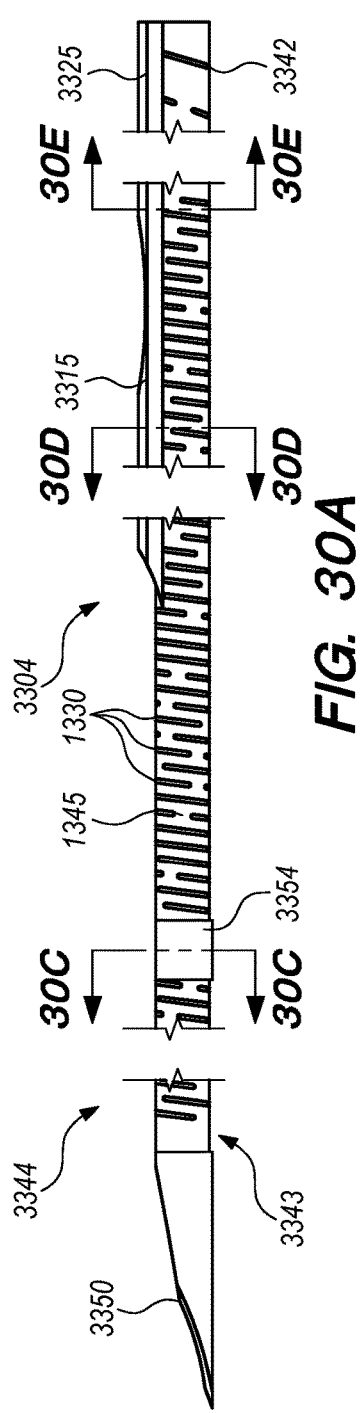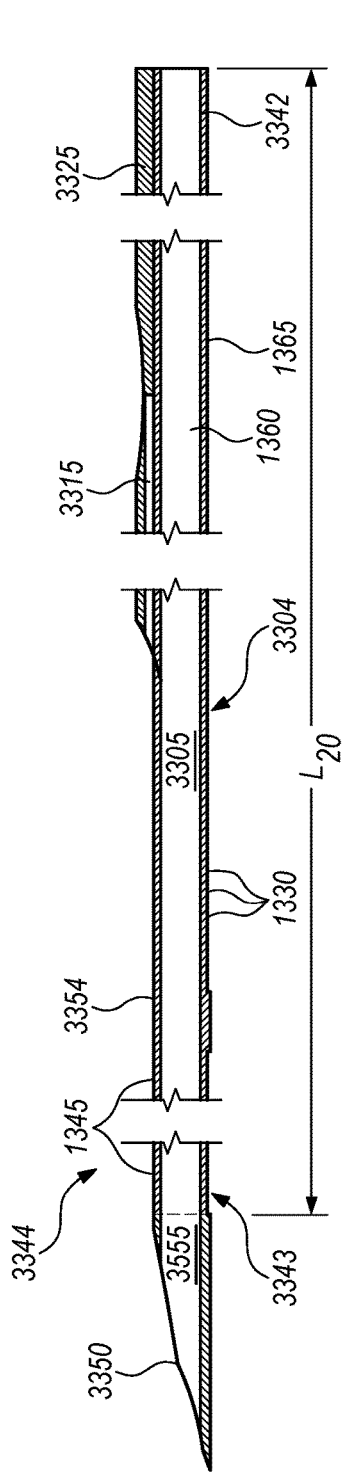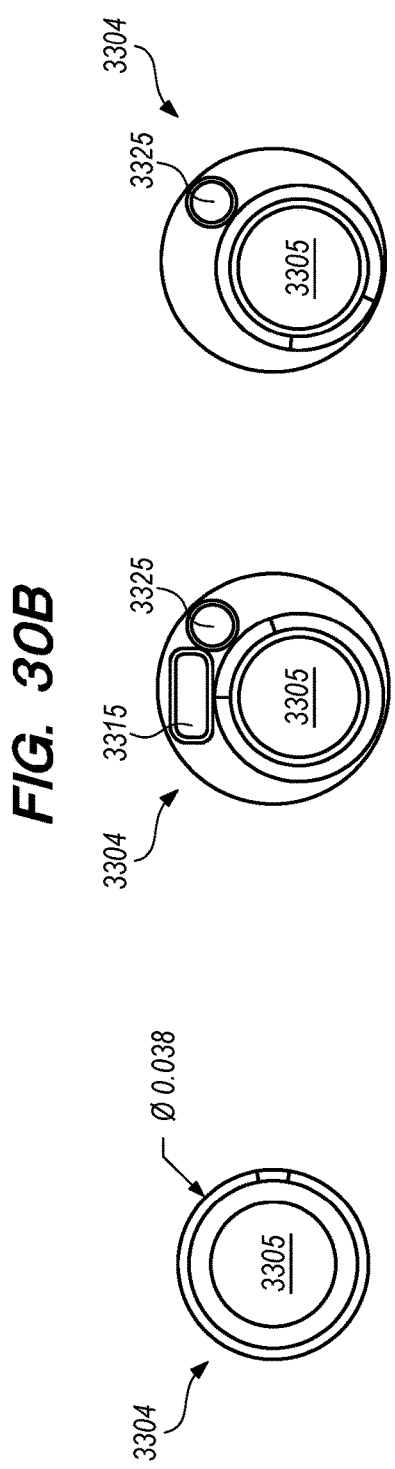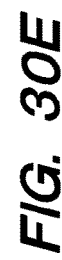

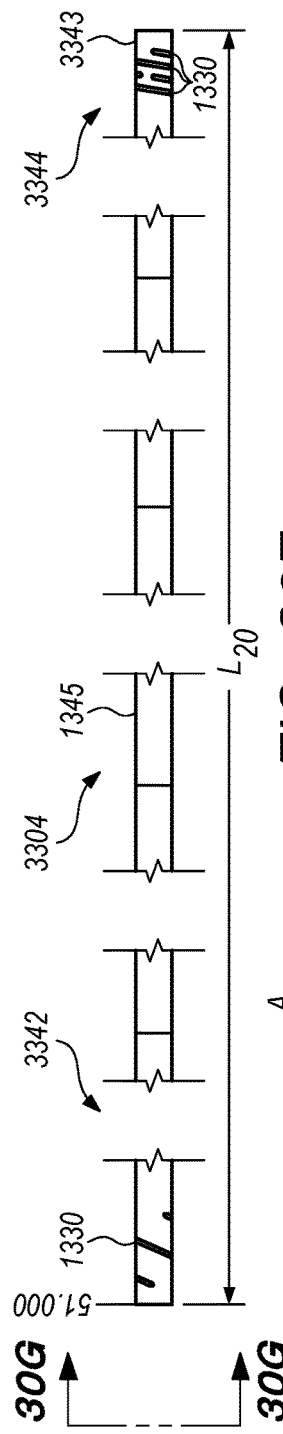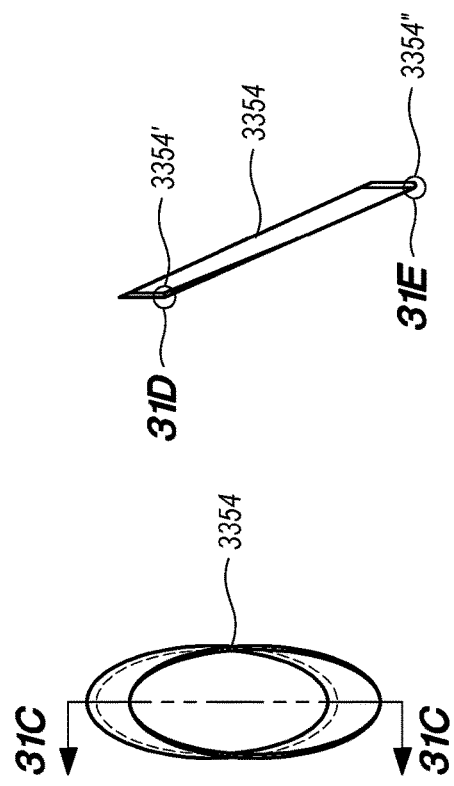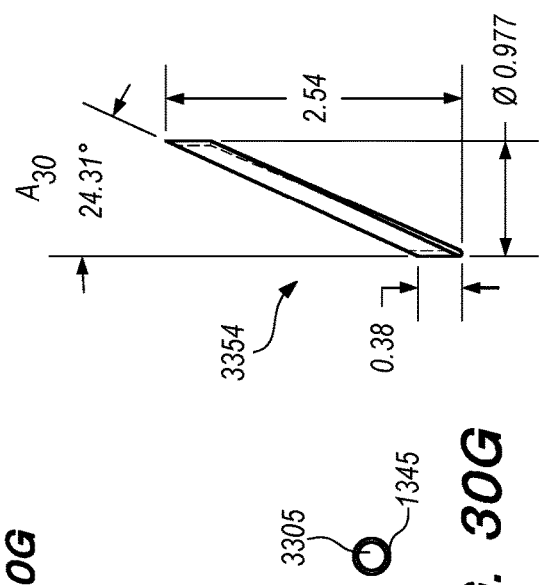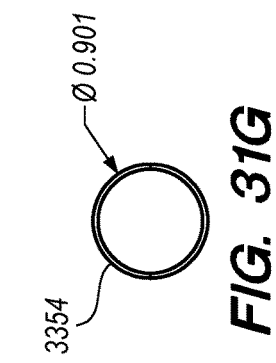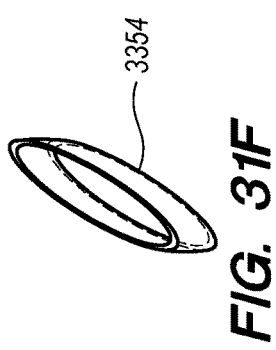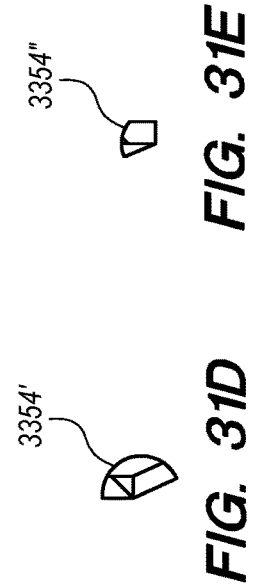

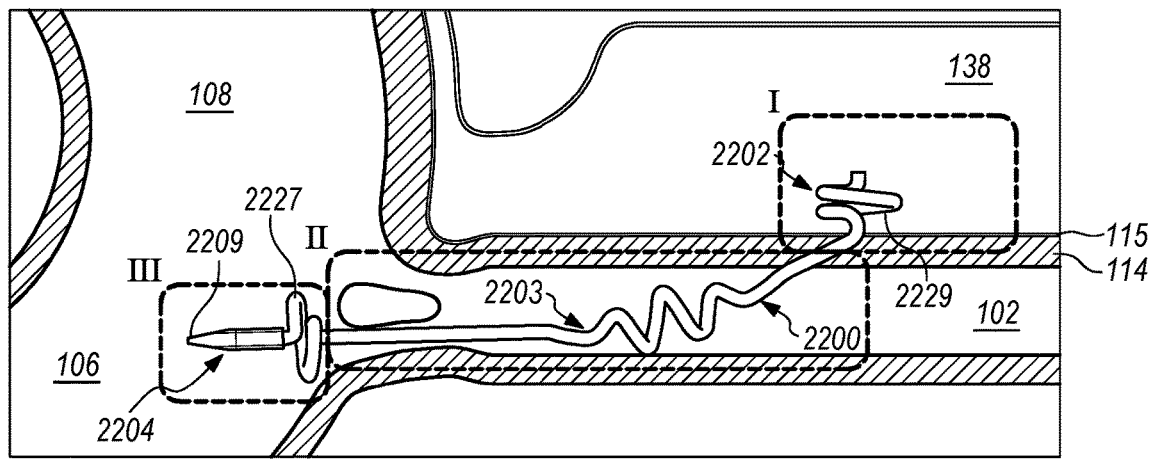
FIG. 32
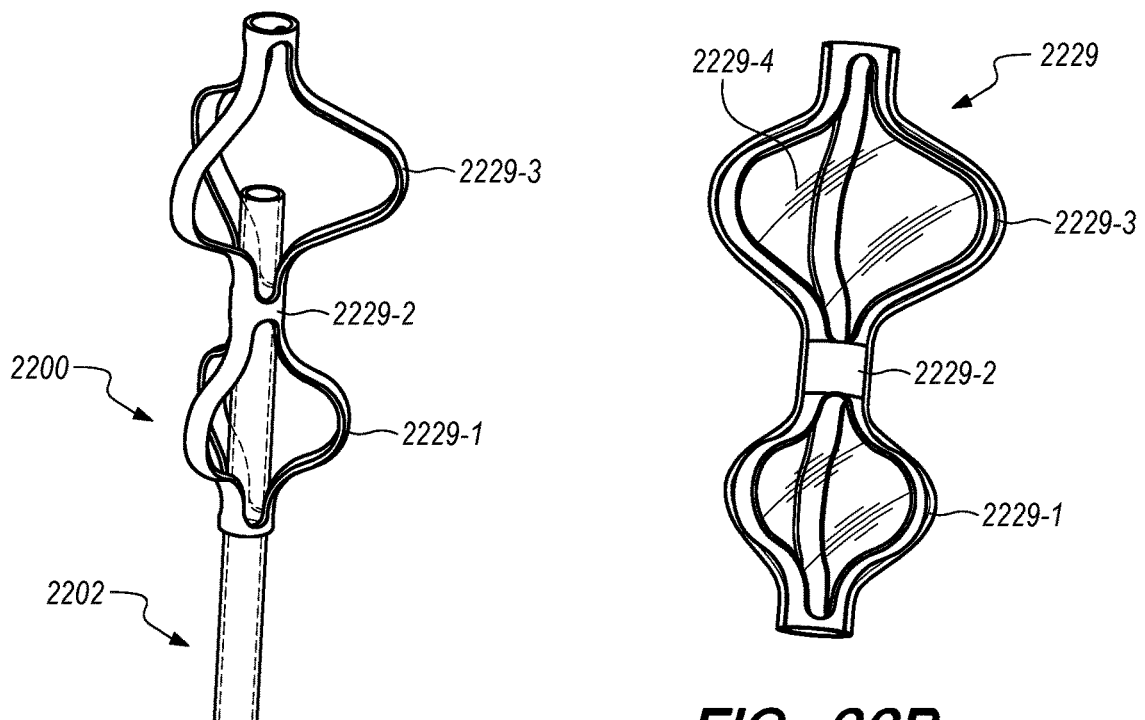
FIG. 33A  FIG. 33B

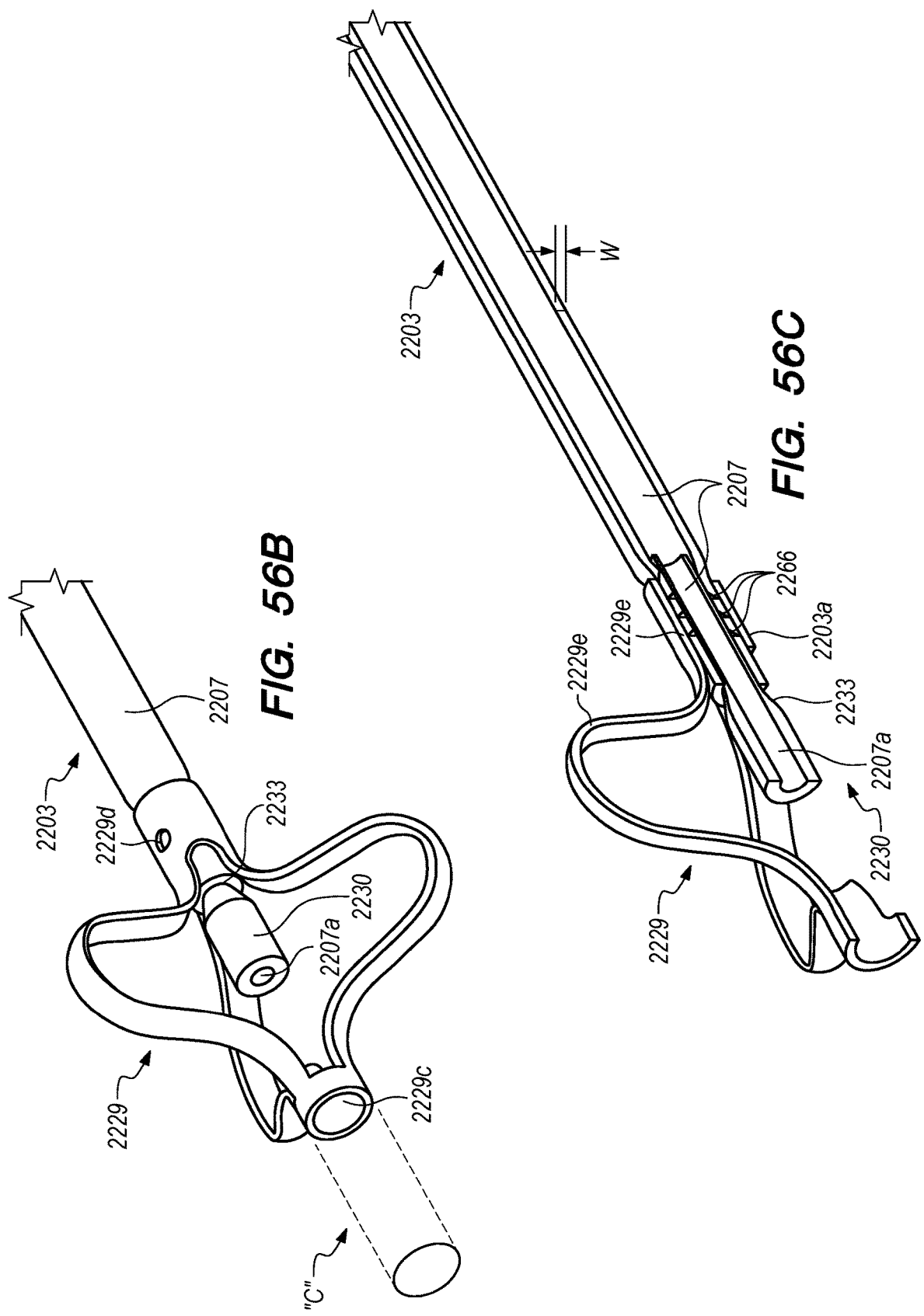

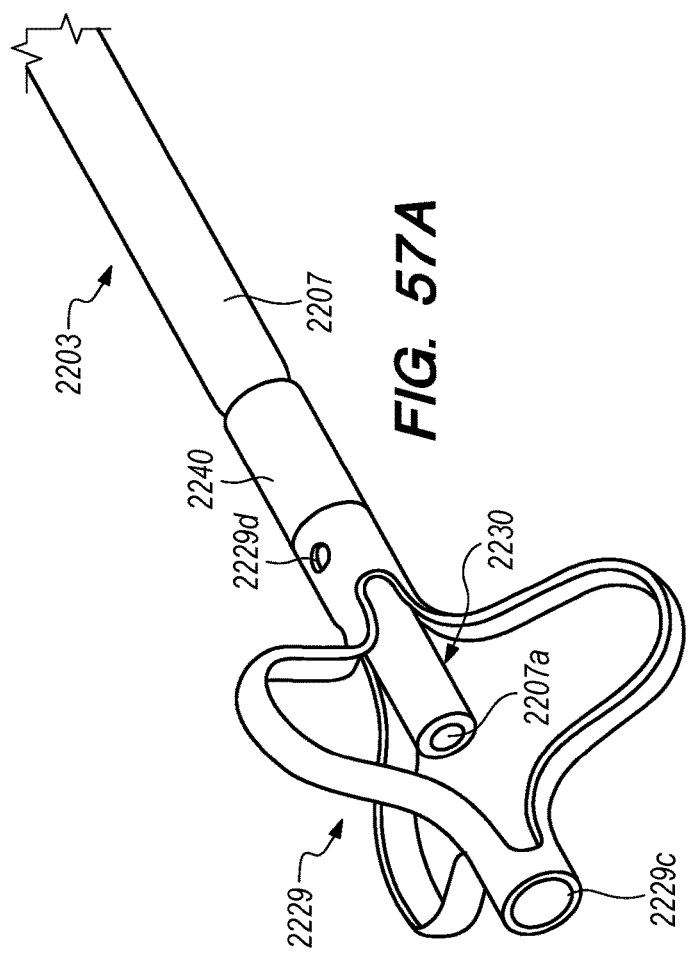
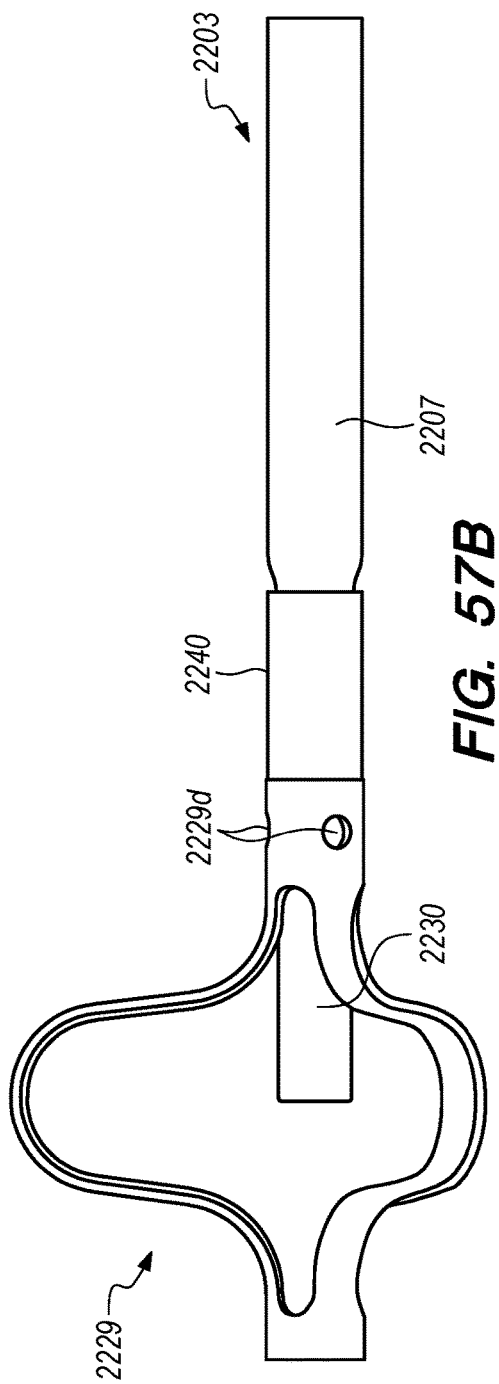

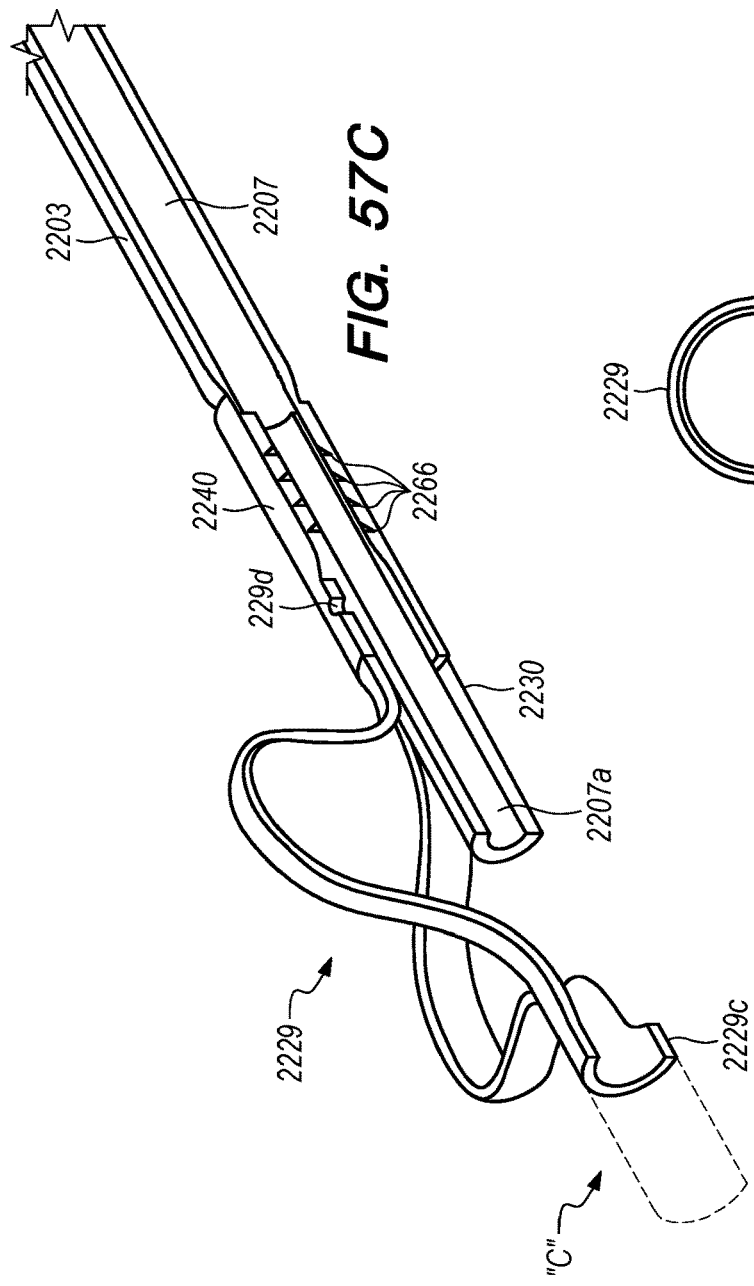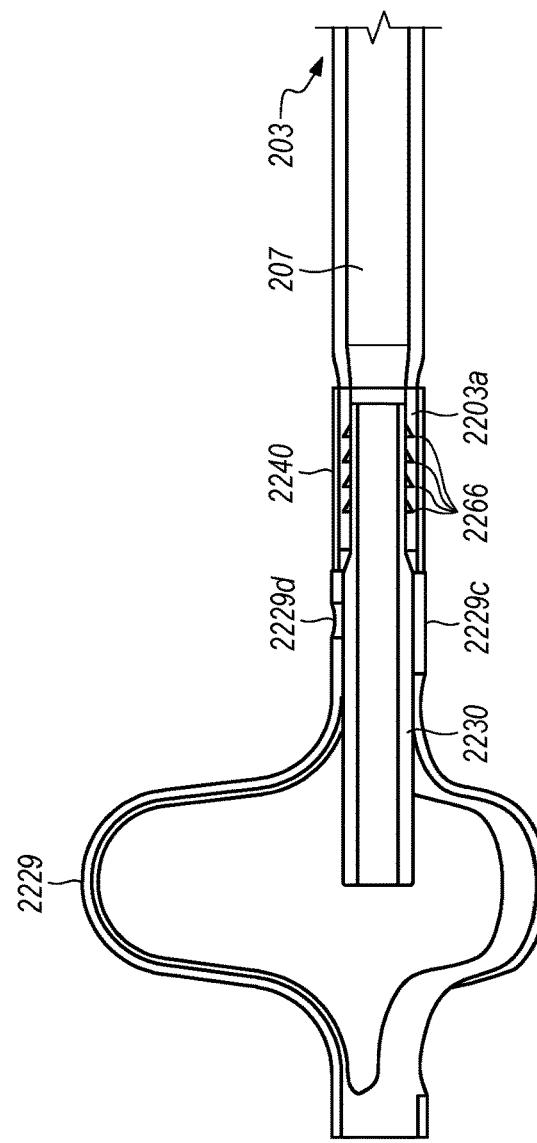

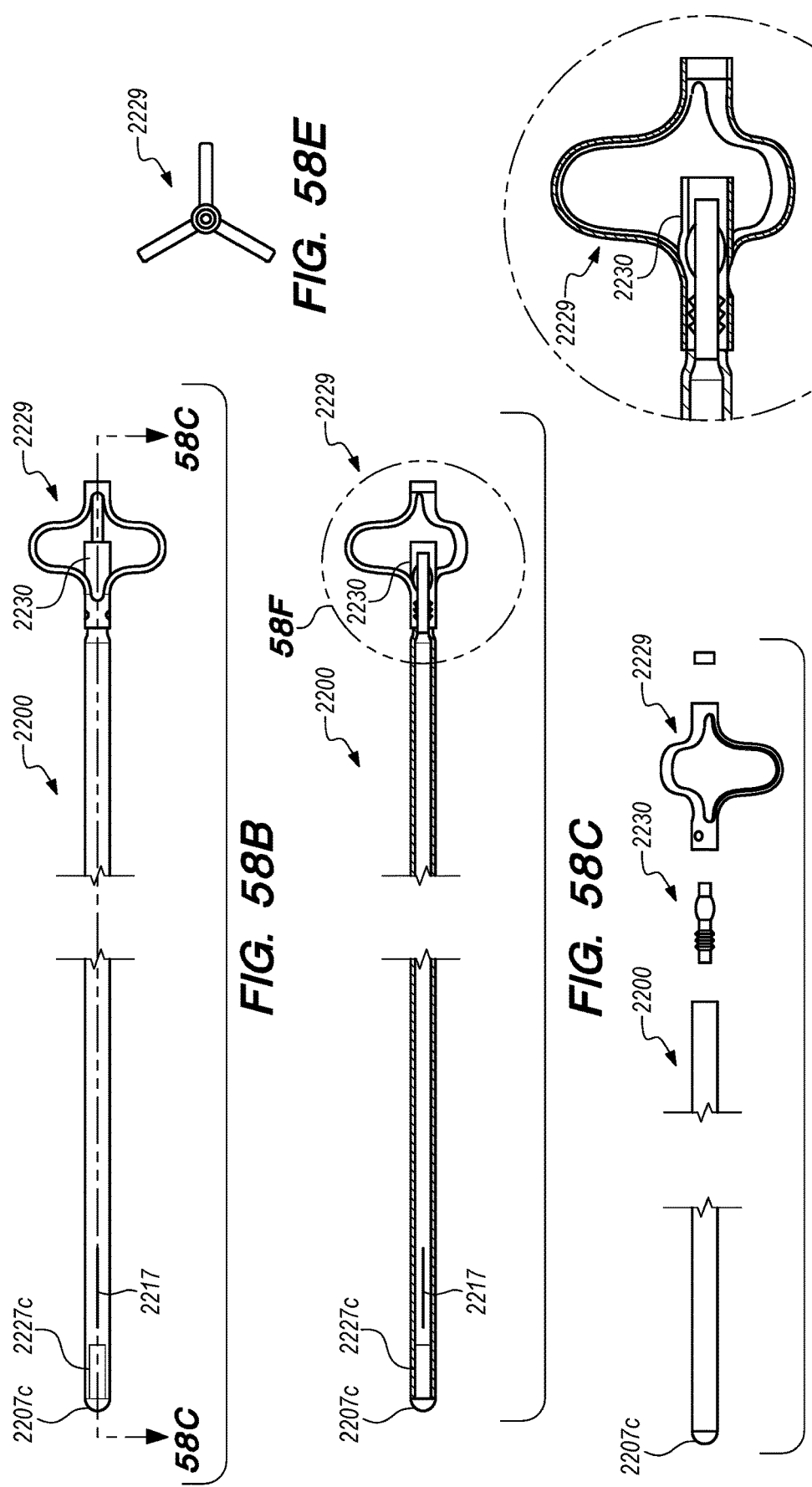

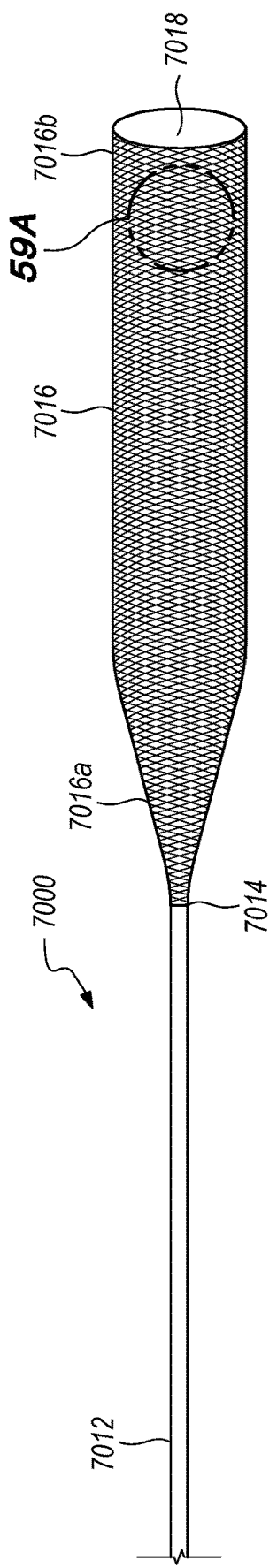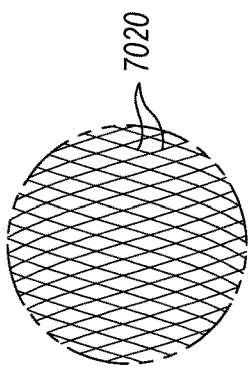
FIG. 59
FIG. 59A

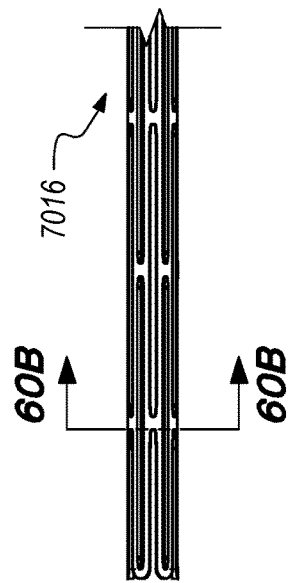
FIG. 60B
FIG. 60A
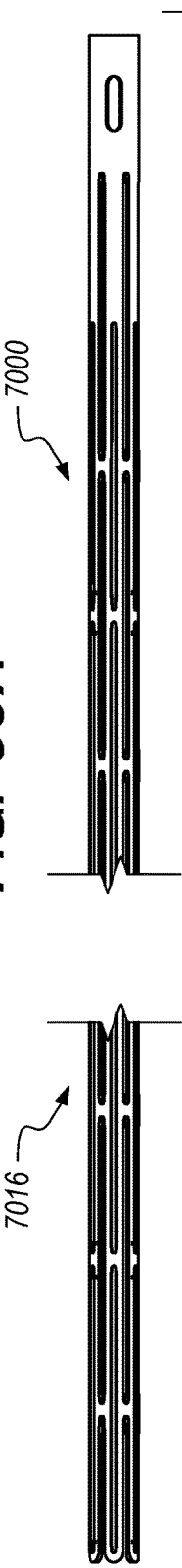
FIG. 60C
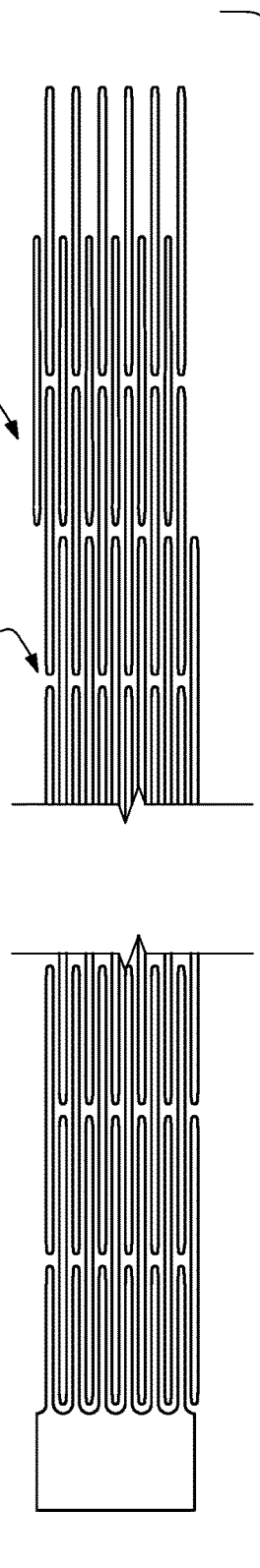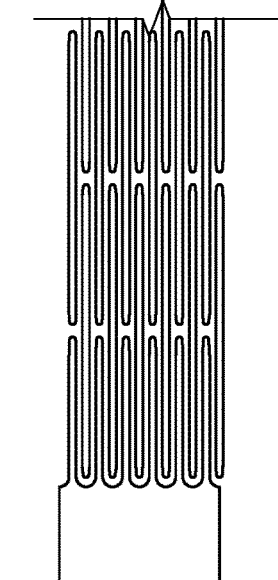
FIG. 60D

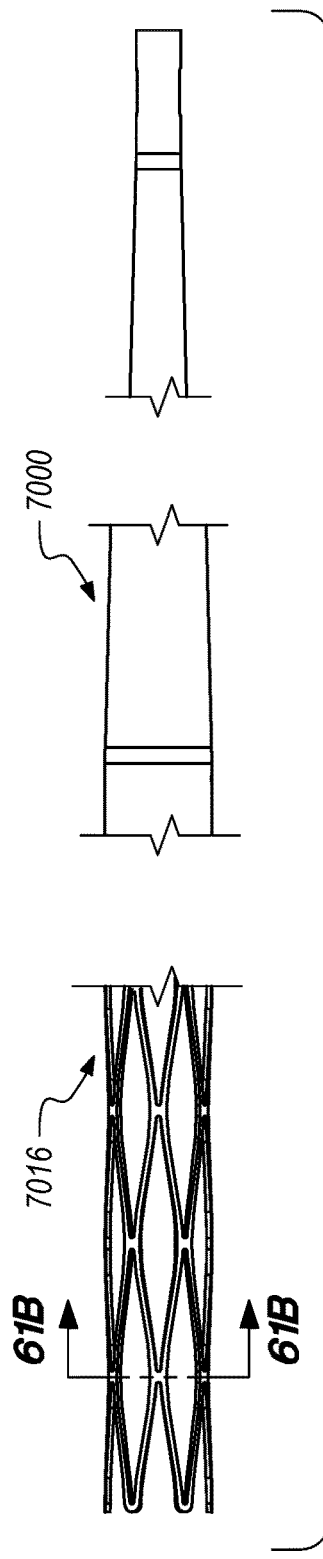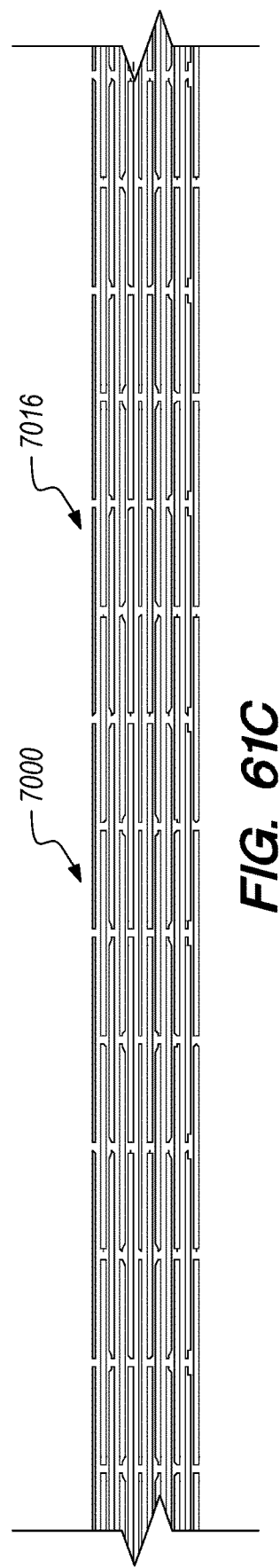
FIG. 61B
FIG. 61A
FIG. 61C

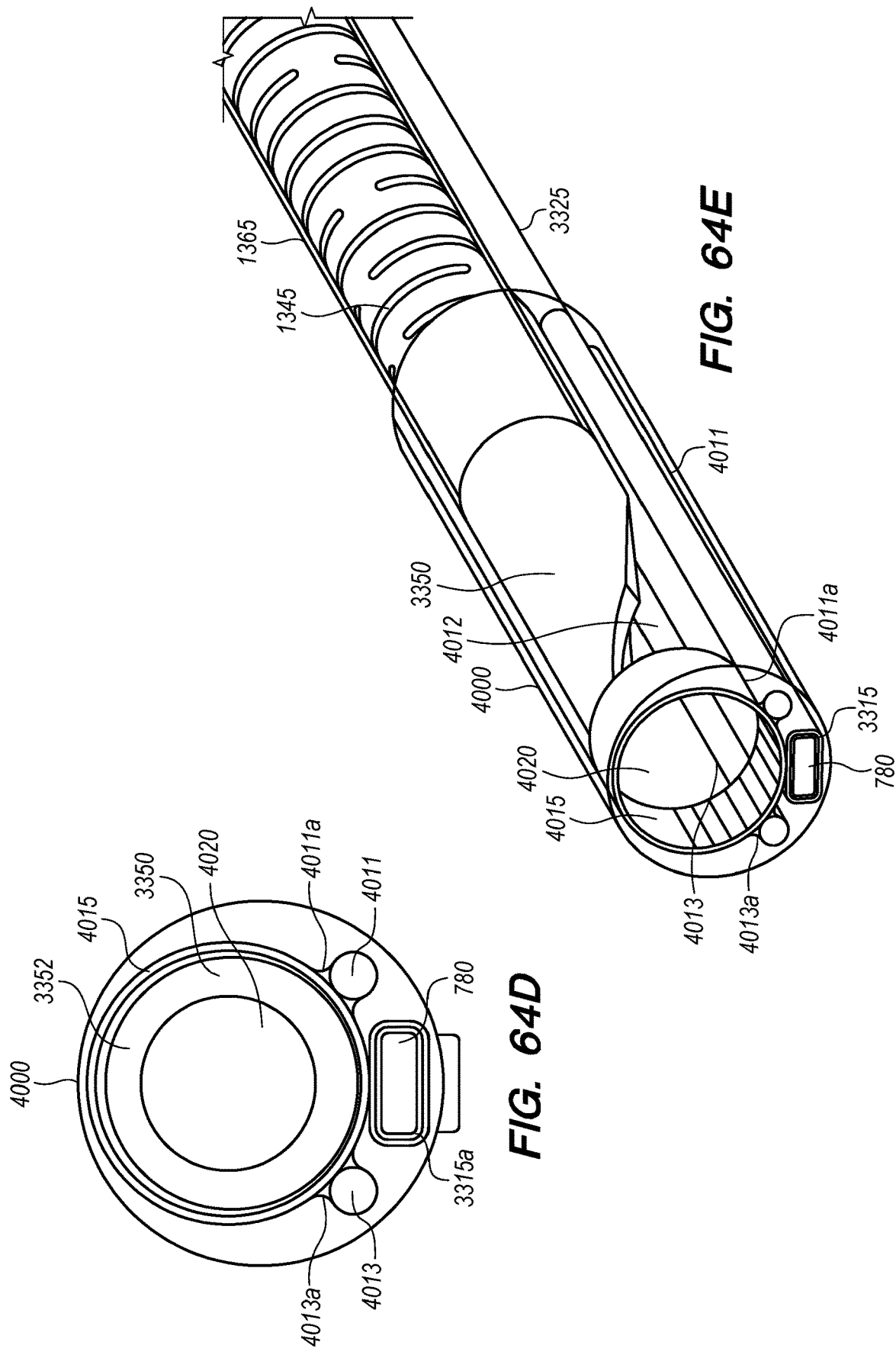

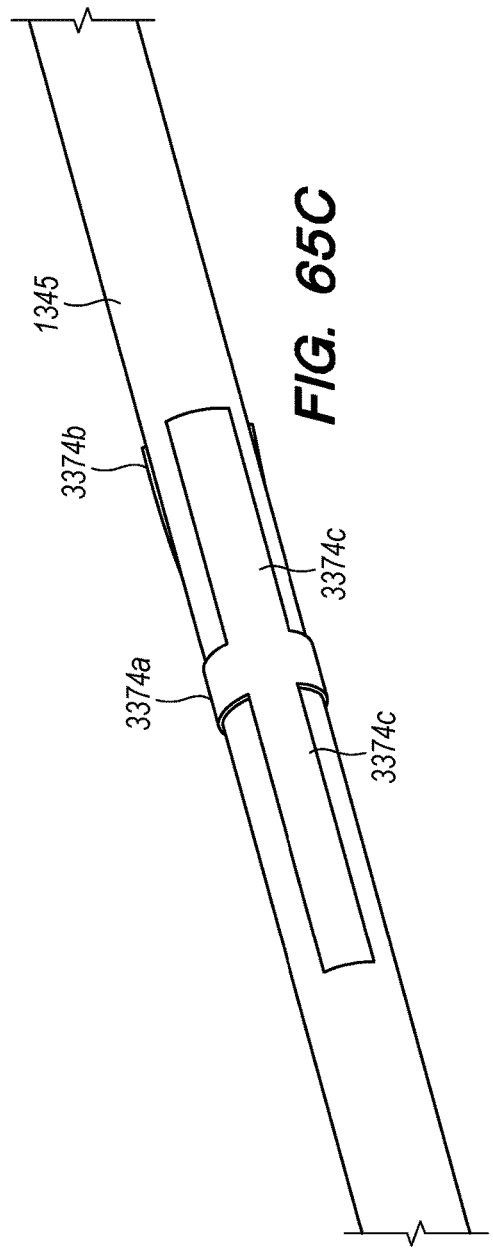
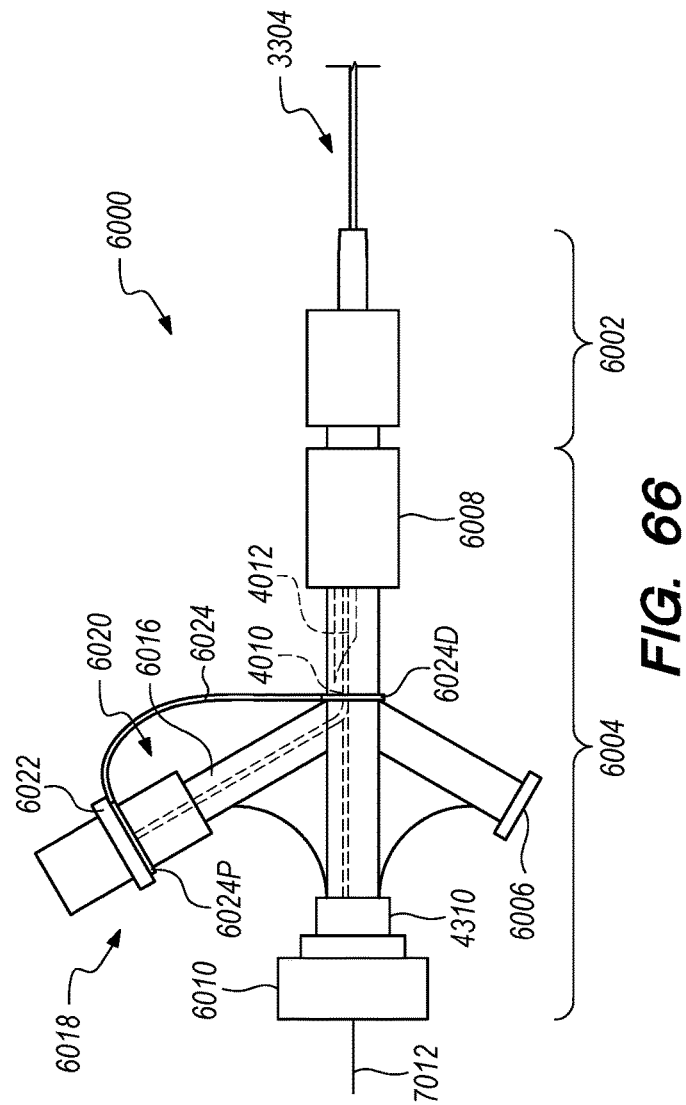

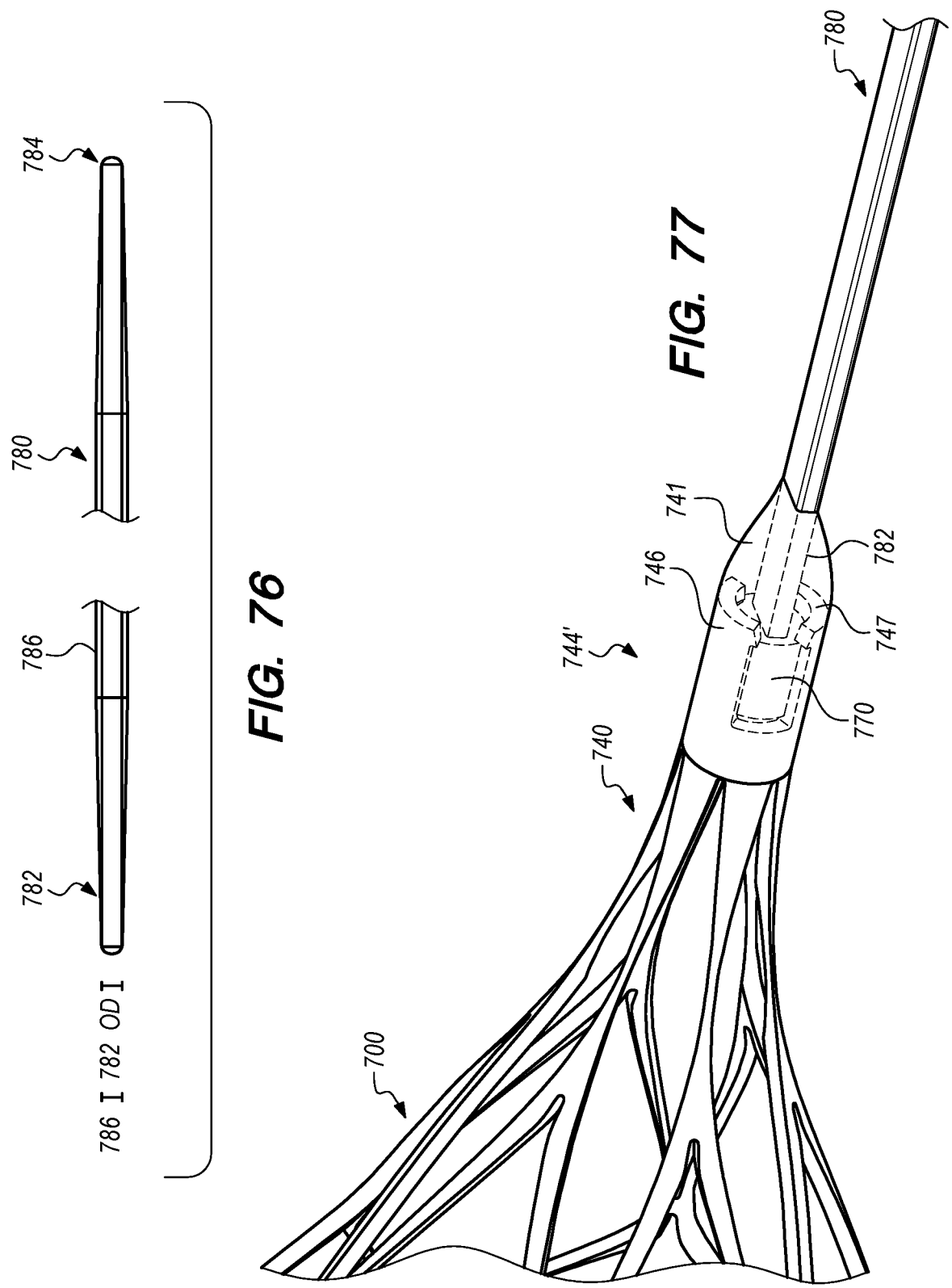

SYSTEMS AND METHODS FOR MINIMALLY INVASIVE DRUG DELIVERY TO A SUBARACHNOID SPACE

RELATED APPLICATION DATA

The present application is a continuation of U.S. patent application Ser. No. 16/976,057, filed Aug. 26, 2020, now issued as U.S. Pat. No. 11,013,900, which is a National Phase entry under 35 U.S.C § 371 of International Patent Application No. PCT/US2019/021471, having an international filing date of Mar. 8, 2019, which claims the benefit under 35 U.S.C. § 119 to each of U.S. Provisional Patent Application Ser. Nos. 62/640,471, filed Mar. 8, 2018, 62/667,852, filed May 7, 2018, 62/727,401, filed Sep. 5, 2018, 62/755,078, filed Nov. 2, 2018, 62/768,296, filed Nov. 16, 2018, and 62/805,091, filed Feb. 13, 2019. The present application is also related to each of International Patent Application No. PCT/US18/20667, filed Mar. 2, 2018, U.S. Provisional Patent Application Ser. No. 62/472,729, filed Mar. 20, 2017, and International Patent Application No. PCT/US17/56227, filed on Oct. 11, 2017. The contents of the foregoing applications are hereby incorporated by reference into the present application in their entirety.

FIELD OF THE INVENTION

The inventions disclosed herein relate to systems and methods for accessing the subarachnoid space including intracranial cerebral cisterns for the administration of therapeutic agents. More particularly, the present disclosure pertains to systems and methods for using a minimally invasive endovascular approach to the subarachnoid space to deliver therapeutic agents that cannot cross the blood-brain barrier through other delivery applications

BACKGROUND

Intrathecal drug delivery is used to deliver therapeutic agents targeted for the central nervous system to the subarachnoid space. Delivery typically occurs with injection of the therapeutic agent after penetrating into the spinal canal (e.g., by lumbar puncture), or through a burr hole drilled in the skull to access a targeted location in the brain. These delivery techniques are required to provide a therapeutic agent directly to the cerebrospinal fluid (CSF) or brain parenchyma because certain such agents cannot pass through the blood-brain barrier when delivered to the bloodstream. Intrathecal drug delivery is used, for example, to administer spinal anesthesia, chemotherapy, pain management agents, and antibiotics. Prior art techniques and devices for intrathecal drug delivery include potentially significant risks and complications for the patient, and can be ineffective for delivering a therapeutic agent to certain locations within the subarachnoid space.

Despite significant advances in biomedical technology, instrumentation, and medical devices, there has been little improvement in minimally invasive methods and devices for delivering therapeutic agents to the intracranial subarachnoid space.

SUMMARY

In accordance with a first aspect of the disclosed inventions, embodiments of an endovascular drug delivery device configured for being deployed in a dural venous sinus (DVS) of a patient are disclosed and described herein. In an exemplary embodiment, the endovascular drug delivery device includes a self-expanding distal anchor configured for being introduced into, and disposed within, an intracranial subarachnoid space (ISAS) of the patient via the DVS, and an elongate tubular body coupled to the distal anchor and configured for being at least partially disposed within the DVS when the anchor is disposed within the ISAS, the elongate tubular body comprising a lumen that is in fluid communication with a therapeutic agent outflow opening in the distal anchor for allowing a therapeutic agent to flow from the lumen of the elongate tubular body out the therapeutic agent outflow opening and into the ISAS when the distal anchor is secured therein.

The endovascular drug delivery device may include a distal connector having one end secured to the distal anchor and a second end secured to a distal end of the elongate tubular body, the distal connector having a lumen that fluidly couples the lumen of the elongate tubular body with the therapeutic agent outflow opening, wherein the distal connector is preferably radiopaque or otherwise has one or more radiopaque elements coupled thereto. In such embodiments, the distal connector may be secured to the distal anchor in a configuration that maintains the therapeutic agent outflow opening in a position that is separated, apart and/or directed away from an arachnoid layer of the ISAS when the distal anchor is secured therein.

The endovascular drug delivery device may include a valve disposed in or over the therapeutic agent outflow opening and configured to allow the therapeutic agent to flow out of the therapeutic agent outflow opening while preventing cerebrospinal fluid (CSF) in the ISAS from entering into the lumen of the elongate tubular body.

The elongate tubular body of the endovascular drug delivery device may be provided with one or more anchoring mechanisms configured to secure the drug delivery device at a deployment location in the patient.

In some embodiments, the lumen of the elongate tubular body may comprise a reservoir containing the therapeutic agent. In other embodiments, the endovascular drug delivery device is part of system that includes a separate reservoir containing the therapeutic agent, wherein the reservoir is in fluid communication with the lumen of the elongate tubular body. By way of non-limiting example, the therapeutic agent reservoir may be located within an implantable housing that is coupled to a proximal end of the elongate tubular member, and a refilling coupler may be provided, with one end connected to the implantable housing and a second end coupled to a subcutaneous access port, the refilling coupler including a lumen that fluidly couples the reservoir to the access port. In other embodiments, wherein the therapeutic agent reservoir is located outside of the patient's body.

In accordance with another aspect of the disclosed inventions, embodiments of an endovascular drug delivery device implantation system configured for implanting the endovascular drug delivery device are disclosed and described herein. In an exemplary embodiment, the implantation system includes an expandable guide member anchor configured for being deployed in a dural venous sinus location distal to a target penetration site for inserting the distal anchor of the drug delivery device through a curved portion of the DVS wall and into the ISAS, and a guide member having a distal end portion coupled to a tapered proximal end of the guide member anchor via a bending strain relief junction.

In a preferred embodiment, a radiopaque marker body is attached to the distal end of the guide member, the marker body having a slot formed therethrough, the slot having a proximal slot opening, a distal slot opening, and a cross-sectional profile and dimensions configured to receive therethrough the distal end portion of the guide member, wherein the guide member distal end portion extends distally through the proximal slot opening, and wherein the guide member distal end portion is welded or otherwise secured to the marker body only proximate the distal slot opening. A distal end portion of the bending strain relief junction may be an integral portion of, or is otherwise secured to, the proximal end of the guide member anchor, and wherein a proximal portion of the strain relief junction comprises a pair of opposing, proximally-extending protrusions defining a passageway therebetween having a cross-sectional profile and dimensions configured to receive the marker body in a specific orientation. The marker body extends distally into the passageway in the specific orientation defined by the proximally extending protrusions, and wherein only a distal portion of the marker body is welded or otherwise secured to one or both of the opposing protrusions and/or a proximal facing surface of the junction the extends between the opposing protrusions. Without limitation, in one preferred embodiment, the distal end portion of the guide member and the marker body slot have respective rectangular cross-sections in which a respective width of the distal end portion of the guide member and marker body slot is substantially greater than a respective height of the distal end portion of the guide member and marker body slot, wherein the specific orientation defined by the proximally extending protrusions is such that the guide member bends proximally of the junction in a bending plane that passes through the respective proximally-extending protrusions.

In accordance with yet another aspect of the disclosed inventions, embodiments of an anchor assembly for securing a guide member in a body lumen are disclosed and described. In an exemplary embodiment, the anchor assembly includes an expandable anchor configured for being deployed in a body lumen, the expandable anchor having a tapered proximal end, an elongate guide member, a radiopaque marker body having a slot formed therethrough, the slot having a proximal slot opening, a distal slot opening, and a cross-sectional profile and dimensions configured to receive therethrough a distal end portion of the guide member, wherein the guide member distal end portion extends distally through the proximal slot opening, and wherein the guide member distal end portion is welded or otherwise secured to the marker body only proximate the distal slot opening, and a strain relief junction having a distal portion that is an integral portion of, or is otherwise secured to, the tapered proximal end of the expandable anchor, wherein a proximal portion of the strain relief junction comprises a pair of opposing, proximally-extending protrusions defining a passageway therebetween having a cross-sectional profile and dimensions configured to receive the marker body in a specific orientation. The marker body preferably extends distally into the passageway in the specific orientation defined by the proximally extending protrusions, and wherein only a distal portion of the marker body is welded or otherwise secured to one or both of the opposing protrusions and/or a proximal facing surface of the junction the extends between the opposing protrusions. Without limitation, in one preferred embodiment, the distal end portion of the guide member and the marker body slot have respective rectangular cross-sections in which a respective width of the distal end portion of the guide member and marker body slot is substantially greater than a respective height of the distal end portion of the guide member and marker body slot, wherein the specific orientation defined by the proximally extending protrusions is such that the guide member bends proximally of the junction in a bending plane that passes through the respective proximally-extending protrusions.

In accordance with still another aspect of the disclosed inventions, embodiments of a method for accessing an intracranial subarachnoid space (ISAS) through a blood vessel wall of a patient are disclosed and described herein. In an exemplary embodiment, the method includes acquiring a 3D volumetric reconstruction of the vessel wall, identifying a target location in the 3D reconstruction for accessing the ISAS through the vessel wall with a delivery catheter, overlaying a portion of the 3D reconstruction including the target location on a fluoroscopy imaging display of the patient's anatomy including the vessel wall, using the overlaid portion of the 3D reconstruction and fluoroscopy imaging display to visually track movement of the delivery catheter within the vessel to the target location, penetrating the vessel wall at the target location to create an anastomosis between the vessel and the ISAS, and accessing the ISAS through the anastomosis with the delivery catheter.

Without limitation, the 3D volumetric reconstruction of the vessel wall may be acquired by 3D-rotational venography or angiography.

The method may further include comprising administering a therapeutic agent from the delivery catheter into the ISAS.

The method may further include deploying a drug delivery device in the anastomosis, wherein the drug delivery device is connected to an access port, and wherein a therapeutic agent is administered (delivered) through the access port, the drug delivery device, and into the ISAS, respectively. The method may further include administering a therapeutic agent into the ISAS from a reservoir of the drug delivery device.

In one embodiment, the method also includes overlaying an MR imaging data set of the patient's anatomy including the vessel wall onto the respective portion of the 3D reconstruction and fluoroscopy imaging display.

Other and further aspects and features of embodiments will become apparent from the ensuing detailed description in view of the accompanying figures.

BRIEF DESCRIPTION OF THE DRAWINGS

FIG. 2A-D are cross-sectional views of a portion of the head of a human patient;

FIG. 3A-J are side, perspective and cross-sectional views of an anchor and elongate guide member, according embodiments of the disclosed inventions;

FIGS. 12A-E are side, perspective and cross-sectional views of an elongated reinforcing member of the delivery catheter, constructed according to other embodiments of the disclosed inventions;

FIG. 16 is a cross-sectional views of an alternative delivery catheter, constructed according to embodiments of the disclosed inventions;

FIGS. 17A-17O are side, perspective and cross-sectional views of an elongated reinforcing member of the delivery catheter, constructed according to other embodiments of the disclosed inventions;

FIGS. 18A-E are side, perspective and cross-sectional views of the interface between the elongated guide member and the anchor, according to embodiments of the disclosed inventions;

FIGS. 19A-I are perspective and cross-sectional views of a delivery assembly having a penetrating element guard, according to embodiments of the disclosed inventions;

FIG. 20 is a side view of an penetrating element guard, constructed according to an alternative embodiment of the disclosed inventions;

FIGS. 21A-N are side, perspective and cross-sectional views of a delivery catheter, constructed according to alternative embodiments of the disclosed inventions;

FIGS. 26A-D are side, perspective and cross-sectional views of another valve constructed according to embodiments of the disclosed inventions;

FIGS. 30A-E are side, perspective and cross-sectional views of another drug delivery device delivery catheter, constructed according to alternative embodiments of the disclosed inventions; FIGS. 30F-G are side and cross-sectional views of a reinforcing member of the drug delivery device delivery catheter of FIGS. 30A-E, constructed according to embodiments of the disclosed inventions.

FIGS. 31A-G are perspective and side views of a marker constructed according to embodiments of the disclosed inventions;

FIG. 32 is a perspective view of an implanted drug delivery device according to the embodiments of the disclosed invention;

FIGS. 56A-58F are perspective, side and cross-sectional views of drug delivery devices constructed according to alternative embodiments of the disclosed inventions;

FIGS. 59-62E are perspective and cross-sectional views of drug delivery device delivery shuttles constructed according to embodiments of the disclosed inventions;

FIGS. 64A-E are perspective and cross-sectional views of a penetrating element guard constructed according to alternative embodiments of the disclosed inventions;

FIGS. 65A-C are side and perspective views of radiopaque markers constructed according to embodiments of the disclosed inventions;

FIG. 66 is perspective view of a handle assembly constructed according to embodiments of the disclosed inventions;

FIGS. 76-81 are side, perspective and cross-sectional views of the interface between the elongated guide member and the anchor, according to other embodiments of the disclosed inventions.

DETAILED DESCRIPTION OF THE ILLUSTRATED EMBODIMENTS

Figure 1:
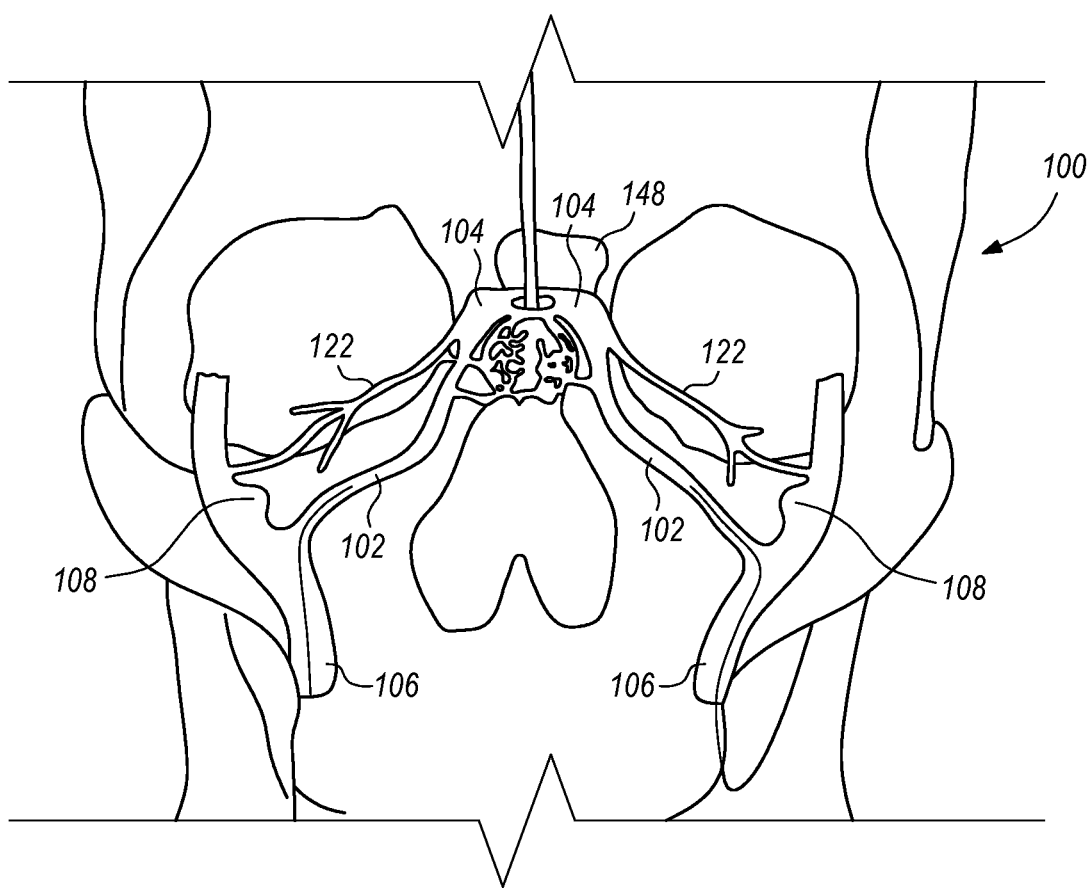
FIG. 1 is a schematic diagram of a head of a human patient.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a schematic diagram showing the head 100 of a human patient. Within each side of the patient's head, an inferior petrosal sinus (IPS) 102 connects a cavernous sinus (CS) 104 to a jugular vein 106 and/or a jugular bulb 108. For clarity, the acronym "IPS" is used herein to refer generally to the inferior petrosal sinus and more particularly to the interior space (or lumen) of the inferior petrosal sinus. The IPS 102 facilitates drainage of venous blood into the jugular veins 106. In some patients, the junction of the IPS 102 and the jugular vein 106 occurs within the jugular bulb 108. However, in other patients, this junction can occur at other locations in the jugular vein 106. Moreover, while the IPS 102 in FIG. 1 is a single sinus passageway, in some patients the IPS can be a plexus of separate channels that connect the CS to jugular vein 106 (not shown) and/or jugular bulb 108.

Embodiments of the disclosed inventions are described with respect to an exemplary target penetration site in the IPS 102 to access the CSF-filled CP angle cistern 138 for administering a therapeutic agent via a delivery catheter or an implanted drug delivery device (FIGS. 1, 2A-B) while avoiding contact or injury to critical structures within the intracranial subarachnoid space including, but not limited to, basilar artery 110, brain stem 112, and cranial nerves. Embodiments of the disclosed inventions can access the intracranial subarachnoid space (SAS) from target penetration sites located in other dural venous sinuses (e.g., cavernous sinus, superior petrosal sinus, sagittal sinus, transverse sinus, sigmoid sinus, etc.) and are not limited exclusively to IPS 102. Embodiments of the delivery assemblies and drug delivery devices described herein can access a target penetration site in the IPS 102 (or other dural venous sinus) through a venous access location in the patient (e.g., femoral vein, cephalic vein, brachial vein, subclavian vein, internal jugular vein). As used herein, it should be appreciated that the term drug(s) or therapeutic agent(s) refer to any type of agent(s), therapeutic, diagnostic, combination thereof or the like, in any state, such as fluid, solid, semisolid or combination thereof and/or include any type of dosage form(s) including modified-release dosage, sustained-release dosage, controlled-release dosage or combinations thereof.

Embodiments of the delivery assemblies, drug delivery devices, catheters and other endovascular componentary can penetrate, for example, the dura mater IPS wall 114 and the arachnoid layer 115 to access the CP angle cistern 138 from within an inferior petrosal sinus 102 or from within a superior petrosal sinus (SPS) 122 (FIG. 1) for delivery of a therapeutic agent to the SAS or implantation of a drug delivery device at the target site. The dura mater IPS wall 114 is also referred to herein as the dura IPS wall 114, or simply as the IPS wall 114. The SPS is a small diameter venous sinus that connects from the sigmoid sinus (distally located to jugular bulb 108) to the cavernous sinus 104 (FIG. 1). Further, the delivery assemblies and drug delivery devices described herein can be advanced through the IPS 102 and into the cavernous sinus 104, so that an anastomosis (not shown) can be created in the upper portion or roof of the cavernous sinus 104 to access the CSF-filled suprasellar cistern 148, shown in 1, for implantation of the drug delivery device at such target site. Whether penetration to access a target site, or deployment and implantation of a drug delivery device occurs from the lumen of the IPS, SPS, cavernous sinus or other dural venous sinus to access CSF in the subarachnoid space, the embodiments of the inventions described herein provide minimally invasive means for delivering therapeutic agents to the intracranial SAS.

Therapeutic agents delivered to the intracranial SAS (e.g., CP angle cistern 138) with embodiments of the delivery catheters and drug delivery devices disclosed herein can include any drug or compound delivered by conventional intrathecal or intraspinal delivery methods including, but not limited to, lumbar puncture delivery methods and intraventricular, intra-cerebral, or intra-parenchymal delivery methods requiring, in part, a burr hole drilled through the skull and catheter or other delivery device passed through brain tissue. Non-limiting examples of therapeutic agents that can be delivered to the intracranial SAS with embodiments of the delivery catheters and drug delivery devices disclosed herein can include compositions comprising anti-sense RNA or anti-sense oligonucleotides, anti-bodies, antibiotics, anti-vasospasm agents, biosimilars, chemotherapy agents, GABA receptor agonists, therapies intended for the treatment of neurodegenerative diseases (e.g., Alzheimer's disease, Parkinson's disease, Huntington's disease, prion disease, motor neurone diseases, spinocerebellar ataxia, and spinal muscular atrophy), therapies intended for the treatment of trigeminal neuralgia, therapies intended for the treatment of pontine glioma, tissue plasminogen activator, and any other composition(s) intended to have a therapeutic effective on all or a portion(s) of the central nervous system.

Figure 2A:
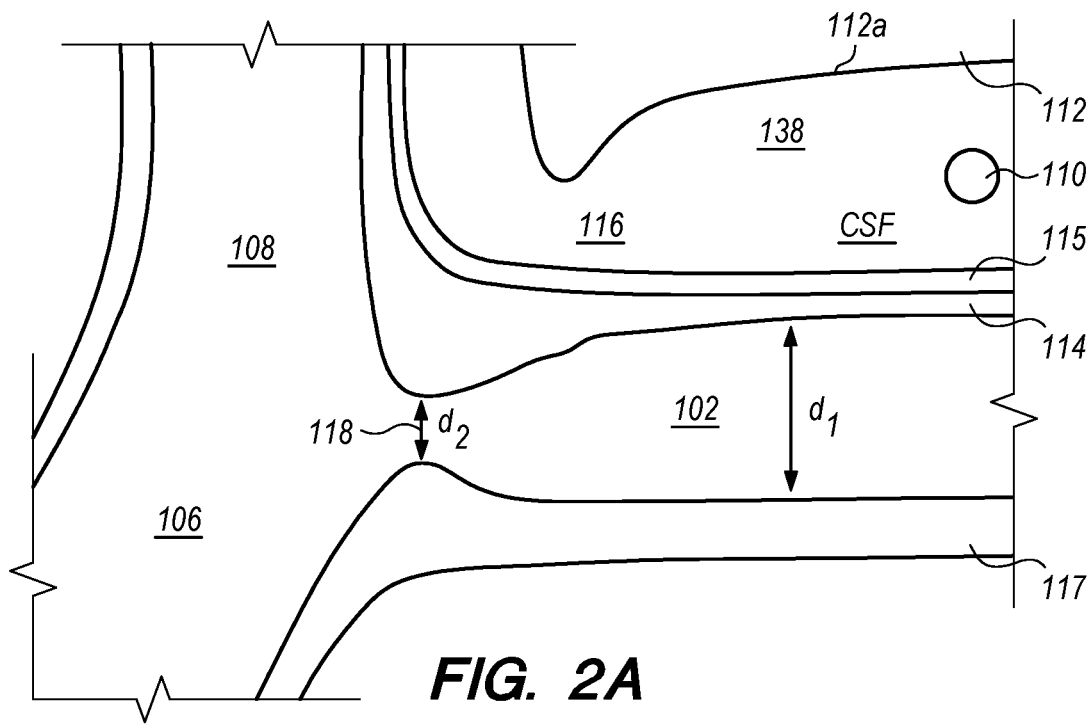

FIG. 2A shows a cross-sectional view of a portion of head 100, including IPS 102, jugular vein 106, and jugular bulb 108. In addition, basilar artery 110, brain stem 112, pia 112a, and IPS wall 114 are also shown in FIG. 2A. The IPS is a relatively small diameter intracranial venous sinus that facilitates drainage of cerebral venous blood into the jugular vein; the IPS is formed by a cylindrical layer of dura mater, typically about 0.9 mm to 1.1 mm thick for the portion of IPS wall 114 shown in FIG. 2A, which creates a hollow lumen through which blood flows. In the cross-section view of FIG. 2A, the hollow lumen of the IPS resides between upper IPS wall 114 and a lower IPS wall 117, also comprised of dura mater; the IPS itself lies in a bony groove or channel in the clivus bone (not shown) beneath IPS wall 117 in FIG. 2A.

A cross-section of the IPS 102 orthogonal to the plane depicted in FIG. 2A would show that the cylindrical layer of dura mater forming IPS 102 is surrounded by bone for about 270° of its circumference with the remaining portion of the IPS circumference (i.e., IPS wall 114 in FIGS. 2A-B) covered by arachnoid matter 115 and facing CP angle cistern 138. Arachnoid mater 115 (also referred to herein as the arachnoid layer) is a delicate and avascular layer, typically about 0.05 mm to 0.15 mm thick, that lies in direct contact with the dura mater comprising the exterior of IPS wall 114; arachnoid layer 115 is separated from the pia mater surrounding brain stem 112 by the CSF-filled subarachnoid space 116 (e.g., CP angle cistern 138). The lower portion of the IPS 102, opposite to the IPS wall 114 is the IPS wall 117 formed by dura mater that sits in a channel in the clivus bone (not shown).

It should be appreciated that for the embodiments of the disclosed inventions, the methods and devices are configured to create an anastomosis via an endovascular approach by piercing or penetrating from within a hollow dural venous sinus such as IPS 102 to pass through the intracranial venus sinus dura, e.g., dura of IPS wall 114, and continue penetrating through the arachnoid layer 115 until reaching the CSF-filled subarachnoid space (e.g., CP angle cistern 138). For ease of illustration, it should be appreciated that the arachnoid matter 115 covering the IPS wall 114 is present, although, not shown in certain figures.

The diameter $d_1$ of IPS 102 is approximately 3 mm but can range from approximately 0.5 mm to about 6 mm. As shown in FIG. 2A, at the junction 118 between the IPS 102 and the jugular bulb 108 and/or jugular vein 106, the diameter $d_2$ of the IPS 102 can narrow. For example, $d_2$ is approximately 2 mm, but can be as small as about 0.5 mm. The length of the IPS 102 from the junction 118 with the jugular vein 106 to the cavernous sinus 104 (shown in FIG. 1) is approximately in a range between 3.5 cm to 4 cm.

Figure 2B:
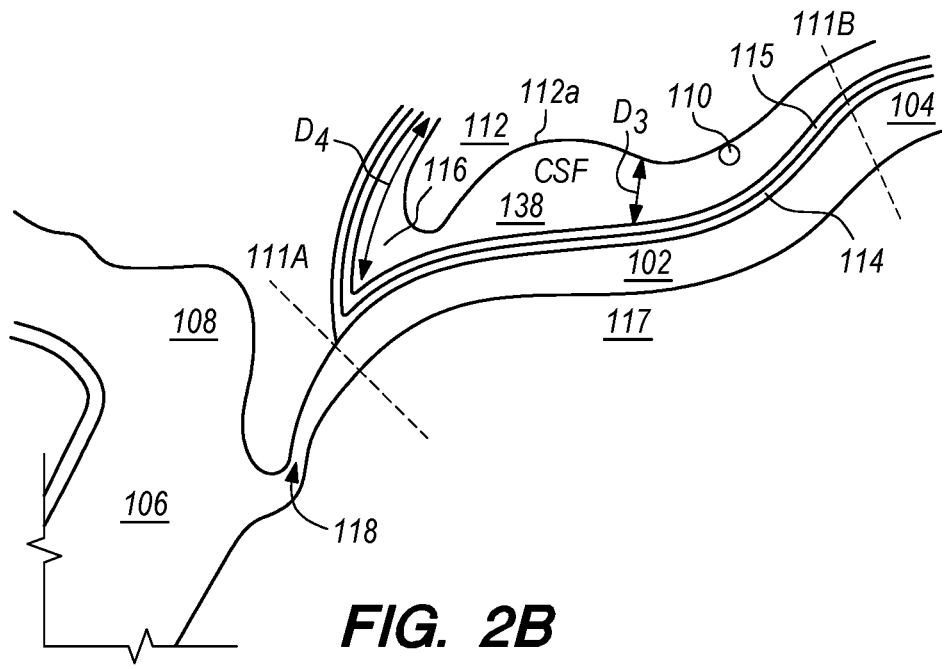

In many patients, the IPS 102 is coupled to the jugular vein 106 at a location disposed below of the jugular bulb 108, depicted as junction 118, shown in FIG. 2B. The IPS 102 extends distally from the junction 118 in the medial wall of the jugular vein 106, past the 9th cranial nerve 111A and jugular tubercle (not shown) while curving rostral-medially through a first curved portion 102A shown in FIG. 2C, and then further curving medial-superiorly through a second curved portion 102B shown in FIG. 2C before connecting at the connection point 111B with the cavernous sinus (CS) 104. The IPS 102 extends distally from the junction 118 through a curvature of approximately 45° to 100° in the first and second curved portions 102A and 102B until the IPS 102 connects with the CS 104. The CSF-filled CP angle cistern 138 lies immediately above the curved portion of the IPS 102.

Figure 2C:
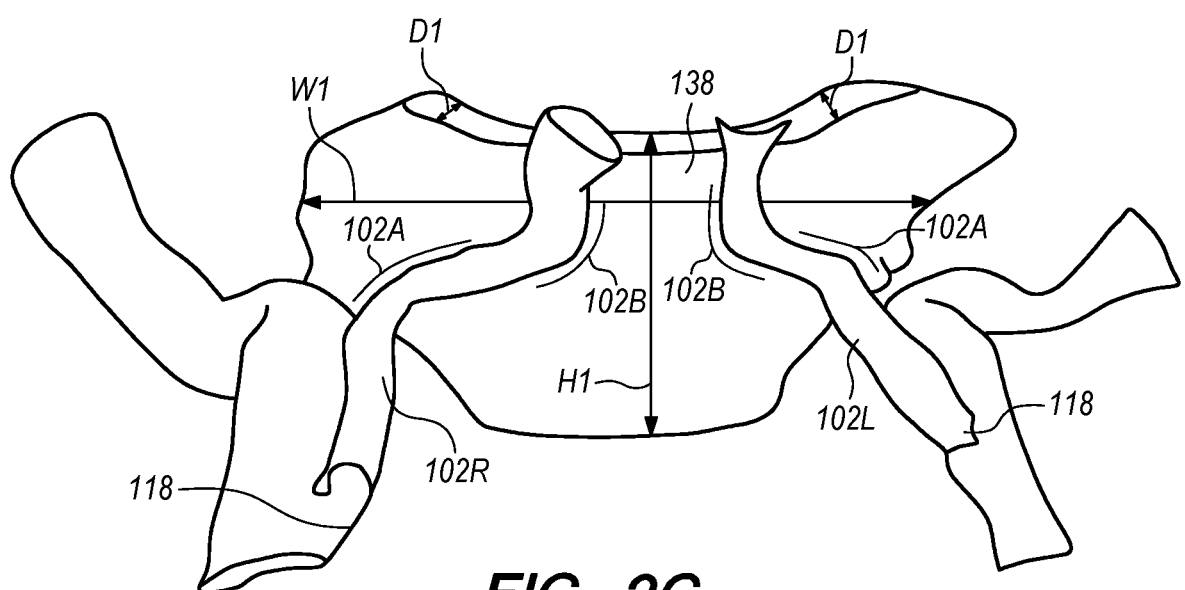

Anatomical features of CP angle cistern 138 provide a large extent of unobstructed, CSF-filled subarachnoid space to accommodate a penetrating element of a delivery catheter or drug delivery device distal anchoring mechanism as further described herein. FIG. 2C shows a portion of CP angle cistern 138 and the relative proximity of the cistern to a patient's right IPS 102R and left IPS 102L. Beyond the lateral boundaries of the cistern depicted in the figure, the CSF-filled subarachnoid space continues circumferentially around the base of the skull, albeit with a lesser extent of CSF space than in CP angle cistern 138. CP angle cistern 138 comprises a depth of free CSF space labelled D1 in FIG. 2C between the skull base and brainstem (not shown, but, e.g., between the anterior portions of the occipital and sphenoid bones and the brain stem). CP angle cistern 138 also comprises a height of free CSF space labelled H1 in FIG. 2C that extends superiorly along the base of the skull (not shown, but extending superiorly from the jugular foramen). CP angle cistern 138 further comprises a width extent of free space labelled W1 in FIG. 2C (e.g., extent of free CSF space extending laterally between the right and left jugular foramina, not depicted). CP angle cistern 138 contains a relatively large volume of CSF, as defined by the exemplary depth D1, height H1, and width W1 dimensions. FIG. 2D shows an alternative view of the same patient anatomy depicted in FIG. 2C, albeit with the D1 cistern dimension portions of left IPS 102L obscured by the view.

As shown in FIGS. 1 and 2C, most patients have two IPS 102 and two jugular veins 106 (left and right). In a very small percentage of patients (e.g., less than 1%), there is no connection between one IPS and the corresponding jugular vein. It is highly unlikely, however, that any given patient will lack connections to the corresponding jugular veins on both left and right IPS.

Subarachnoid spaces are naturally occurring separations between the pia mater and the arachnoid layer where the CSF pools. Typically, the CSF is passed into a subarachnoid space over the cerebral hemispheres and then into the venous system by arachnoid granulations. The subarachnoid space 116 in FIG. 2A corresponds to a cerebellopontine (CP) angle cistern 138, which acts as a reservoir for CSF and a location for delivering therapeutic agents to the intracranial SAS.

A detailed assessment of anatomical constraints of IPS 102 and CP angle cistern 138 relevant to embodiments of the disclosed inventions is reported in Heilman C B, Basil G W, Beneduce B M, et al., Anatomical characterization of the inferior petrosal sinus and adjacent cerebellopontine angle cistern for development of an endovascular transdural cerebrospinal fluid shunt. *Journal of Neurointerventional Surgery* Published Online First: 9 Jan. 2019. doi: 10.1136/neurintsurg-2018-014445, incorporated by reference herewith.

As will be further described herein, embodiments of the disclosed inventions deliver therapeutic agents to the intranial SAS using a minimally invasive, endovascular approach. The therapeutic agents are delivered to the intranial SAS (e.g., CP angle cistern 138) through embodiments of a delivery catheter configured to access the intracranial SAS from a dural venous sinus. In addition, therapeutic agents can be delivered to the intranial SAS through embodiments of a drug delivery device deployed from a delivery catheter, through a target penetration site in a dural venous sinus to access the incranial SAS.

Embodiments of the disclosed inventions can reduce or eliminate the complications associated with conventional intrathecal drug delivery methods and devices, and can provide a more effective administration of therapeutic agents based on, among other factors, target delivery locations and their relative proximity to the brain stem in comparison to other delivery approaches. Conventional intrathecal drug delivery techniques deliver therapeutic agents via lumbar puncture to the lumbar SAS or directly to brain parenchyma through a burr hole drilled in the skull. Delivery to the lumbar SAS typically requires a specialized Tuoy needle to penetrate the dura and access the SAS. Patients often experience persistent headaches, e.g., for one to nine or days following the procedure, often caused by CSF leaking from puncture site. In addition, patients can develop CSF collections outside the SAS and under the skin from CSF leaking from the puncture site, typically requiring an elastic corset or other compression means to prevent further CSF leaks. Concentrations of the therapies must be specifically formulated to account for dilution in circulating CSF within the entirety of the SAS, which can diminish the efficacy of certain compounds when delivered in a lumbar location; often, higher concentrations of therapies are required to disperse through the SAS from a lumbar delivery location, which can increase the risk and/or duration of side effects for the patient. Intrathecal drug delivery techniques to the brain parenchyma require an invasive craniotomy to expose cranial dura, followed by passing a catheter through the brain tissue to deliver the therapy to a target site. Risks include intra-parenchymal bleeding and other more serious complications from misguided catheters passing through brain tissue. Infection and post-procedural pain at the lumbar puncture or craniotomy site are common risks and complications of conventional intrathecal drug delivery techniques. The systems, devices, and methods disclosed herein advantageously deliver therapeutic agents directly to the intracranial SAS surrounding the brain using a minimally invasive, endovascular approach thereby improving efficacy and eliminating or reducing risks of conventional delivery techniques such as headaches, CSF leaks, intra-parenchymal hemorrhage, pain, and infection.

A variety of different imaging methods can be used to ensure accurate positioning and navigation of endovascular componentry (e.g., guide wire, guide catheter, delivery catheter, anchor with elongate guide member, etc.) though a patient's vasculature to a location within a subarachnoid space. Examples of suitable imaging methods include biplane fluoroscopy, digital subtraction angiography with road mapping technology, venous angiography with road mapping technology, 3D-rotational angiography or venography (3DRA or 3DRV), and cone-beam computed tomographic angiography or venography (CBCTA or CBCTV). Both 3DRA/V and CBCTA/V enable volumetric reconstruction showing the relationship between the bony anatomy, the vascular anatomy and the endovascular componentry used in minimally invasive procedures to cross a blood vessel wall (e.g., by penetrating through the vessel wall) to access the subarachnoid space. A 3DRA/V and CBCTA/V volumetric reconstruction can be overlaid, registered, combined and/or matched to real-time fluoroscopy imaging using a 3D roadmap technique (e.g., using Siemens syngo 3D Roadmap and syngo Toolbor, or Phillips Dynamic 3D Roadmap) that facilitates an overlay, registration, combination, and/or matching of a point(s) of interest from the 3D or volumetric reconstruction (e.g., DynaCT from Siemens Healthcare, XperCT from Phillips) with real-time 2D fluoroscopy images. Magnetic resonance imaging (MRI) provides additional valuable information about the anatomy surrounding intended or target access locations to the subarachnoid space, which MRI can also be overlaid, registered, combined and/or matched with real-time fluoroscopy and a 3D reconstruction.

The imaging methods described herein provide improved visualization during endovascular procedures where catheters and other endovascular componetary are navigated extra-vascularly to a target location. In turn, the imaging methods facilitate safer, more efficient patient interventions by providing the practitioner with real-time imaging guidance of endovascular componentry relative to critical anatomical structures of interest such as the brain stem or bony barriers surrounding a target procedure location. The disclosed imaging methods will be illustrated in connection with example endovascular procedures for navigating to and penetrating the wall of a venous vessel, i.e., an inferior petrosal sinus, to access a specific location within the intracranial subarachnoid space, i.e., a cerebellopontine angle cistern. However, the imaging methods described herein can be used for any procedure conducted from within a venous or arterial lumen to access a location within the subarachnoid space (e.g., penetrating from within the cavernous sinus, superior petrosal sinus, sagittal sinus, transverse sinus, sigmoid sinus, basilar artery, anterior inferior cerebellar artery, or other arterial vessel to access an intracranial subarachnoid space). Still further, the imaging methods described herein can be used for any procedure conducted from within any venous or arterial lumen to access a location outside of the vasculature and not limited to the intracranial subarachnoid space.

Combining, overlaying, registering, and/or matching a 3D or volumetric reconstruction of a target anatomic location for an endovascular drug delivery or drug delivery device implantation procedure with real-time fluoroscopy acquired during the procedure and, optionally, further combining, overlaying, registering, and/or matching MRI data of the target location with the volumetric reconstruction and fluoroscopy imaging, advantageously provides the operator with improved visualization of componentry used in the procedure and surrounding anatomy. The combination volumetric reconstruction and fluoroscopy or 3D road mapping technique facilitates navigation of endovascular delivery componentry tracking within the vasculature and through a vessel wall at the target location for the intended drug delivery procedure; this provides the operator with important information and guidance on the presence of anatomic landmarks relative to such target location and other local structures of interest including bones, nerves, critical organs (e.g., brain tissue), and venous and arterial structures.

Figure 68:
FIGS. 68-71 are imaging views within the head of a human patient for visualizing endovascular access to the subarachnoid space, according embodiments of the disclosed inventions.

During an endovascular procedure intended to access a target location within the intracranial subarachnoid space (e.g., CP angle cistern 138 from the IPS 102), including embodiments of the disclosed endovascular drug delivery and endovascular drug delivery device implantation procedures, an operator can generate a 3D or volumetric reconstruction image 130 of the patient's head. FIG. 68 depicts a 3D reconstruction 130 of a portion of the clivus bone where an IPS 102 (not shown in FIG. 68) extending between connection points with IJV 106 and CS 104. A contrast injection through a micro catheter placed in IPS 102 or CS 104 administered prior to obtaining the volumetric reconstruction image 130 can improve visualization of the IPS 102 pathway in the reconstruction. Alternatively, the 3D reconstruction 130 can be generated from an imaging study that was obtained previously, independent of the endovascular procedure, for example, from a computed tomography scan of the relevant patient anatomy or from an MRI data set.

Figure 69:
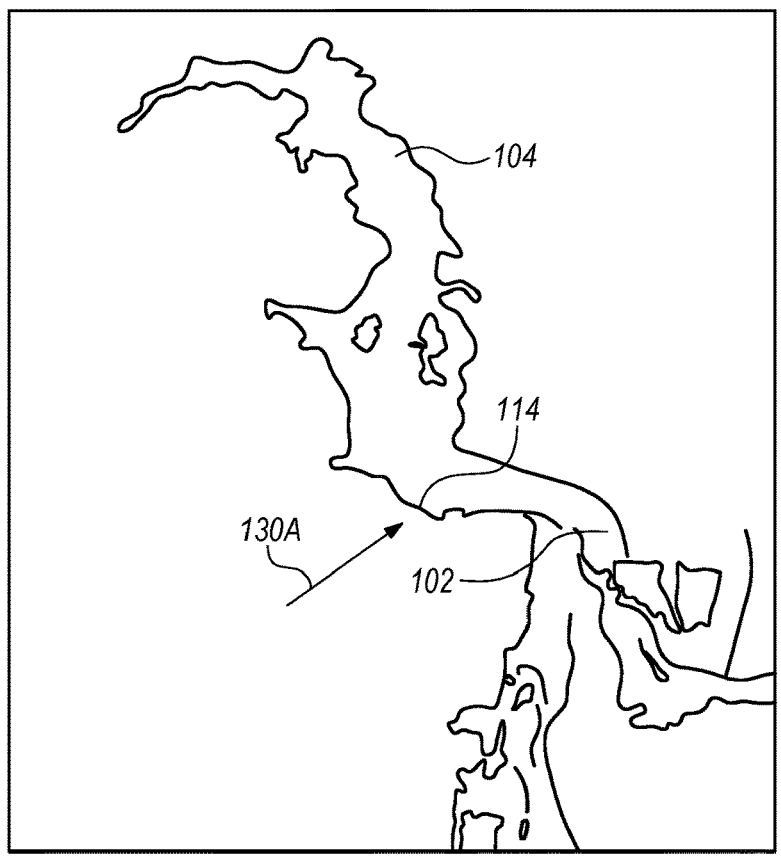

The operator can further review, orient or rotate the 3D reconstruction 130 when identifying a target location for the procedure. For example, the operator can reorient the reconstruction 130 so that the IPS 102 can be visualized along its course as the vessel 102 extends between the CS 104 and jugular bulb 108 as depicted in FIG. 69. The operator can use the 3D reconstruction 130 to identify local bony anatomy (e.g., petrous bone) that could obstruct a catheter passing through IPS wall 114 into CP angle cistern 138. The operator selects a target location 130A within the 3D reconstruction 130 and along IPS wall 114 between CS 104 and jugular bulb 108 where the operator intends to penetrate IPS wall and access CP angle cistern 138 as shown in FIG. 69. If the operator has further combined MRI data with the 3D reconstruction 130, the presence or absence of local arterial, venous, nerve, or brain tissues identified by the MRI data can also be considered when selecting a target location 130A to access CP angle cistern 138 and/or as anatomic landmarks to assist navigation of endovascular componentry during the procedure.

Figure 70A:
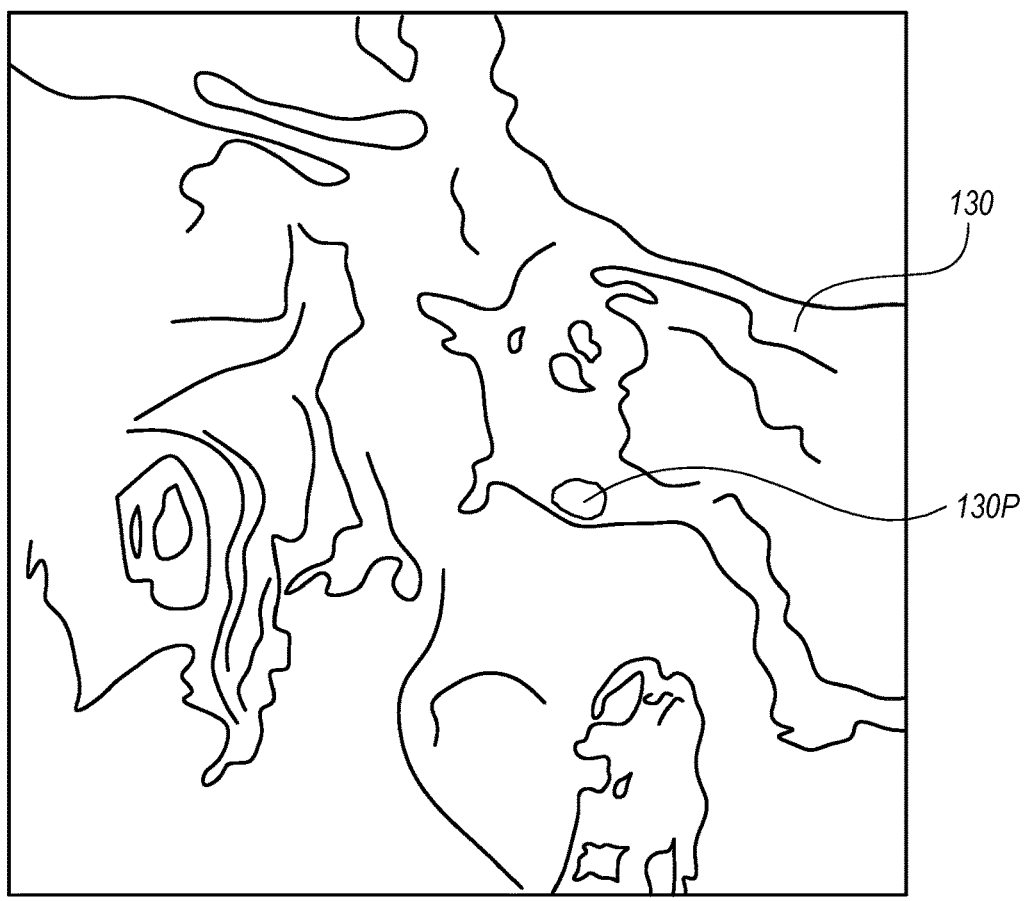
Figure 70B:
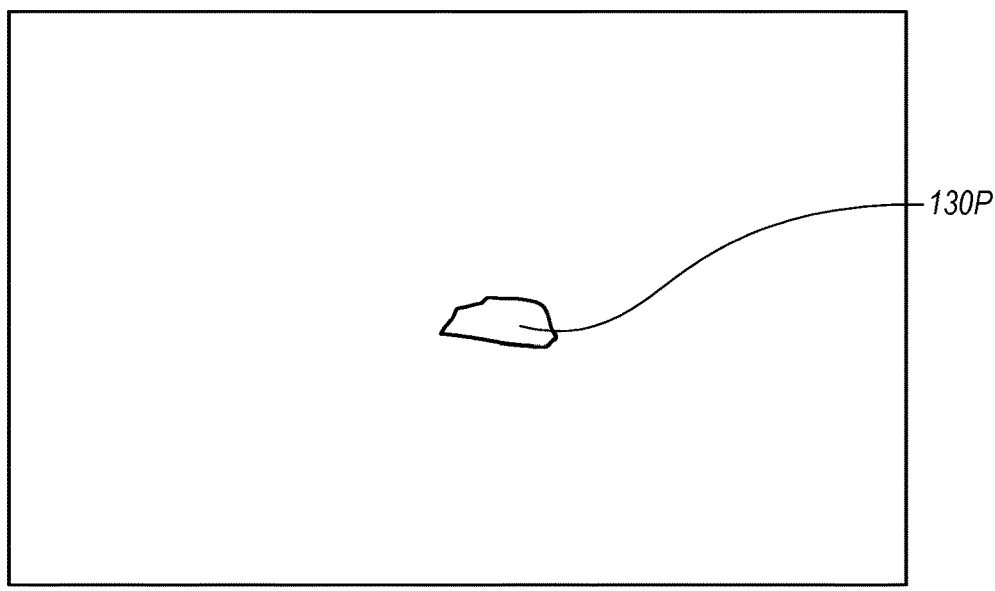
Figure 71:
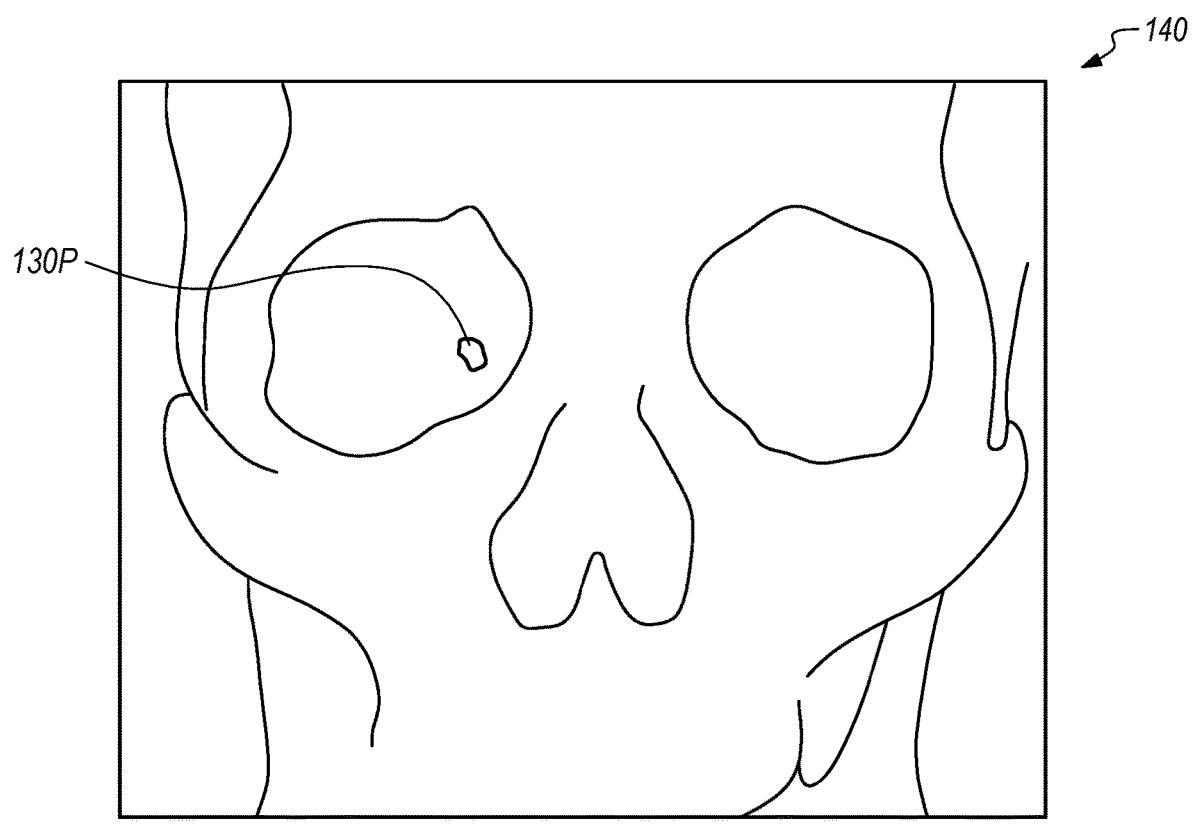

From the 3D reconstruction, the operator can crop or select a portion 130P of the reconstruction that pinpoints the target location along IPS wall 114 where the operator intends to penetrate the IPS and access CP angle cistern 138. FIG. 70A shows a portion 130P selected from the larger 3D reconstruction 130; the portion 130P comprise a three dimensional volume encompassing the target location on IPS wall 114. Within the anatomic region of interest, portion 130P can represent a sphere having a diameter less than 1 mm, 1-3 mm, or more. The cropped or selected portion 130P of the 3D reconstruction can include a portion of CP angle cistern 138 and define a window within which the operator intends to access the SAS with endovascular componentry and/or devices. Portion 130P maintains its spatial relationship to the patient anatomy using the underlying data acquired when the operator generated the volumetric reconstruction 130. All other portions of the 3D reconstruction 130 can be discarded for subsequent steps of the procedure, with the operator relying solely on the portion 130P that pinpoints the target location along IPS wall 114 where the operator intends to access CP angle cistern 138. FIG. 70B shows portion 130P after the operator has discarded all other portions of 3D reconstruction 130.

Figure 72:
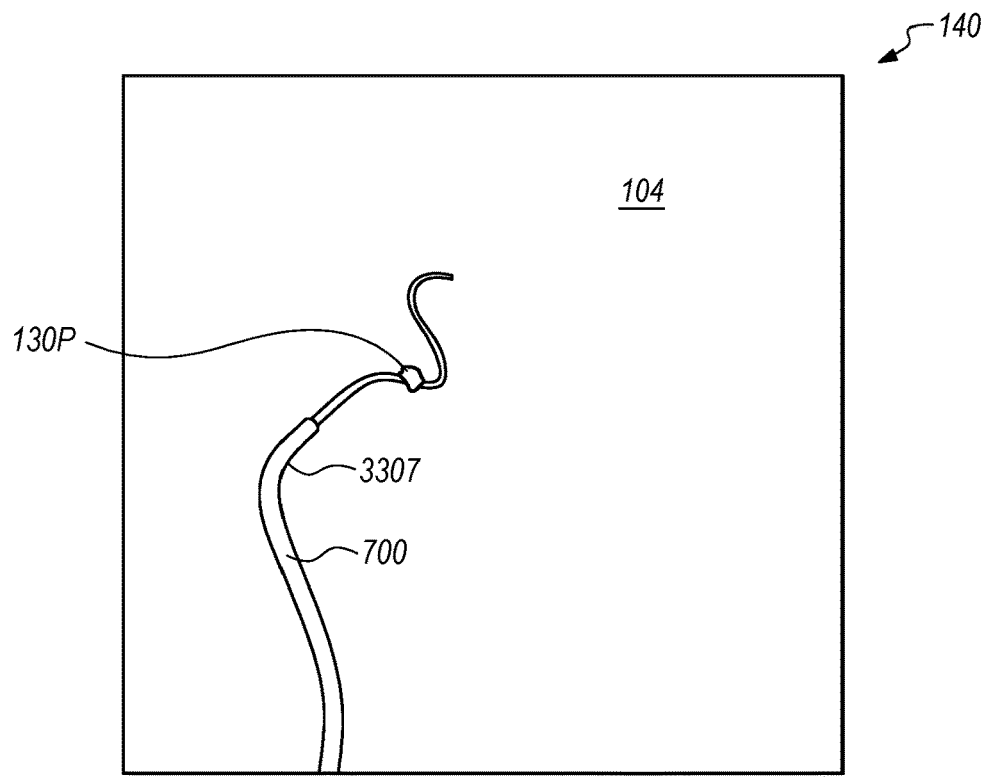
FIGS. 72-75 are imaging views of exemplary methods for visualizing endovascular access to the subarachnoid space.
Figure 73:
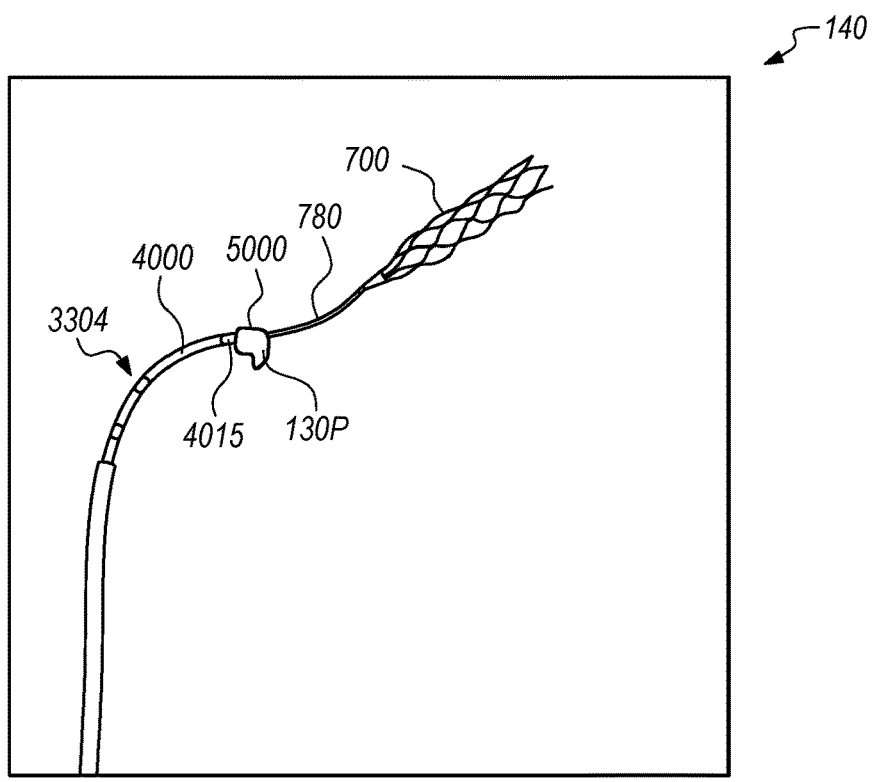

The operator can combine, overlay, register, and/or match portion 130P of the 3D reconstruction 130 with live fluoroscopy imaging 140 using a 3D road mapping technique as shown in FIGS. 71-75. Thus, the operator will observe a combination of the fluoroscopy imaging 140 acquired in real-time during the procedure and the portion 130P highlighting the selected location to access CP angle cistern 138 from IPS 114. 3D road mapping software maintains image registration of the portion 130P to the live fluoroscopy such that portion 130P maintains its spatial relationship to the patient anatomy regardless of patient movement, magnification of the fluoroscopy imaging, and rotation of the patient gantry during the procedure. As the operator navigates endovascular componentry through IPS 114 with the guidance of live fluoroscopy, the 3D road mapping technique maintains the overlaid portion 130P in spatial relation to the live fluoroscopy imaging 140. Using portion 130P with a 3D road mapping technique presents a more streamlined view to the operator during the procedure compared to an approach where the operator combines or overlays all of reconstruction 130 with the live fluoroscopy imaging 140. The operator can use reconstruction portion 130P as a navigational guide to deliver endovascular componentry to and access CP angle cistern 138 at target location 130A under live fluoroscopy (e.g., navigating a guidewire beyond portion 130P along IPS wall 114 between CS 104 and jugular bulb 108 as shown in FIG. 72, advancing a delivery catheter 3304 to portion 130P via elongate guide member 780 as shown in FIG. 73, advancing the delivery catheter 3304 penetrating element 3350 through IPS wall 114 at portion 130P shown in FIG. 75). Radiopaque markers present on the endovascular componentry also facilitate visualizing the delivery catheter pass through IPS wall 114 at the target location 130A (e.g., retracting guard member 4000 to expose penetrating element 3350 in IPS 102 observed by the proximal transition of marker band 4015 shown in FIGS. 73-74, distal advancement of delivery catheter 3304 visualized through distal advancement of marker band 4015 within guard member 4000 to portion 130P shown in FIGS. 74-75); further, if the operator intends to deploy a device within the CP angle cistern 138, the operator can visualize the device radiopaque markers on live fluoroscopy as the device deploys in CP angle cistern 138. With this improved imaging method, the operator can more precisely and safely navigate endovascular componentry and devices to a target location in the intracranial subarachnoid space while avoiding nearby arteries, nerves, and brain tissue. If portion 130P was obtained from a prior imaging study of the patient, the operator can register portion 130P to the live fluoroscopy imaging to facilitate the 3D road mapping technique; this can improve procedural efficiency by eliminating the need to generate a volumetric reconstruction during the endovascular procedure to access the subarachnoid space.

Figure 15A:
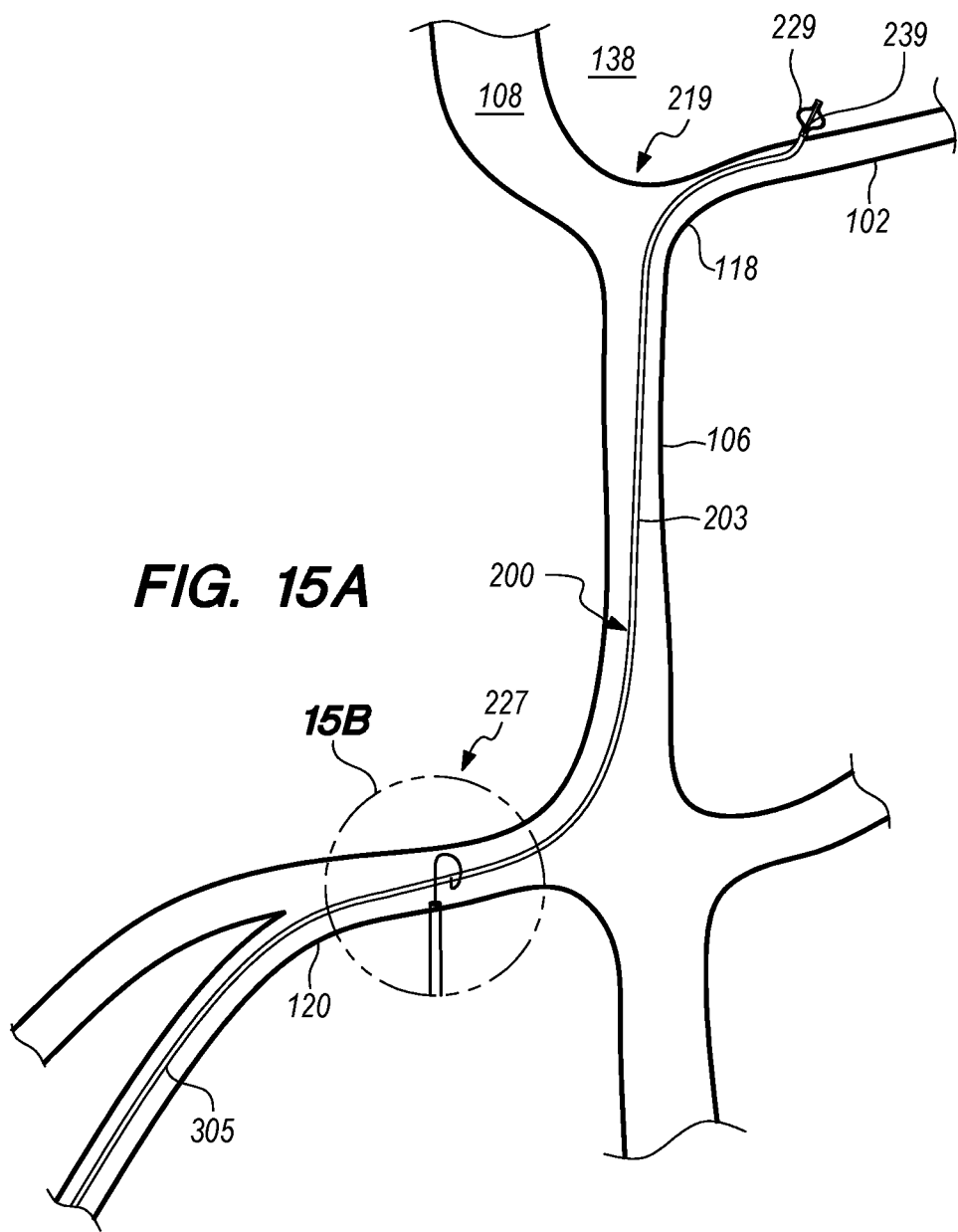
FIG. 15A is a perspective view of a drug delivery device, constructed according to embodiments of the disclosed inventions.

FIG. 15A illustrates a drug delivery device 200, according to embodiments of the disclosed inventions. As shown in FIG. 15A, the device 200 has been deployed from a subclavian vein 120 access point in the patient through an introducer sheath 305. The drug delivery device 200 extends from the subclavian vein 120 through the jugular vein 106, and into the IPS 102 and CP angle cistern 138.

With reference to FIG. 15A, the drug delivery device 200 comprises an elongate device body 203 that extends from the device proximal portion 227 to the device distal portion 219. The drug delivery device 200 also includes one or more drug delivery lumens 207 that extend from a proximal end opening 217 to a distal end opening 239 in device 200. Drug delivery devices lumens 207 can be used to deliver therapeutic agents through the drug delivery device 200 to a targeted delivery location in the patient; for example, the drug delivery device lumen 207A can be used for delivery of therapeutic agent A from proximal end opening 217A to distal end opening 239A; the drug delivery device lumen 207B can be used for delivering therapeutic agent B from proximal end opening 217B to distal end opening 239B, and so on. One or more drug delivery device lumens 207 can also be used for aspirating CSF from the intracranial SAS though the device (e.g., to collect CSF samples for diagnostic purposes, to remove a known volume of CSF from the SAS before delivering an equivalent volume of therapeutic agent to the SAS to maintain a relatively constant intracranial pressure within the SAS). The drug delivery device body 203 can include one or more anchoring mechanisms at one or more locations along body 203 (e.g., a self-expanding stent at the location of reference line 203 shown in FIG. 15A, any other anchoring mechanism disclosed herein or in the related applications) to secure the deployed device in the venous system of a patient.

The distal portion 219 of the drug delivery device 200 includes a distal anchoring mechanism 229. As shown in FIG. 15A, distal anchoring mechanism 229 has been deployed in the CP angle cistern 138 through an anastomosis in IPS wall 114 (not shown) created by embodiments of the delivery catheter disclosed herein. Anchoring mechanism 229 can comprise a self-expanding malecot configured to deploy in the intracranial SAS upon deployment from delivery catheter 3304 (not shown), or any other anchoring mechanism 229, 2229, 227, 2227 disclosed herein. The anchoring mechanism secures the distal end opening 239 of the drug delivery lumen 207 (not shown) in the intracranial SAS, prevents the device from withdrawing through IPS wall 114 into the IPS 102, and maintains the distal end opening 239 of the drug delivery lumen 207 away from arachnoid layer 115 to prevent growth or scarring that could obstruct the flow of therapeutic agents from device 200 into the intracranial SAS.

Figure 22:
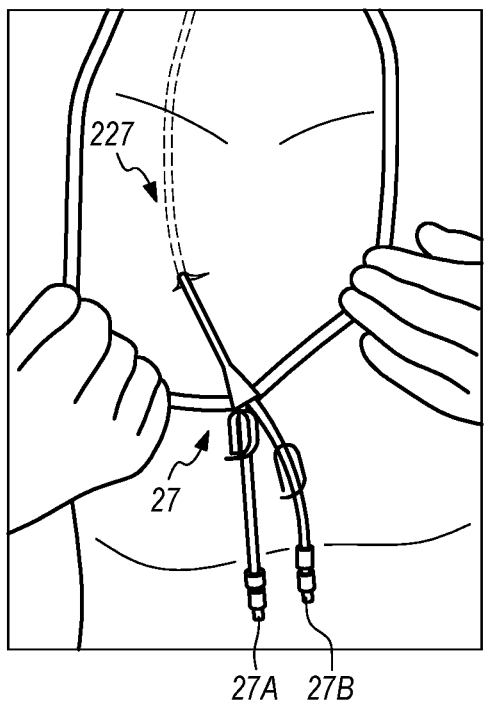
FIGS. 22-24 illustrate drug delivery systems access ports, constructed according to embodiments of the disclosed inventions.
Figure 23:
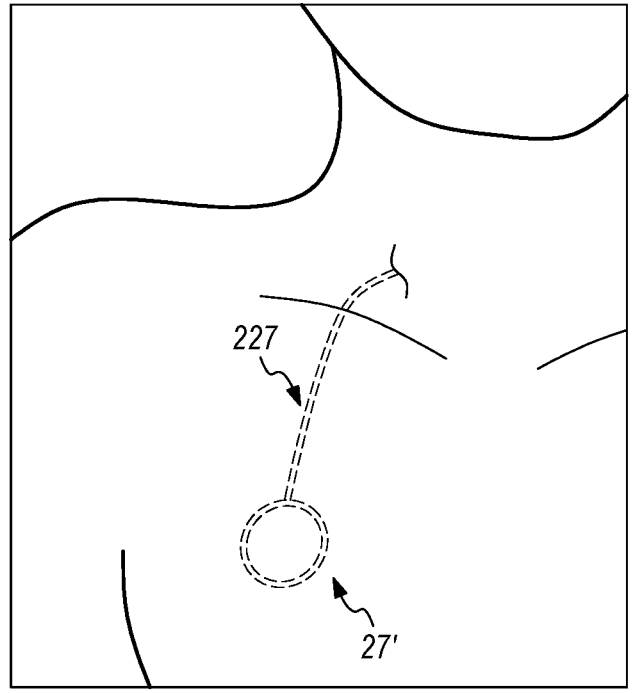
Figure 24:
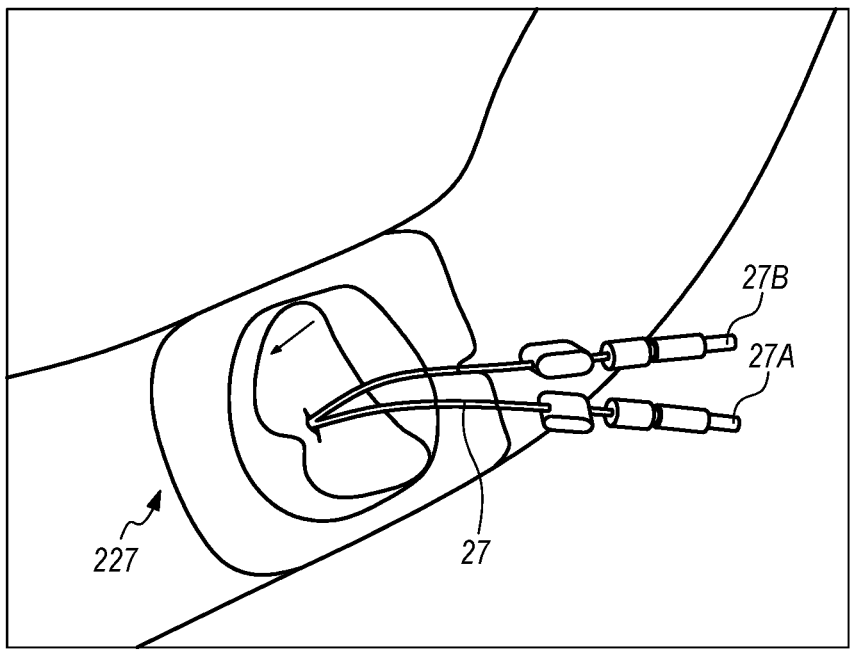

Therapeutic agents are delivered from the proximal end opening 217 of drug delivery lumen 207 through device 200 and the distal end opening 239 of the drug delivery lumen to a target location in the patient. An access port 27 can be connected to the proximal portion 227 of drug delivery device 200 and the proximal portion of drug delivery device 2200 embodiments described in connection with FIGS. 56A-58D. The access port 27 provides for aspiration of CSF from and administration of therapeutic agents into drug delivery device 200 left indwelling at its deployed location in the vasculature. FIGS. 22 and 24 depict a dual access port 27 having access ports 27A and 27B configured for aspirating from and/or delivering fluid into patients (e.g., drugs, therapeutic agents) through the delivery device lumens 207A and 207B via the respective proximal end openings 239A and 239B. It should be appreciated that a variety of suitable access port configurations may be used (e.g., single port, three or more ports). The proximal portion 227 of drug delivery device 207 has been advanced subcutaneously from the subclavian vein 120 to a connection point with access port 27 shown in FIG. 22. In FIG. 24, proximal portion 227 of drug delivery device 207 has been advanced subcutaneously from the brachial vein to a connection point with access port 27 FIG. 23 shows a subcutaneous access port 27' connected to the proximal end portion 227 of drug delivery device 200.

Figure 15B:
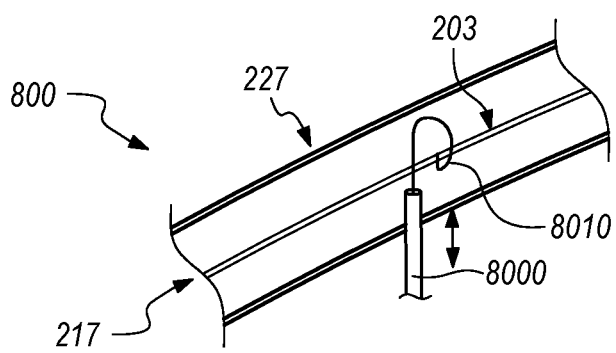
FIG. 15B illustrates an exemplary method of accessing a deployed drug delivery device, according to embodiments of the disclosed inventions.

FIG. 15B illustrates a method of connecting the proximal portion 227 of drug delivery device 200 to an access port 27 or other reservoir of therapeutic agent to be administered to the patient. Following drug delivery device 200 deployment in CP angle cistern 138, IPS 102, JV 106, and subclavian vein 120 (illustrated in FIG. 15A and as will be further described below in connection with FIGS. 55A-L), an operator can access the proximal portion 227 of the device (distal of the introducer sheath 305) through a hypodermic needle 8000 or other atraumatic access tool advanced through the skin and into the venous lumen. The operator can then use a snare, loop or guidewide 8010 advanced through needle 8000 to engage, grasp, grab the proximal portion 227 of the drug delivery device 2000 and pull, retract, withdraw such portion 227 proximally through needle 8000 for connection with an access port 27. For access ports comprising a subcutaneous port 27', the foregoing method can be used to connect proximal portion 227 of drug delivery device 200 to subcutaneous port 27' while the port is being implanted in the patient.

Embodiments of the drug delivery device 200 can include a one-way valve 209 at the distal end opening 239 of the drug delivery lumen 207. Valve 209 prevents CSF reflux into drug delivery device 200, while facilitating controlled delivery of a therapeutic agent through the drug delivery device into the intracranial SAS. Additional valves 209 can be placed along the length of drug delivery lumens 207 to further prevent CSF reflux into drug delivery device 200 and control delivery of a therapeutic agent through the drug delivery device into the intracranial SAS. Any of the one-way valve embodiments described herein can be used for valve 209 of a drug delivery device 200.

Figure 17D:
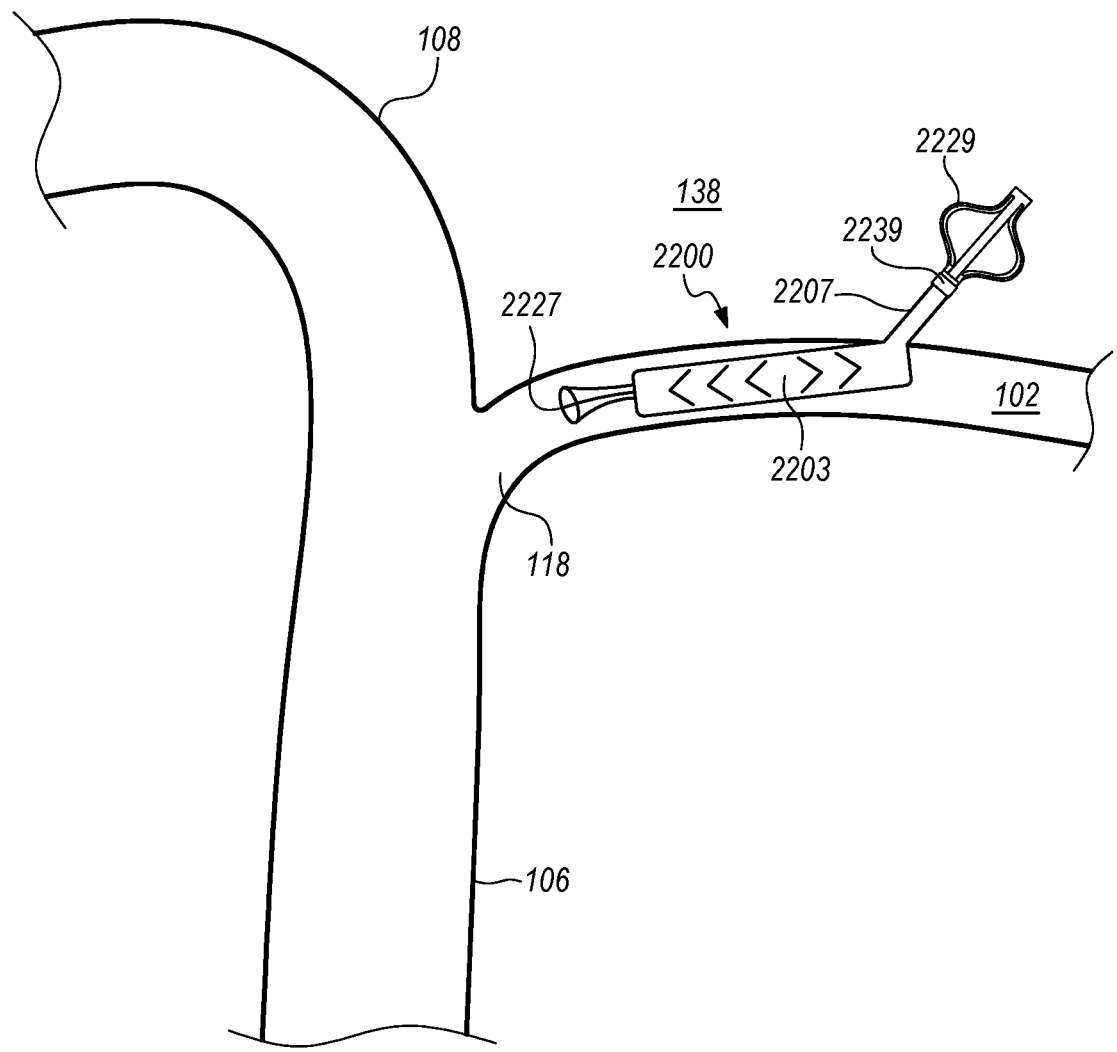
FIG. 17D is a perspective view of a drug delivery device, constructed according to embodiments of the disclosed inventions.

FIG. 17D shows another drug delivery device 2200, according to embodiments of the disclosed inventions. Drug delivery device 2200 can be deployed in a dural venous sinus for delivering one or more therapeutic agents to the intracranial SAS by any of the delivery catheter embodiments disclosed herein. Device 2200 in FIG. 17D has been deployed in IPS 102, with the distal end opening 2239 of drug delivery lumen 2207 and distal anchoring mechanism 2239 disposed in CP angle cistern 138. Drug delivery device 2200 includes a reservoir 2203 for holding a therapeutic agent to be delivered to the intracranial SAS. In alternative embodiments of drug delivery device 2200, reservoir 2203 can comprise an expandable reservoir (e.g., a balloon, a member) disposed in the dural device sinus and in fluid communication with one or more drug delivery lumens. In further alternative embodiments of drug delivery device 2200, reservoir 2203 can comprise a helical coil including a lumen in fluid communication with one or more drug delivery lumens of device 2200; the helical coil can be coupled to a distal portion of the drug and intended for deployment in the dural venous sinus lumen and to provide an anchoring means for the deployed drug delivery device 2200.

In drug delivery device 2200 embodiments with two or more drug delivery lumens 2207, multiple or partitioned reservoirs can be included to administer two or therapeutic agents (or different concentrations or formulations of the same agent) to the intracranial SAS. Device 2200 can include a programmable control system (not shown, but e.g., a microelectricalmechanical system) to operate a pump or other fluidic delivery means to deliver a therapeutic agent from reservoir 2203, through drug delivery lumen 2207 and distal end opening 2239 continuously, on a pre-determined schedule, or in response to 22 commands received from a controller external to the patient (e.g., via Bluetooth). In alternative embodiments, device 2200 contains mechanical means for continuous or periodic delivery of a therapeutic agent from reservoir 2203 to the intracranial SAS (e.g., a piston within reservoir to drive therapeutic agent from the device actuated by a spring or lead screw powered by blood flow through IPS 102). Reservoir 2203 of drug delivery device 2200 can be filled with therapeutic agent(s) prior to device deployment in the patient, and/or after deployment via catheter or other refilling delivery device that connects to a refilling coupler 2227. Refilling coupler 2227 can also be used as a point to connect a snare or other interventional retrieval device to remove device 2200 from the patient.

Figure 3E:
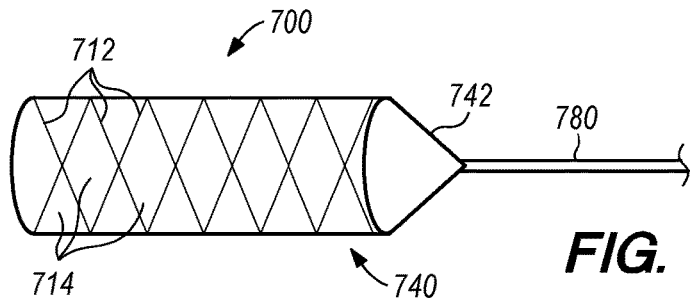
Figure 3F:
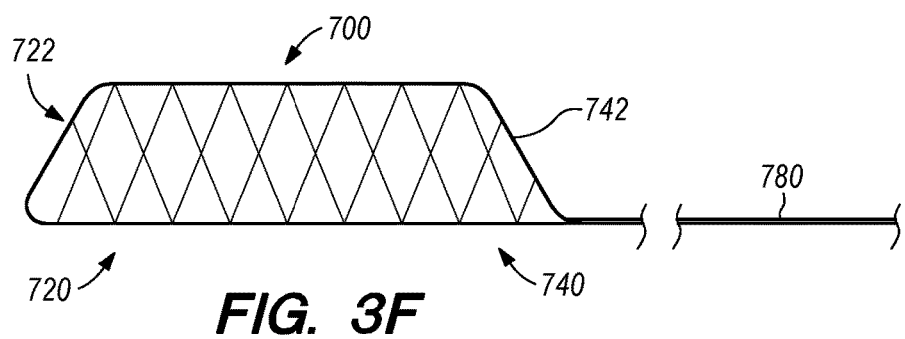
Figure 3G:
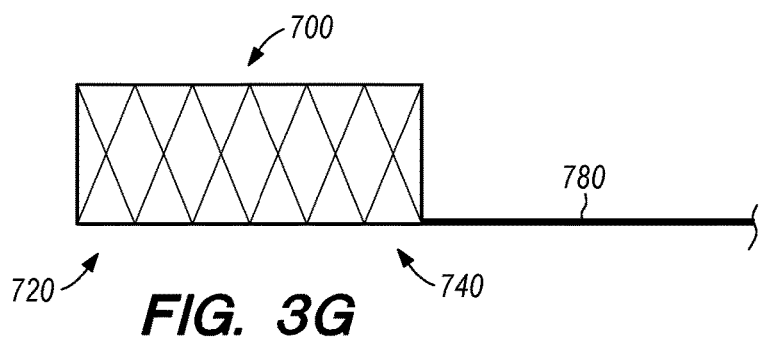
Figure 3H:
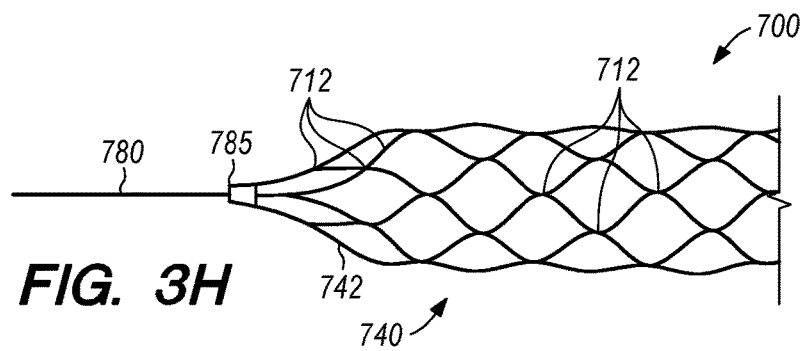

Embodiments of the drug delivery assemblies disclosed herein can include an anchor 700. FIGS. 3A-J illustrates exemplary anchor 700 according to the embodiments of the disclosed inventions. The anchor 700 comprises a proximal portion 740, a middle or body portion 730, a distal portion 720 (FIG. 3A), and a lumen 750 extending therebetween (FIG. 3A-B). The proximal portion 740 of FIGS. 3A, 3C, 3E, 3F includes a beveled or tapered proximal section 742. The anchor 700 further comprises an elongate guide member 780 coupled to the proximal portion 740 and/or beveled/tapered proximal section 742. As shown in FIGS. 3A, 3C and 3F, the beveled/tapered proximal section 742 is offset, as the taper transitions to the bottom of proximal portion 740 and the elongate guide member 780. Alternatively, the beveled/tapered proximal section 742 may be symmetrical having the elongate guide member 780 centrally disposed, as shown in FIGS. 3E and 3H. Additionally, the distal portion 720 of the anchor 700 may include a beveled/tapered distal section 742, as shown in FIG. 3F. The proximal portion 740 and distal portion 720 of the anchor 700 may taper at a variety of suitable angles. The proximal portion 740 of the anchor 700 may comprise a strut or plurality of struts 712 directly or indirectly coupled to the elongate guide member 780 (e.g., FIG. 3E, 3H). In an alternative embodiment, the anchor 700 proximal portion 740 and distal portion 720 terminates at approximately 90° angle (i.e., without tapering), as shown in FIG. 3G.

The anchor 700 may be composed of suitable materials, such as, platinum, Nitinol®, gold or other biocompatible metal and/or polymeric materials, for example, silicon, or combinations thereof. In some embodiments, the anchor 700 may include materials that are compatible with magnetic resonance imaging and have radiopacity sufficient to allow the use of known imaging techniques. In some embodiments, the anchor 700 is composed of shape memory, self-expandable and biocompatible materials, such as Nitinol®, or other super-elastic alloys, stainless steel, or cobalt chromium, and comprises a stent-like configuration. In other embodiments, the anchor 700 may include other suitable configurations, such as tubular prosthesis, flow diverter, clot retriever, or the like. Alternatively, the anchor 700 can be composed of magnesium, zinc, or other bio-absorbable or dissolvable components.

Figure 3I:
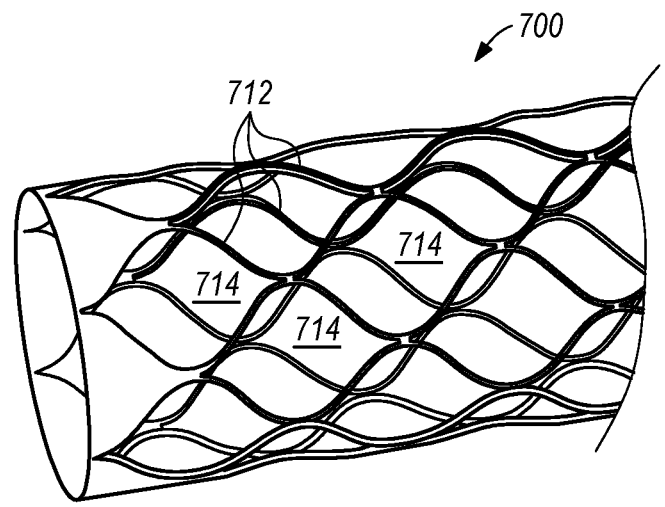
Figure 3J:
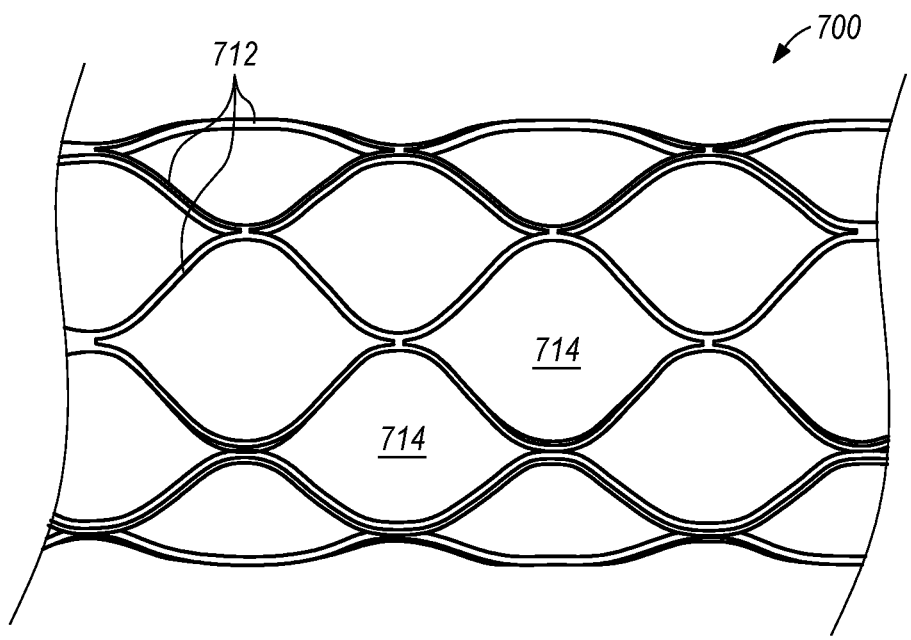

The anchor 700 may be formed by laser cutting a flat sheet, a tubular member, or other suitable configuration of the described materials into interconnected struts 712 forming an open or closed cell pattern having a plurality of cells 714, as shown by the closed cell patterns in FIGS. 3A and 3C-H. Detailed portions of exemplary closed cell patterns of the anchor 700 having the plurality of struts 712 defining the plurality of cells 714 are shown in FIGS. 3I-J. Other suitable techniques may be used to form the closed (or open) cell pattern of the anchor 700, such as etching, or having a plurality of wires braided, woven, or coupled together (not shown). The anchor 700 further comprises a radially collapsed or delivery configuration and, a radially expanded or deployed configuration. In the deployed configuration the anchor 700 is configured to radially expand and anchor itself within the IPS 102 or CS 104. The anchor 700 may include a length Li of approximately 2 mm to approximately 20 mm, in the radially expanded configuration (FIG. 3C). The anchor 700 may include an outer diameter $OD_1$ of approximately 2 mm to approximately 6 mm or larger, in the radially expanded configuration (FIG. 3D). The anchor 700 is radially compressible about the axis 751 of the lumen 750, and configured to collapse within a delivery catheter (e.g., a delivery catheter having an inner diameter of approximately 0.014" to approximately 0.040") such that a clinician can navigate the collapsed anchor 700 through one or more catheters into the IPS 102 or CS 104.

The anchor 700 and the elongate guide member 780 coupled to the proximal portion 740 of the anchor 700 can be manufactured from the same piece of material (e.g., a super-elastic alloy such as Nitinol®), or may comprise separate parts joined at a joint 744 between anchor 700 and the elongate guide member 780. As shown in FIGS. 3A, 3C, 3E-H, the elongate guide member 780 is coupled (e.g., directly or indirectly, attached, secured, joined, or their like) to the proximal portion 740 of the anchor 700. Alternatively, the elongate guide member 780 can be coupled to the distal portion 720, middle portion 730, and/or to any strut or plurality of struts 712 (FIG. 3E, 3H) of the anchor 700 (not shown). The elongate guide member 780 can have a flat, rectangular, or otherwise non-circular, cross-sectional profile, as shown for example in FIG. 3D and FIG. 11. By way of non-limiting example, the elongate guide member 780 can have a rectangular cross-sectional profile with dimensions of approximately 0.001"×0.003" to 0.008"×0.040". An elongate guide member 780 with rectangular cross-sectional profile can provide increased column strength to facilitate navigation of the anchor 700 through a delivery catheter to a target location in IPS 102 or CS 104 and, if necessary, to assist with the re-sheathing of the anchor 700 into a delivery catheter for re-deployment of the anchor 700 prior to penetration of the IPS wall 114/arachnoid layer 115 and deployment of the drug delivery device, or when removing the anchor 700 from the patient's vasculature after administration of a therapeutic agent from a delivery catheter or deployment of a drug delivery device as disclosed herein. When used with the delivery catheter 3304 including a dedicated lumen 3315 configured to conform to the rectangular cross-sectional profile of the guide member 780 (e.g., as shown in FIG. 10), the elongate guide member 780 maintains the trajectory of the delivery catheter 3304 over the guide member and at the target penetration site by limiting or preventing rotation of the delivery catheter 3304 about or around the guide member 780.

Alternatively, embodiments of elongate guide member 780 can have a circular cross-sectional profile, as shown in FIGS. 17A-C. By way of non-limiting example, an elongate guide member 780 with circular cross-sectional profile can have a diameter of about 0.005" to 0.018" or more. The elongate guide member 780 having a tubular configuration may include a plurality of cuts to increase flexibility, as shown by the exemplary spiral cut pattern of kerf, pitch, cuts per rotation and cut balance depicted in sections of FIGS. 17A-C. Such configurations of the elongate guide member can improve the "trackability" of a delivery catheter over the guide member (e.g., a delivery catheter with a dedicated lumen configured to conform to the guide member profile), and provide the ability to radially orient the delivery catheter and penetrating element about the guide member in the lumen of IPS 102 or CS 104. An elongate guide member 780 with circular cross-sectional profile can provide increased column strength to facilitate navigation of the anchor 700 through a catheter to a target location in IPS 102 or CS 104 and, if necessary, to assist with the re-sheathing of the anchor 700 into a catheter for re-deployment of the anchor 700 prior to penetration of the IPS wall 114/arachnoid layer 115, or when removing the anchor 700 from the patient's vasculature after administration of a therapeutic agent from a delivery catheter or deployment of a drug delivery device. Further, the ability to radially orient the delivery catheter and penetrating element about the guide member in the lumen of IPS 102 or CS 104 can be used to correct the orientation of a mis-loaded delivery catheter over the guide member.

The profile, dimensions, and material for the elongate guide member 780 are configured to resist kinking along the length of the elongate guide member 780 and provide sufficient column strength for anchor deployment and re-sheathing, while still allowing sufficient flexibility for deployment through a catheter by tracking through the curved portion of the IPS 102. Alternatively, the elongate guide member 780 can have a pre-curved distal portion, disposed closer to the joint 744 between anchor 700 and the elongate guide member 780, so as to bias the elongate guide member 780 towards IPS wall 114 or IPS wall 117 when the elongate guide member 780 is deployed through the curved portion of the IPS 102. Further, the joint 744 between the anchor 700 and the elongate guide member 780 may include a rotatable element (FIGS. 18E-F) allowing the elongate guide member 780 to assume a desirable orientation through the curved portion of the IPS 102.

Radiopaque markings, biocompatible coatings, and/or lubricious coatings can be incorporated into the anchor 700 and/or elongate guide member 780 to assist with navigation and deployment of the anchor 700 in a sinus lumen distal to a target penetration site on IPS wall 114. The radiopaque markings may be placed on one or more of the following locations along the anchor 700 and elongate guide member 780, as shown in FIG. 3C: in a plurality of struts 712 at the distal portion 720 of the anchor 700; along Li, with or without rotationally varying marker placement along the middle or body portion 730 of the anchor 700 to further aid navigation and orientation; at the joint 744 between anchor 700 and the elongate guide member 780, and/or on or around the first full-diameter portion of anchor 700 at the proximal portion 740.

Figure 4A:
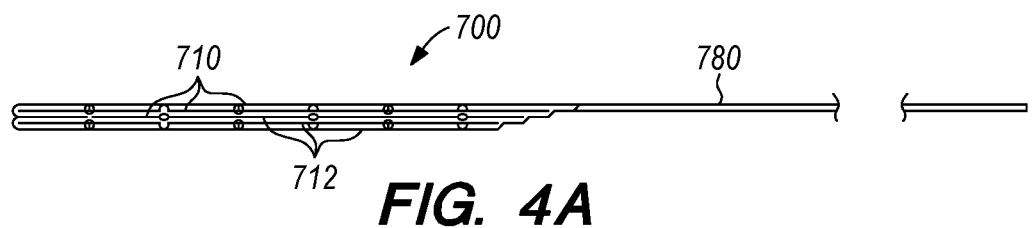
FIG. 4A-C are perspective and cross-sectional views of an anchor and elongate guide member, according another embodiment of the disclosed inventions.
Figure 4B:
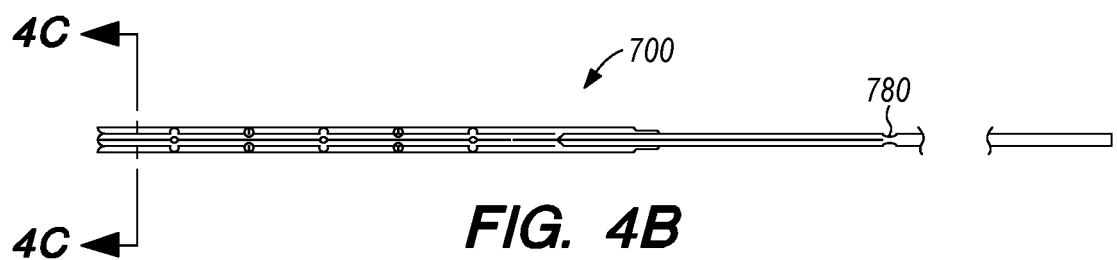
Figure 4C:
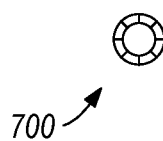
Figure 5A:
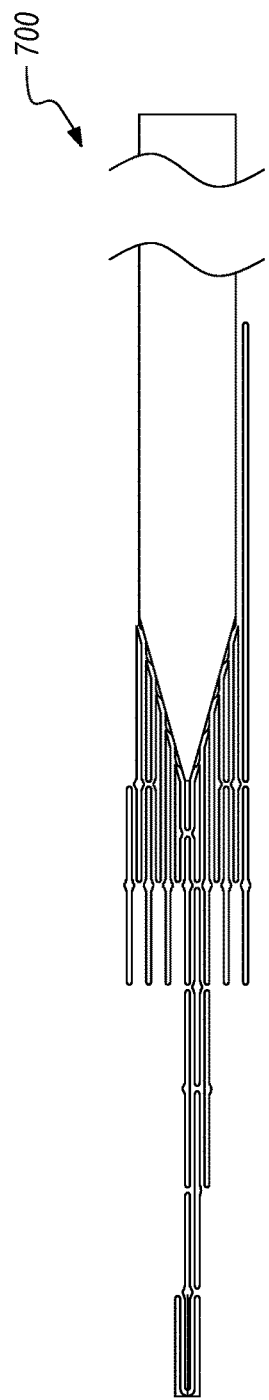
FIGS. 5A-W are perspective and cross-sectional views of an anchor, according other embodiments of the disclosed inventions.
Figure 5B:
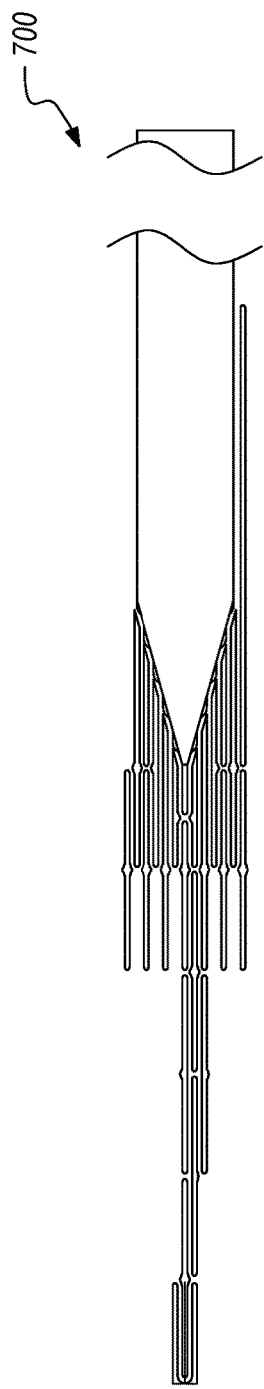
Figure 5C:
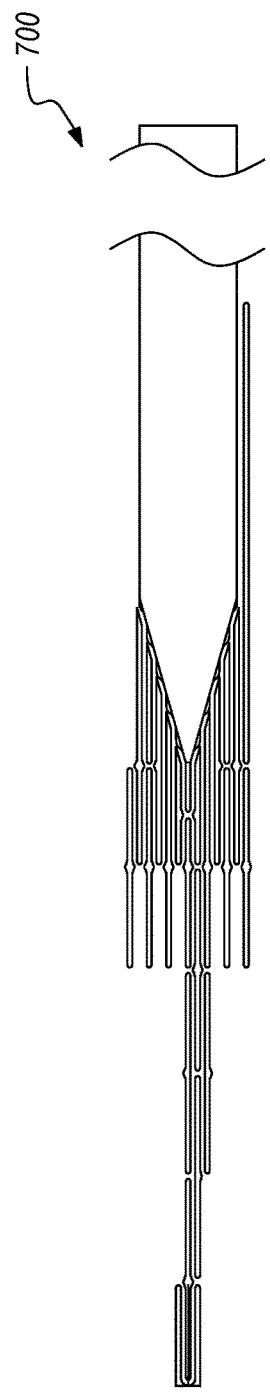
Figure 5G:
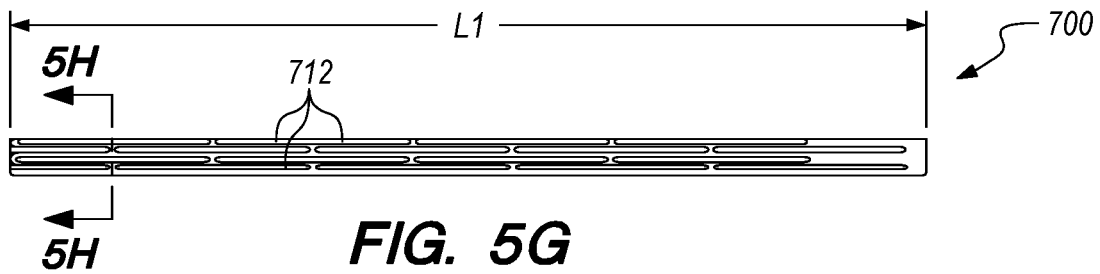
Figure 5H:
Figure 5I:
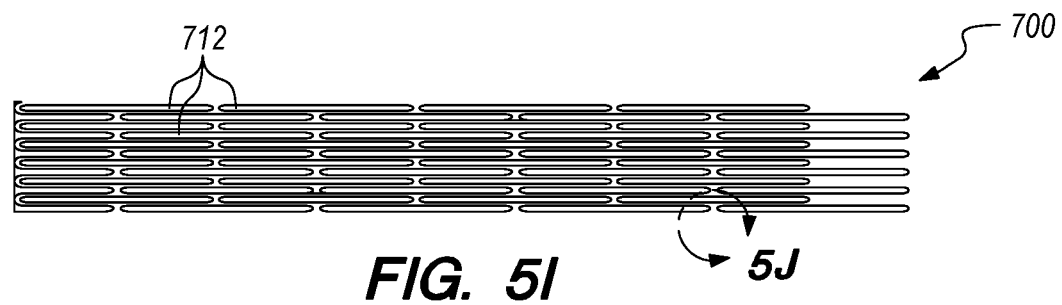
Figure 5J:
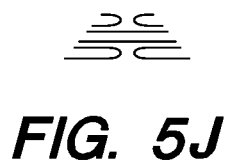
Figure 5K:
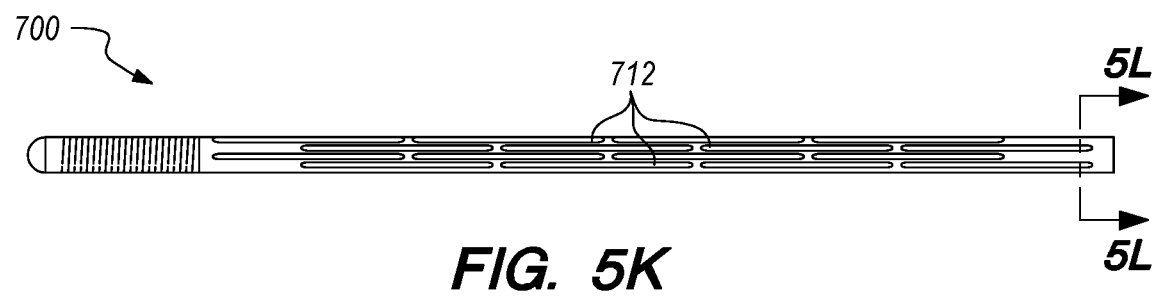
Figure 5L:
Figure 5M:
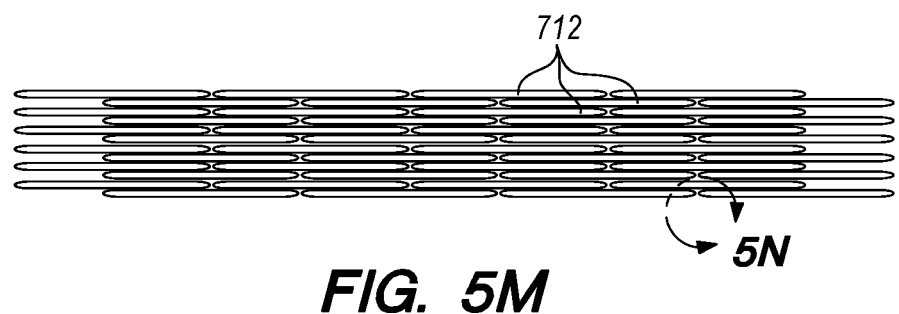
Figure 5N:
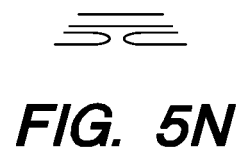
Figure 5U:
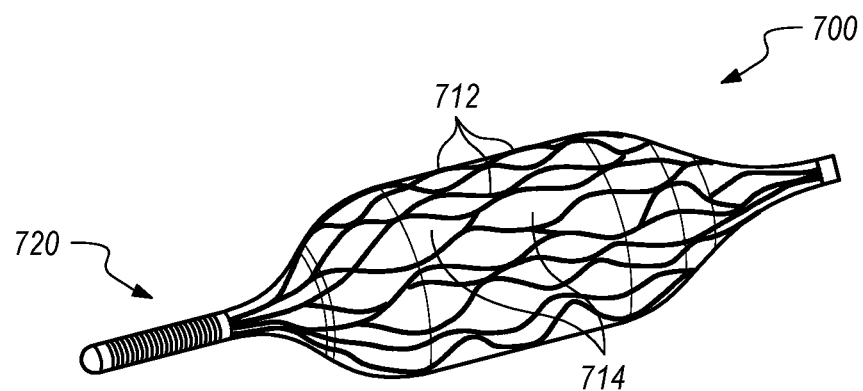
Figure 5V:
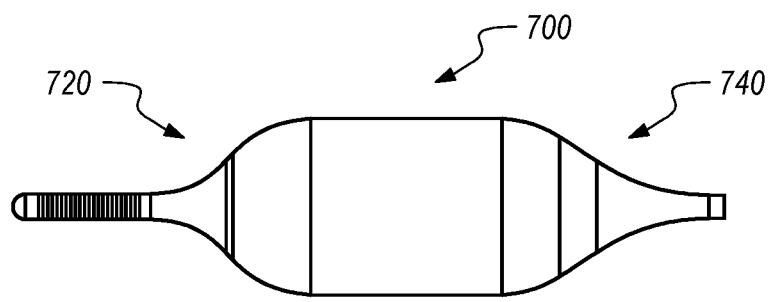
Figure 5W:
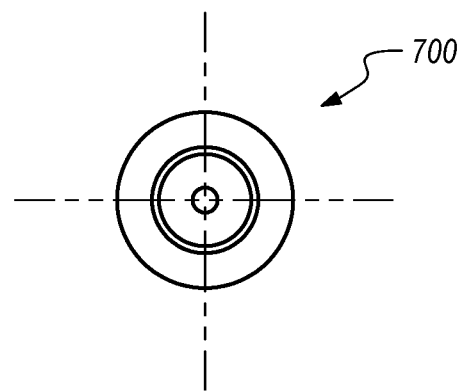

FIGS. 4A-C illustrate another exemplary anchor 700, constructed according to embodiments of the disclosed inventions. FIG. 4A-B depict respective side views, and FIG. 4C depicts a cross-sectional view of the anchor 700, comprising a plurality of cuts 710 forming a stent-like configuration, having a plurality of struts 712. The anchor 700, the elongate guide member 780, cuts 710 and/or the patterns of the cuts 710 may be manufactured by selectively cutting a tubular element using any suitable cutting method (e.g., laser cutting, etching or their like). FIGS. 5A-W depicts exemplary dimensions and cut patterns of the anchor 700, constructed according to embodiments of the disclosed inventions. The struts 712 of the anchor 700 form a plurality of spaces or cells 714 therebetween. The cells 714 include a closed cell pattern when the anchor 700 is in the radially expanded configuration, as for example shown in FIGS. 3E, 3H-J, 5O and 5U, and a closed cell pattern when the anchor 700 is in the radially compressed configuration, as for example shown in FIGS. 4A, 5G, and 5K. In one embodiment of the anchor 700, the cut pattern shown in the radially compressed configuration in FIG. 5G, is configured to form the radially expanded configuration of the anchor 700 shown in FIG. 5O. FIGS. 5P-T illustrate exemplary dimensions and properties of the anchor 700 of FIGS. 5G and 5O, such as the variations of the beveled/tapered proximal portions 740. Varying the taper in the proximal portion 740 (e.g., as described by the transition length measurements of FIG. 5T) can facilitate smooth anchor deployment and retrieval when paired with an appropriately sized catheter (e.g., catheter with 0.027" inner diameter, for example, as disclosed in the above-referenced International Patent Application PCT/US18/20667 filed on Mar. 2, 2018). In an alternative embodiment of the anchor, the cut pattern shown in the radially compressed configuration in FIG. 5K, is configured to form the radially expanded configuration of the anchor 700 shown in FIG. 5U. FIGS. 5V-W illustrate exemplary dimensions and properties of another embodiment of anchor 700 of FIG. 5U, such as having beveled/tapered proximal portion 740 and distal portion 720. The beveled/tapered distal portion 720 of anchor 700 depicted in FIG. 5U, and corresponding flexibility provided by the spiral cut pattern of such distal portion shown in FIG. 5K, facilitates access to remote, narrowing, and/or tortuous regions of the intracranial venous anatomy such as IPS 102 and CS 104. For illustration purposes, FIGS. 5P-S and 5V-W are depicted without the struts 712 and cells 714 of the anchor 700 to better appreciate the dimensions and properties of the anchor 700 in said figures (in a radially expanded configuration). However, it should be appreciated that the anchor 700 of FIGS. 5P-S and 5V-W includes the struts 712 and cells 714 of their respective FIGS. 5O and 5U The struts 712 and cells 714 of the anchor 700 substantially extend along the length Li, as for example shown in FIG. 3C in the radially expanded configuration, and in FIG. 5G in the radially compressed configuration. However, the struts 712 and cells 714 may extend along selected portions of the anchor 700, as for example shown in FIG. 5U at the distal portion 720. Additionally, the anchor 700 can include a mesh framework between the struts 712 to increase the friction between the anchor 700 and IPS 102 (or CS 104), further securing the anchor 700 at or about the target site when deployed. The struts 712 of anchor 700 can have flat, round, elliptical, or irregularly shaped profiles or suitable cross-sections. The width of the struts 712 can vary from approximately 0.0030" to 0.0045", or larger. Additionally, the struts 712 can be configured to exhibit a negative Poisson's ratio under strain such that, after deployment in a sinus lumen (e.g., IPS 102 or CS 104), applying a retrograde force to anchor 700 (e.g., by pulling proximally on the anchor 700 via the elongate guide member 780) further expands the struts 712 radially outward to secure the anchor 700 at the target site.

Dimensions referenced in FIGS. 5A-5W in brackets (e.g., [14.67]) are provided in millimeters, while all other dimensions referred without brackets are provided in inches. It should be appreciated that the dimensions depicted in FIGS. 4A-5W are exemplary dimensions of the anchor 700, which are not intended to limit the embodiment of the anchor 700 disclosed herein.

Figure 6:
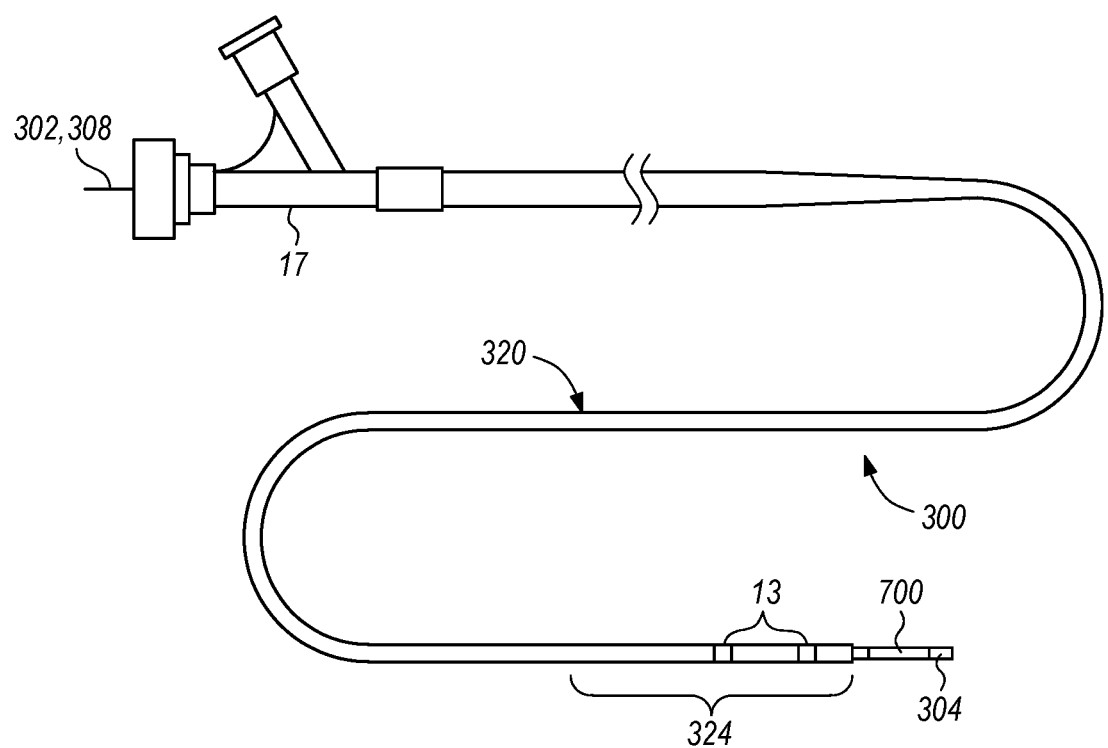
FIG. 6 is a side view of a delivery assembly according to embodiments of the disclosed inventions.

FIG. 6 is a side view of a delivery assembly 300 for delivering the anchor 700 and administering a therapeutic agent and/or deploying a drug delivery device into a target site of a patient, constructed in accordance with embodiments of the disclosed inventions. The delivery assembly 300 includes the anchor 700 and the drug delivery device (not shown) detachably coupled to or disposed within the delivery assembly 300. The delivery assembly 300 and the drug delivery device may be composed of suitable biocompatible materials. The delivery assembly 300 is dimensioned to reach remote locations of the vasculature and is configured to deliver the anchor 700 and the drug delivery device percutaneously to the target location (e.g., inferior petrosal sinus). The delivery assembly 300 includes a tubular member interface having an outer tubular member 320 (i.e., guide catheter) and an inner tubular member 304 (i.e., delivery catheter/micro catheter) coaxially disposed within the outer tubular member 320 and movable relative to the outer tubular member 320. The delivery assembly 300 may include a guidewire 302 coaxially disposed within the guide catheter 320 and/or the delivery catheter 304. The guidewire 302 can be, for example, 0.035" (0.889 mm) in diameter. Additionally to the guidewire 302, the delivery assembly 300 may include a delivery guidewire 308 disposed within the delivery catheter 304. The delivery guidewire 308 has a smaller diameter (e.g., approximately 0.010" (0.254 mm) to 0.018" (0.4572 mm) or other suitable dimension to facilitate accessing intracranial venous vasculature with other components of delivery assembly 300) compared to guidewire 302.

The guide catheter 320, delivery catheter 304, and guidewires 302/308 (FIG. 6) may be formed of suitable biocompatible materials, and may include markings 13 for purposes of imaging (e.g., markers composed of radio-opaque materials). Various known and often necessary accessories to the delivery assembly 300, e.g., one or more radiopaque marker bands 13 at the distal portion 324 of the guide catheter 320 to allow viewing of the position of the distal portion under fluoroscopy and a Luer assembly 17 for guidewires and/or fluids access, are shown in FIG. 6. The delivery assembly 300 and/or the delivery catheter 304 may include a penetrating element (not shown) configured to pierce and/or penetrate a dural venous sinus wall to access the intracranial SAS, e.g., penetrate the IPS wall 114 and arachnoid layer 115 to access the CP angle cistern 138, for administration of a therapeutic agent and/or implantation of a drug delivery device 200.

FIGS. 7A-F illustrate exemplary methods of delivering the anchor 700, the elongate guide member 780 and delivery catheter 3304 for administration of a therapeutic agent and/or deployment of a drug delivery device 200 at a target site, according embodiments of the disclosed inventions. The anchor 700 is configured to be deployed and disposed within the IPS 102 or the CS 104 prior to penetration of the IPS wall 114 with a micro catheter. In some embodiments, the anchor 700 is configured to be distally disposed to a target penetration site in IPS wall 114, as to provide support (e.g., foundation) for subsequent IPS wall 114 penetration, and therapeutic agent administration and/or drug delivery device deployment step. The anchor 700 may be deployed in the IPS 102 or CS 104 by advancing the anchor 700 out of the distal end opening of a micro catheter 304, or by withdrawing the micro catheter 304, and/or by a combination of advancing the anchor 700 and withdrawing the catheter 304 for deployment of the anchor 700 in the IPS 102 or CS 104 (not shown).

When the anchor 700 is deployed into the target site (e.g., IPS 102 or CS 104), the anchor 700 transitions from its delivery configuration (e.g., radially constrained by an inner lumen of the micro catheter 304) to its deployed configuration (e.g., expanding radially outwards, so as to engage the walls of the IPS 102 or CS lumen 131). When deployed (FIG. 7A), the struts 712 of the anchor 700 are biased to exert an outward radial force that engages and secures the anchor 700 within the IPS 102, against IPS walls 114 and 117, or against the equivalent walls of the CS 104. The ratio of the resting anchor 700 diameter (i.e., expanded, unconstrained configuration) to the reference vessel diameter (i.e., diameter of the sinus lumen where the anchor will be deployed) can range from about 1:1 up to about 2:1. In addition, the exterior surface of anchor 700 can include anchoring elements, spikes, burrs, barbs or other features to engage the dura mater of IPS walls 114 and 117 (or the walls of CS lumen 131), which further secures the anchor in IPS 102 or CS 104.

The micro catheter 304, with or without a delivery guide wire, facilitates navigation and delivery of the anchor 700 within the patient's vasculature through the junction 118 and into the IPS 102 and/or CS 104. The compressible nature of the anchor 700 allows the clinician to deploy the anchor 700 from the catheter 304 within the IPS 102 (or CS 104), re-sheath the anchor 700 into the catheter 304 (when needed), and redeploy the anchor 700 within the applicable sinus lumen (e.g. IPS 102 and/or CS 104) until the clinician is satisfied with the deployment location and orientation of the anchor 700 and/or elongate guide member 780 in the patient.

Figure 7A:
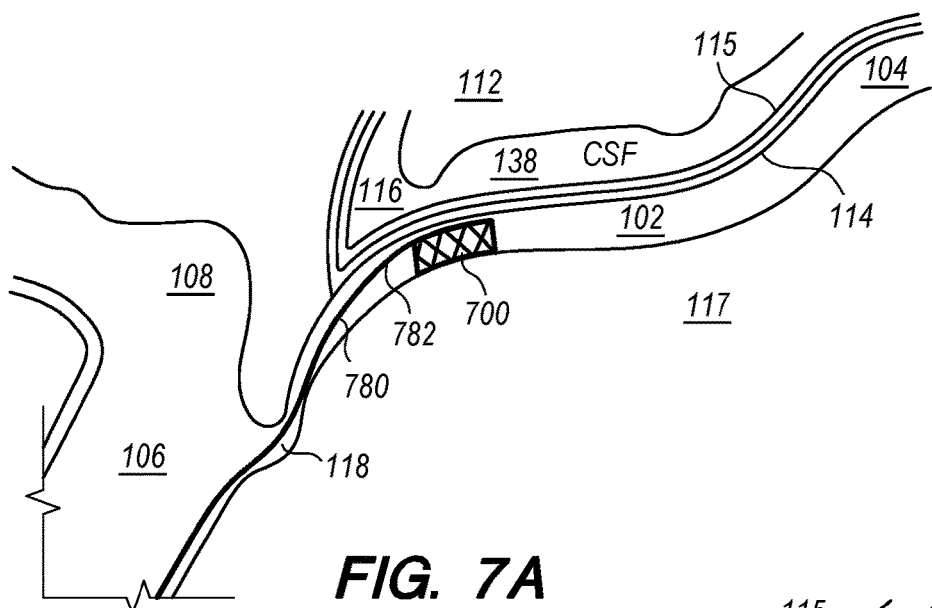
FIGS. 7A-F are cross-sectional views of exemplary methods of delivering the anchor, the elongate guide member and the drug delivery device at a target site, according embodiments of the disclosed inventions.

As shown in FIG. 7A, the anchor 700 is deployed in the IPS 102. The anchor 700 is disposed in the IPS 102 distal to a target penetration site in IPS wall 114. The elongate guide member 780 coupled to the anchor 700 extends from the IPS 102 through the curved portion of IPS 102 into the junction 118. The elongate guide member 780 further extends into the jugular vein 106, and can extend further through venous vasculature and out of the patient's body at the peripheral access site (e.g., femoral vein, subclavian vein, cephalic vein, brachial vein). The micro catheter 304 used to deploy the anchor 700 may be withdrawn from the patient to allow for other delivery system components to access the IPS 102 after deployment of the anchor. Alternatively, the micro catheter 304 used to deploy the anchor 700 may allow further deployment of other components (e.g., piercing or penetrating elements, drug delivery devices, or their like) into the IPS 102 without needing withdrawal of the micro catheter 304 for other delivery systems. As previously disclosed, the anchor 700 can be deployed in a more distal location, such as CS 104.

Figure 7B:
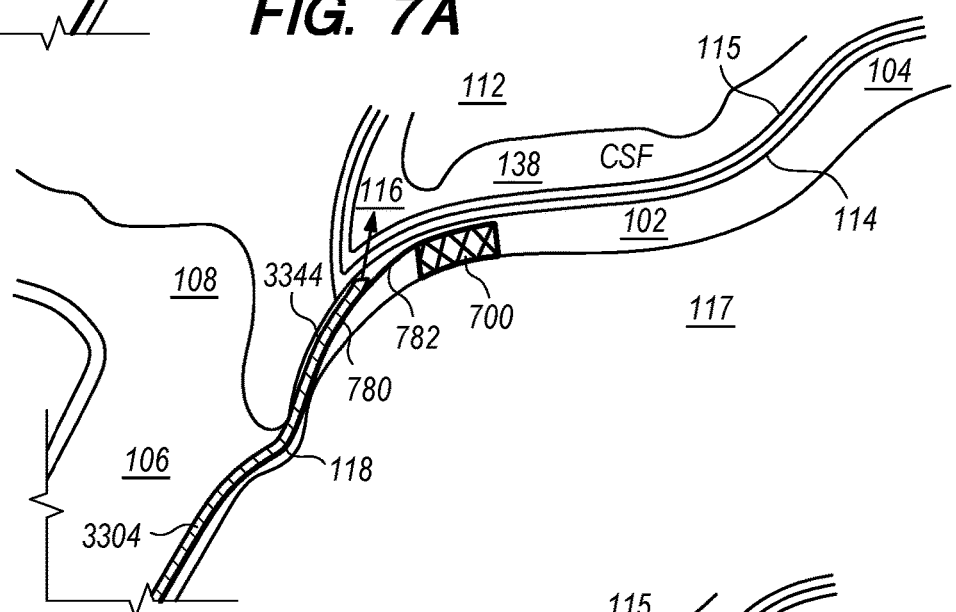
Figure 7C:
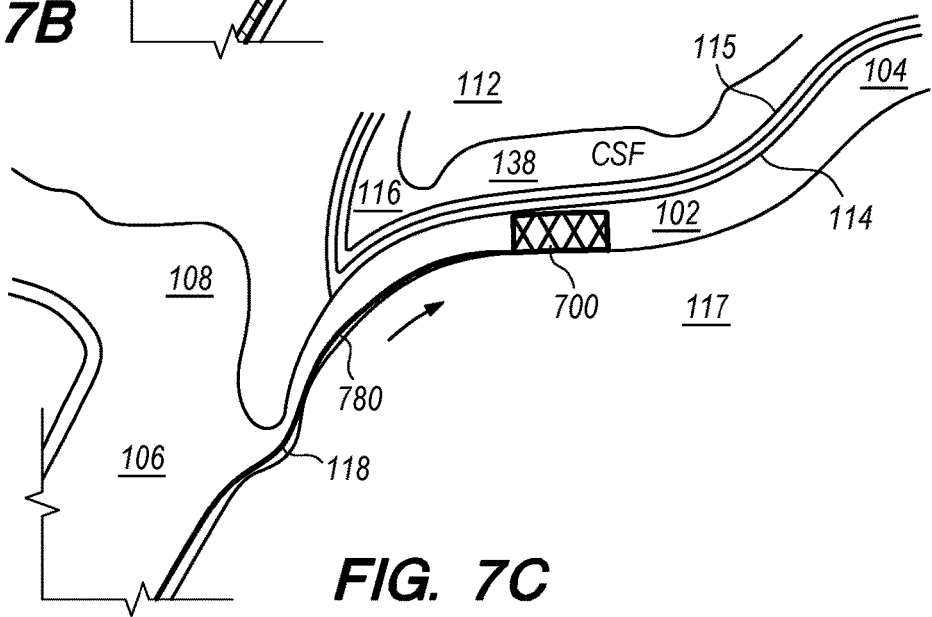
Figure 7D:
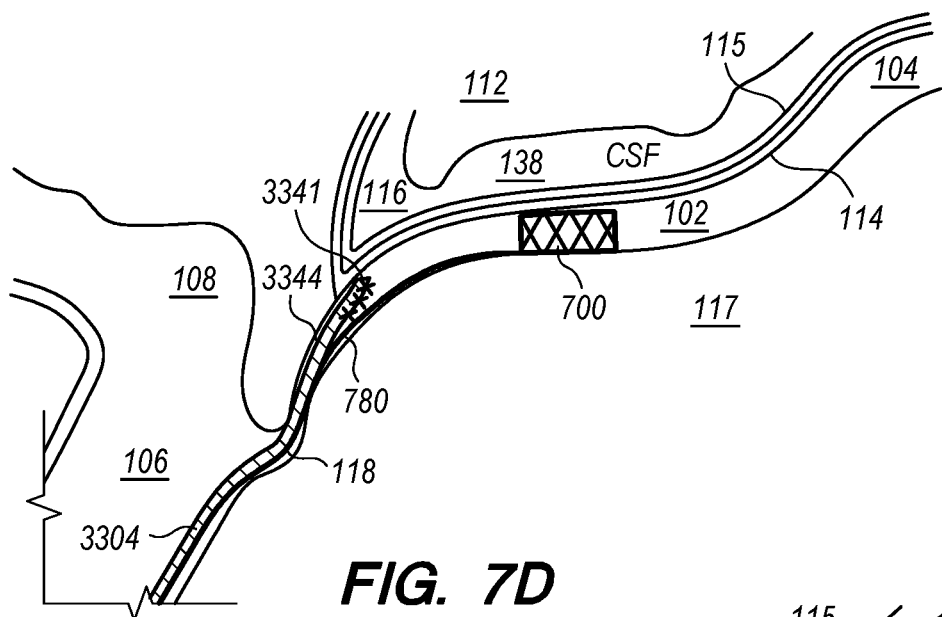
Figure 8A:
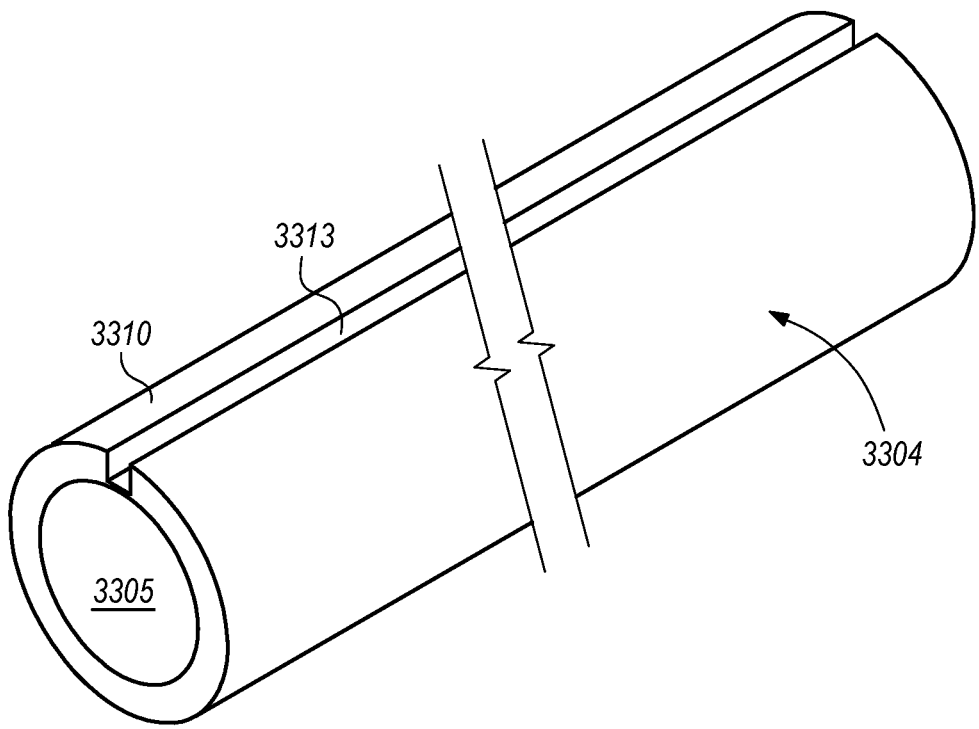
FIGS. 8A-B are perspective and cross-sectional views of a delivery catheter, constructed according to embodiments of the disclosed inventions.
Figure 8B:
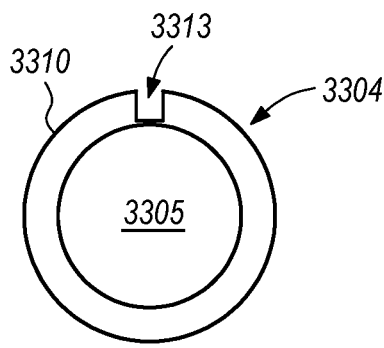

In some embodiments, a delivery catheter 3304 can include one or more features that allow for accurate guidance, navigation and/or control of the deployment of the penetrating element, a therapeutic agent, and/or a drug delivery device, particularly when passing through the junction 118 into the IPS 102. FIGS. 8A-B illustrate perspective and cross-sectional views of the delivery catheter 3304, according to one embodiment of the disclosed inventions. The delivery catheter 3304 comprises a recess 3313 formed in the outer surface 3310 of the catheter. The recess 3313 is configured to slidably engage the elongate guide member 780 of the anchor 700, so that the delivery catheter 3304 rides on the elongate guide member 780 of the previously deployed anchor 700 (e.g., "side car" configuration), allowing the catheter 3304 to be guided in a desired orientation and location within the target site in the IPS 102, as shown in FIG. 7B. The elongate guide member 780 is dimensioned and configured to engage the recess 3313 in the delivery catheter 3304. The elongate guide member 780 is further configured to guide the delivery catheter 3304 into the target penetration site, as shown in FIGS. 7B and 7D. The embodiment shown in FIGS. 8A-B is an exemplary control feature that can be implemented in connection with the catheter 3304. In some embodiments, the catheter 3304 and anchor 700 can include a plurality of such features (e.g., a plurality of elongate guide members that engage with a plurality of recesses).

Figure 9:
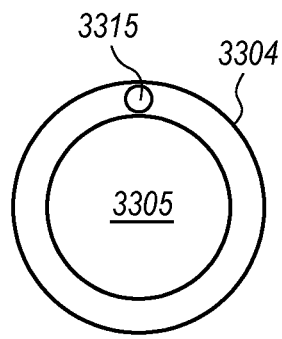
FIG. 9 is cross-sectional view of another delivery catheter, constructed according to another embodiment of the disclosed inventions.

As shown in FIG. 7B, the delivery catheter 3304 has been advanced over, in or on the elongate guide member 780 of the previously deployed anchor 700. Alternatively to the recess 3313 disclosed above, the delivery catheter 3304 can have a dedicated lumen 3315 extending between the delivery catheter proximal and distal portions configured to accommodate the elongate guide member 780 of the anchor 700. Alternatively, the delivery catheter 3304 can include a broken or incomplete lumen extending between the proximal and distal portions of the catheter that captures the elongate guide member 780 against IPS wall 117 and allows the catheter to travel over the elongate guide member 780. At least one other lumen 3305 of delivery catheter 3304 extends between the proximal and distal portions of the catheter 3304 (FIGS. 8A-B, and FIG. 9), which allows for navigation and delivery of the penetrating elements (e.g., surgical tool, needles, RF stylets, or the like), administration of therapeutic agents into the incranial SAS, and/or deployment of drug delivery devices. The distal portion 3344 of the delivery catheter 3304 intersects the IPS wall 114 at an angle of approximately 75° (or any other suitable angle) at the target penetration site, as shown in FIG. 7B.

FIGS. 10A-K depict additional embodiments of a dual lumen delivery catheter 3304. As shown in FIGS. 10A-E, a distal portion 3344 of the delivery catheter includes a penetrating element 3350. Each catheter of FIG. 10 includes a first lumen 3315 extending between the ends of the catheter, which is configured to receive the elongate guide member 780 and, optionally, conforms to the profile of the elongate guide member. A second lumen 3305 of the foregoing catheter embodiments extends between the ends of the catheter, which allows for navigation and delivery of the penetrating elements (e.g., surgical tool, needles, RF stylets, or their like), administration of therapeutic agents into the incranial SAS, and/or deployment of drug delivery devices. Further, one or both lumens of delivery catheter 3304 shown in FIGS. 10A-K can include a liner and/or can be coated with a hydrophilic agent to increase the lubricity of such lumens with respect to other delivery assembly components as described in the related application previously incorporated by reference herewith. FIGS. 10B, 10D, and 10E-J show elongate guide member 780 disposed within first lumen 3315, and FIGS. 10B, 10E-J show the drug delivery device 200 with a hollow inner lumen 207 disposed within second lumen 3305 for the exemplary delivery catheter 3304 embodiments. It should be appreciated that the dimensions depicted in 10A-K are exemplary dimensions of the delivery catheter 3304, first lumen 3315, second lumen 3305, penetrating element 3350, drug delivery device 200, and drug delivery device lumen 207, which are not intended to limit the scope of embodiments disclosed herein. For example, embodiments of delivery catheter 3304 can have a second lumen 3305 with an inner diameter in a range of about 0.012" (0.3048 mm) to 0.040" (1.016 mm) or more.

The anchor 700 and the elongate guide member 780 can be optimized to orient the penetrating element or a drug delivery device advancing via the catheter 3304 over the elongate guide member 780 towards a target penetration site on the IPS wall 114 along the curved portion of IPS 102. For example, the elongate guide member 780 coupled to the anchor 700 at a location along the top edge of anchor 700, is configured to orient a distal portion 782 of the elongate guide member 780 proximate or adjacent to the IPS wall 114, as shown in FIGS. 7A-B. Alternatively, the anchor 700 and the elongate guide member 780 can be configured such that the elongate guide member 780 orients (e.g., "hugs") nearest the IPS wall 117 through the curved portion of IPS 102, as shown in FIGS. 7C-D, when the anchor 700 is deployed distally to a target penetration site along the IPS wall 114.

Additionally, the deployment location of the anchor 700 in the sinus lumen can vary the path of the elongate guide member 780 through the curved portion of IPS 102, regardless of how the elongate guide member 780 is oriented with respect to the top, midline, or bottom portions of the anchor 700. For example, deploying the anchor 700 more distally than the deployment location shown in FIGS. 7A-B will orient the elongate guide member 780 more proximate to the IPS wall 117 than IPS wall 114.

Additionally, embodiments of the delivery catheter 3304 (or a drug delivery device if delivered over the elongate guide member 780 without a delivery catheter) can be optimized to orient a penetrating element and/or drug delivery device advancing through or over the elongate guide member 780 towards a target penetration site in the IPS wall 114 along the curved portion of IPS 102. The distal portion 3344 of the delivery catheter 3304 can have multiple interface points to accommodate the elongate guide member 780, as denoted by the "x" markings in FIG. 7D. The interface point on the distal portion 3344 of delivery catheter 3304 for the elongate guide member 780 provides a penetration stop to limit the distance the penetrating element 3350 can travel through IPS wall 114 and into CP angle cistern 138 (e.g., the maximum penetration depth corresponds to the distance between the distal tip of penetrating element 3350 and the interface point on delivery catheter 3304 for receiving elongate guide member 780). Introducing the elongate guide member 780 into or along the delivery catheter 3304 at a more proximal location on the catheter 3304 allows for more separation between the penetrating element 3350 and/or a distal open end 3341 of the delivery catheter 3304 and the elongate guide member 780. The greater extent of separation between the penetrating element 3350 and elongate guide member 780 provides a relatively longer depth of penetration through IPS wall 114 and arachnoid layer 115 along the curved portion of IPS 102. Conversely, a more distal entrance point or connection along the delivery catheter 3304 and the elongate guide member 780 decreases the separation between the elongate guide member 780 and the penetrating element 3350 and/or distal open end 3341 of delivery catheter 3304. The lesser extent of separation between the penetrating element 3350 and elongate guide member 780 provides a relatively shorter depth of penetration through IPS wall 114 and arachnoid layer 115 along the curved portion of IPS 102. A clinician can adjust the interface point between the elongate guide member 780 and delivery catheter 3304 to optimize the trajectory of a penetrating element from the delivery catheter 3304 and penetration depth at a target penetration site along the IPS 114. The interface point between the elongate guide member 780 and delivery catheter 3304 can range from the distal end 3341 of delivery catheter 3304 (e.g., where the distal end of the delivery catheter includes a distal opening to a dedicated rail lumen) to an interface point about 10 cm proximal from the distal end of delivery catheter 3304.

Once deployed, the anchor 700 and the elongate guide member 780 provide a stable, intra-sinus platform that creates an off-axis trajectory for the penetrating element to pass through the IPS wall 114 and access the intracranial SAS. The deployed anchor 700 and elongate guide member 780, along with other aspects of the delivery system, afford clinicians controlled access to the greatest extent of CSF-filled space in the CP angle cistern 138 for administration of a therapeutic agent from delivery catheter 3304 or drug delivery device deployment from the delivery catheter. The elongate guide member 780 extending through the curved portion of IPS 102 advantageously orients the penetrating element 3350 (i.e., advancing via the guide member) toward IPS wall 114 into CP angle cistern 138. As shown in FIG. 7D, the portion of delivery catheter 3304 distal of the interface point separates from the axis of the elongate guide member 780 as the delivery catheter advances over the guide member through the curved portion of the IPS; that is, the distal most portion of delivery catheter 3304 including penetrating element 3350 travel off-axis from elongate guide member 780 to puncture IPS wall 114 and access the CSF-filled CP angle cistern 138. This orienting feature of the elongate guide member with respect to delivery catheter 3304 ensures that advancement of the penetrating element will: (a) intersect the IPS wall 114 at a target penetration site along the curved portion of IPS 102 at an angle of approximately 90° (i.e., oriented orthogonal to IPS wall 114) to approximately 30° (although, other suitable angles may be provided), and (b) continue on a trajectory through the dura mater of the IPS wall 114 and through the arachnoid layer 115 to access at least 2-3 mm of unobstructed, CSF-filled space of CP angle cistern 138 as measured distally from the penetration point on the IPS wall 114. Features of anchor 700 and the elongate guide member 780 disclosed herein allow clinicians to access the intracranial SAS and administer a therapeutic agent or deploy a drug delivery device in a relatively large extent of free CSF-filled space in the cistern, often more than 3 mm to 5 mm of unobstructed CSF-filled space.

After the anchor 700 and the elongate guide member 780 have been deployed at a desired location in the sinus lumen and the penetrating element has been advanced over the elongate guide member 780 to a target penetration site along the IPS wall 114, the clinician can proceed by creating anastomosis between the IPS 102 and the CP angle cistern 138, followed by administration of the therapeutic agent into the incranial SAS and/or deployment of a drug delivery device from delivery catheter 3304. For example, after penetrating IPS wall 114 and accessing CP angle cistern 138, a therapeutic agent can be administered to the intracranial subarachnoid space through second lumen 3305 of delivery catheter 3304. For example a bolus or loading dose of a therapeutic agent typically delivered via lumbar puncture can be delivered directly to CP angle cistern 138 proximate the brain stem. Alternatively, embodiments of a drug delivery device disclosed herein can be deployed in the anastomosis so as to provide a continuous or extended release of therapeutic agent to the intracranial SAS.

The clinician can penetrate the IPS wall 114 to access the CP angle cistern 138 with the penetrating element (e.g., penetrating element advanced via the catheter, or carried by the catheter distal end) by pulling the elongate guide member 780 in the proximal direction (or locking the elongate guide member 780 in place relative to other delivery system components) while advancing the penetrating element over the elongate guide member 780, toward the IPS wall 114. The retrograde force on the elongate guide member 780 during the penetration step further secures the guide member and anchor 700 in the sinus lumen, thereby stabilizing the elongate guide member 780 in the curved portion of the IPS 102 while it orients a penetrating element towards IPS wall 114 and off-axis from the trajectory of elongate guide member 780 in the curved portion of the IPS lumen. And by simultaneously advancing the penetrating element through the IPS wall 114 and arachnoid layer 115 until a distal anchoring mechanism 229 of the drug delivery device 200 is deployed in the CP angle cistern 138 (i.e., without an exchange of delivery system components between the penetration and drug delivery device deployment steps) eliminates the risk of bleeding from the sinus lumen into the subarachnoid space.

Radiopaque markings or coatings can be incorporated on the penetrating element 3350 (e.g., penetrating element advanced via the catheter, on the drug delivery device, or carried by the distal end of the delivery catheter) and/or the delivery catheter to assist the clinician visualize the orientation of delivery system elements in the sinus lumen and the trajectory of such elements prior to or during the penetration step of the drug delivery procedure. For example, a semicircle piece or half-band of radiopaque material can be coupled to or incorporated within the penetrating element 3350 and/or in the distal portion 3344 of the delivery catheter 3304. Depending on the location of the marker in the penetrating element 3350 and/or distal portion 3344 of the delivery catheter 3304 (e.g., distal section or proximal section of the penetrating element to assist with the visualization of the respective section of the inner diameter or lumen), the clinician can confirm whether the penetrating element 3350 is properly oriented toward the IPS wall 114 and/or improperly oriented toward the IPS wall 117.

After the distal anchoring mechanism 229 of the drug delivery device 200 has been deployed in the CP angle cistern 138, the delivery catheter 3304 can be withdrawn (i.e., pull in the proximal direction) from the curved portion of IPS 102. The distally anchored drug delivery device 200 emerges from the distal end opening 3341 of the delivery catheter 3304 as the catheter is withdrawn through the IPS 102 into the junction 118; the distal anchoring mechanism of the drug delivery device disposed within the CP angle cistern 138 retains, secures and/or anchors the drug delivery device in its deployed location within the subarachnoid space 116 as the delivery catheter 3304 is withdrawn from the IPS 102. Thereafter, the delivery catheter 3304 can be further withdrawn through the junction 118 to allow the proximal anchoring mechanism 227 of drug delivery device 200 to be deployed in the jugular vein 106, as shown in FIG. 7E.

After the drug delivery device 200 has been fully deployed and/or secured at the target site by the drug delivery device 200 respective anchoring mechanisms 227, 229, the clinician can advance the delivery catheter 3304 and/or a micro catheter (e.g., catheter having an inner diameter of 0.027" or 0.021") over the elongate guide member 780 to re-sheath the anchor 700, and then withdraw the catheter 3304 containing anchor 700 and elongate guide member 780 from the patient (e.g., via a femoral access point). Alternatively, the elongate guide member 780 can include an electrolytic detachment element 785 in or around the joint 744 with anchor 700 (FIG. 3C, 3H) or at any other suitable portion of the elongate guide member 780 (e.g., FIG. 7F), so as to detach the elongate guide member 780 from the anchor 700. After detachment of the elongate guide member 780 from the anchor 700, the elongate guide member 780 can be withdrawn from the patient while anchor 700 remains deployed in the IPS 102 or CS 104. This configuration can be advantageous to avoid accidental pullout of an implanted drug delivery device from CP angle cistern 138 while retrieving the anchor 700 from its distal deployment location by snagging the anchor 700 on a portion of the deployed drug delivery device, as the anchor 700 is withdrawn through the IPS 102 and the junction 118.

Figure 7E:
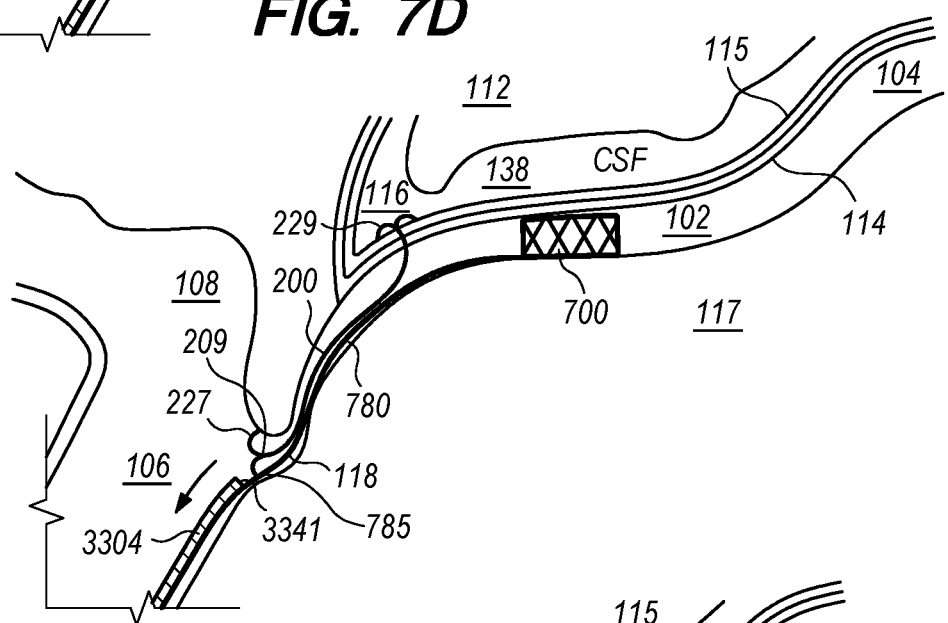
Figure 7F:
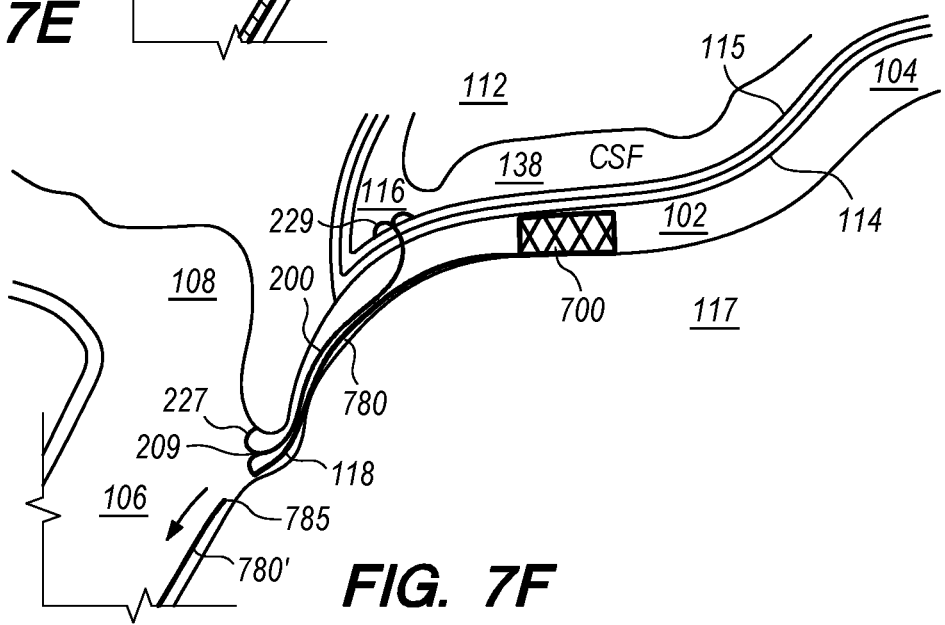

In further alternative embodiments, the electrolytic detachment element 785 can be proximately disposed from the joint 744 (e.g., at the elongate guide member 780 portion configured to be disposed around the junction 118), as shown in FIGS. 7E and 7F. The anchor 700 and a portion of the elongate guide member 780 can be part of the implanted drug delivery system where a deployed drug delivery device includes one or more connection points or interfaces with the elongate guide member 780, or is otherwise secured in a venous sinus lumen by anchor 700, allowing the deployed anchor 700 and/or portion of the elongate guide member 780 to further anchor the drug delivery device at its deployed location. In such embodiments, the elongate guide member 780 can include the electrolytic detachment element 785 at a portion of the elongate guide member 780 configured to be disposed around the junction 118 or about the connection point or joint between elongate guide member 780 and anchor 700. So that, for example, a proximal portion 780' (i.e., proximately to the electrolytic detachment element 785) of the elongate guide member 780 is withdrawn from the patient after deployment of the drug delivery device, while the distal portion of the elongate guide member 780 remains coupled to the anchor 700. In this embodiment, the anchor 700 may further provide a scaffold support for the deployed drug delivery device 200, as shown in FIG. 7F. Alternatively, if the electrolytic detachment element is configured at the connection point or joint between the elongate guide member 780 and anchor 700, the elongate guide member 780 is withdrawn from the patient after deployment of the drug delivery device 200, while the anchor 700 secures the device at a target implant location in the sinus wall.

The anchor 700 and the elongate guide member 780 system advantageously facilitate endovascular deployment of drug delivery device and/or administration of therapeutic agents to the intracranial SAS based on one or more features of the disclosed embodiments:

Separate anchor 700 and drug delivery device 200 deployment steps preserve critical working and deployment space in the IPS 102 and/or CS 104 around the target penetration site to accommodate delivery system components such as delivery catheter 3304 and drug delivery device 200 compared to a delivery system configured for a single anchor and drug delivery device 200 deployment step comprising multiple, concentric elements (e.g., a delivery catheter, delivery system anchor and/or guide wire, a drug delivery device, and a penetrating element).

The anchor 700 and the elongate guide member 780 system provides a stable platform to secure delivery system components during (a) penetration through the dura mater IPS wall 114 and arachnoid layer 115 into CP angle cistern 138, and (b) deployment of the drug delivery device distal anchoring mechanism 229 in the cistern compared to a conventional delivery catheter and guide wire system.

The anchor 700 and the elongate guide member 780 system resists "kickout" of delivery system components (e.g., delivery catheter 3304) from the IPS 102 and/or CS 104 into the jugular vein 106 resulting from tortuous anatomy during critical procedure steps such as penetrating dura mater IPS wall 114 and arachnoid layer 115 and deploying the drug delivery device and its distal anchoring mechanism 229.

In some embodiments of anchor 700, for example when the anchor is left behind in the sinus lumen (IPS 102 or CS 104) to secure that the implanted drug delivery device 200, the anchor can be configured for hydraulic expansion using stainless steel or cobalt chromium materials, thereby simplifying system design and reducing product manufacturing costs.

The elongate guide member 780 extending proximally from a deployed anchor 700 along the IPS wall 117 eliminates or decreases the risk that an uncovered or unprotected penetrating element inadvertently snags a portion of the IPS wall 114 as the penetrating element is delivery to the target penetration site.

FIGS. 12A-F illustrate an alternative delivery catheter 1304 for delivering a therapeutic agent to the intracranial SAS and/or deploying a drug delivery device into a target site of a patient, constructed in accordance with embodiments of the disclosed inventions. For ease in illustration, the features, functions, and configurations of the delivery catheter 1304 that are the same as in the delivery catheters 304 and 3304 of the present disclosure and the delivery catheters 304, 304' in the related application previously incorporated by reference herewith, are given the same reference numerals. The delivery catheter 1304 comprises an elongated configuration having a proximal portion 1342, a distal portion 1344 and a lumen 1341 extending therebetween. The delivery catheter 1304 is dimensioned to reach remote locations of the vasculature and is configured to deliver a therapeutic agent or drug delivery device percutaneously to the target site (e.g., IPS, CS, CP angle cistern, or the like). The delivery catheter 1304 comprises variable stiffness sections (e.g., varying ratio of material, including selective reinforcement, varying the properties or distribution of the materials used and/or varying the durometer or thickness of the materials during the process of manufacturing) suitable to provide sufficient "pushability" (e.g., exhibits sufficient column strength to enable delivery to target locations such as IPS 102 or CS 104; in embodiments of reinforcing member 1345 further comprising a tissue penetrating element 1350 as shown in FIG. 12A and FIG. 12D, provides sufficient column strength to transmit about 0.1 N to 2.0 N force or more for the penetrating or piercing element to penetrate dura of IPS wall 114 and arachnoid layer 115) and "torqueability" (e.g., in the vasculature exhibits a torque response of about 1:1 such that a single clockwise turn of the catheter at the patient's groin or proximal portion results in approximately single clockwise turn of the distal portion of the catheter at a target location such as IPS 102 or CS 104) to allow the catheter 1304 to be inserted, advanced and/or rotated in the vasculature to position the distal portion 1344 of the catheter at the target site within the IPS 102 or CS 104. Further, the distal portion 1344 has sufficient flexibility so that it can track and maneuver into the target site, particularly in tortuous anatomy.

Known components, such as embedded coils or braids, are often used to provide selective reinforcement to delivery catheters. Delivery catheters including embedded coils can provide suitable flexibility, however, the embedded coils usually fail to provide the necessary column strength for the catheter, particularly at the distal portion of micro-catheters. Delivery catheters including embedded braids can provide with suitable column strength, while sacrificing flexibility, particularly if the embedded braids are disposed at the distal portion of the catheter.

In the embodiments of FIGS. 12A-E, the delivery catheter 1304 comprises an reinforcing member 1345 configured to reinforce the catheter 1304 while providing a suitable balance between column strength and flexibility (e.g., "pushability" and "torqueability"). The reinforcing member 1345 is composed of suitable biocompatible and elastomeric materials such as, stainless steel, Nitinol® or the like. In some embodiments, the reinforcing member 1345 comprises a stainless steel or Nitinol hypotube providing suitable column strength, the hypotube further comprises selective cuts 1330, which provides suitable flexibility.

The reinforcing member 1345 may extend along a substantial length of the catheter 1304 (e.g., the reinforcing member 1345 extends from the proximal portion 1342 to the distal portion 1344 of the catheter 1304). In the embodiment of FIG. 12A, length $L_{10}$, measured along a central axis 1349 of the reinforcing member 1345 is approximately 59" (150 cm). Alternatively, the reinforcing member 1345 can extend along a section of the catheter 1304 (e.g., the reinforcing member 1345 extends along the distal portion 1344 without extending to the proximal portion 1342 of the catheter 1304). For example, $L_{10}$ can range between 1.9" (5 cm) to 6" (15.2 cm), or any other suitable length.

Further, in the embodiment of FIGS. 12A-C, the inner diameter (ID) of the reinforcing member 1345 (e.g., lumen 1341) measured in a direction orthogonal to axis 1349 can range between 0.0205" (0.5207 mm) to 0.024" (0.6096 mm), and the outer diameter (OD) of the reinforcing member 1345 measured in the same direction (i.e., orthogonal to axis 1349) can range between 0.026" (0.6604 mm) to 0.03" (0.762 mm). It should be appreciated that the ID, OD and/or the $L_{10}$ and any other length, width, or thickness of the reinforcing member 1345 of the delivery catheter 1304 may have any suitable dimension for delivering a therapeutic agent to the intracranial SAS and/or deploying a drug delivery device in the target site (e.g., IPS, CP angle cistern, or the like). Exemplary dimensions (in inches) and properties of the reinforcing member 1345 are shown in FIG. 12G, which are not intended to limit the embodiment of FIGS. 12A-C.

In the embodiments of FIGS. 12A and 12C, the reinforcing member 1345 comprises one or more cuts 1330 (e.g., kerfs, slots, key-ways, recesses, or the like) selectively disposed at the proximal portion 1342 and the distal portion 1344 of the reinforcing member 1345. Additionally, the one or more cuts 1330 can be disposed in sections of the reinforcing member 1345 along $L_{10}$, as shown by the exemplary spiral cut pattern of kerf, pitch, cuts per rotation and cut balance depicted in sections of FIG. 12A. Alternatively, the cuts 1330 can be continuously disposed substantially along $L_{10}$ (not shown), and the continuously disposed cuts 1330 can have variable spiral cut patterns of kerf, pitch, cuts per rotation and cut balance along $L_{10}$ or combinations thereof.

The cuts 1330 of the reinforcing member 1345 can have a variety of suitable patterns, and can be manufactured by laser cutting the reinforcing member 1345 of the delivery catheter 1304. Alternatively, the cuts 1330 and their patterns can be manufactured by etching or other suitable techniques. FIGS. 12E-F depict an exemplary cut pattern of the reinforcing member 1345 of FIGS. 12A-C. In these embodiments, the laser cutting of the reinforcing member 1345 creates between 1.5 to 2.5 cuts 1330 per rotation of the reinforcing member 1345, having a cut balance of between 100° to 202° of rotation with laser on, and then 34° to 38° of rotation with laser off.

As shown in FIG. 12A, the cuts 1330 of the reinforcing member 1345 that are disposed at the proximal portion 1342 comprise a larger pitch (e.g., 0.015) than the pitch (e.g., 0.006) of the cuts 1330 disposed at the distal portion 1344 of the reinforcing member 1345. The smaller the pitch of the cuts 1330 (i.e., smaller separation between cuts) provides for an increase in flexibility of the reinforcing member 1345, such as at the distal portion 1344 of the delivery catheter 1304. The transition between the larger pitch to the smaller pitch cuts 1330 can be subtle, providing for a progressively more flexible delivery catheter towards the distal portion. By way of non-limiting examples, the spiral cut pattern to create the cuts 1330 disposed at the proximal portion 1342 of the reinforcing member 1345 comprise a kerf of 0.001, a pitch of 0.015, creating 2.5 cuts per rotation, having a cut balance of 100° of rotation with laser on, and then 34° rotation with laser off. The spiral cut pattern applied to create the cuts 1330 disposed between the proximal portion 1342 and the distal portion 1344 of the reinforcing member 1345 comprises a kerf of 0.001, a pitch transition from 0.006 to 0.015, creating 1.5 cuts per rotation, having a cut balance of 202° of rotation with laser on, and then 38° rotation with laser off. The spiral cut pattern applied to create the cuts 1330 disposed at the distal portion 1344 of the reinforcing member 1345 comprises a kerf of 0.001, a pitch of 0.004, creating 1.5 cuts per rotation, having a cut balance of 202° of rotation with laser on, and then 38° rotation with laser off. The cuts 1330 may have a width that ranges between 0.0005" (0.0127 mm) to 0.002" (0.0508 mm), or any other suitable width. It should be appreciated that the width, length and depth of the cuts 1330 and patterns of the cuts 1330 in the reinforcing member 1345 of the delivery catheter 1304, can comprise any suitable dimensions. By way of non-limiting example, the pattern of cuts 1330 can transition to a larger pitch (e.g., greater than 0.004) in the distal portion 1344 of reinforcing member 1345 to increase column strength and provide support to a delivery catheter during the penetration step of the therapeutic agent administration and/or deployment of a drug delivery device.

Additionally, the reinforcing member 1345 comprises an inner liner 1360 and an outer jacket 1365, as better seen in FIG. 12C. The inner liner 1360 and outer jacket 1365 are composed of suitable implantable polymeric materials, such as polytetrafluoroethylene "PTFE", polyethyleneterephthalate "PET", High Density Polyethylene "HDPE", expanded polytetrafluoroethylene "ePTFE", urethane, silicone, or the like. The inner liner 1360 and outer jacket 1365 are configured to cover—completely or partially—the cuts 1330 of the reinforcing member 1345, from within lumen 1341 and over the elongated coated member outer surface 1370, respectively. In such configuration, the reinforcing member 1345 becomes an impermeable tubular element having the cuts 1330 covered by the respective inner liner 1360 and outer jacket 1365, while maintaining the flexibility provided by the selective cuts 1330 and column strength afforded, in part, by the reinforcing member 1345.

The inner liner 1360 provides a smooth inner surface in the lumen 1341 of the reinforcing member 1345 that facilities translation and delivery of the drug delivery device (and/or a therapeutic agent, other delivery systems or devices delivered through the lumen). Further, the inner liner 1360 can be configured to line the interior reinforcing member 1345 using an extrusion process. Alternatively, the liner material can be deposited (e.g., using a dispersion technique) on a mandrel (e.g., nickel coated copper); thereafter, the liner-coated mandrel can be placed within the reinforcing member 1345 for application of outer jacket 1365 and adhering the inner liner 1360 to the reinforcing member 1345, after which the mandrel can be withdrawn from the reinforcing member 1345 leaving inner liner 1360 in place within the lumen 1341 of the reinforcing member 1345.

The outer jacket 1365 provides a smooth outer surface to the reinforcing member 1345, which facilitates the navigation of the delivery catheter 1304 through tortuous vasculature. As noted above, the outer jacket 1365 can comprise one or more implant-grade polymers including, but not limited to, polyurethane or silicone-polyurethane blends. In some embodiments, a gas or liquid dispersion of polymer is applied to the reinforcing member 1345 and inner liner 1360, which forms the outer jacket 1365 and bonds the inner liner 1360, the reinforcing member 1345, and outer jacket 1365 together in an integrated configuration of the delivery catheter 1304.

The outer jacket 214 can substantially cover the entire outer surface of the reinforcing member 1345; however, in some embodiments, the outer jacket can be placed selectively along sections of reinforcing member 1345 to adhere the inner liner 1360 to the reinforcing member 1345. By way of non-limiting example, a liquid dispersion of polymer or an epoxy-based adhesive can be placed at discrete locations along $L_{10}$. Alternatively, the outer surface of inner liner 1360 can be coated with polymer or adhesive, and then placed within reinforcing member 1345; the polymer or adhesive can seep into the cuts 1330, completely or partially filling some or all of the cuts 1330 along $L_{10}$.

In the embodiment of FIG. 12C, the inner liner 1360 can have a thickness of 0.0005" (0.0127 mm); though the thickness of inner liner 1360 can range from 0.0005" (0.0127 mm) to 0.0015" (0.0381 mm) in other embodiments. In the embodiment of FIG. 12C, the outer jacket 1365 can have a thickness of 0.001" (0.0254 mm); though the thickness of outer jacket 1365 can range from 0.0001" (0.00254 mm) to 0.001" (0.0254 mm) in other embodiments. It should be appreciated that the inner liner 1360, and the outer jacket 1365 of the reinforcing member 1345 may comprise any suitable dimensions.

Embodiments of delivery catheter 1304 can have a middle portion 1343 that is relatively stiffer than the proximal portion 1342 and distal portion 1344 of the catheter. For example, reinforcing member 1345 can have a middle segment with cuts 1330' comprising a relatively larger pitch than the pitch of cuts 1330 proximal and distal to the middle segment, but otherwise comprising cuts 1330 on reinforcing member 1345 providing a progressively more flexible delivery catheter 1304 from the proximal portion 1342 towards the distal portion 1344. The relatively stiffer middle portion 1343 of delivery catheter 1304 can also be accomplished using a relatively thicker and/or higher durometer outer jacket 1365 at middle portion 1343 compared to the proximal portion 1342 and the distal portion 1344 of delivery catheter 1304. Embodiments of delivery catheter 1304 with a relatively stiffer middle portion 1343 can advantageously maintain overall delivery catheter trackability, torqueability and pushability when advanced through the junction of the subclavian vein into the jugular vein (e.g., middle portion 1343 can span the sharply curved junction between the subclavian vein and jugular vein to enable catheter tracking distally into the venous sinuses while maintaining sufficient pushability and torquability to complete a drug delivery procedure).

Referring back to FIG. 12A, the reinforcing member 1345 further comprises a penetrating element 1350 (e.g., sharp, tapered, cannula-like end, bevel, pencil, or Quincke tip needle, or the like) extending or disposed at the distal portion 1344 of the elongated member, as also depicted in FIG. 12D. The penetrating element 1350 is configured to penetrate the dura mater of the IPS wall 114 and the arachnoid layer 115 creating an anastomosis between the IPS 102 and the CSF-filled CP angle cistern 138 for administration of a therapeutic agent and/or deployment of a drug delivery device, as previously disclosed herein, and in the related application previously incorporated by reference herewith. The cuts 1330 proximately disposed to the penetrating element 1350 are configured to provide suitable flexibility to the distal portion 1344 of the delivery catheter 1304, allowing the distal portion 1344 to bend, curve and/or orient the penetrating element 1350 towards the IPS wall 114, while maintaining suitable column strength to support the penetrating element 1350 at the distal portion 1344 as it penetrates through the IPS wall 114 and arachnoid layer 115. The penetrating element 1350 extending from, integrated with and/or incorporated to the distal portion 1344 of the reinforcing member 1345 allows for a secure withdrawal of the penetrating element 1350 when the delivery catheter 1304 is withdrawn from the patient.

Figure 13:
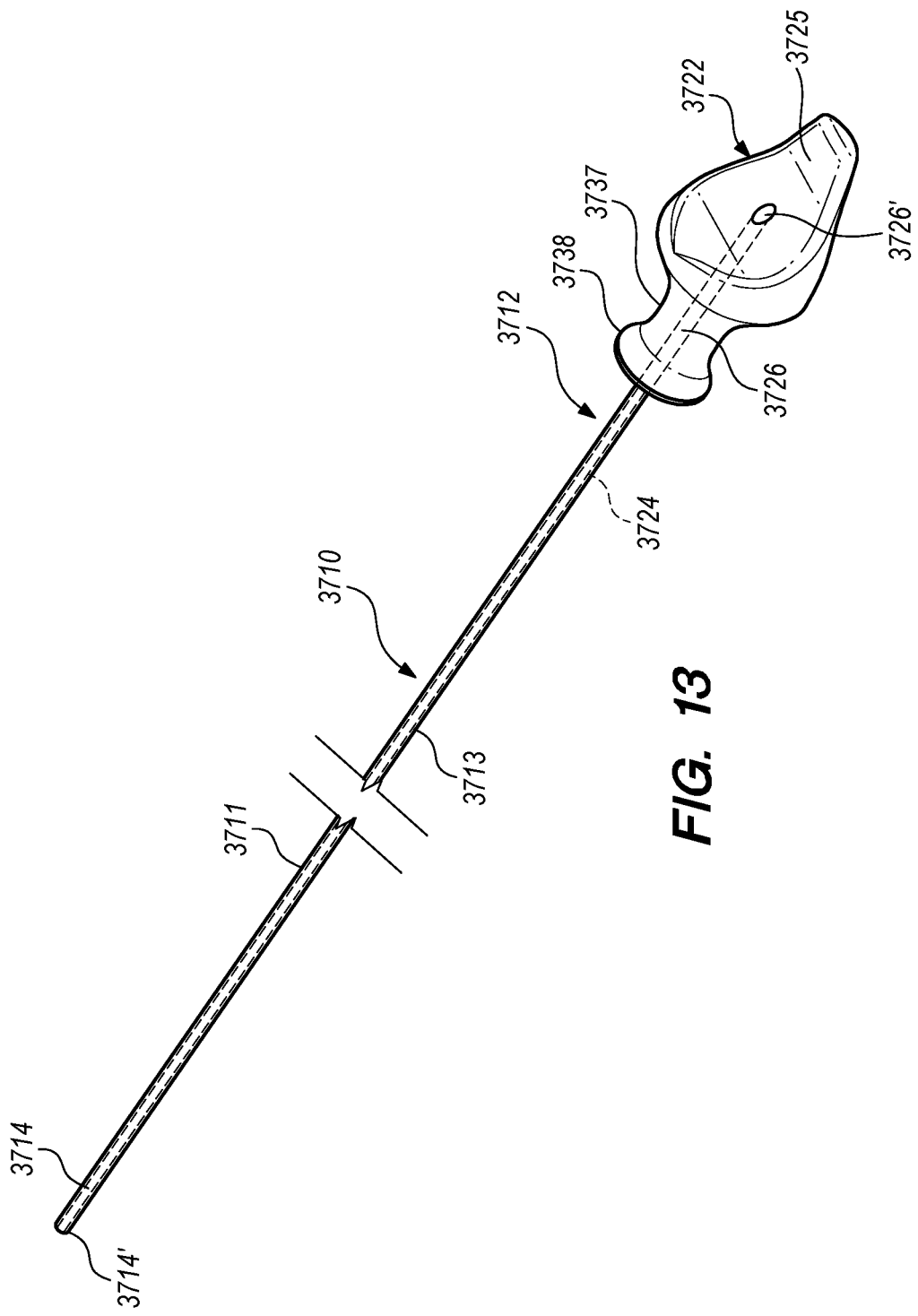
FIG. 13 is a perspective view of an elongated pusher constructed according to embodiments of the disclosed inventions.

FIG. 13 illustrates an elongated pusher 3710, constructed in accordance with embodiments of the disclosed inventions. The elongated pusher 3710 comprises a support tubular member 3711, having a proximal portion 3712, a middle portion 3713 and a distal portion 3714, and a lumen 3724 extending therebetween. The proximal portion 3712 of the support tubular member 3711 is coupled to a handle 3722, which will be described in further detail below. The pusher 3710 provides telescoping support to a guidewire or other interventional devices as a clinician translates such guidewire or device through a catheter to a target site.

The elongated pusher 3710 is configured to translate (e.g., advance, push) interventional access/treatment devices (e.g., stent anchor 700, guide member 780, guidewires, thrombectomy devices, or the like) into the IPS 102 or any other target site, through a catheter (e.g., delivery catheter 304/3304, or the like) disposed in a patient's vasculature. The pusher 3710 is further configured to receive the elongated guide member 780, and the handle 3722 is configured to assist the clinician hold a portion of the guidewire or interventional devices extending proximally through the handle lumen 3724 thereby advancing the guidewire and/or interventional devices through a catheter.

The length of the support tubular member 3711 can range from about 1" (2.54 cm) to about 60" (152.4 cm) or larger. The support tubular member 3711 comprises an inner wall defining the lumen 3724, the inner wall can include an annular, circular or any other suitable shape or dimension suitable for advancing guidewires and/or interventional devices therebetween. The inner diameter of the support tubular member 3711 can range from about 0.010" (0.254 mm) to about 0.024" (0.6096 mm). In some embodiments, the inner diameter of the of the support tubular member 3711 is larger than 0.024" (0.6096 mm), such that the pusher 3710 is configured to receive and translate larger guidewires and/or other interventional devices (e.g., 2-24Fr). The outer diameter of the support tubular member 3711 is configured to be received into the proximal hub 3377 of a catheter or hemostasis valve through which guidewires and/or other interventional devices will be advanced into the patient's target site. The support tubular member 3711 can have a thin-walled configuration, comprising a wall thickness that ranges from about 0.001" (0.0254 mm) to about 0.005" (0.127 mm), which allows the support tubular member 3711 to fit within the catheter hub while maintaining maximum clearance within the tubular member lumen 3724 for receiving guidewires and/or interventional devices. By way of non-limiting example, an embodiment of the pusher 3710 configured for translating embodiments of anchor 700 and guide member 780 through an 0.027" micro catheter into a distal portion of the IPS can have a support tubular member 3711 that is 6" to 8" (15.25 to 20.32 cm) long, with an outer diameter of 0.025" (0.635 mm) and inner diameter of 0.020" (0.508 mm). Alternative embodiments can be configured for translating larger or smaller interventional devices through larger or smaller catheters; for example, embodiments of the pusher can be configured for translating neuro-interventional devices such as 0.010", 0.014", or 0.018" guidewires through 0.014", 0.018", or 0.021" micro catheters.

The support tubular member 3711 of the elongated pusher 3710 can be composed of metal (e.g., stainless steel, titanium, Nitinol) or plastic (e.g., polyamide, polyimide, PTFE, PEEK, polyester), or combinations thereof. The support tubular member 3711 can have a multi-layered construction, for example, stainless steel exterior with an HDPE inner layer. In embodiments of the support tubular member 3711 composed by metal, the tubular member 3711 can include progressive spiral cut or articulated construction, where cut pattern or articulations are configured to create stiffness that transitions along the length of the support tubular member 3711 (e.g., stiffness transitions over its length and becomes stiffer nearer to the handle 3722. In such embodiments, the distal portion 3714 of the support tubular member 3711 is more flexible than the proximal portion 3712 (e.g., stiffer near the handle 3722). Further, the inner wall of the support tubular member 3711 can include a PTFE liner or a lubricious coating such as PTFE, parylene, or other suitable hydrophilic coatings, configured to reduce friction or facilitate smooth translation of the guidewires and/or interventional devices through the tubular member lumen 3724.

Referring back to the handle 3722 coupled to the proximal portion 3712 of the support tubular member 3711, the handle 3722 comprises an outer surface 3725, and a lumen 3726 in fluid communication with the lumen 3724 of the support tubular member 3711 of the pusher 3710. The handle lumen 3726 is configured for receiving a proximal end 3712' of the proximal portion 3712 of the support tubular member 3711. The handle 3722 can be coupled to the proximal end 3712' of the tubular member 3711 by an adhesive (e.g., an ultraviolet light-cured adhesive, cyanoacrylate, or epoxy), using a press-fit connection, or any other suitable techniques. In alternate embodiments, the proximal end 3712' of the tubular member 3711 can be radially flared (e.g., outwardly flared, flared out, funnel-like configuration, or the like) with the handle 3722 molded around the flared proximal end 3712' of the tubular member 3711. The handle 3722 can be composed of polyethylene, HDPE, PTFE, PEEK, ABS, polycarbonate, ABS-polycarbonate, thermoplastic polyamide, or polyoxymethylene, or the like. In alternative embodiments of the pusher 3710, the handle can comprise PEEK, polyvinylidene difluoride, or other thermoplastic polymers or materials suitable for autoclaving treatments that can be used with a metal tubular member 3711.

The handle 3722 further comprises a lumen opening 3726' configured for receiving the guidewire and/or interventional devices for advancement into a target site in a patient through the support tubular member lumen 3724. In some embodiments, the handle 3722 can range in diameter (at its widest portion) from about 0.75" to 1.5" (0.75 mm to 38.1 mm) or more, and have a length of about 0.5" to 1.5" (12.7 mm to 38.1 mm) or more. The handle lumen 3726 defines an annular, circular or any other shaped space suitable for advancing the guidewire and/or interventional devices therebetween. The handle 3722 can comprise an ergonomic configuration, as shown in FIG. 13. The ergonomic configuration of the handle 3722 is suitable for providing a resting portion (i.e., surface 3725) for the clinician's fingers, typically sized for the clinician's thumb or finger, while using the pusher 3710. The resting surface 3725 is configured to be contoured for resting a human thumb or finger, such that the clinician can use the surface 3725 to hold, pinch, press or maintain a portion of the guidewire and/or the interventional devices extending out from the handle 3722 while using the pusher 3710, with one hand only. By pinching the guidewire and/or interventional device against the resting surface 3725 of the handle 3722, the clinician can advance the pusher 3710, the guidewire or the interventional devices into the catheter. Then, the clinician can release the pinch and withdraw the pusher 3710 over the guidewire. The clinician may perform a sequence of pinching the guidewire, advancing the pusher and pinched guidewire, releasing the pinch and withdrawing the pusher over the guidewire (as shown in FIGS. 14C-E), which sequence can be repeated until the guidewire and/or the interventional devices translates through the catheter and reach their target site. The handle 3722 may include other contour shapes or configurations (e.g., scallop, ramp, slopes or the like) that allow the clinician to hold, pinch, press or maintain the guidewire and/or the interventional devices against the surface 3725 of the handle 3722. The surface 3725 can include a traction pad (e.g., a thin strip of silicone, swallow ribs or the like) configured to increase the friction coefficient between the handle and the clinician, to assist with the holding of the guidewire and/or the interventional devices against the handle 3722. The traction pad may comprise a single silicone pad disposed on the surface 3725 of the handle 3722 or a silicone tab that folds over and sandwiches the guidewire and/or interventional devices pinched against the surface 3725 of the handle 3722.

The handle 3722 can further comprise features that facilitate use of the pusher 3710. In the embodiment of FIG. 13, the handle 3722 comprises a neck 3737 (e.g., annular indentation, or the like) configured to be held or gripped by the clinician's fingers during use of the pusher 3710, as shown in FIGS. 14C-D. The handle 3722 further comprises a flange 3738 (e.g., annular outward rim, protruding collar, or the like) distally disposed from the neck 3737 of handle 3722. The neck 3737, either alone or in combination with the flange 3738, is configured to assist the clinician's hold of the pusher 3710 and to control the push and pull motions of the pusher 3710 relative to the guidewire, interventional devices and/or catheter, while maintaining the position of the pusher 3710 at a desired location. Additionally, the handle 3722 can include a scalloped or tapered lead in to lumen opening 3726' for additional support for guidewire and/or interventional devices used with the pusher 3710. In alternative embodiments, a portion of the handle 3722 can include a guidewire torque features (e.g., rotating collet to lock wire or device in place).

During advancement of the guidewire and/or interventional devices into a target site of a patient using the elongated pusher 3710 of FIG. 13, the clinician introduces the guidewire and/or interventional devices through the lumen opening 3726' of the handle 3722. Then, the clinician distally translates the guidewire and/or interventional devices into the pusher 3710 (i.e., handle lumen 3726 and tubular member lumen 3724) while maintaining the proximal portion of the guidewire or interventional devices extending out of the handle 3722.

FIGS. 14A-F illustrate a method of use an elongated pusher according with embodiments of the disclosed inventions. By way of non-limiting example, FIGS. 14A-E illustrate the pusher 3710 of FIG. 13 to translate a guide member 780 through a catheter 3307 (e.g., micro catheter, introducer sheath or the like). In these embodiments, the catheter 3307 has been advanced into the vasculature (e.g., the IPS) from a femoral vein access point in the patient. It should be appreciated that the elongated pusher 3710 constructed according to embodiments of the disclosed inventions may be used in other interventional procedures including, but not limited to, stent retriever delivery, distal protection device delivery, foreign body retrieval, delivery loops and snares, pacemaker implantation, and any other suitable medical procedure.

Figure 14A:
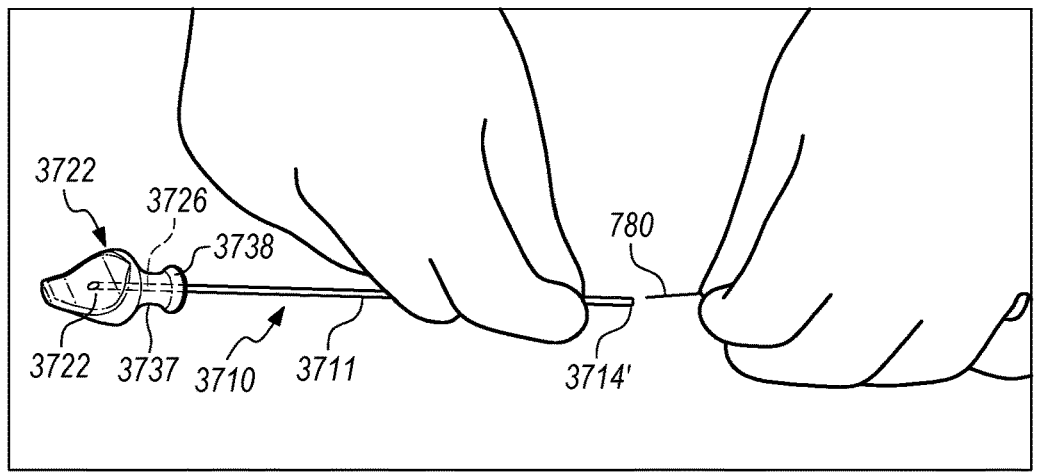
FIGS. 14A-F are perspective views of exemplary methods for the elongated pusher of FIG. 13 use, according to embodiments of the disclosed inventions.
Figure 14B:
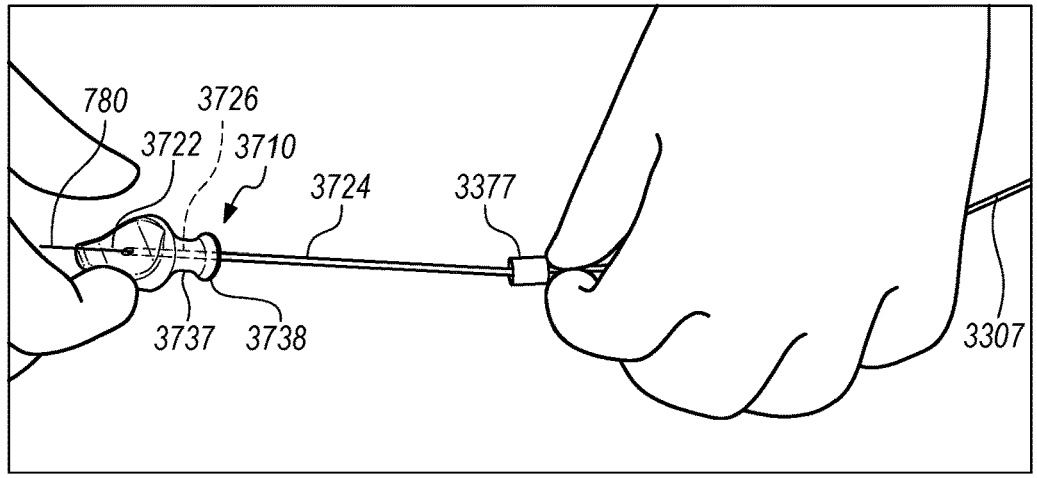
Figure 14C:
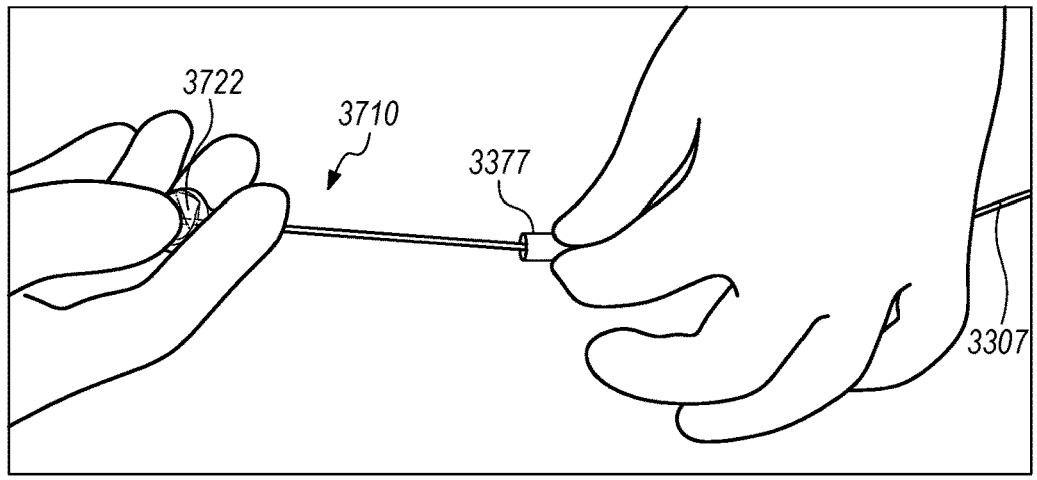
Figure 14D:
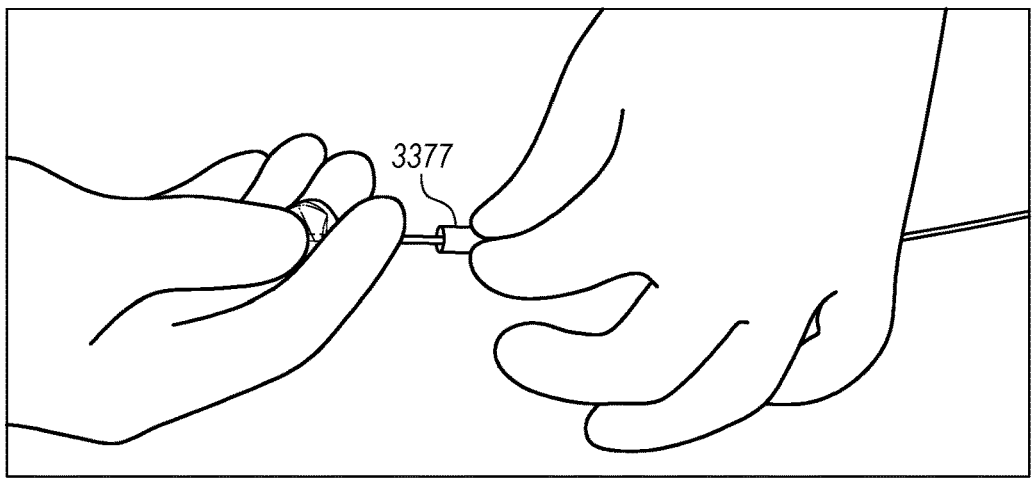
Figure 14E:
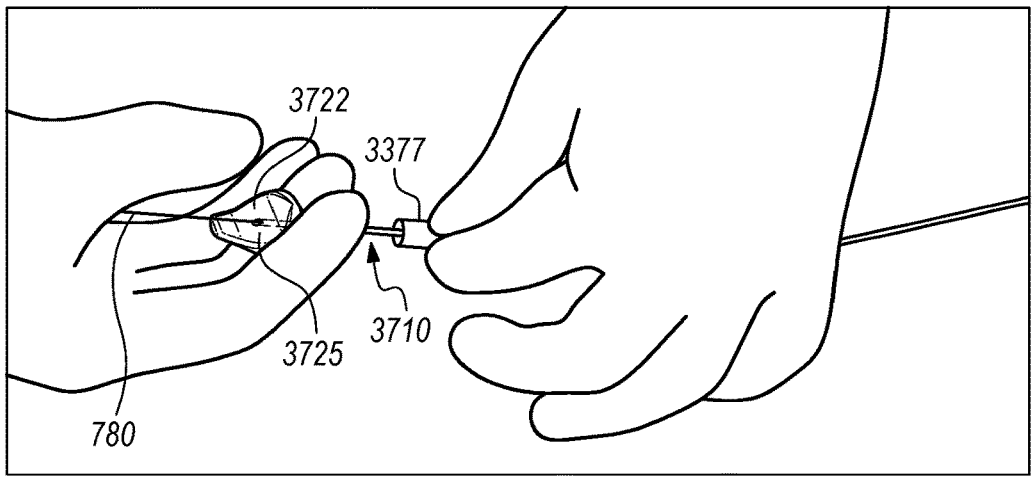
Figure 14F:
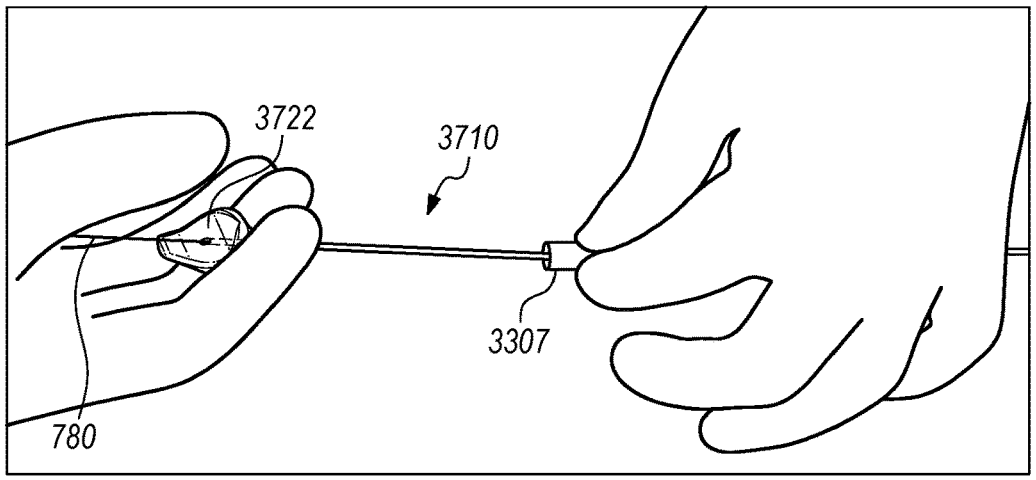

FIG. 14A depicts the guide member 780 being advanced into the distal opening 3714' of the support tubular member 3711. It should be appreciated that anchor 700 coupled to the guide member 780 has already been inserted and translated through the catheter hub 3377 into the proximal portion of the catheter 3307 (not shown). Alternatively, the pusher 3710 and guide member 780 can be introduced simultaneously into the catheter hub 3377. As shown, the clinician feeds the guide member 780 through pusher 3710, via the distal opening 3714' of the support tubular member 3711, through tubular member lumen 3724 and handle lumen 3726, such that the guide member 780 emerges from the opening 3726' of the handle 3722. Alternatively, the clinician may feed the guide member 780 through pusher 3710, via the opening 3726' of the handle 3722, through the handle lumen 3726, into the tubular member lumen 3724. Then, the clinician advances the pusher 3710 over guide member 780 until distal portion 3714 of support tubular member 3710 accesses the catheter hub 3377 of catheter 3307 (FIG. 14B).

In instances in which the body lumen is a blood vessel, the elongate guide member 780 is normally advanced into the blood vessel through an introducer sheath 3307 having a proximal opening outside of the patient and a distal opening (not shown) within the blood vessel, in which case advancing the pusher tool 3710 may include advancing the distal portion 3714 of the tubular body 3711 into the proximal opening of the introducer sheath 3307. The proximal opening of the introducer sheath is normally accessed via the proximal introducer hub 3377, in which case the method may further include grasping to thereby stabilize the introducer hub 3377 while advancing the distal portion 3714 of the tubular body 3711 through the hub 3377.

The clinician then holds, pinches, or presses the guide member 780 against the handle 3722, as described above, and further advances the pusher 3710 and guide member 780 into catheter hub 3377 of catheter 3307. (FIGS. 14C-14D). By pinching the guide member 780 against the resting surface 3725 of the handle 3722, the clinician can advance the pusher 3710 and guide member into the catheter 3307. Then, the clinician can release the pinch and withdraw the pusher 3710 over the guide member 780, preferably while maintaining the distal portion 3714 of the support tubular member 3711 within the catheter hub 3377. The clinician may perform a sequence of pinching the guide member 780, advancing the pusher 3710, releasing the pinch and withdrawing the pusher 3710 over the guide member 780 (as shown in FIGS. 14C-F), which sequence can be repeated until the guide member 780 translates through the catheter 3307, with the support tubular member 3711 telescoping into the catheter hub 3377 and guide member 780 reaching the target site. The clinician releases the pinch of the guide member 780 against the handle 3722 and withdraws the pusher 3710 over the guide member 780 after the guide member reaches the target site.

It should be appreciated that the disclosed embodiments have exemplary dimensions, angles and properties of the drug delivery device 2200, which are not intended to limit the embodiment of FIG. 17D As previously disclosed, embodiments of the disclosed drug delivery devices can include an anti-thrombotic coating on all or a portion of the exterior of the device, to minimize clotting in the IPS and/or other dural venous sinus and venous location(s) after drug delivery device deployment. Such anti-thrombotic coatings may comprise phosphorylcholine (e.g., Lipidure® products available from NOF Corporation) or Heparin-based compositions (e.g., CBAS® Heparin Surface available from Carmdea AB, Astute® from BioInteractions, Ltd.). Anti-thrombotic coatings can also be applied to anchor 700 and/or elongate guide member 780 to further minimize the risk of clotting in the IPS during the drug delivery device implant procedure.

FIG. 16 illustrates a delivery catheter 3300, constructed according to embodiments of the invention. The delivery catheter 3300 (or distal most portion of the delivery catheter) can include an oversheath member 3300" (e.g., a larger, concentric sheath that covers the outer diameter of the delivery catheter and/or the penetrating element). The oversheath 3300" can translate longitudinally about the delivery catheter, and can be retracted proximally to expose the needle tip 3350" for the penetration step of the drug delivery procedure. The oversheath 3300" of FIG. 16 is disposed over a delivery catheter 3304 and penetrating element 3350 advanced over a guide member 3308"; the bands 3303" located proximal of the penetrating element comprise radiopaque markings to confirm orientation of the penetrating element and assess penetration trajectory during a drug delivery procedure. The oversheath member covers the penetrating element as the delivery system navigates through the patient's vasculature, thereby preventing inadvertent vessel punctures. The operator can position the distal portion of the oversheath adjacent or abutting the target penetration site along a dural venous sinus wall (e.g., IPS wall 114) until the operator is ready to expose the penetrating element or advance the penetrating element through the tissue into the CP angle cistern 138.

Figure 18D:
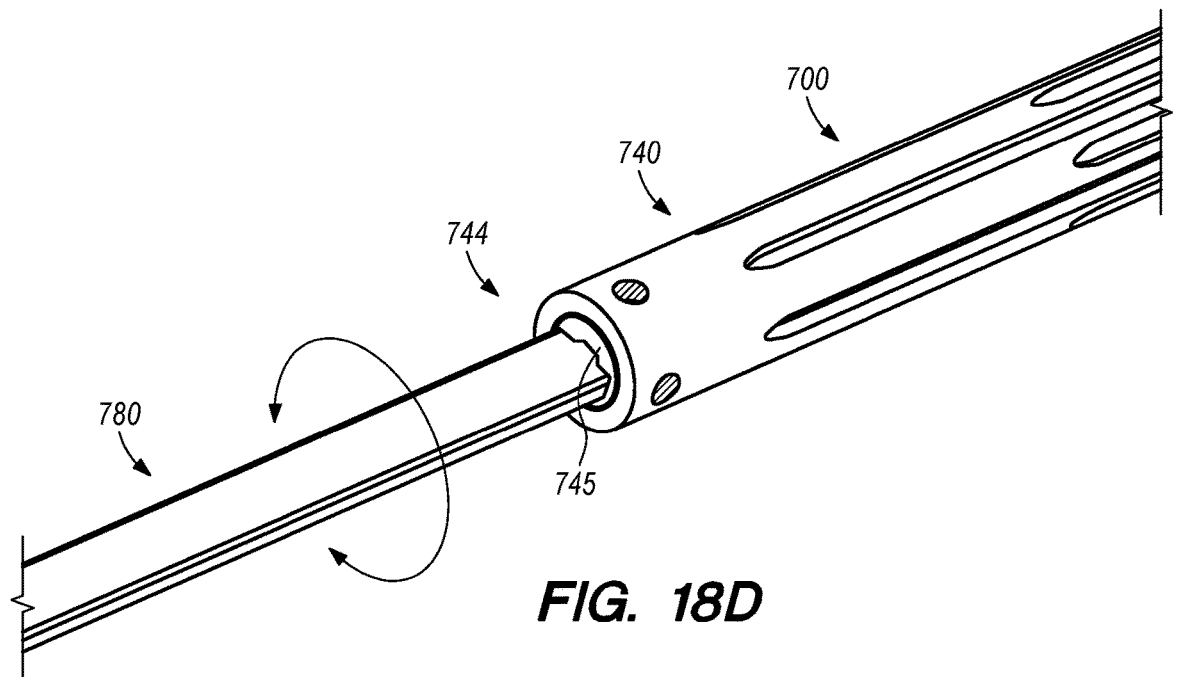
Figure 18E:
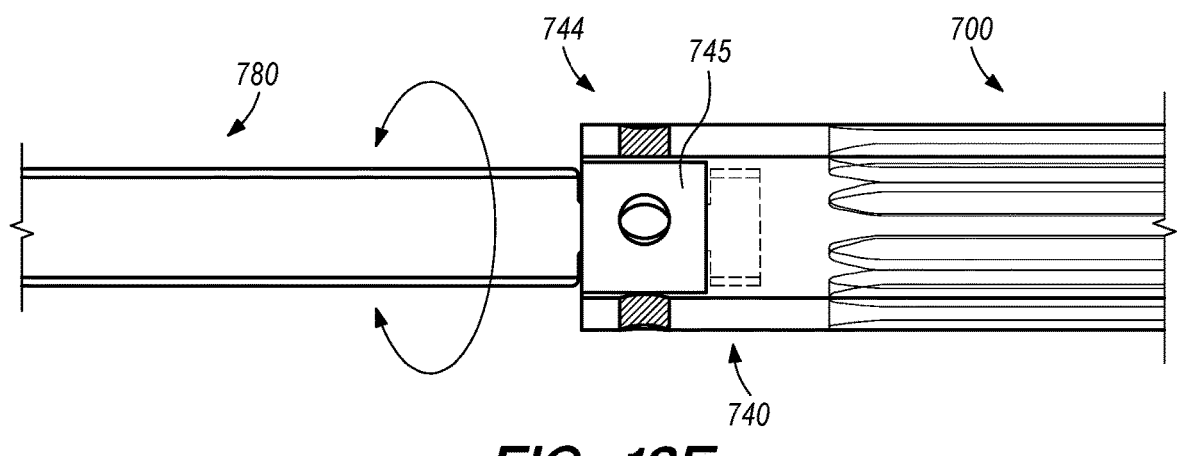

FIGS. 18A-E illustrate another exemplary elongate guide member 780 for guiding a deliver catheter to a target site for administering a therapeutic agent and/or deploying a drug delivery device, constructed according to the disclosed inventions. The elongate guide member 780 of FIGS. 18A-E includes a flat, rectangular cross-sectional profile, as described in FIG. 3D and FIG. 11. As shown in FIGS. 18A-E, the elongate guide member 780 is coupled to the proximal portion 740 of anchor 700 via joint 744, as previously described (e.g., directly or indirectly, fixedly or detachably coupled or the like). FIGS. 18A-E illustrate exemplary dimensions and properties of the interface of the elongate guide member 780 with the anchor 700, which are not intended to limit the embodiment of the interface disclosed herein. In the embodiments of FIGS. 18D-E, the joint 744 between the anchor 700 and the elongate guide member 780 includes a rotatable element 745 configured to allow the elongate guide member 780 to rotate clockwise and/or counter-clockwise with respect to the anchor 700. The independent rotation of the elongate guide member 780 relative to the anchor 700 via the rotatable element 745 at the joint 744 allows for the elongate guide member 780 to assume a desirable orientation through the curved portion of the IPS 102 during delivery and/or after deployment of the anchor 700. For example, the anchor 700 may be delivered at a random orientation at the IPS 102, yet the elongate guide member 780 would assume a desirable orientation by rotating (if needed).

FIGS. 19A-I depict an embodiment of a delivery assembly 300 comprising delivery catheter 3304 and penetrating element guard or guard member 4000. The guard member 4000 covers the penetrating element 3350 during navigation of the delivery catheter 3304 (FIG. 19A) through the patient's vasculature to the target penetration site on a dural venous sinus wall (e.g., IPS wall 114) and during withdrawal of delivery catheter 3304 after administration of a therapeutic agent and/or drug delivery device deployment, thereby preventing inadvertent puncture or damage to other components of delivery assembly (e.g., guide catheter) and the patient's vasculature. As will be further described below, the clinician can actuate a pull wire 4010 to retract guard 4000 proximally and expose the penetrating element 3350 to the dura of IPS wall 114 prior to the penetration step of the drug delivery procedure and, optionally, then re-cover the penetrating element 3350 after the penetration step (e.g., after distal anchoring mechanism 229 of the drug delivery device has been deployed). Radiopaque markers located on the guard 4000 and delivery catheter 3304 provide an indication of whether the guard has been retracted and penetrating element 3350 is exposed or the guard remains in a delivery configuration, covering the penetrating element 3350 for navigation through the patient's vasculature, as will be further described below.

Figure 19A:
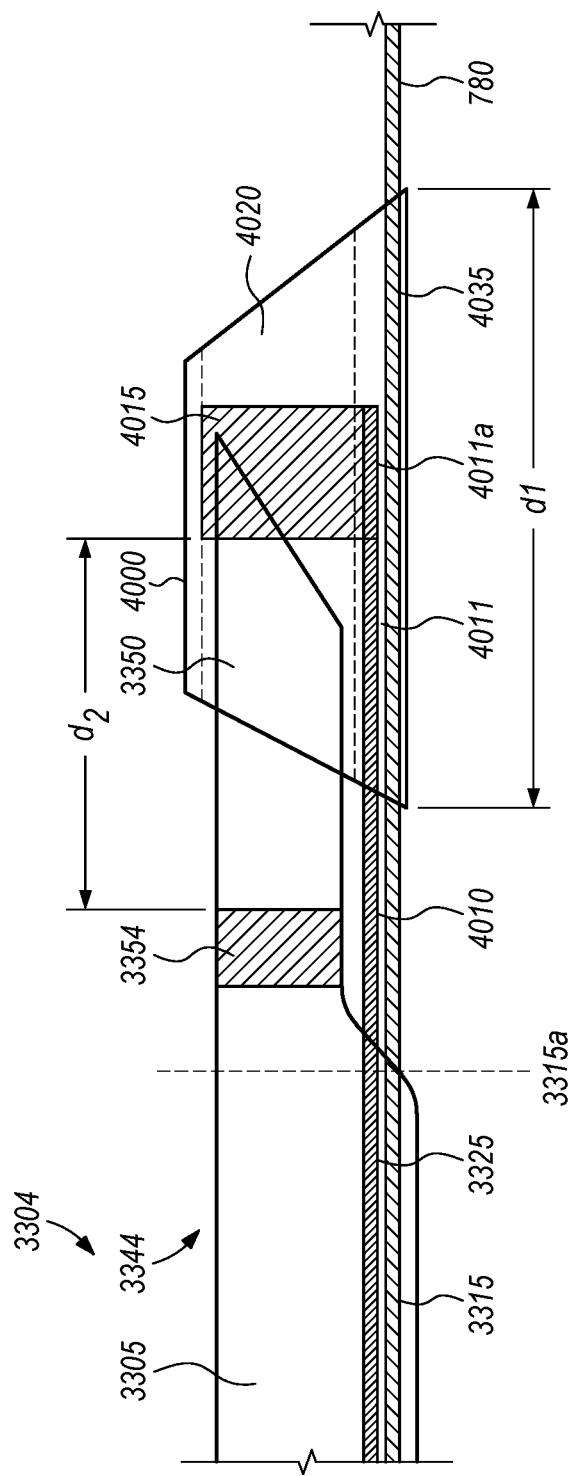

With reference to FIG. 19A, the distal portion 3344 of delivery catheter 3304 comprises penetrating element 3350 and a radiopaque marker 3354. As previously described, delivery catheter 3304 includes a first lumen 3315 to accommodate elongate guide member 780 and a second lumen 3305 to accommodate a drug delivery device 2200 (not shown). The guard member 4000 comprises a pull wire 4010, the pull wire 4010 having a distal portion 4011 attached to a guard body 4000, where the pull wire 4010 is configured to translate the guard body 4000 proximally or distally relative to the delivery catheter 3304 so as to at least partially expose or cover, respectively, the penetrating element 3350. The distal portion 4011 of pull wire 4010 is embedded or encased within guard 4000 (as will be further described below) and includes an attachment point 4011a (e.g., a weld) to radiopaque marker 4015 also embedded within guard 4000 (as will be further described below). The guard 4000 further comprises a first lumen 4020 configured to receive the penetrating element 3350 and allows the guard 4000 to retract proximally (direction of left-hand arrow d2 in FIG. 19A) over the penetrating element 3350 and distal portion of 3344 of delivery catheter and distally (e.g., to re-cover penetrating element 3350, direction of right-hand arrow d2 in FIG. 19A) via pull wire 4010. The enlarged circumference in the distal portion 3344 of delivery catheter 3304 at interface point 3315a where the elongate guide member 780 enters the first lumen 3315 of the delivery catheter prevents guard 4000 from retracting further proximally over the delivery catheter. Guard 4000 can advance distally, via pull wire 4010 and as will be further described below, to re-cover penetrating element 3350. As shown in FIG. 19A, the delivery catheter 3304 includes a third lumen 3325 that extends throughout the length of the delivery catheter, from the distal portion 3344 to the proximal portion 3342; third lumen 3325 accommodates pull wire 4010 of guard 4000.

FIGS. 19B and 19C show cross section and perspective views, respectively, of penetrating element guard or guard member 4000. FIG. 19B depicts a guard member 4000 in a delivery configuration with respect to the distal portion 3344 of delivery catheter 3304 (represented by dashed lines in the figure), covering penetrating element 3350. Penetrating element 3350 is positioned within lumen 4020 of the guard 400 and inside of radiopaque marker 4015 embedded or encapsulated within the walls of guard 4000 (as will be further described below). The guard member 4000 can be approximately 0.5" (1.27 cm) long or other suitable dimensions sufficient to cover penetrating element 3350 on the distal portion 3344 of the delivery catheter. The guard lumen 4020 is sized to allow guard 4000 to retract proximally over the penetrating element 3350 and distal portion 3344 of the delivery catheter, indicated by the direction of the left-hand arrow d2 shown in FIG. 19A. For example, the inner diameter of guard lumen 4020 can be approximately 0.0385" (0.09779 cm).

Marker 4015 comprises a cylindrical profile (as can be seen in FIGS. 19B-D and 19G) such that penetrating element 3350 can reside inside of marker 4015 and the guard first lumen 4020 as depicted in FIG. 19A; the alloy material of marker 4015 shields the concentrically disposed penetrating element 3350 and can prevent the penetrating element from inadvertently puncturing through the guard 4000 when the distal portion of 3344 of delivery catheter 3304 bends as the clinician navigates the delivery assembly 300 through tortuous anatomy to the target penetration site along a venous sinus wall such as IPS wall 114. The distal portion 4004 of the guard 4000 has a beveled/tapered edge, as shown in FIGS. 19B and 19C. The bevel/taper facilitates access to narrow or tortuous vasculature as the clinician navigates the delivery assembly distally beyond the inferior vena cava through the internal jugular vein and into narrower venous sinuses (e.g., to access and navigate through junction 118 of jugular vein 106 and IPS 102). The guard 4000 may comprise a second lumen 4035 to accommodate elongate guide member 780 as shown in FIG. 19C. The delivery assembly 300 comprising delivery catheter 3304 and guard 4000 can advance along the elongate guide member 780 distally, toward the target penetration site; that is, the guide member 780 passes through second lumen 4035 of the guard 4000 and lumen 3315 of delivery catheter 3304 to assist delivery catheter navigation through the patient's vasculature.

FIG. 19D depicts the pull wire 4010 and radiopaque marker 4015 subassembly of guard 4000. Pull wire 4010 can comprise PFTE-coated stainless steel or other suitable materials. The diameter of pull wire 4010 can range from about 0.003" to 0.012" (0.0762 mm to 0.3048 mm). While pull wire 4010 depicted in FIG. 19B-D has a circular cross-sectional profile, other pull wire embodiments can include non-circular cross-sectional profiles (e.g., rectangular, crescent). The PTFE coating on pull wire 4010 increases the lubricity of the wire within the third lumen 3325 of delivery catheter 3304, thereby facilitating smooth proximal and distal actuation of guard 4000 to expose and re-cover penetrating element 3350 (not shown in FIG. 19D). Radiopaque marker 4015 can comprise platinum-iridium 90/10 alloy or other suitable materials that provide sufficient radiopacity and allow for a connection point 4011a between the marker and distal portion 4011 of pull wire 4010. The inner diameter of marker 4015 can be 0.0385' or other suitable dimensions compatible with a guard lumen 4020 sufficient to accommodate the distal portion of delivery catheter 3344 and penetrating element 3350. As shown in FIG. 19D, the distal portion 4011 of pull wire 4010 does not include the PTFE coating depicted on the body portion of pull wire 4010; the uncoated stainless steel distal portion 4011 of pull wire allows for a weld or other connection point 4011a to radiopaque marker 4015.

Figure 19E:
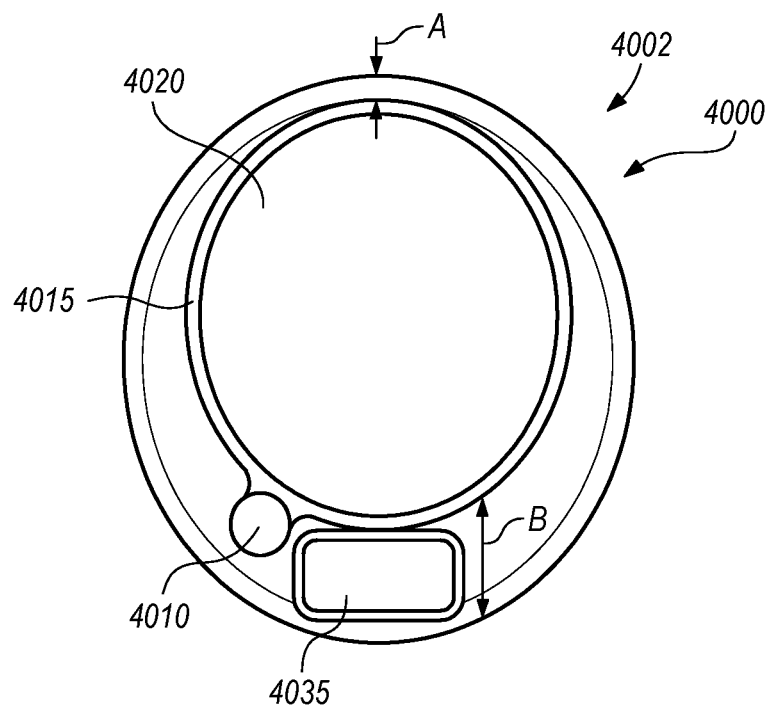
Figure 19F:
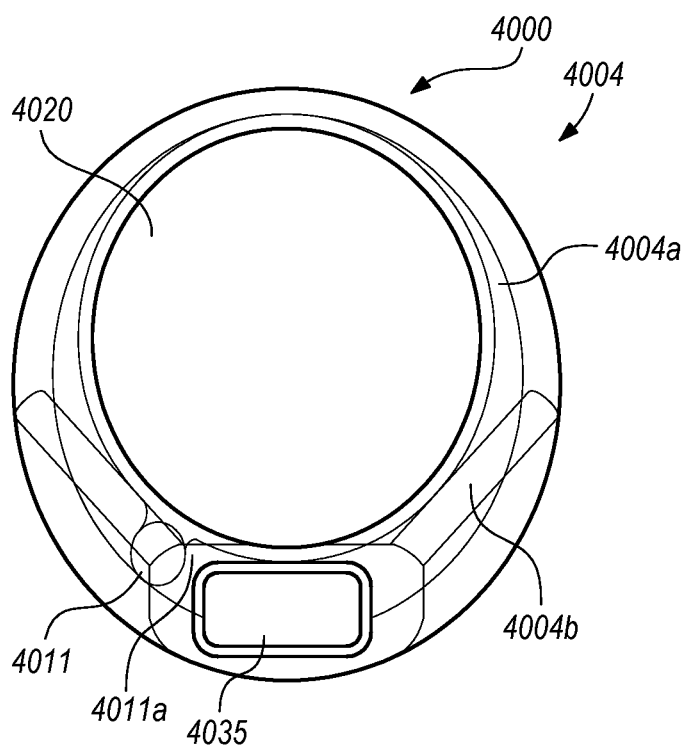

FIGS. 19E and 19F show cross section views of the proximal portion 4002 and distal portion 4004, respectively, of the guard member 4000. As depicted in FIG. 19E, marker 4015 and pull wire 4010 are embedded or encapsulated within the wall of guard 4000. Guard 4000 can comprise polymeric materials such as polyether block amide (Pebax® available from Arkema Group), HTPE, PTFE, urethanes or the like. Pebax embodiments of guard 4000 can range from 27D to 70D hardness (e.g., Pebax 63D). The wall thickness of guard 4000 can vary depending on top-to-bottom orientation of the guard. The top portion of guard 4000 (represented by line A in FIG. 19E) can range from about 0.002" to 0.006" (0.0508 mm to 0.1524 mm) or larger. The bottom portion of guard 4000 (represented by line B in FIG. 19E) can range from about 0.008" to 0.014" (0.2032 mm to 0.3556 mm) or larger.

As previously disclosed and during the drug delivery procedure, a clinician can deploy an anchor 700 distal to a target penetration site along IPS wall 114. Thereafter, the clinician advances a delivery assembly 300 comprising delivery catheter 3304 and penetrating element guard 4000 via elongate guide member 780 to the target penetration site. The radiopaque marking 3354 on the distal portion 3344 of the delivery catheter 3304 and radiopaque marking 4015 within guard 4000 provide reference points for the clinician to visualize the location of the delivery assembly and penetrating element 3350 at the target penetration site. When the clinician is prepared to penetrate IPS wall 114, the clinician can pull the proximal end of pull wire 4010 proximally, which retracts guard 4000 proximally over the distal portion 3344 of delivery catheter (indicated by the direction of the left-hand arrow d2 shown in FIG. 19A) and exposes penetrating element 3350 from the delivery assembly 300. Observing the transition of marker 4015 in guard 4000 proximally towards and/or until it abuts marker 3354 on the distal portion 3344 of the delivery catheter (e.g., in the direction of arrow d2 shown in FIG. 19A) confirms that guard 4000 actuated properly and penetrating element 3350 is exposed from the delivery assembly in the patient's vasculature. The clinician can then advance delivery catheter 3304 distally via elongate guide member 780 until the penetrating element accesses the CP angle cistern 138. The CP angle cistern 138 access can be confirmed by imaging and/or aspiration of CSF from the cistern through a lumen of the delivery catheter (e.g., second lumen 3305). Simultaneously or after the CP angle cistern 138 access is confirmed, a therapeutic agent can be delivered to CP angle cistern 138 (e.g., by flushing the agent through second lumen 3305), and/or a drug delivery device 200 can be deployed from the delivery catheter. After application of a therapeutic agent and/or drug delivery device implantation, the clinician can distally translate or advance the pull wire 4010 to re-cover the penetrating element 3350 and confirm (e.g., via imaging) that the guard 4000 is in a delivery or withdrawal configuration (e.g., penetrating element not exposed in IPS 102 or jugular vein 106 lumens).

FIG. 20 depicts an alternate embodiment of penetrating element guard 4000. For ease in illustration, like features of the penetrating element guard 4000 and delivery catheter 3304 shown in FIG. 20 have been given the same reference numerals from FIGS. 19A-F. Guard 4000 comprises a guard 4000 having a full-length, "oversheath" configuration; that is, guard 4000 is a sheath that extends along the length of and over the delivery catheter 3304 disposed concentrically within guard lumen 4020. Guard 4000 can be retracted proximally (direction of left-hand arrow D2 in FIG. 20), e.g., by a clinician pulling on the proximal portion of guard 4000 to uncover and expose a protected penetrating element 3350. Optionally, guard 4000 can include a scored or weakened portion (e.g., indicated by dotted line d1 in FIG. 20) that splits or tears (e.g., along the longitudinal axis of the guard) to facilitate guard retraction.

Guard 4000 includes a second lumen 4035 that accommodates elongate guide member 780. Lumen 4035 can extend from the distal portion or end of guard 4000 and include an exit port 4035a located in the distal portion of guard 4000, as shown in FIG. 20. As compared to the guard configuration described in connection with FIGS. 19A-F, the guard configuration shown in FIG. 20 simplifies the design of the delivery assembly 300 by eliminating pull wire 4010 and a corresponding pull wire lumen 3325 in the delivery catheter 3304.

FIGS. 21A-L depict an alternate embodiment of delivery catheter 3304. FIGS. 21C and D show longitudinal side and cross section views, respectively, of delivery catheter 3304. FIGS. 21A and B show cross section views of delivery catheter 3304 at reference lines in FIG. 21C, respectively, looking from the distal portion 3344 of the catheter towards the proximal portion. FIG. 21I shows another longitudinal side view of the delivery catheter of FIGS. 21A-L. FIGS. 21F-L depict cross section views of delivery catheter 3304 at various points along the longitudinal axis corresponding to the reference line designations in FIG. 21I.

With respect to FIGS. 21C, D, and I, the depicted delivery catheter 3304 includes a beveled-needle penetrating element 3350 on the distal portion 3344 of the delivery catheter. The penetrating element 3350 can be fixed to the delivery catheter and, as depicted, is welded to reinforcing member 1345 (further described below). Delivery catheter includes three distinct radiopaque marker bands: a distal most marker 3354 located about the proximal portion of penetrating element 3350, an intermediate marker 3354a, and proximal most marker 3345b. A first lumen 3315 in the delivery catheter accommodates elongate guide member 780 and lumen 3315 can include a polymeric liner 3306 material such as PTFE (FIG. 21B) to increase the lubricity of the lumen and facilitate smooth motion of the delivery catheter 3304 over guide member 780.

As depicted, first lumen 3315 has a rapid-exchange configuration and does not span the entire longitudinal axis of deliver catheter 3304, although such a configuration is possible in other embodiments. Marker bands 3354a and 3354b reinforce the distal 3315a and proximal 3315b openings of lumen 3315, as shown in FIGS. 21A and 21K-L. FIG. 21D includes longitudinal dimensions along the length of delivery catheter 3304, measured from the proximal portion of penetrating element 3350 to the distal opening 3315a of first lumen 3315 (0.16"/0.4064 cm), to the distal edge of marker band 3354a (0.17"/0.4318 cm), to the distal edge of marker band 3354b (7.95"/20.193 cm), to the proximal opening 3315b of first lumen 3315 (8"/20.32 cm), and to the proximal portion of delivery catheter 3304 (39.37"/100 cm). Further, delivery catheter 3304 includes a second lumen 3305 to accommodate delivery of a therapeutic agent into the intracranial SAS via the delivery catheter and/or deployment of a drug delivery device. For example, after delivery of a therapeutic agent, the drug delivery device may be deployed from the second lumen 3305 by a pusher delivery assembly as disclosed herein. Second lumen 3305 includes a polymeric liner material 3306 as indicated in FIGS. 21E, 21E-1, 21E-2 to FIG. 21N, such as PTFE.

The outer diameter of delivery catheter 3304 of FIGS. 21A-M varies along the longitudinal axis. The cross section views of FIGS. 21F-M, working from the distal most cross-section to the proximal most cross-section along the axis of delivery catheter 3304, correspond to the reference lines shown in FIG. 21I as follows: FIG. 21J at reference line E-E in FIG. 21I; FIG. 21F at reference line F-F in FIG. 21I; FIG. 21K at reference line G-G in FIG. 21I; FIG. 21G at reference line H-H in FIG. 21I; FIG. 21L at reference line I-I in FIG. 21I; FIG. 21H at reference line J-J in FIG. 21I; and FIG. 21M at reference line K-K in FIG. 21I. In an alternative embodiment of FIG. 21M, FIG. 21N illustrates dual lumens 3305A and 3305B, as described in further detailed below; other embodiments of delivery catheter 3304 can have three or more lumens 3305A, 3305B, 3305C, and so on. Each of FIGS. 21A-B and F-M specify the maximum outer diameter along the longitudinal axis of the delivery catheter 3304 at the location of the particular cross section depicted, which varies depending on the longitudinal location of the cross section along the axis of the catheter (e.g., ranging from 0.036" to 0.046"/0.09144 cm to 0.11684 cm). FIGS. 21K, 21F, and 21J depict a gradually tapering outer diameter in the distal portion of the delivery catheter 3304, moving in the distal direction along the axis of the catheter (i.e., from 0.046" to 0.036"/0.11684 to 0.09144 cm), which facilitates access to tortuous anatomy and narrowings in the vasculature (e.g., junction 118 of jugular vein 106 and IPS 102).

While FIGS. 21A-M and the foregoing description reference a two-lumen delivery catheter 3304, additional embodiments of the delivery catheter can include a third lumen (e.g., lumen 3325 of 19A, FIGS. 29A-D to accommodate, for example, a pull wire of a penetrating element guard 4000, as further described below) and fourth lumen (e.g., lumen of to accommodate, for example, a second pull wire of a penetrating element guard 4000, as further described below and shown in FIGS. 64D-E). In addition, while the foregoing description references a second lumen 3305 of the delivery catheter, in some embodiments of the delivery catheter 3304 can include a partitioned second lumen 3305 having a plurality of lumens (e.g. 3305A, 3305B of FIG. 21N) extending from the penetrating element 3350 to the proximal end or handle of the delivery catheter 3304. Embodiments of delivery catheter 3304 with the partitioned lumen 3305 having multiple lumens (e.g., 3305A, 3305B of FIG. 21N) can be used for dedicated drug delivery steps. By way of non-limiting example, one of the partitioned portion (e.g., lumen 3305A) can be used for CSF aspiration from the intracranial SAS, while the other partitioned portion (e.g., lumen 3305B) can be used to facility delivery of a therapeutic agent from the delivery catheter and/or deployment of a drug delivery device into the intracranial SAS. In alternative embodiments of the delivery catheter 3304, each of a plurality of lumens (e.g., 3305A, 3305B) can be used for providing a particular therapeutic agent to the intracranial SAS or deploying a drug delivery device through a dural venous sinus wall for delivery of a therapeutic agent to the intracranial SAS.

Criteria for selecting a particular needle as the penetrating element 3350 of a delivery assembly 300 include bevel length, force required to penetrate a dural venous sinus wall (e.g., IPS wall 114), and needle wall thickness. Bevel length is inversely related to the puncture force required to penetrate IPS wall, though longer bevels can make navigation of delivery assembly 300 more difficult as compared to shorter bevels, particularly in tortuous anatomy, given that needles do not flex as the distal portion 3344 of the delivery catheter 3304 navigates through the vasculature. Lower puncture forces facilitate a smooth penetration step of the drug delivery procedure, as the penetrating element passes through IPS wall 114 into the subarachnoid space. Puncture force for candidate penetrating element embodiments can be assessed in vitro using a dura surrogate, e.g., DuraGuard® Dural Repair Patch available from Synovis Surgical Innovations, and force gauge as further described in U.S. patent application Ser. No. 14/929,066 filed on Oct. 30, 2015. Penetrating element embodiments comprising a needle configuration can have a puncture force of about 0.1 pounds-force or less. A thinner needle wall minimizes the gap between the anastomosis through IPS wall 114 and the outer surface of deployed drug delivery device 2200. Reducing this gap is clinically significant to minimize or eliminate venous blood from leaking from the IPS 102 or CS 104 through the anastomosis (e.g., between the penetration tract through IPS wall 114 and the outer surface of implanted drug delivery device 2200) into the subarachnoid space and, conversely, CSF leaking from the subarachnoid space into the IPS lumen. For applications where a therapeutic agent is delivered to the intracranial SAS without deploying a drug delivery device, embodiments of delivery catheter 3304 can use relatively smaller hypodermic needles for penetrating element 3350 (e.g., smaller than a 20 gauge needle) to minimize the risks of CSF leaking from the intracranial SAS and venous blood refluxing through the anastomosis into the SAS after the drug delivery procedure.

FIGS. 25A-O illustrate embodiments of the valve 2209" constructed according to embodiments of the disclosed inventions. Embodiments of drug delivery device 200, 2200 can include at least one valve 209, 2209 or 2209" on a distal end opening 239, 2239 of the drug delivery lumen. Further, embodiments of delivery catheter 304, 3304 can include one or more valves 209, 2209 or 2209" in a distal portion of second lumen 3305 (e.g., single, dual, tri, or other second lumen configurations). Exemplary valve embodiments are shown in FIGS. 25A-29. The valves 209, 2209, 2209" can be used to further regulate the rate of therapeutic agent flow into the intracranial SAS through the drug delivery device 2200 (e.g., from an access port 27) or delivery catheter, while minimizing or preventing CSF reflux into the drug delivery device (or delivery catheter) so as to maintain a relatively constant intracranial pressure in the SAS space. The valve 2209 may be disposed at any suitable location within the body 2203 of the drug delivery device 2200 or second lumen 3305 of the delivery catheter. For example, valve 2209 may be disposed within the body 2203 of the drug delivery device 2200 proximate to or at the proximal portion 227, to the distal portion 219, and/or in between said portions 227, 219 (not shown). In certain embodiments, multiple valves can be disposed at different locations within the drug delivery device 2200 or delivery catheter.

The valves 209, 2209, 2209" can include a specific cracking pressure that, when met or exceeded by the positive pressure gradient applied from an operator providing therapeutic agent to an access port 27 (or from the reservoir 2203 for embodiments of drug delivery device depicted in FIG. 17D, or via one or more second lumens 3305 of a delivery catheter), opens the valve thereby facilitating therapeutic agent flow from the device into the intracranial SAS. Embodiments of valves 209, 2209, 2209" can be configured to withstand 3-5 mm Hg or more backpressure to minimize or prevent CSF reflux into drug delivery device 2000; 3-5+mm Hg reflects typical positive pressure gradients between the intracranial SAS and the venous blood pressure in the dural venous sinuses.

Figure 25E:
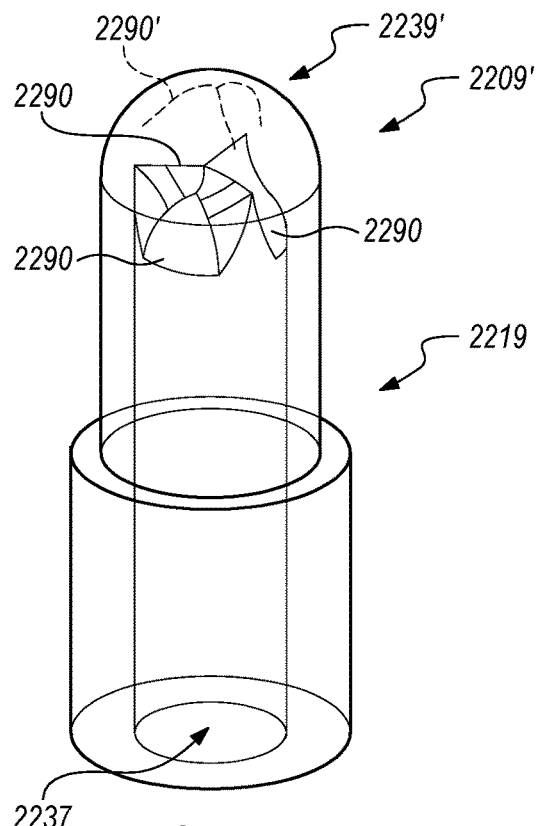
FIGS. 25A-O are side, perspective and cross-sectional views of valves constructed according to embodiments of the disclosed inventions.

The valve 2209 may have a variety of suitable features, and can comprise a molded silicone element configured to be coupled to the drug delivery device 2200 in fluid communication with the drug delivery device lumen 2207 (or within a second lumen 3305 of a delivery catheter 3304). For example, the valve 2209' of FIG. 25E is a one-way valve 2209' having a cylindrical body 2219 comprising a lumen 2237 and an end portion dome 2239. The dome 2239' comprises two or more leaflets 2290' on the outer portion of the dome (FIG. 25E) formed from cutting or slitting the part, and two or more leaflets 2290 on the inner portion of the dome 2239' (FIG. 30H) formed through the silicone molding process. The leaflets 2290 and 2290' are configured to open the valve 2209' facilitating therapeutic agent flow through the lumen 2237 into the intracranial SAS. The outer leaflets 2290' may be formed by creating cuts or slits in the molded silicone element of the valve 2209'. As shown in FIGS. 25E and 25H, the valve 2209' includes three inner leaflets 2290, similar to a heart valve, molded into the valve. In addition, as shown in FIGS. 25E and 25H, the inner surface of the dome 2239 of valve 2209' can include various tiling patterns to increase the available surface area that therapeutic agent flowing through the valve contacts to crack or open the valve from its resting or closed state. Other tiling patterns on the interior portion of the valve dome are possible to accommodate specific valve cracking pressures.

Figure 25F:
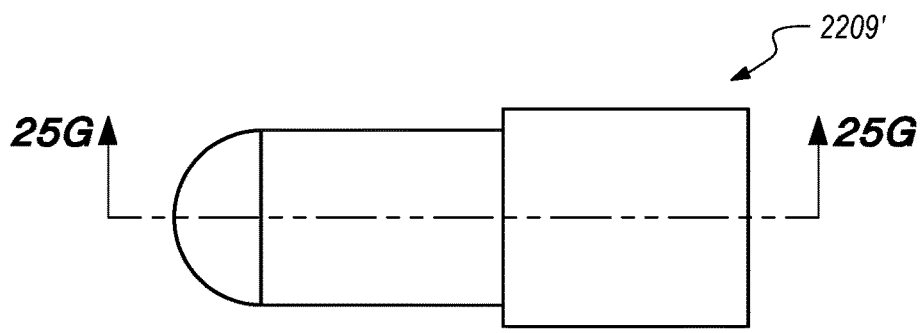
Figure 25G:
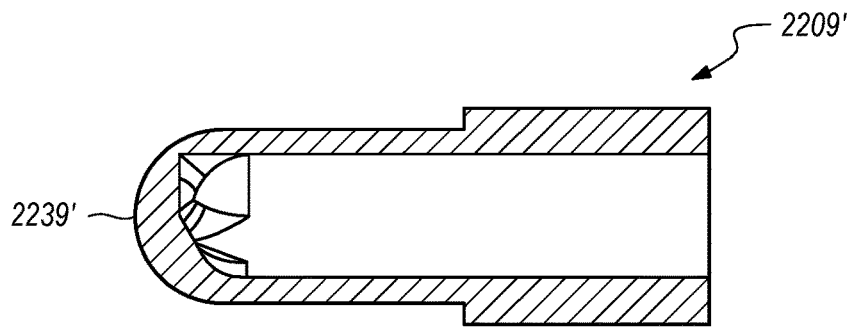
Figure 27A:
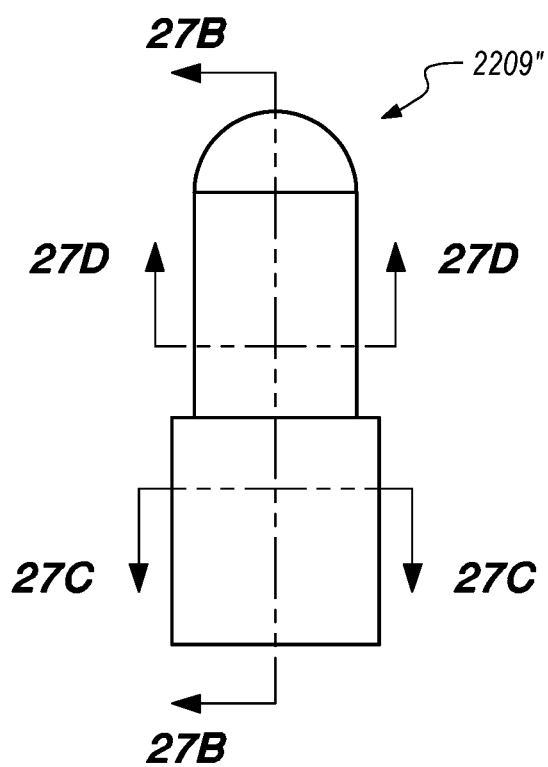
FIGS. 27A-D are side, perspective and cross-sectional views of yet another valve constructed according to embodiments of the disclosed inventions.
Figure 27B:
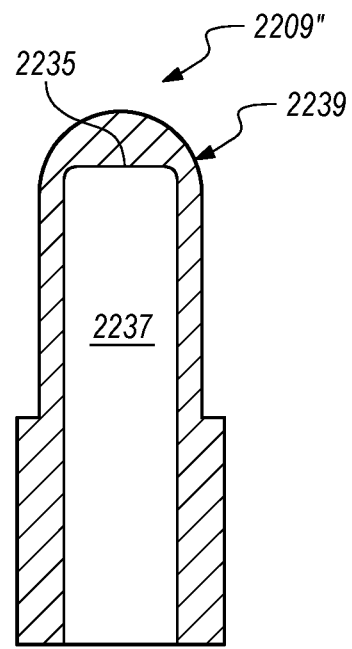
Figure 27C:
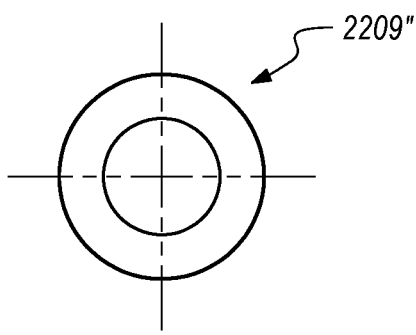
Figure 27D:
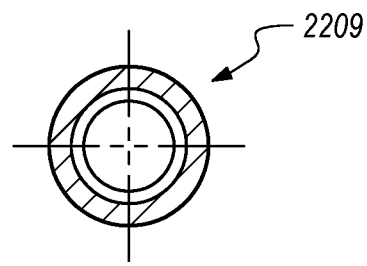

FIG. 25A illustrates an alternate embodiment of valve 2209" comprising a simple dome 2239". Two or more leaflets (not shown) can be created in the dome 2239" in FIG. 25A (e.g., by cutting or slitting with a trocar or blade, using an excimer laser, etc.) to achieve the desired cracking pressure of the valve (e.g., varying the extent of slitting across the surface of the valve dome and/or along the wall of valve 2209"). FIGS. 25B-D illustrate exemplary dimensions (in inches) of the valve 2209"; exemplary dimensions of the dome thickness for molded silicone valves can also range from about 0.001" to 0.004" (0.0254 mm to 0.1016 mm). As shown in FIG. 25B, the cylindrical body 2219 of embodiments of the valve 2209" comprises at least two portions 2219a and 2219b with variable wall thickness, the portion 2219a comprises a larger wall thickness of approximately 0.006" (0.1524 mm) that the portion 2219b having a wall thickness of approximately 0.003" (0.0762 mm), as shown in FIGS. 25B and 25G for valve 2209'. The thicker portion of the valve wall thickness can be used for handing the part during manufacturing or assembly steps, or can be an intended feature of the design (e.g., to allow incorporation with the distal end opening 2239 of the drug delivery lumen 2207). The length of the portions 2219a of the valve 2209'/2209" is approximately 0.030" (0.762 mm), while the length of the portions 2219b including the dome 2239'/2239" is approximately to 0.040" (1.016 mm), as shown in FIGS. 25B and 25F. The dome 2239' comprises a wall thickness with variable ranges shown in FIGS. 25G and 25I.

FIGS. 25J-O illustrate alternative embodiments of valve 2209 including exemplary dimensions (in inches) having outer leaflets 2290'. As shown in FIGS. 25J-L, the valve 2209''' includes three inner leaflets 2290 (FIG. 25M) and three outer leaflets 2290' (FIG. 25N). FIG. 25J illustrates a perspective view of an embodiment of the valve 2209''' including the three sets of inner and outer leaflets 2290 and 2290', respectively. In addition, the exterior portion of the valve dome 2239" includes three ribs 2293 as shown in FIGS. 25J and 25N; the outer ribs 2293 can increase the outer surface area of the valve 2209''' to provide more robust backflow resistance of CSF through the valve (e.g., resisting or preventing CSF backflow from the intracranial SAS into the drug delivery lumen 2207 of device 2000 or second lumen 3305 of delivery catheter 3304). FIGS. 25K-O illustrate exemplary dimensions (in inches) of embodiments of the valve 2209''' depicted in FIG. 25J. Similarly to FIG. 25C, the cylindrical body 2219 of the valve 2209''' of FIG. 25L comprises at least two portions 2219a and 2219b with variable wall thickness, the portion 2219a comprises a larger wall thickness that the wall thickness of the portion 2219b. For example, the wall thickness of portion 2219a can range from approximately 0.006" (0.1524 mm) to 0.001" (0.0254 mm), and the wall thickness of portion 2219b can range from approximately 0.003" (0.0762 mm) to 0.0003" (0.00762 mm). The length of the portions 2219a of the valve 2209 can range from approximately 0.030" (0.762 mm) to 0.005" (0.127 mm), while the length of the portions 2219b including the dome 2239 can range from approximately to 0.040" (1.016 mm) 0.003" (0.0762 mm), as shown in FIG. 25K. The dome 2239''' comprises a wall thickness with variable ranges shown in FIG. 25O, though alternate embodiments can include thinner or thicker wall thicknesses, e.g., in the dome portion of the valve.

FIGS. 26A-28Q illustrate alternative embodiments of the valve constructed according to embodiments of the disclosed inventions. The valve regulates the rate of therapeutic agent flow through the drug delivery device lumen 2207 (or second lumen 3305 of delivery catheter 3304), while allowing preventing or resisting CSF backflow into the device 2200 (or delivery catheter 3304) from the intracranial SAS. Features, functions, and configurations of the valve of FIGS. 26A-28Q that are the same as in the valve of the present disclosure (e.g., FIGS. 25A-O) and in the related application, are incorporated by reference herewith, the differences will be described in further detail below. The valve may have a variety of suitable features, such as comprising a molded silicone element configured to be coupled to the drug delivery device in fluid communication with the drug delivery device lumen. For example, the valve 2209" of FIGS. 26A-D is a one-way valve having a cylindrical body comprising a valve lumen 2237 and an end portion dome 2239. The valve 2209" includes a transitional core 2236 (e.g., inner tapered surface of the dome 2239), as better appreciated in the cross-sectional portion of the dome (FIG. 26B). By contrast, the valve 2209" of FIGS. 27A-D include a non-transitional core 2235 (e.g., inner square or flat inner surface of the dome 2239), as better appreciated in the cross-sectional portion of the dome 2239 (FIG. 27B). Either valve 2239", having transitional (FIG. 26A-D) or non-transitional (FIGS. 27A-D) cores 2236 or 2235, respectively, include cuts, slits, holes, perforations or the like (FIGS. 28A-Q) configured to open the valve 2209" and allow for fluid communication facilitating therapeutic agent flow through the drug delivery device when deployed in the target site.

Figure 28A:
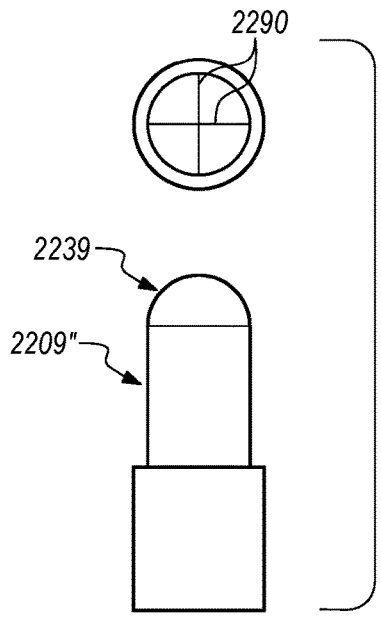
FIGS. 28A-Q are side, perspective and cross-sectional views of valves constructed according to further embodiments of the disclosed inventions.
Figure 28B:
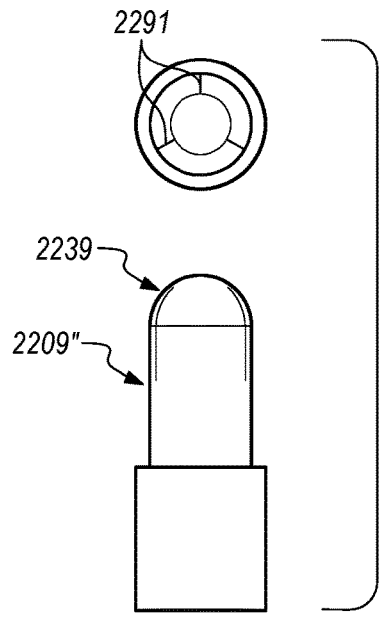
Figure 28C:
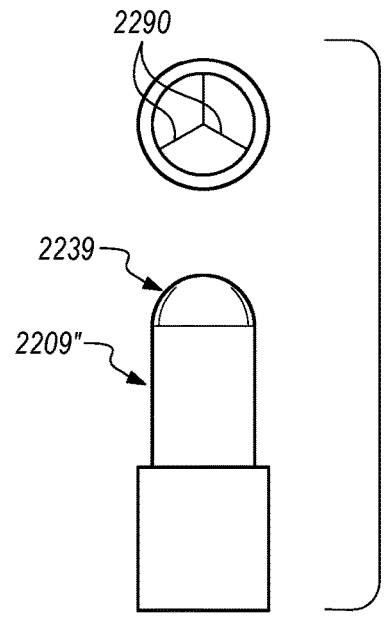
Figure 28D:
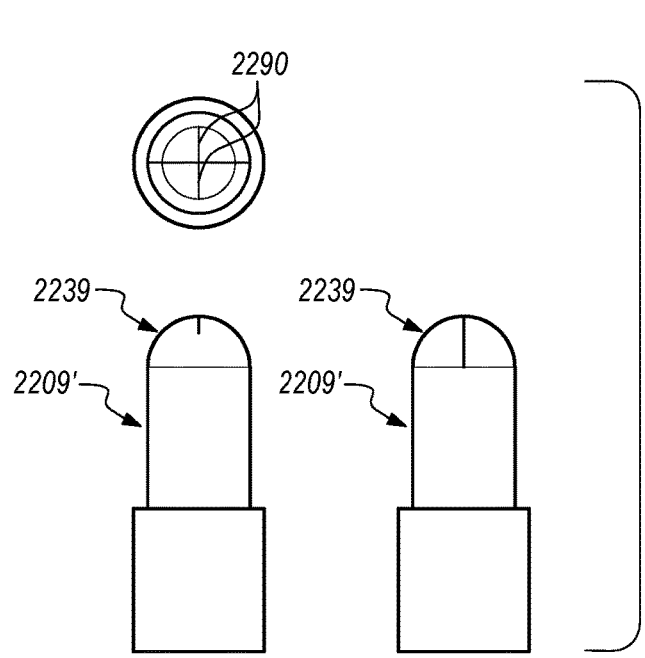
Figure 28E:
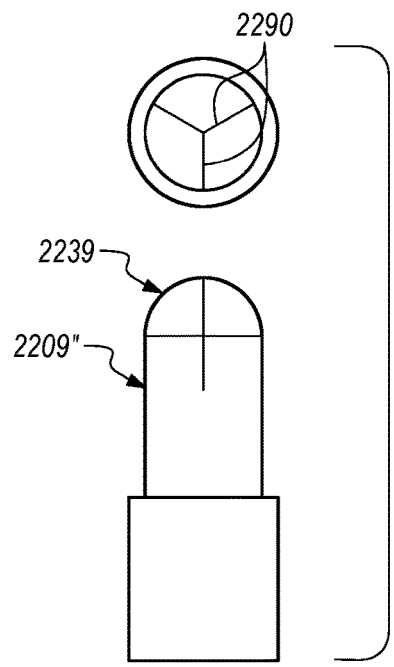
Figure 28F:
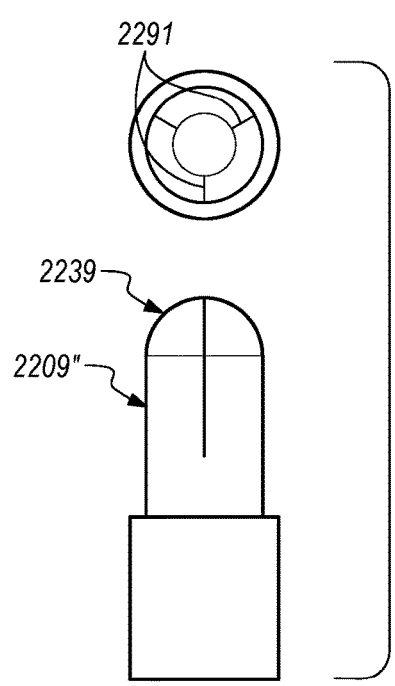
Figure 28G:
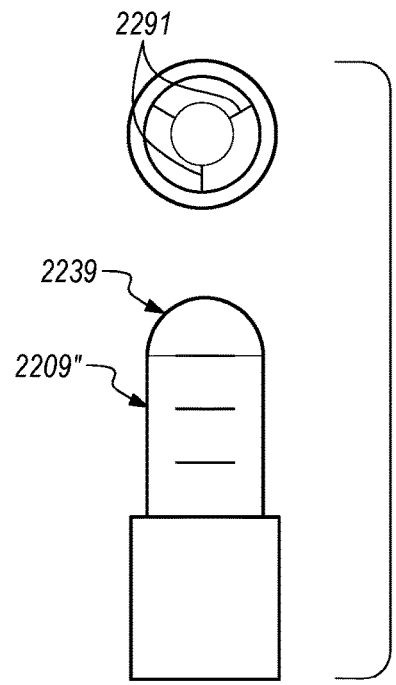
Figure 28H:
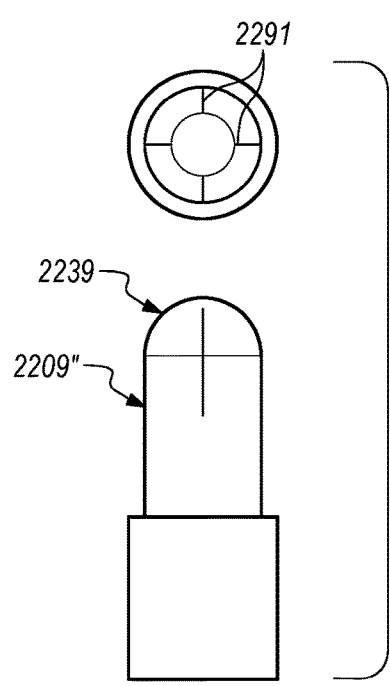
Figure 28I:
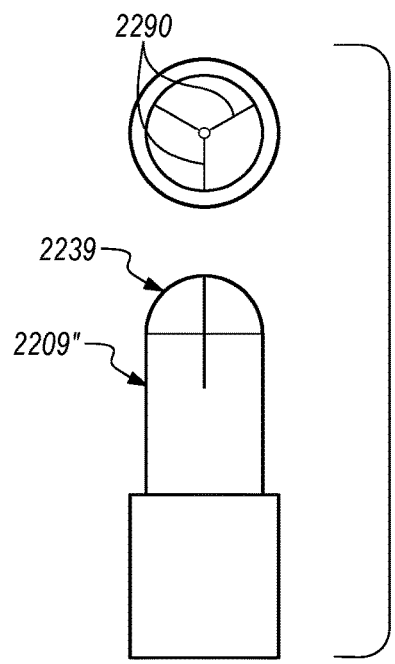

FIGS. 28A-Q illustrate exemplary valve cuts at the end portion dome 2239 of the valves 2209" constructed according to embodiments of the disclosed inventions. The dome 2239 may be cut to include two or more leaflets 2290 formed from cutting or slitting, as shown in FIGS. 28A, 28C-E and 28I. The leaflets 2290 may be similar to a heart valve, as shown in FIGS. 25E and 25H. Alternatively, the cuts at the end portion dome 2239 may not form leaflets, such as when linear cuts do not intersect 2291, as better appreciated in FIGS. 28B and 28F-H. These non-intersecting cuts 2291 of the dome 2239 allow for opening of the valve 2209" while also allowing the valve 2209" to fully close.

FIG. 28J-Q illustrate further exemplary valve cuts at the end portion dome 2239. In contrast with the linear cuts of FIGS. 28A-I, FIGS. 28J-Q shows arcuate, circular-shaped, concave and convex cuts or the like, that may extend along the cylindrical body of the valve 2209" forming two or more leaflets 2290.

Figure 29:
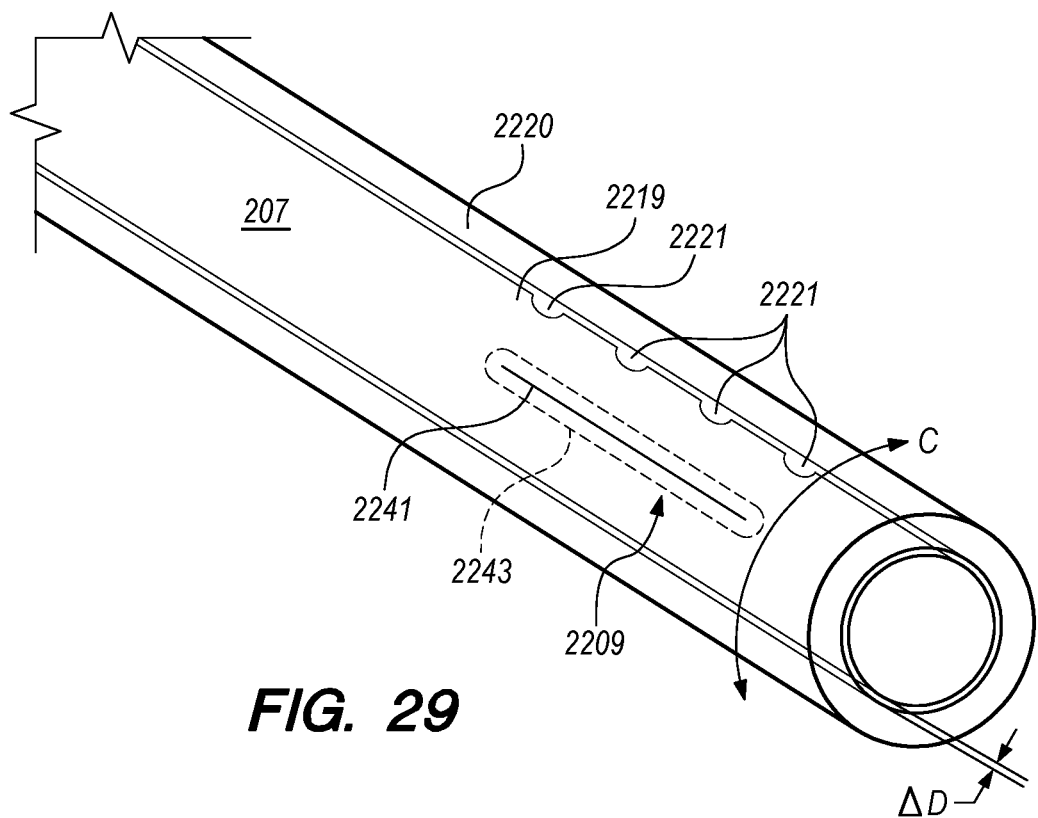
FIG. 29 is a perspective of another valve constructed according to embodiments of the disclosed inventions.

FIG. 29 illustrates valve embodiments that include an internal support member and exterior layer. For example, valve 2209 can include a relatively rigid internal support member 2219 comprising a gold (or other radiopaque metal or alloy), Nitinol, stainless steel, or polymeric hypotube (e.g., any of the polymers previously described herein or disclosed in the applications incorporated by reference). The internal lumen of the support member 2219 provides the drug delivery device lumen 207 for a distal portion 219 of the drug delivery device 2200 and can comprise the entire length of the drug delivery device lumen in other embodiments. As shown in FIG. 29, the support member 2219 can include one or more apertures (e.g., four apertures 2221 as shown in the figure). Exterior layer 2220 can include a silicone, polyurethane, or other suitable polymeric material hypotube or layer disposed concentrically over the internal support member 2219. The distal ends of internal support member 2219 and the exterior layer 2220 can be closed as depicted in the FIG. 29. Exterior layer 2220 can include one or more slits 2241 (e.g., slit created by a blade or trocar) or apertures 2243 (e.g., apertures created by a laser that removes a portion of the layer material between the opposing edges of the aperture). The rotational or clocking orientation of the exterior layer 2220 and slits or apertures 2243 can be varied with respect to the location of the apertures 2241 of the internal support member 2219 (e.g., indicated by the "C" arrows in the FIG. 29) to achieve a target cracking pressure in these alternate valve 2209. As will be further described below, aspects of the valve 2209 of FIG. 29 allow therapeutic agent within drug delivery device lumen 207 to flow through the apertures 2221 of the internal support member 2219, between the respective outer surface of the internal support member and inner surface of the exterior layer, and out of the slit 2241 or aperture 2243 of exterior layer 2220.

Where exterior layer comprises one or more slits 2241, the opposing edges of the slit(s) provide a sealing interface to maintain the valve 2209 closed below a target opening or cracking pressure. When the drug delivery device lumen 207 and/or internal support fill with therapeutic agent and meet or exceed the cracking or opening pressure of the valve 2209, the one or more slits 2241 of the exterior layer 2220 open to allow therapeutic agent to flow from drug delivery device lumen 207 and out from the valve 2209. When therapeutic agent is not being delivered through drug delivery device 2200, the slits 2241 seal to prevent CSF from entering the drug delivery device lumen 207. Support member 2219 resists compression or collapse of the exterior layer of the valve 2209.

The relative sizing between internal support member 2219 and exterior layer 2220 (e.g., referenced as "AD" in FIG. 29) can be optimized to target a valve cracking pressure, facilitate therapeutic agent flow from within internal support member 2219/drug delivery device lumen 207 and through the exterior layer 2220 and out of the valve 209, and prevent CSF backflow. For example, in embodiments where exterior layer 2220 includes one or more slits 2241, the difference between the outer diameter of internal support member 2219 and the inner diameter of exterior layer 2220 can be about 0.0001" to 0.005" (0.00254 mm to 0.127 mm). In embodiments where exterior layer 2220 includes one or more apertures 2243, the outer diameter of the internal support member 2219 can be sized more closely to or slightly exceed the inner diameter of exterior layer 2220. In such embodiments, the external and internal diameters of the internal support and exterior layer, respectively, can provide a sealing interface to prevent therapeutic agent flow from device 2200 below a target cracking pressure while also preventing or resisting CSF reflux into drug delivery lumen 2207; once pressure within drug delivery device lumen 207 and/or internal support member 2219 meet or exceed a target cracking pressure (e.g., by an operator administering a therapeutic agent through an access port 27), therapeutic agent flows through the one or more apertures 2243 of the internal support and out through the one or more apertures 2243 of the exterior layer 2220. In further embodiments comprising one or more slits in the exterior layer 2220, the inner diameter of such exterior layer 2220 can match the outer diameter of the internal support member 2219; in such embodiments, the exterior layer 2220 will seal against the internal support at the points where the respective inner and outer diameters touch below a target cracking pressure. Where the target cracking pressure is met or exceeded, therapeutic agent flows through the one or more apertures of the internal support 2219 and out through the one or more slits 2241 of the exterior layer 2220.

FIGS. 30A-G illustrate an alternative delivery catheter 3304 for administering a therapeutic agent and/or delivering the drug delivery device 200 into a target site of a patient, constructed in accordance with embodiments of the disclosed inventions. For ease in illustration and disclosure, the features, functions, and configurations of the delivery catheter that are the same as in the catheter of FIGS. 10A-K and in the related application, are incorporated by reference herewith; the differences will be described in further detail below. FIG. 30A show perspective longitudinal side views at various points along the longitudinal axis of the delivery catheter. FIG. 30B shows another perspective longitudinal cross-sectional view of the delivery catheter. The delivery catheter 3304 of FIGS. 30A-E includes a penetrating element 3350 on the distal portion and a distinct radiopaque marker band 3354 proximately disposed to the penetrating element 3350. The radiopaque marker band 3354 may be disposed in an angle with respect to the longitudinal axis of the catheter 3304 to indicate direction/orientation of the catheter distal portion 3344 during navigation of catheter 3304 to a target site in the intracranial venous sinuses. The angled marker 3354 may further include directional features, such as arrow heads, or the like, as shown in FIGS. 31A-G.

Figure 10A:
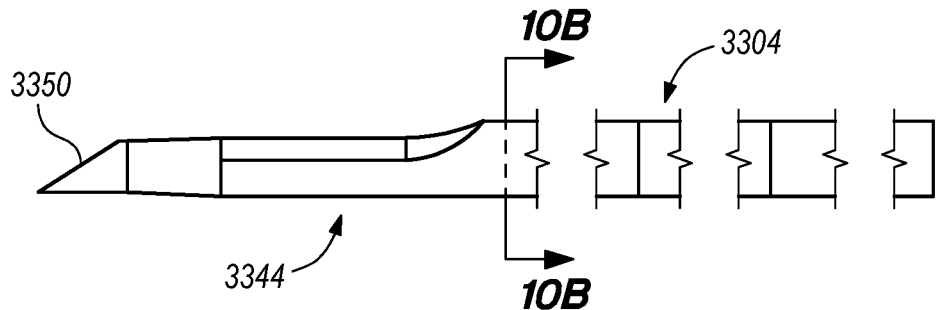
FIGS. 10A-J are perspective, side and cross-sectional views of a delivery catheter, according to another embodiment of the disclosed inventions.
Figure 10B:
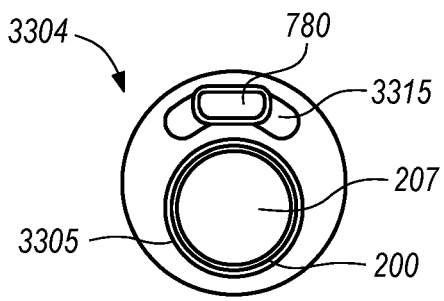
Figure 10C:
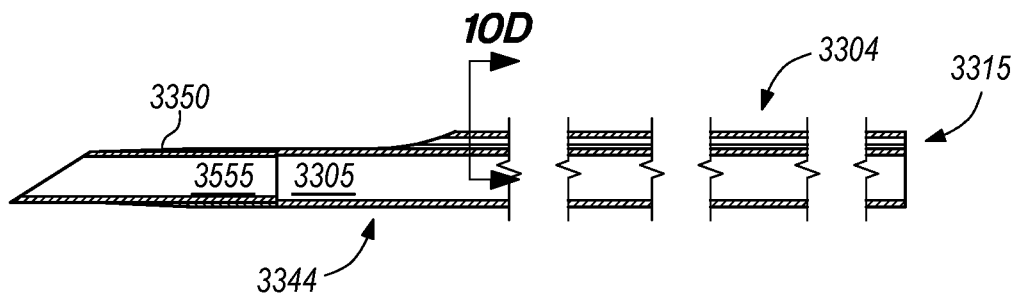
Figure 10D:
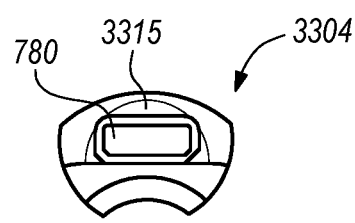
Figure 10E:
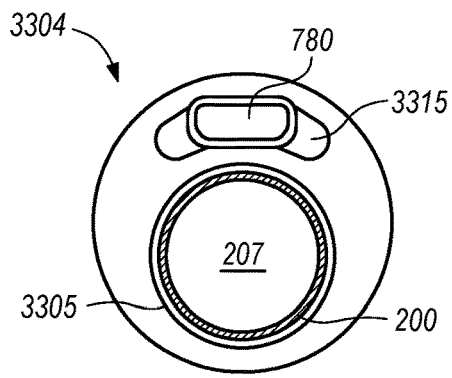
Figure 10F:
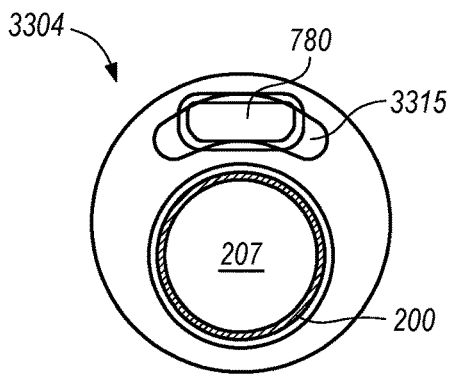
Figure 10G:
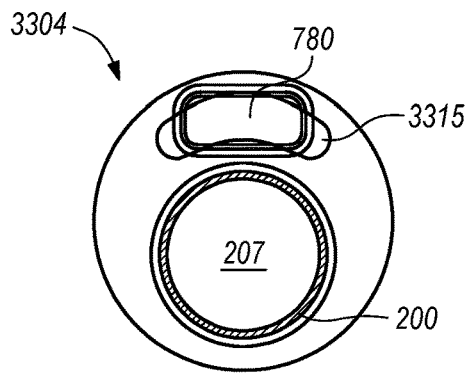
Figure 10H:
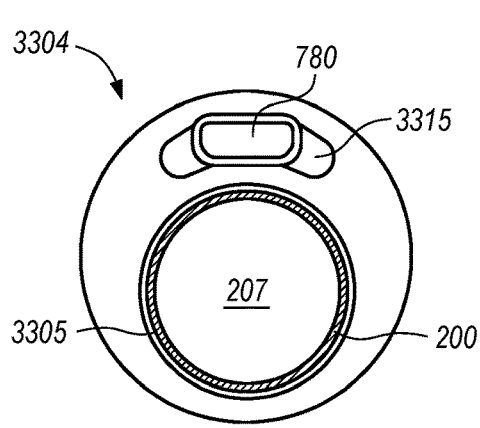
Figure 10I:
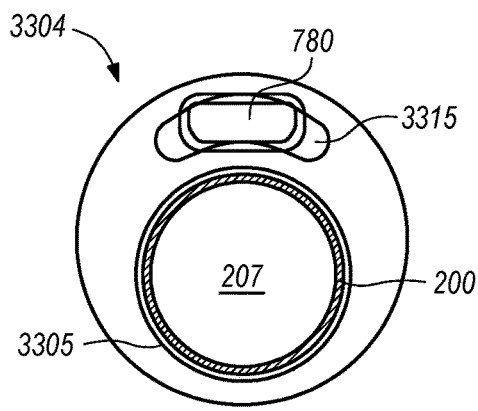
Figure 10J:
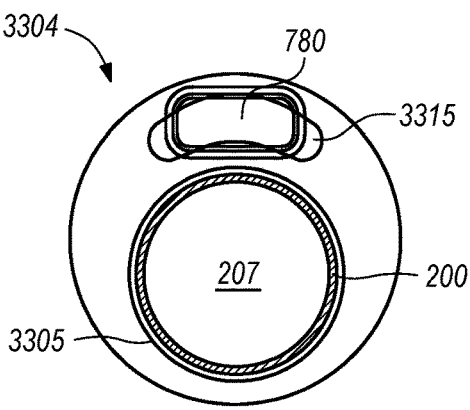
Figure 11:
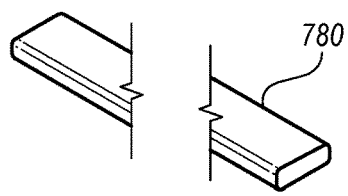
FIG. 11 is a perspective view of an elongate guide member, constructed according to embodiments of the disclosed inventions

Further to the lumen, for administering a therapeutic agent and/or deploying a drug delivery device 200 from the delivery catheter, and the elongated guide member lumen, as shown in FIG. 10C as 3305 and 3315 respectively, the delivery catheter of FIG. 30A includes an additional lumen (FIGS. 30D and 30E) adjacently disposed to the drug delivery device lumen. The additional lumen is configured to allow passage of the guard pull wire, the penetrating element guard, an additional penetrating element, tool, or any other suitable element.

The delivery catheter 3304 includes a reinforcing member 1345 (FIGS. 30A-B, FIGS. 30F-G) configured to reinforce the catheter 3304 while providing a suitable balance between column strength and flexibility (e.g., "pushability" and "torqueability") for access to and maneuverability within the intracranial venous sinuses. The reinforcing member 1345 is composed of suitable biocompatible and/or elastomeric materials such as, stainless steel, Nitinol® or the like. The reinforcing member 1345 includes a plurality of cuts 1330 (e.g., kerfs, slots, key-ways, recesses, or the like) selectively disposed in sections of the reinforcing member 1345 along length $L_{20}$ of the delivery catheter 3304, as shown in FIGS. 30A-B, and FIG. 30F. Alternatively, the cuts 1330 can be continuously disposed substantially along $L_{20}$ (not shown). It should be appreciated that the cuts 1330 can have variable spiral cut patterns of kerf, pitch, cuts per rotation and cut balance along $L_{20}$ or combinations thereof. Additionally, the reinforcing member 1345 of FIGS. 30A-G includes an inner liner 1360 and an outer jacket 1365 (FIG. 30B), as previously described and better appreciated in detail in FIG. 12C. The inner liner 1360 and outer jacket 1365 are configured to cover—substantially completely or partially—the cuts 1330 of the reinforcing member 1345, while maintaining the flexibility provided by the selective cuts 1330 and column strength afforded, in part, by the reinforcing member 1345.

The distal portion of the delivery catheter 3344 of FIGS. 30A-B and FIG. 30F, further includes a stain-relief portion 3343 element proximately disposed to the penetrating element 3350 to avoid, minimize and/or resist kinking of the catheter 3304 at the transition area from the flexible portion of the catheter to the penetrating element, during penetration of the IPS wall and, in some procedures, deployment of a drug delivery device 200. Further, the selective cuts along the length of the delivery catheter are configured to provide a balance between column strength and flexibility of the catheter, such as, having a more rigid proximal portion to a more flexible distal portion (FIGS. 30A-C).

FIGS. 31A-G illustrate an alternative marker, constructed in accordance with embodiments of the disclosed inventions. The marker 3354 is composed of radiopaque material and may be formed by cutting a tubular element in an angle, as shown for example in angle $A_{30}$ of FIG. 31A. Additionally, the marker 3354 may include any other relative size, geometry or configurations (e.g., arrow head, different width of the band, asymmetric band, or the like) suitable to indicate direction and/or orientation of the element where the marker is disposed, such as for example, when the marker is disposed on the delivery catheter to indicate the direction of the penetrating element. FIGS. 31D-E are detailed views of respective edges 3354' and 3354" of the marker of FIG. 31C.

FIG. 32 illustrates yet another exemplary drug delivery device 2200 constructed and deployed in IPS 102 according to embodiments of the disclosed inventions. For ease in illustration and disclosure, the features, functions, and configurations of the drug delivery device 2200 that are the same as in the drug delivery device of the present disclosure (e.g., FIGS. 15A-E, 17D) and in the related application, are incorporated by reference herewith; the differences will be described in further detail below. The implanted drug delivery device 2200 of FIG. 32 shows three distinct zones; zone I (Distal) depicts the distal portion 2202 of the drug delivery device having the distal anchoring mechanism 2229 engaging the dura mater IPS wall 114, the arachnoid layer 115 and/or securing the drug delivery device 2200 at the target site (e.g., intracranial subarachnoid space, CP angle cistern 138), zone II (Mid) depicts the middle or body portion 2203 of the drug delivery device 2200 disposed within the IPS 102 and zone III (Proximal) depicts the proximal portion 2204 of the drug delivery device having a proximal anchoring mechanism 2227 engaging and/or securing the drug delivery device in the venous system (e.g., IPS 102, jugular vein 106, and/or a jugular bulb 108). In some drug delivery device embodiments (e.g., FIGS. 53, 54A, 56A-58F), zone III (Proximal) does not include an anchoring mechanism and the proximal portion 2204 of the implanted drug delivery device is disposed in the IPS 102, jugular vein 106, and/or a jugular bulb 108 (e.g., as also depicted in FIG. 17D), or extends through jugular vein 106 to another venous site for connection to an access port (e.g., as depicted in FIGS. 15A-E). The zone I (Distal) is configured to maintain a patent fluid outlet for therapeutic agent to flow form the device, zone II (Mid) is configured to accommodate a variety of venous sinus anatomies (e.g., length, curvature, width, or the like), maintain a patent fluid lumen (e.g., kink-resistant, non-thrombogenic, protein resistant, or the like), or alternatively function as an anchor within the sinus. Zone III is configured to minimize or prevent thrombus formation on the implanted drug delivery device, and/or further maintain a refilling coupler 2227 separated from the vessel wall to prevent encapsulation (e.g., 2-3 mm away from the wall). FIGS. 33A-54B illustrate exemplary embodiments of zones I-III of the drug delivery device 2200 according to the disclosed inventions. It should be appreciated that the drug delivery device 2200 constructed according to embodiments of the disclosed inventions may include any variety or combinations of zones I-III as disclosed herein and/or in the related application that are incorporated by reference herewith. Furthermore, a drug delivery device 2200 can include one or more anchoring mechanisms at any of the zone I-III locations to secure the deployed device within the venous vasculature and/or intracranial SAS.

Figure 33C:
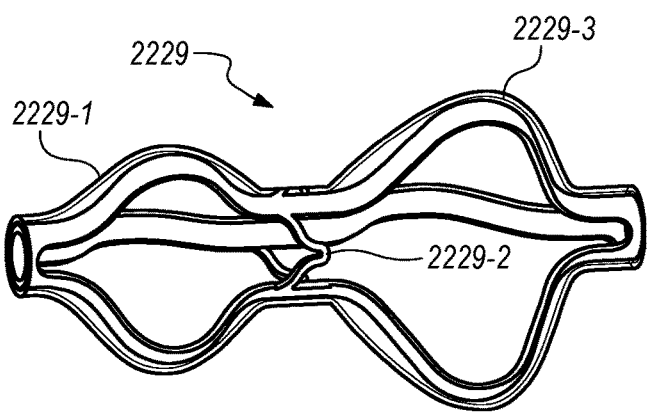
FIGS. 33A-40C are perspective and cross-sectional views of various embodiments of distal anchoring mechanisms of the drug delivery device, constructed according to the embodiments of the disclosed invention.

FIGS. 33A-40C illustrate exemplary embodiments of zone I (Distal) of the drug delivery device 2200, according to the disclosed inventions. FIGS. 33A-C illustrates a distal portion of the drug delivery device 2200 including a double-malecot anchoring mechanism 2229 in a deployed expanded configuration. The double-malecot includes a proximal malecot 2229-1, a distal malecot 2229-3 and a joint element 2229-2 (e.g., collar, band—FIGS. 33A-B—, struts with hinge members—FIG. 33C—or the like) disposed therebetween. The double-malecot is configured to expand into the deployed configuration engaging the arachnoid layer 115 at the CP angle cistern 138 and the dura layer 114 at the IPS 102. The double-malecot configuration of the distal anchoring mechanism 2229 further secures the distal portion of the implanted drug delivery device 2200, while avoiding or minimizing distal or proximal migration/translation of the drug delivery device 2200. Additionally, the double-malecot distal anchoring mechanism 2229 may further include a liner 2229-4 (e.g., membrane, mesh, braid or other suitable permeable material or combinations thereof), as shown in FIGS. 33B-C, configured to avoid or minimize the formation of thrombus.

Figure 34:
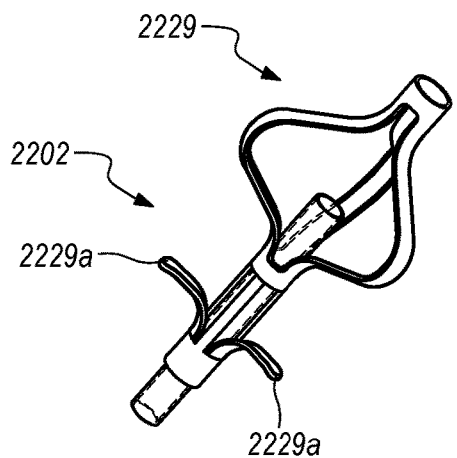
Figure 35:
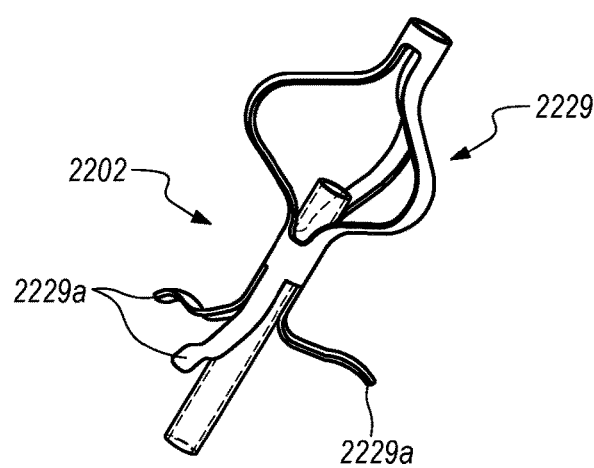

FIGS. 34-35 illustrate distal portions of embodiments of the drug delivery device 2200 including a malecot-flarecot anchoring mechanism 2229 in a deployed expanded configuration. The malecot portion is configured to expand into the deployed configuration engaging the arachnoid layer 115 at the CP angle cistern 138 and the flarecot is configured to engage the dura mater 114 at the IPS 102 (or other intracranial SAS and venous sinus device deployment location). The flarecot arms 2229a of the malecot-flarecot anchoring mechanism 2229 can flare out in the distal direction (e.g., towards the dura mater 114 in the implanted drug delivery device), as shown in FIG. 34 or the flarecot arms 2229a can flare out in the proximal direction (e.g., towards the IPS 102 in the implanted drug delivery device), as shown in FIG. 35, or the flarecot arms 2229a may comprise a combination of the arms 2229a of FIGS. 34 and 35. Similar to the double-malecot configuration, the zone I (Distal) embodiments of FIGS. 34-35 further secure the distal portion of the implanted drug delivery device 2200, while avoiding or minimizing distal or proximal migration/translation of the drug delivery device.

Figure 36:
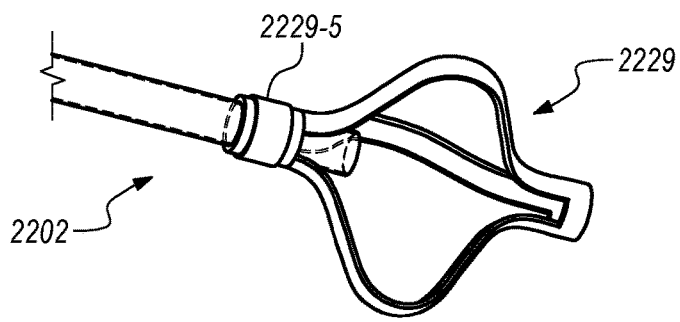

FIG. 36 illustrates a distal portion of embodiments of the drug delivery device including a malecot anchoring mechanism 2229 in a deployed expanded configuration. The malecot anchoring mechanism further includes an annular element 2229-5 composed of expandable material (e.g., foam, swellable or the like). The annular element 2229-5 is configured to expand when disposed within an anastomosis channel formed by piercing the IPS wall 114 and arachnoid layer 115, and further secure the drug delivery device 2200 at the target site.

Figure 37:
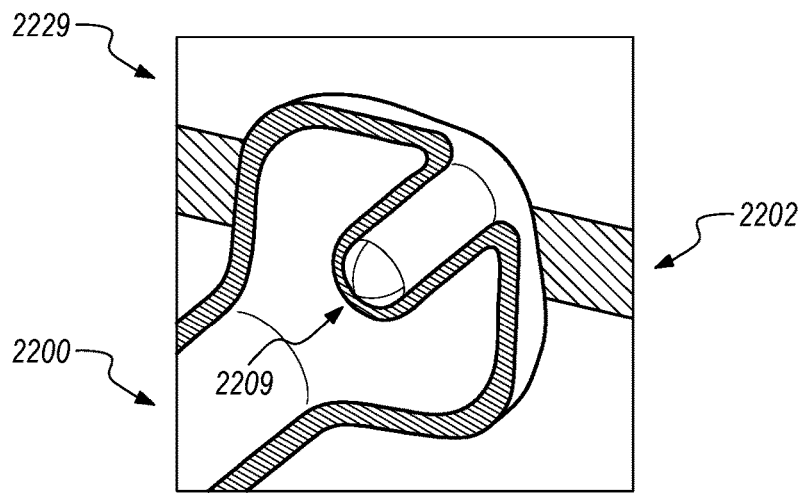
Figure 38:
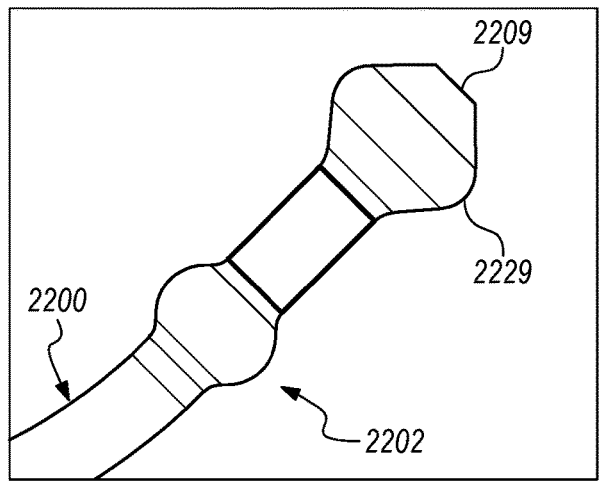
Figure 39A:
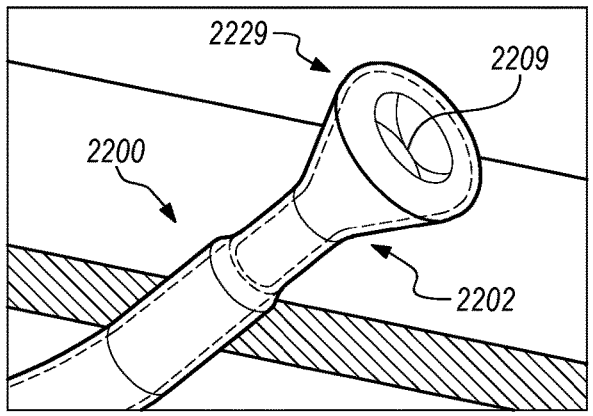
Figure 39B:
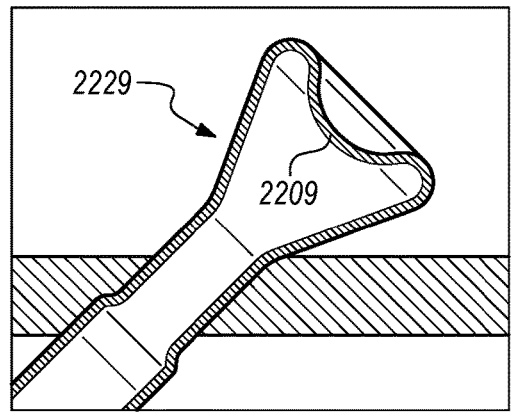

FIGS. 37-39B illustrate distal portions of embodiments of the drug delivery device 2200 including anchoring mechanisms 2229 in a deployed expanded configuration. The anchoring mechanism 2229 is composed of polymeric material, such as silicone, or any other suitable biocompatible non-metallic materials. The anchoring mechanism 2229 includes an expandable element that may have a spheroid, ellipsoid, obloid, diamond-like (FIGS. 37-38), funnel-like (FIGS. 39A-B) or any other suitable shape and dimension configured to anchor the drug delivery device 2200 at the target site when expanded in the intracranial SAS. In some embodiments, the distal anchoring mechanism 2229 includes one expandable element, as shown in FIGS. 37 and 39A-B. In other embodiments, the distal anchoring mechanism includes at least two expandable elements and a portion therebetween, as shown in FIG. 38. The distal anchoring mechanisms 2229 of FIGS. 37-39B can further include a one-way valve 2209, which functions as the valves previously described herein (e.g., FIGS. 25A-28Q).

Figure 40A:
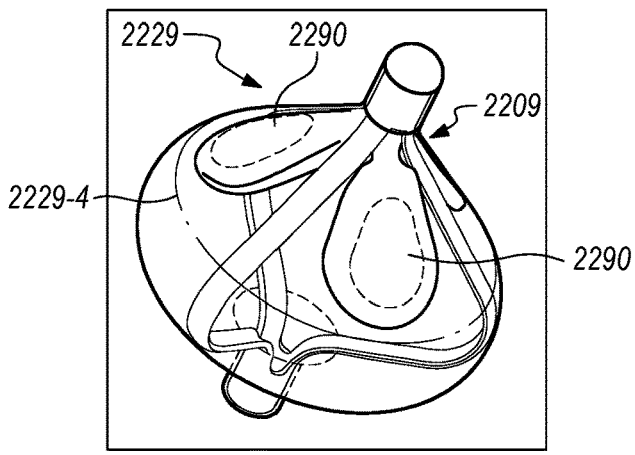
Figure 40B:
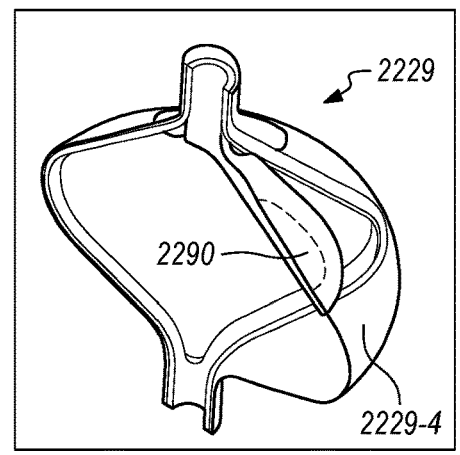
Figure 40C:
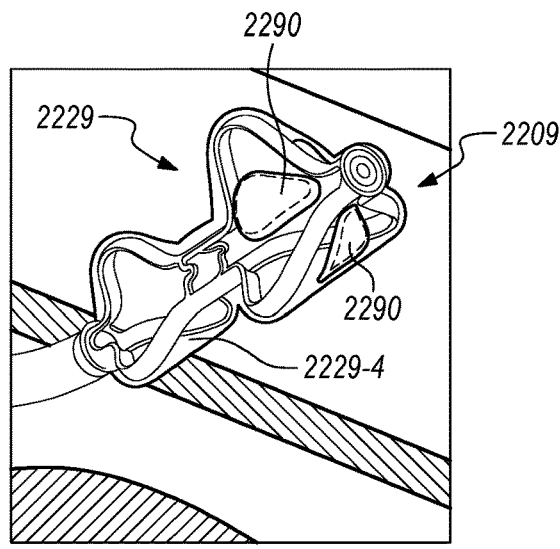

FIGS. 40A-C illustrate another embodiment of the distal portion of the drug delivery device 2200 having an anchoring mechanism 2229 in a deployed expanded configuration. The anchoring mechanism 2229 of FIGS. 40A-B includes a malecot and polymeric cover 2229-4; the polymeric cover 2229-4 further includes a plurality of leaflets 2290. In one embodiment, the polymeric cover 2229-4 is composed of urethane, and the leaflets 2290 are composed of silicone. It should be appreciated that any other suitable biocompatible materials may be used in the distal anchoring mechanisms 2229. The leaflets 2290 are configured as one-way valves, and function as the valves previously described to control therapeutic agent flow into the intracranial SAS and prevent CSF reflux into the device lumen 2207. The leaflets 2290 may further increase the functional valve area, as shown in FIGS. 40A-B. The anchoring mechanism of FIG. 40C includes a double-malecot and polymeric cover 2229-4 having a plurality of leaflets 2290 acting as one-way valve 2209.

Figure 41A:
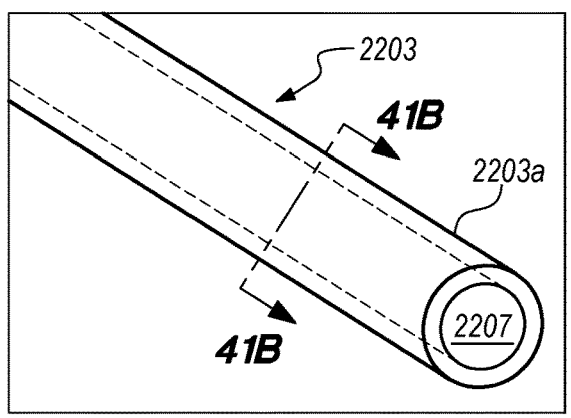
FIGS. 41A-48B are perspective and cross-sectional views of various embodiments of drug delivery device bodies, constructed according to the embodiments of the disclosed invention.

FIGS. 41A-48B illustrate exemplary embodiments of zone II (Mid) of the drug delivery device 2200, according to the disclosed inventions. FIG. 41A illustrates an elongated tubular member 2203 having a proximal portion (not shown), a distal portion 2203a, and a lumen 2207 (FIGS. 41A-B) extending therebetween. FIG. 41B is a cross-sectional view of FIG. 41A. The elongated tubular member 2203 of FIGS. 41A-B is configured to be compressed and/or stretch during delivery of the drug delivery device 2200. The elongated tubular member 2203 of FIGS. 41A-B is composed of silicone and is formed by extrusion. In other embodiments, the elongated tubular member 2203 of zone II (Mid) of the drug delivery device 2200 can be composed of any other suitable biocompatible polymeric material including, for example, polyurethane or silicone-polyurethane blend, and can be formed by any suitable technique.

Figure 41B:
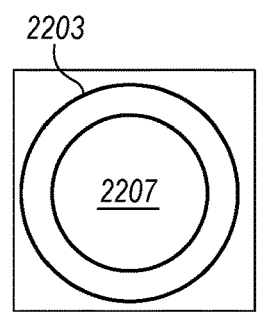
Figure 42A:
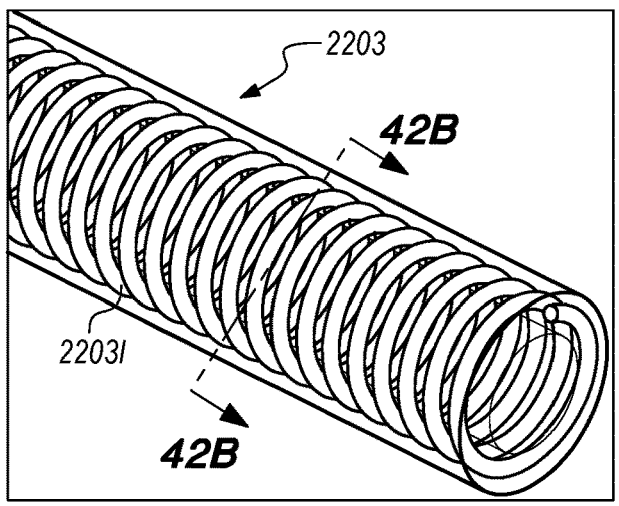
Figure 42B:
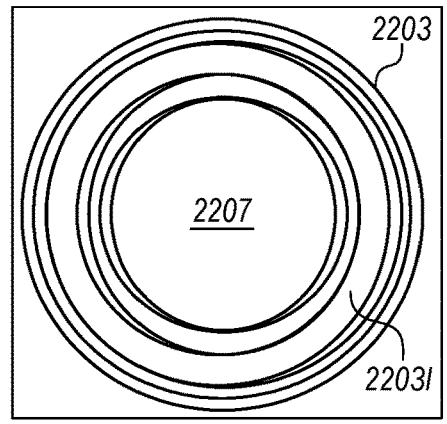

FIG. 42A illustrates the elongated tubular member 2203 of FIGS. 41A-B having an embedded coil element 22031. The coil element 22031 can be composed of any suitable polymeric, metallic material or combination thereof. The coil element 22031 provides reinforcement (e.g., increased column strength) and kink resistance to the zone II (Mid) of the drug delivery device. FIG. 42B is a cross-sectional view of FIG. 42A.

Figure 43A:
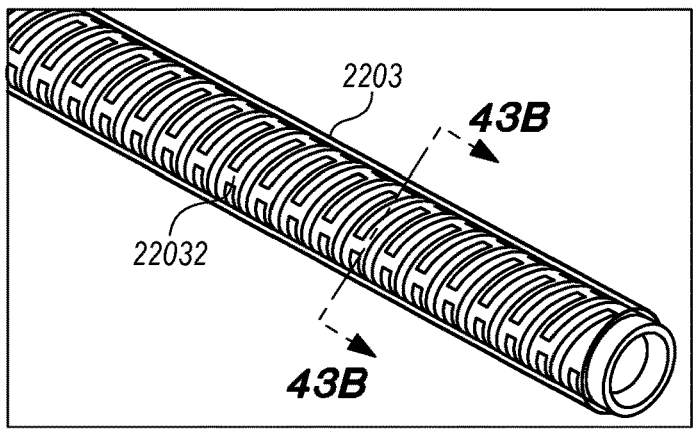
Figure 43B:
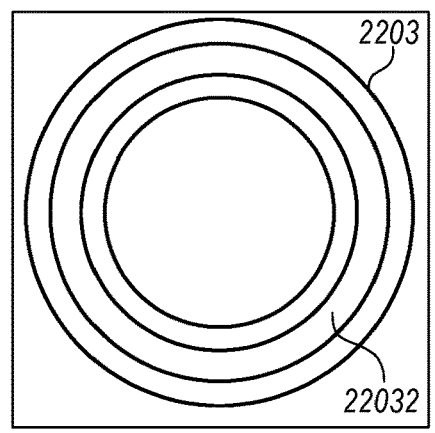

FIG. 43A illustrates the elongated tubular member 2203 of FIGS. 41A-B having an embedded tubular element 22032. The embedded tubular element 22032 can be composed of any suitable materials, such as, platinum, Nitinol®, gold or other biocompatible materials. The embedded tubular element 22032 provides reinforcement (e.g., increased column strength) and kink resistance to the zone II (Mid) of the drug delivery device 2200. Further, the embedded tubular element 22032 includes a plurality of cuts along the length configured to increase flexibility of the element. FIG. 43B is a cross-sectional view of FIG. 43A.

Figure 44A:
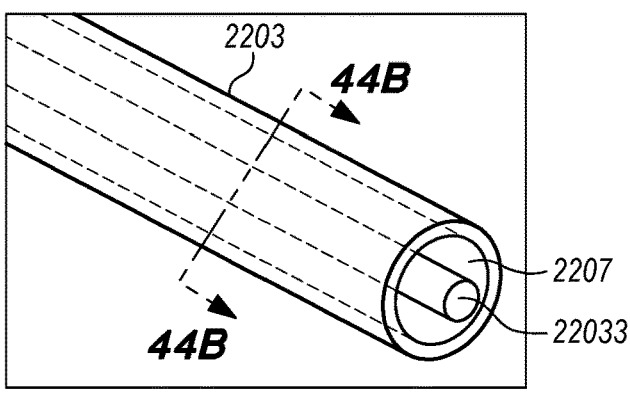
Figure 44B:
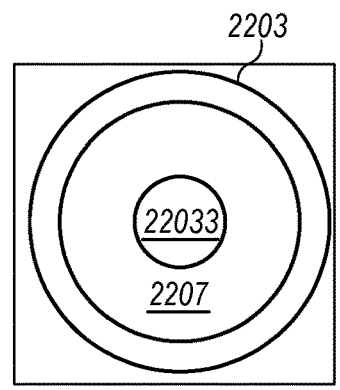
Figure 45A:
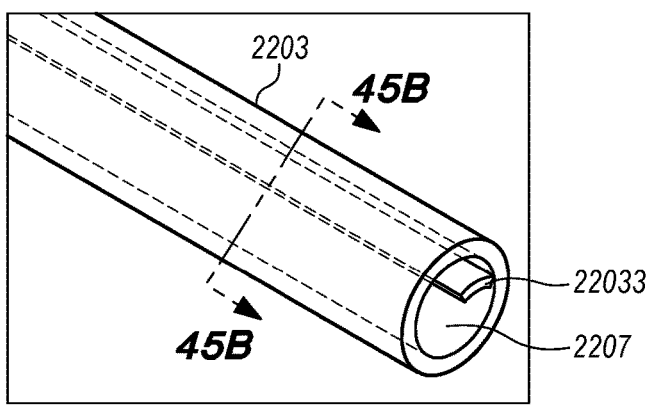
Figure 45B:
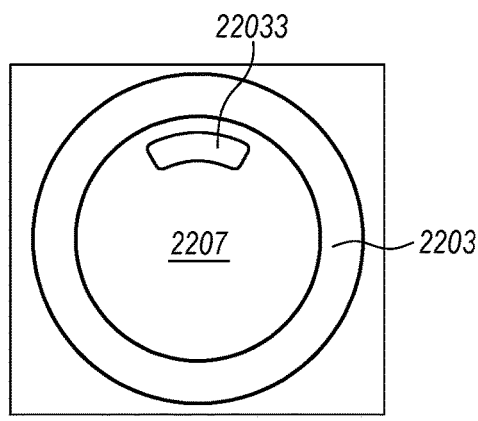
Figure 46A:
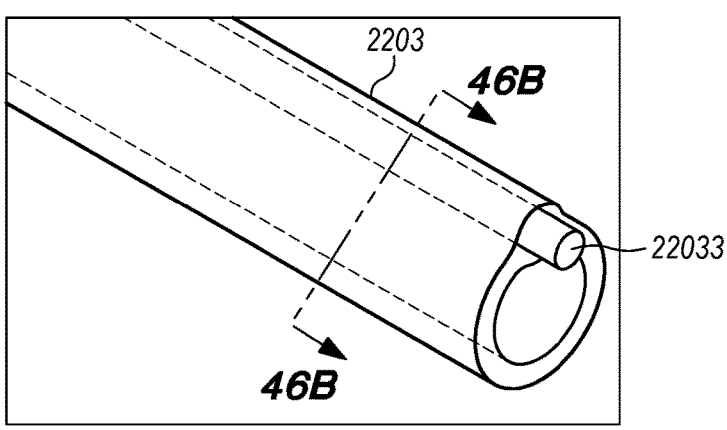
Figure 46B:
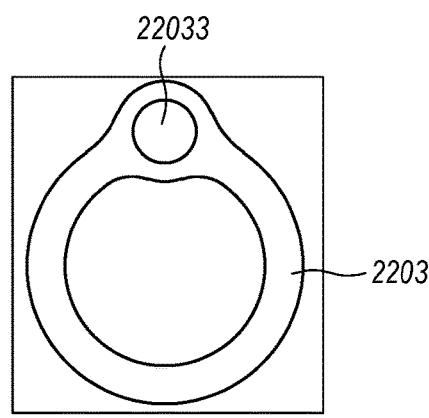
Figure 47A:
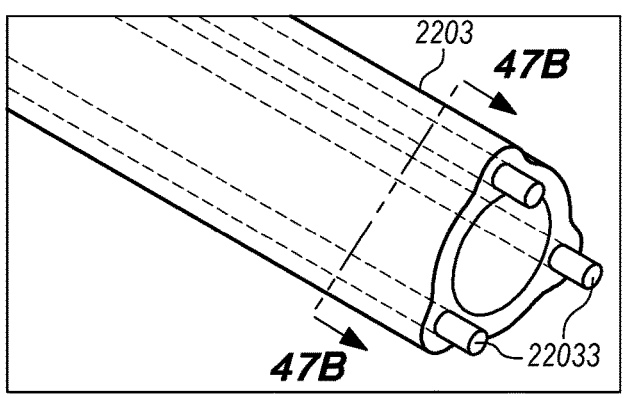
Figure 47B:
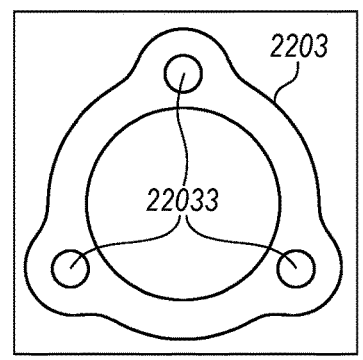
Figure 48A:
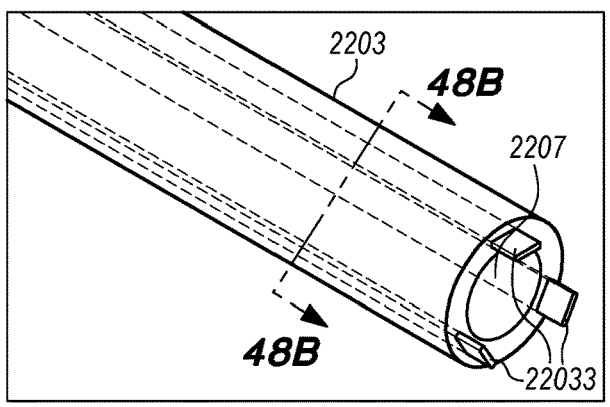
Figure 48B:
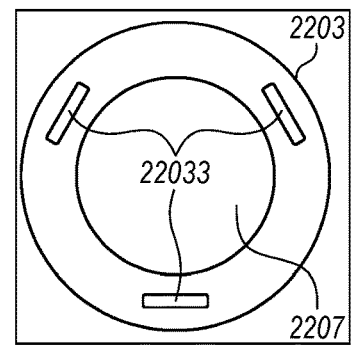

FIGS. 44A-48B illustrate the elongated tubular member 2203 of FIGS. 41A-B having one or more spine elements 22033. The spine element 22033 can be composed of any suitable materials, such as, platinum, Nitinol®, gold or other biocompatible materials. The spine element 22033 is configured to provide reinforcement (e.g., increased column strength) and kink resistance to the zone II (Mid) of the drug delivery device 2200. In some embodiments, the spine element 22033 can be used as drug delivery device shaping stylets. The spine element 22033 can be an elongated rod or cylindrical member (FIGS. 44A-B, 46A-B), an arcuate elongated member (FIGS. 45A-B), a flat elongated member (FIGS. 48A-B), or can have any other suitable configuration. In the embodiments of FIGS. 44A-B, the spine element 22033 is disposed in the lumen 2207 of the tubular element, such as concentrically disposed (FIGS. 44A-B) or laterally disposed (FIGS. 45A-B). In the embodiments of FIGS. 46A-48B, a plurality of spine elements 22033 is embedded in the tubular element 2203. FIGS. 44B-48B are a cross-sectional view of the respective FIGS. 44A-48A.

FIGS. 44A-48B illustrate the elongated tubular member 2203 of FIGS. 41A-B having one or more spine elements 22033. The spine element 22033 can be composed of any suitable materials, such as, platinum, Nitinol®, gold or other biocompatible materials. The spine element 22033 is configured to provide reinforcement (e.g., increased column strength) and kink resistance to the zone II (Mid) of the drug delivery device 2200. In some embodiments, the spine element 22033 can be used as drug delivery device shaping stylets. The spine element 22033 can be an elongated rod or cylindrical member (FIGS. 44A-B, 46A-B), an arcuate elongated member (FIGS. 45A-B), a flat elongated member (FIGS. 48A-B), or can have any other suitable configuration. In the embodiments of FIGS. 44A-B, the spine element 22033 is disposed in the lumen 2207 of the tubular element, such as concentrically disposed (FIGS. 44A-B) or laterally disposed (FIGS. 45A-B). In the embodiments of FIGS. 46A-48B, a plurality of spine elements 22033 is embedded in the tubular element 2203. FIGS. 44B-48B are a cross-sectional view of the respective FIGS. 44A-48A.

Figure 49A:
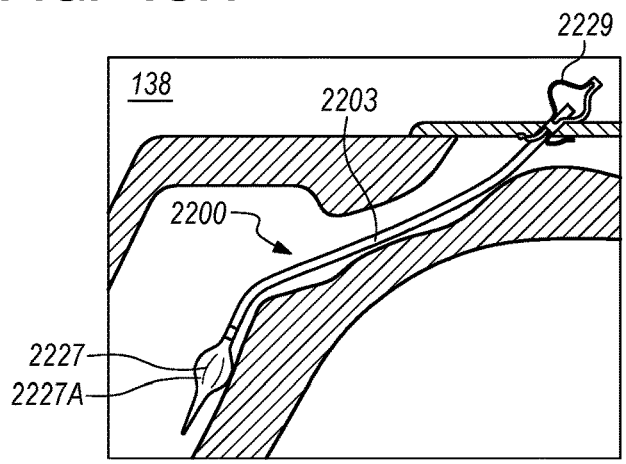
FIGS. 49A-54B are perspective and cross-sectional views of various embodiments of drug delivery devices according to the embodiments of the disclosed invention.
Figure 49B:
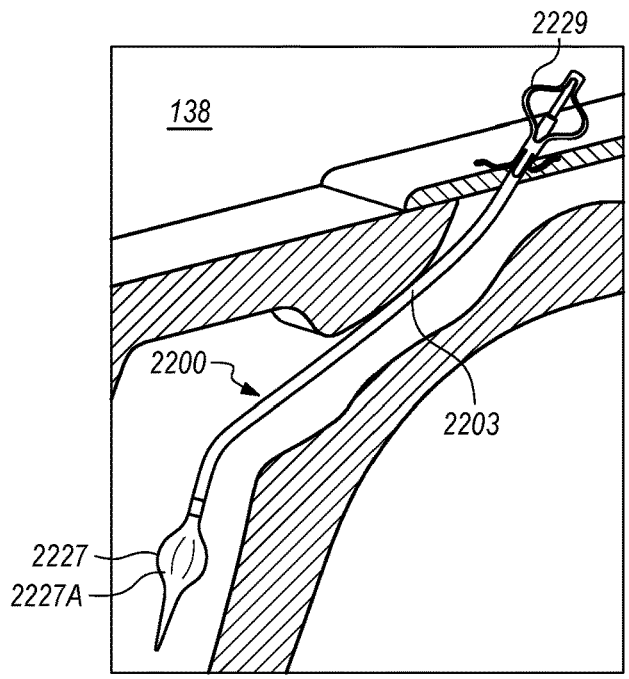

FIGS. 49A-B illustrate exemplary embodiments of zone III (Proximal) of the drug delivery device 2200 according to the disclosed inventions. Additionally, FIGS. 49A-B illustrate deployed drug delivery devices 2200 having previously disclosed zones I and II, in combination with zone III of the drug delivery devices that will be described below. As shown in FIGS. 49A-B, a proximal anchoring mechanism 2227 of device 2200 includes an expandable member and having a bulb-like configuration. The proximal portion of the drug delivery device further includes a refilling coupler 2227A proximally disposed to the anchoring mechanism 2227. FIGS. 49A-B are perspective views of the drug delivery device 2200; the device further having the elongated tubular member 2203 of FIGS. 41A-B in zone II, and the malecot-flarecot anchoring mechanism 2229 of FIG. 35 in zone I.

Figure 50A:
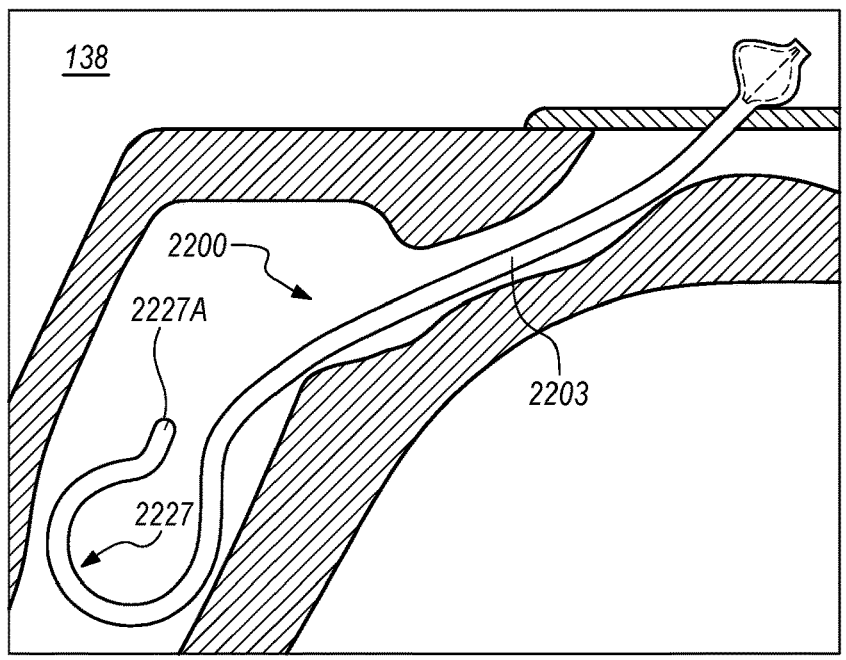
Figure 50B:
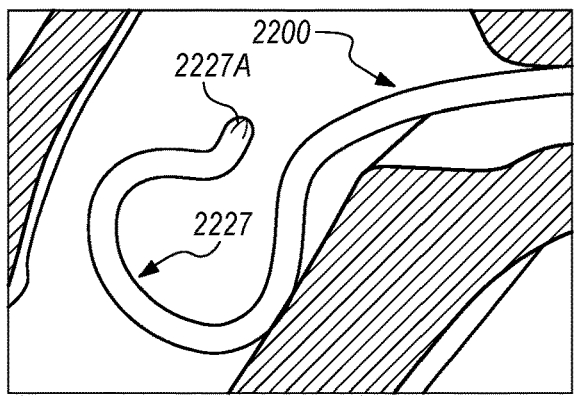
Figure 50C:
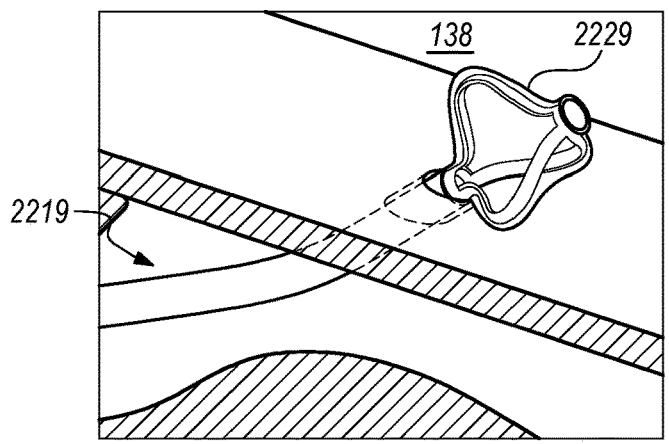

FIGS. 50A-C illustrate another exemplary embodiment of zone III (Proximal) of the drug delivery device 2200 having a proximal anchoring mechanism 2227. As shown in FIGS. 50A-B, the proximal anchoring mechanism 2227 includes a spine composed of shape memory material, such as Nitinol®, or other super-elastic alloys. For example, as shown in FIG. 50B, the spine is configured to form the loop in zone III (Proximal) when the drug delivery device is in the deployed configuration. The proximal anchoring mechanism 2227 of FIGS. 50A-B is configured to facilitate device retrieval (e.g., the loop allows for snaring, grabbing, engaging of a retrieval system to the device) and/or further maintain a refilling coupler 2227A (if present in the particular device embodiment) separated from the vessel wall to prevent encapsulation. FIGS. 50A-C are perspective views of the drug delivery device 2200; the device 2200 further having the elongated tubular member of FIGS. 45A-B or 46A-B in zone II, and a single malecot-liner distal anchoring mechanism in zone I, as better appreciated in FIG. 50C.

Figure 51A:
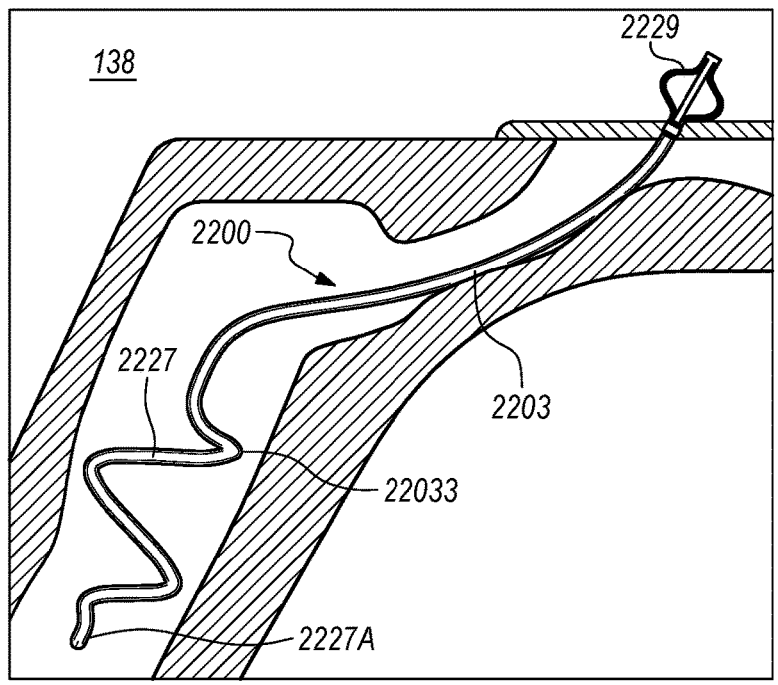
Figure 51B:
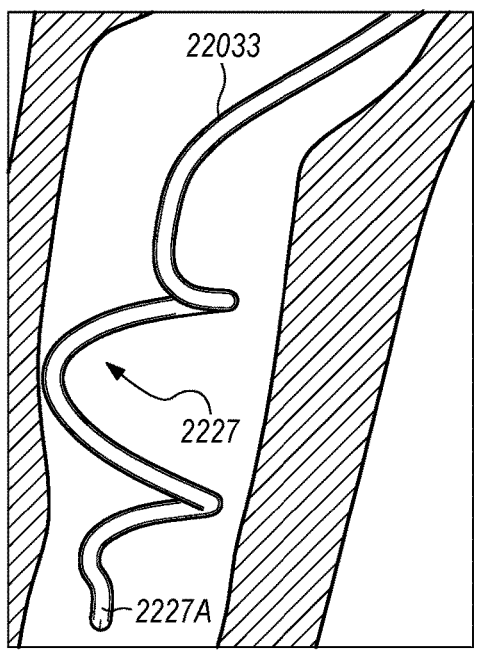
Figure 51C:
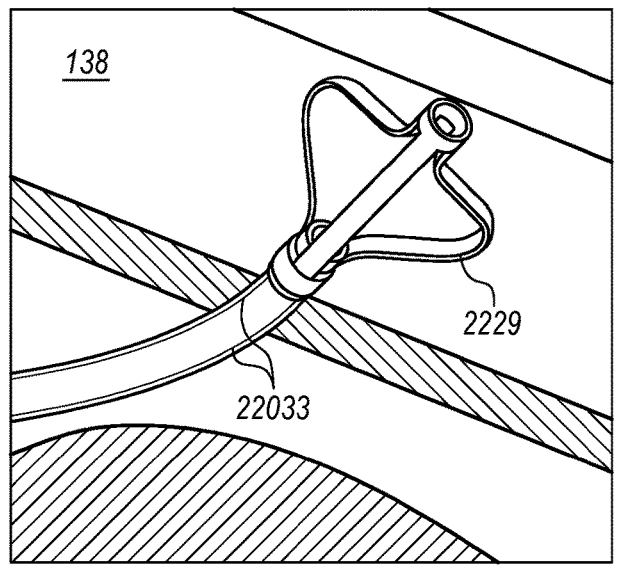

FIGS. 51A-C illustrate yet another exemplary embodiment of zone III (Proximal) of the drug delivery device 2200 having a proximal anchoring mechanism 2227. As shown in FIGS. 51A-B, the proximal anchoring mechanism 2227 includes a plurality of spine elements 22033 composed of shape memory material, such as Nitinol®, or other super-elastic alloys, configured to form a coil when the drug delivery device 2200 is deployed. The proximal anchoring mechanism 2227 of FIGS. 51A-B is configured to secure the drug delivery device in the venous lumen where deployed (e.g., IPS, jugular vein, subclavian vein, etc.) and/or maintain a refilling coupler 2227A (if present in the particular device embodiment) separated from the vessel wall to prevent encapsulation. FIGS. 51A-C are perspective views of the drug delivery device 2200; the drug delivery device further having the elongated tubular member 2203 of FIGS. 46A-B or 47A-B in zone II, and the malecot distal anchoring mechanism 2229 of FIG. 36 in zone I.

Figure 52A:
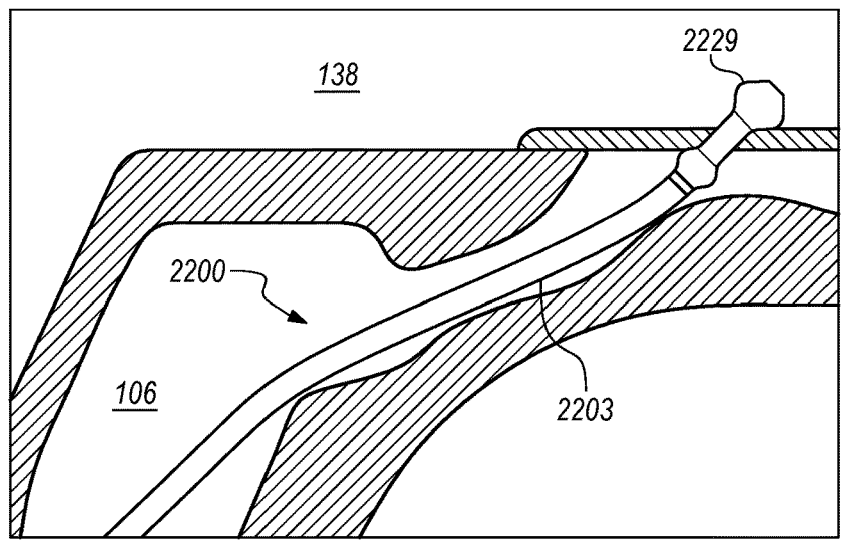
Figure 52B:
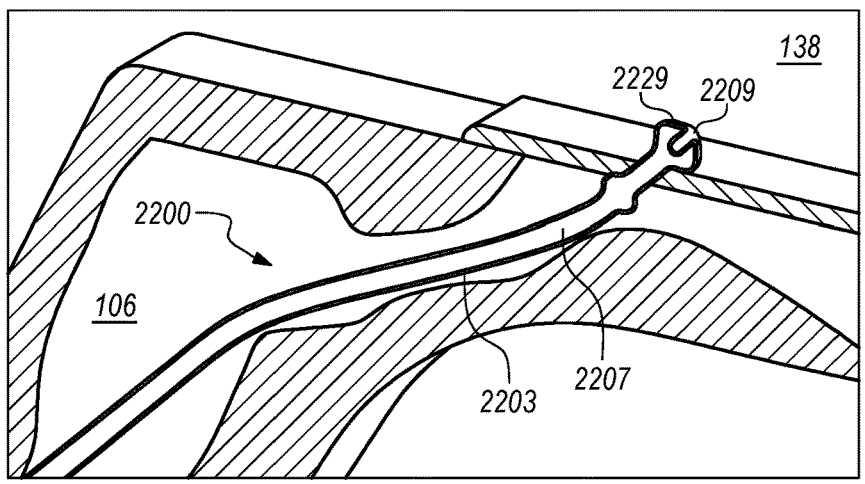
Figure 52C:
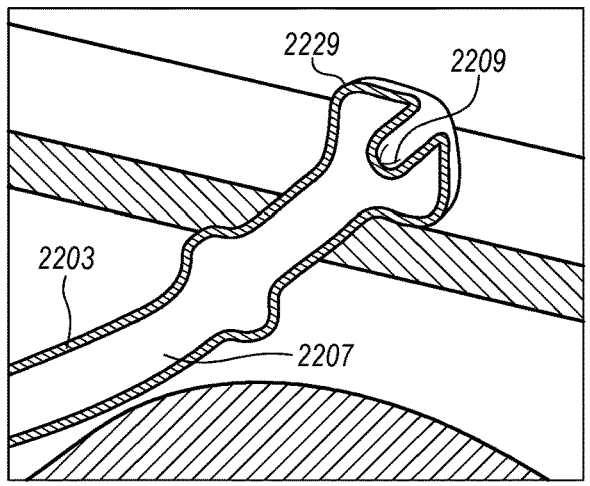

FIGS. 52A-C illustrate another exemplary embodiment of drug delivery device 2200. As shown in FIGS. 52A-B, the zone III (Proximal) includes the configuration of the elongated tubular element 2203 of zone II (Mid) of FIGS. 41A-B, and can extend to proximal portion connecting with an access port 27 as disclosed herein. FIGS. 52A-C are perspective views of the drug delivery device 2200; the device 2200 having the elongated tubular member 2203 and drug delivery lumen 2207 of FIGS. 41A-B in zone 2, and the anchoring mechanism 2229 of FIG. 38 in zone 1. In the embodiments of FIGS. 52A-C a one-way valve 2209 is disposed in the distal anchoring mechanism 2229.

Figure 53:
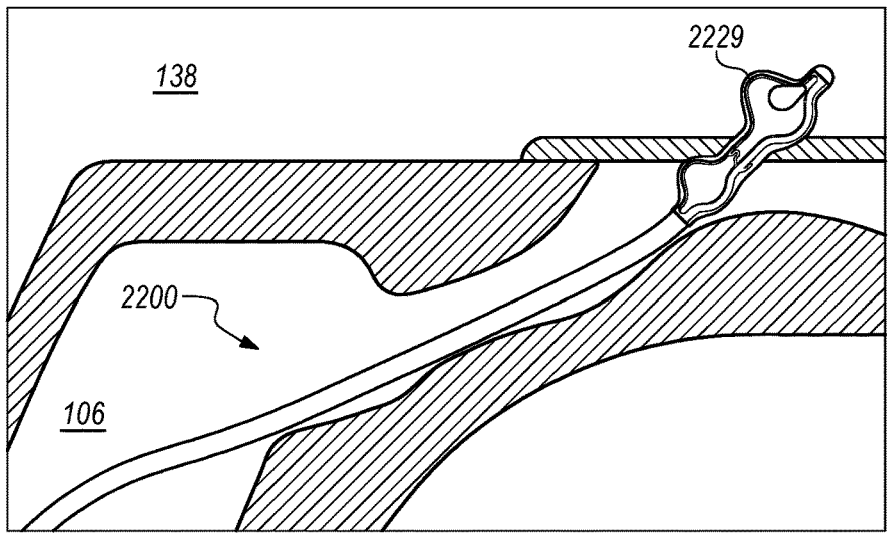

FIG. 53 illustrates the embodiment of zone III (Proximal) of the drug delivery device 2200 of FIGS. 52A-B having the distal anchoring mechanism 2229 of FIG. 40C.

Figure 54A:
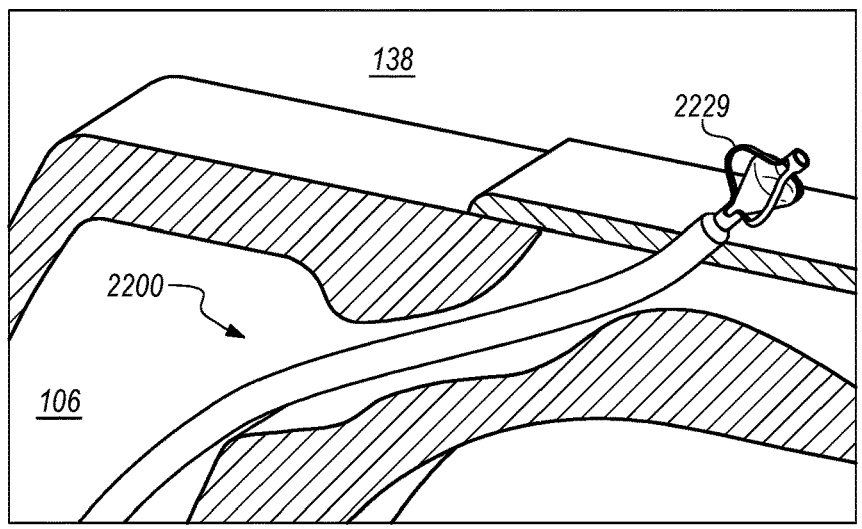
Figure 54B:
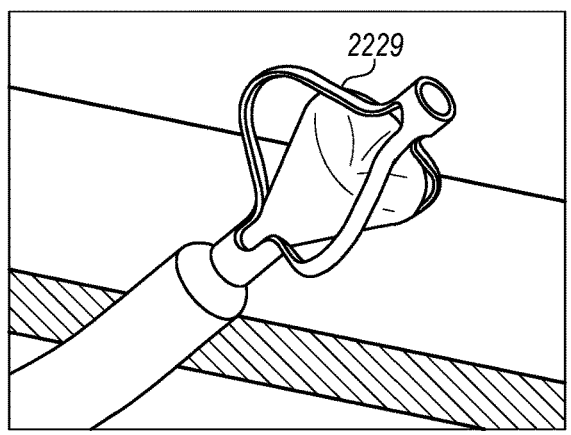

FIGS. 54A-B illustrates the embodiment of zone III (Proximal) of FIGS. 52A-B having the distal anchoring mechanism 2229 of combined FIGS. 36 with 39A-B. Embodiments of drug delivery device 200, 2200 can be prepared and loaded into embodiments of delivery catheter 304, 3304 (e.g., during device manufacturing or in a clinical setting, e.g., prior to the drug delivery device implantation procedure) using one or more embodiments of a device loading tool disclosed in U.S. Provisional Patent Application No. 62/755,078 filed on Nov. 2, 2018, and U.S. Provisional Patent Application No. 62/805,091 filed on Feb. 13, 2019, incorporated by reference herewith.

Figure 55A:
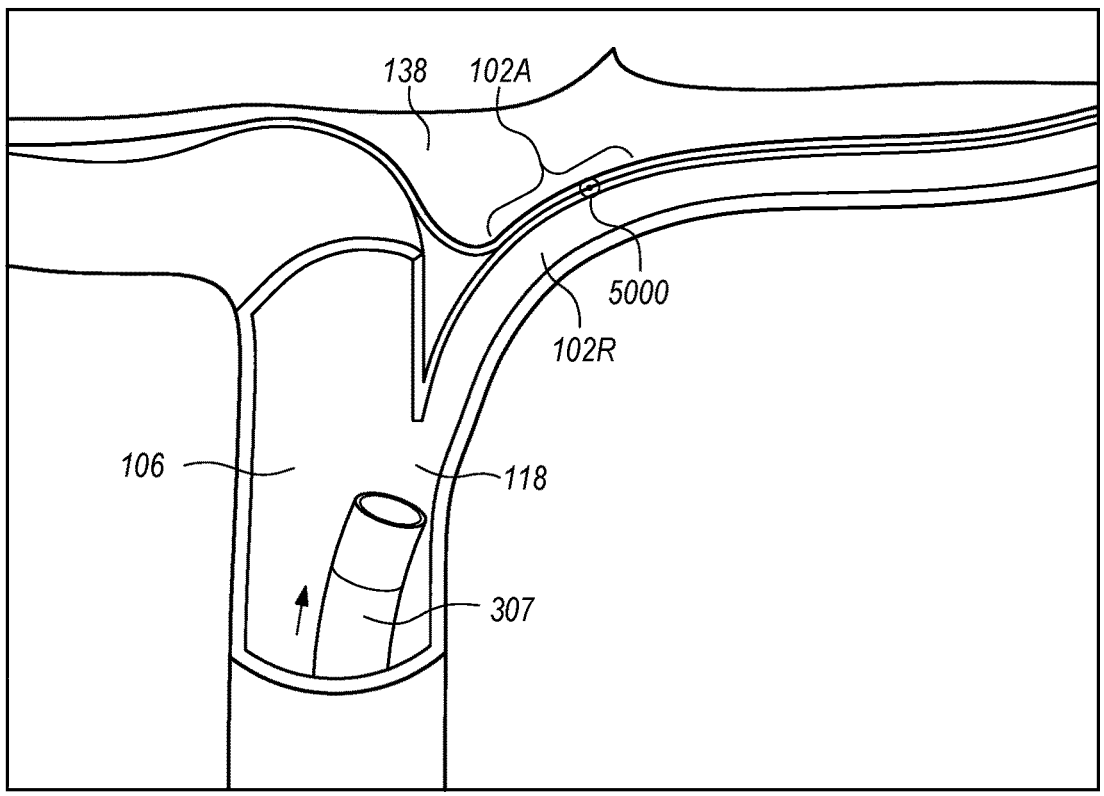
FIGS. 55A-P are perspective and cross-sectional views of exemplary methods for endovascular drug delivery and endovascular drug delivery device deployment procedures, according embodiments of the disclosed inventions.
Figure 55B:
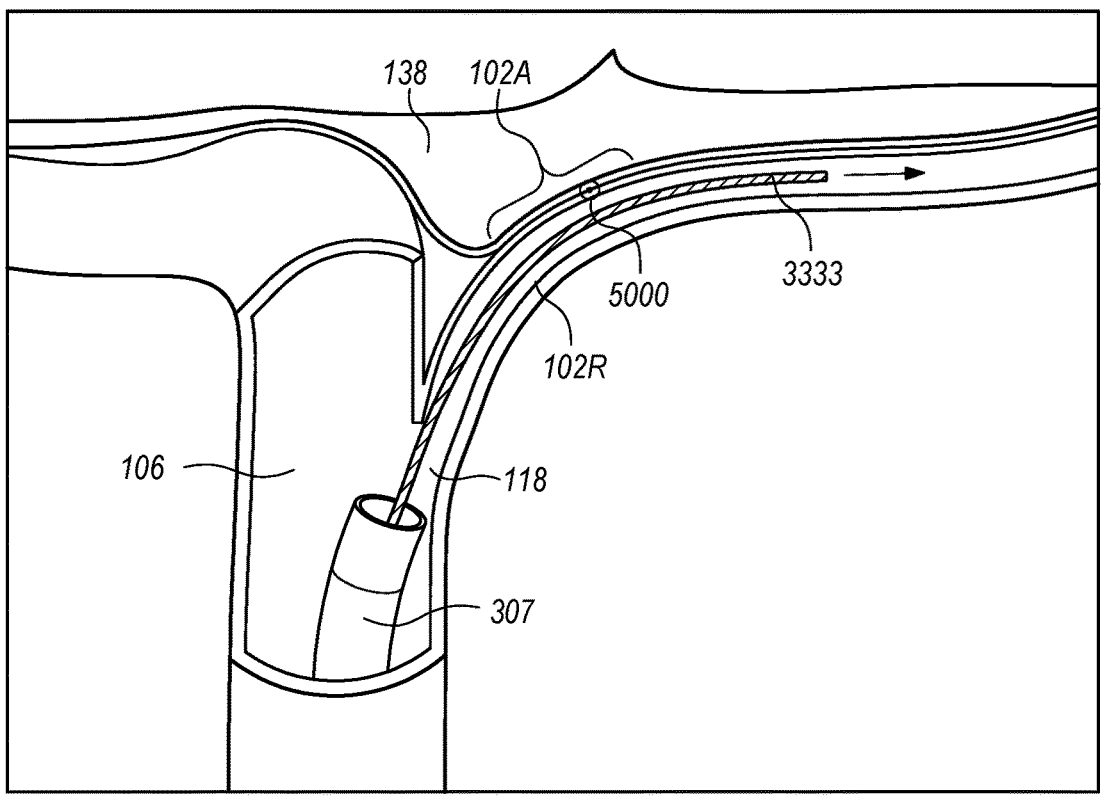
Figure 55C:
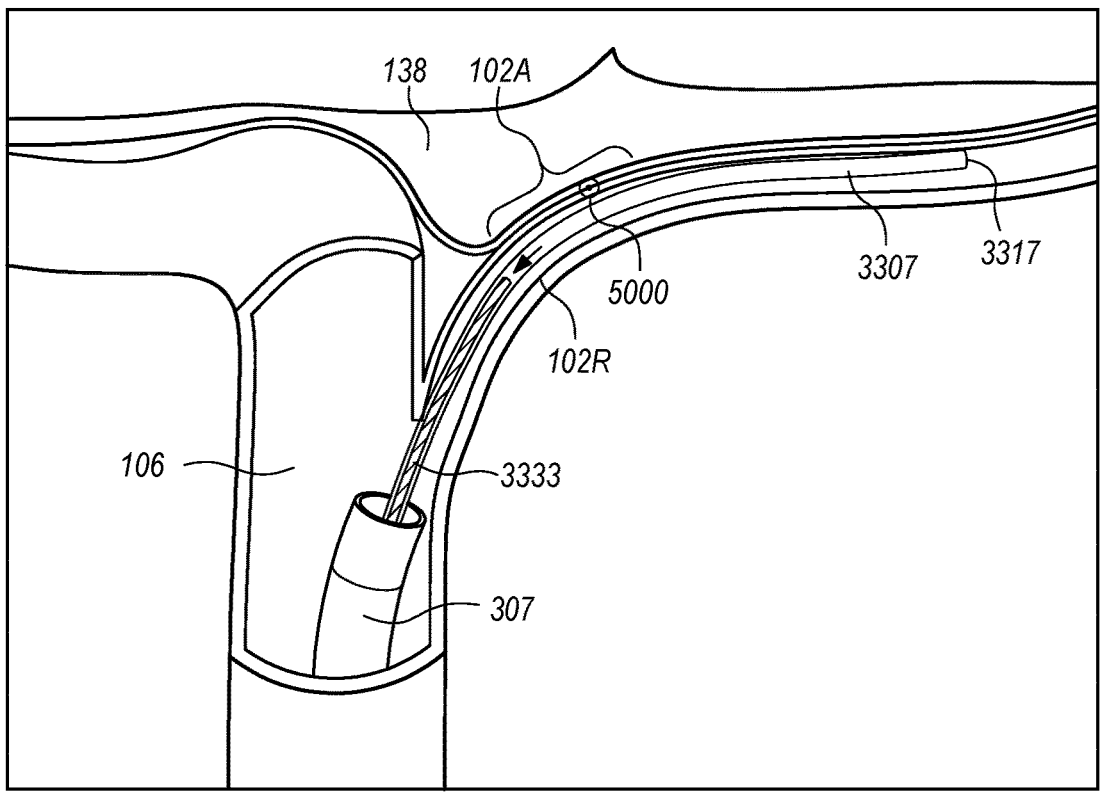
Figure 55D:
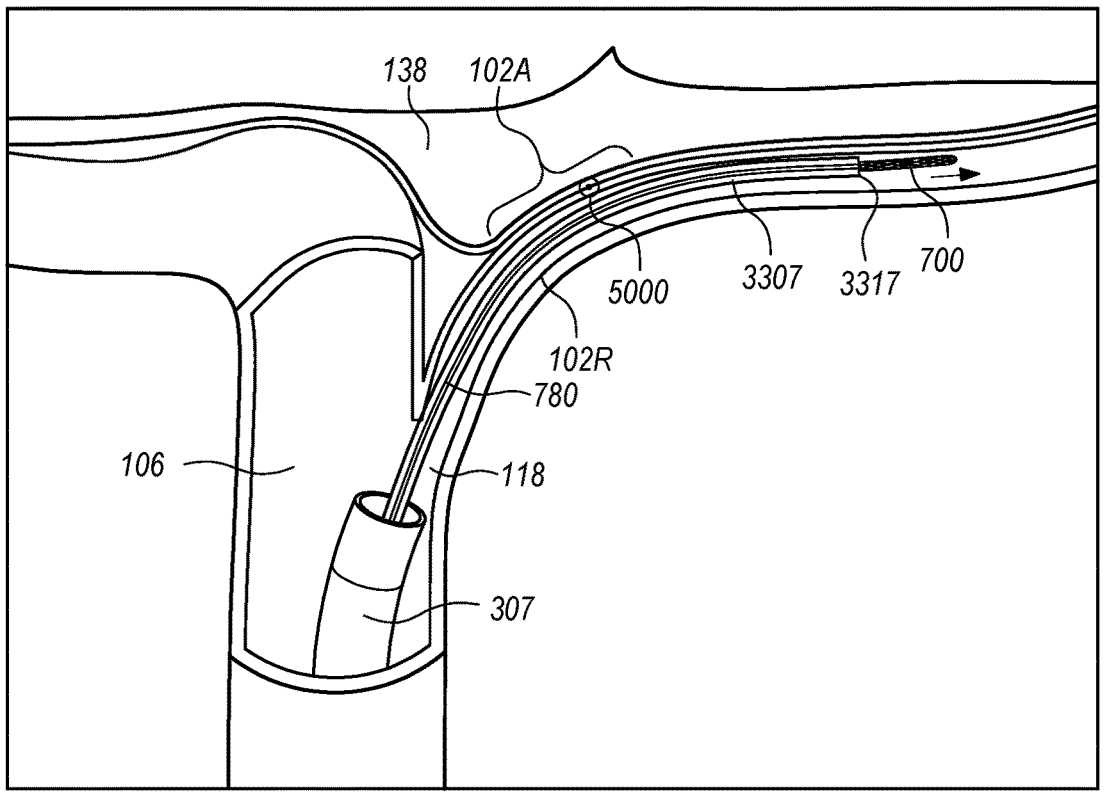
Figure 55E:
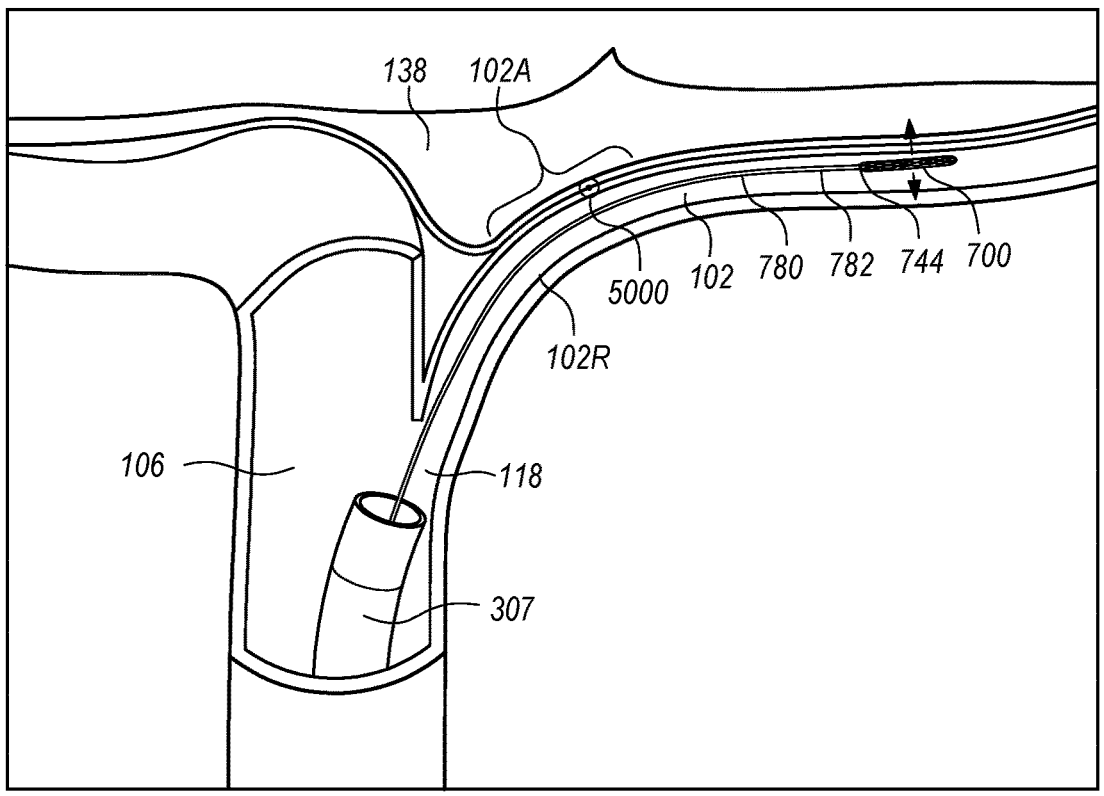
Figure 55F:
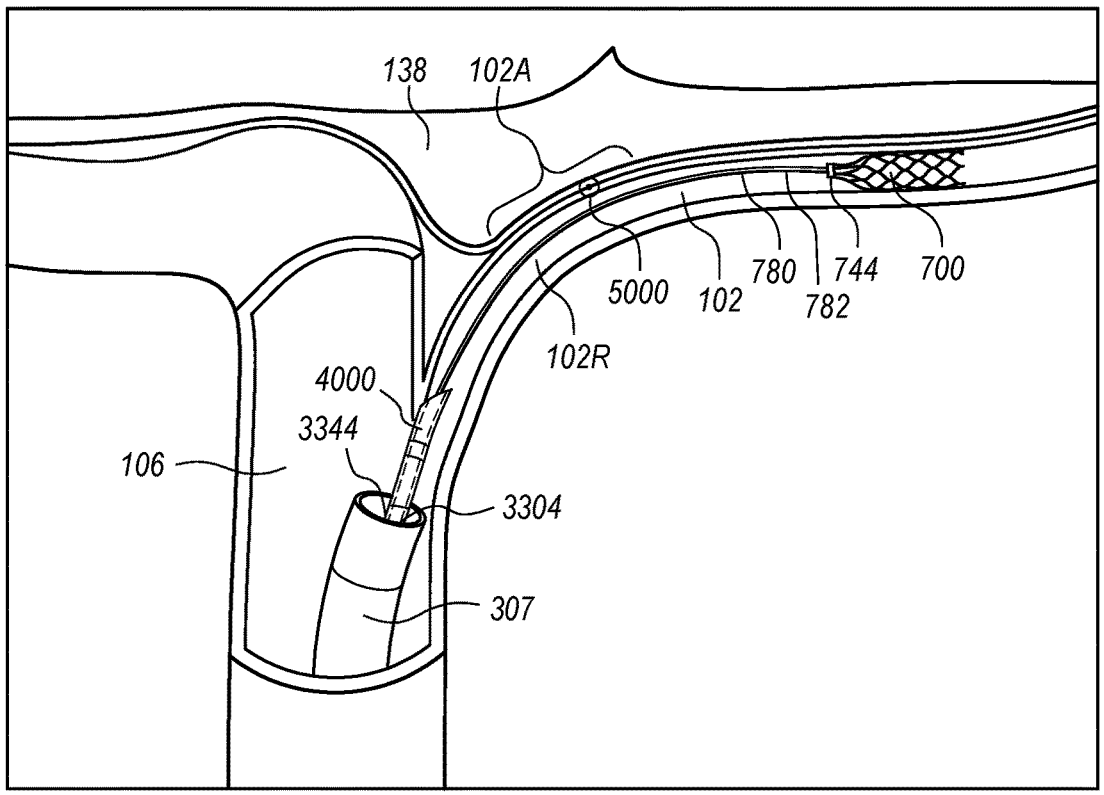
Figure 55G:
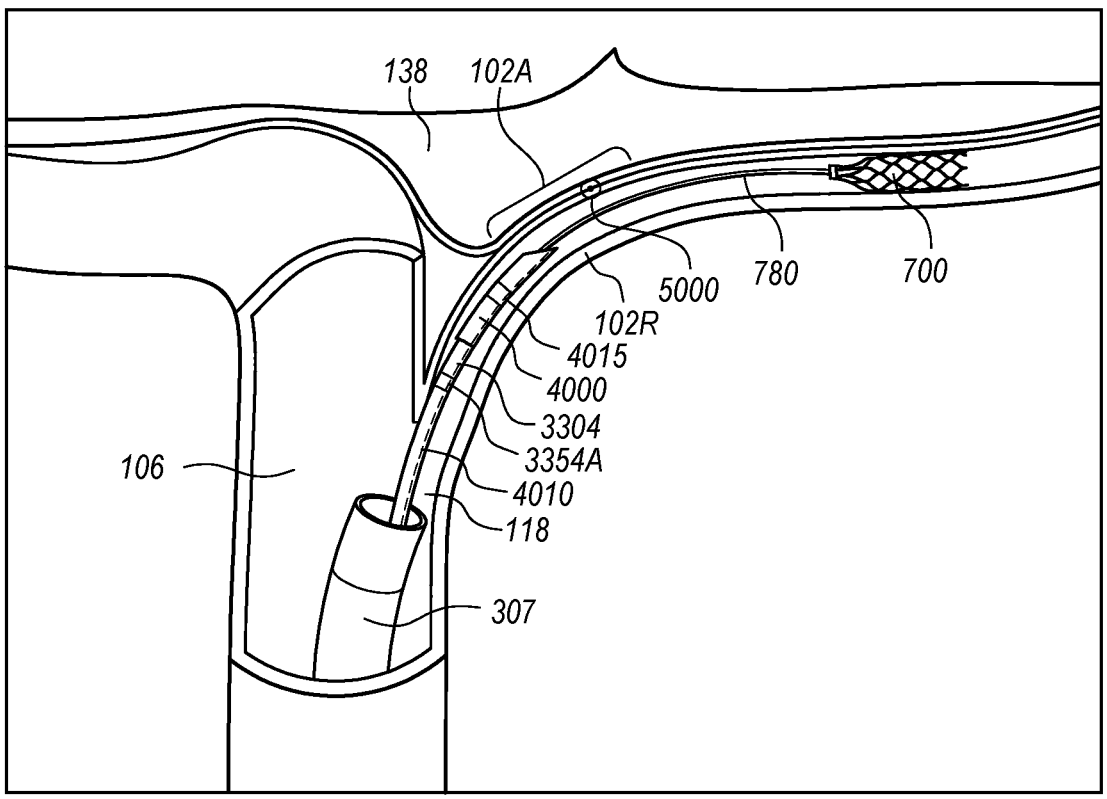
Figure 55H:
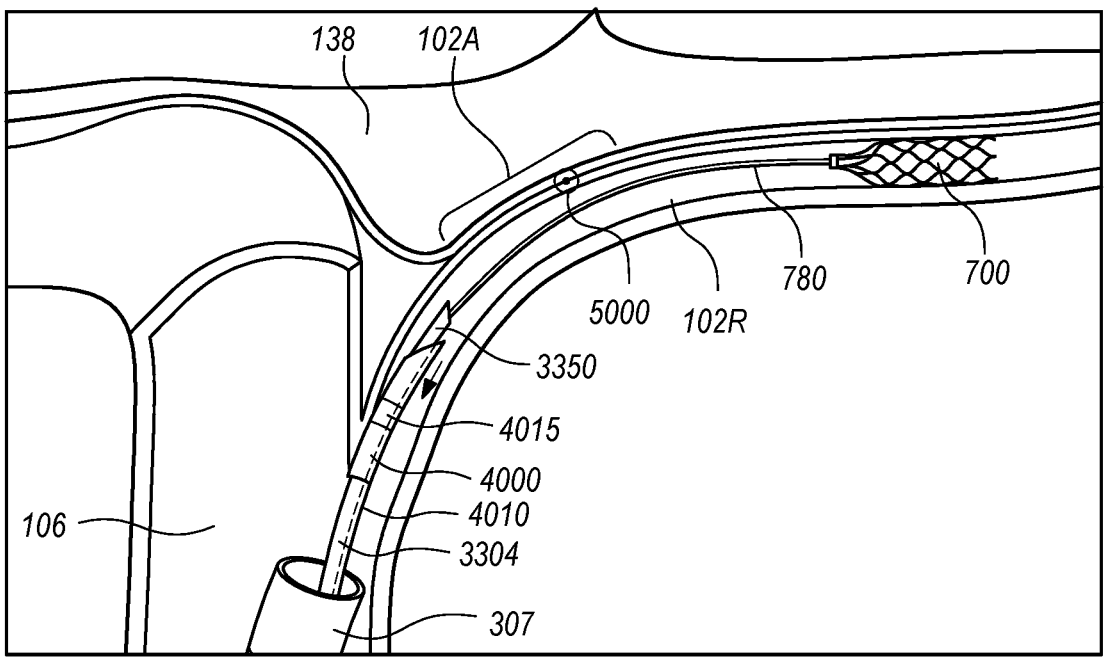
Figure 55I:
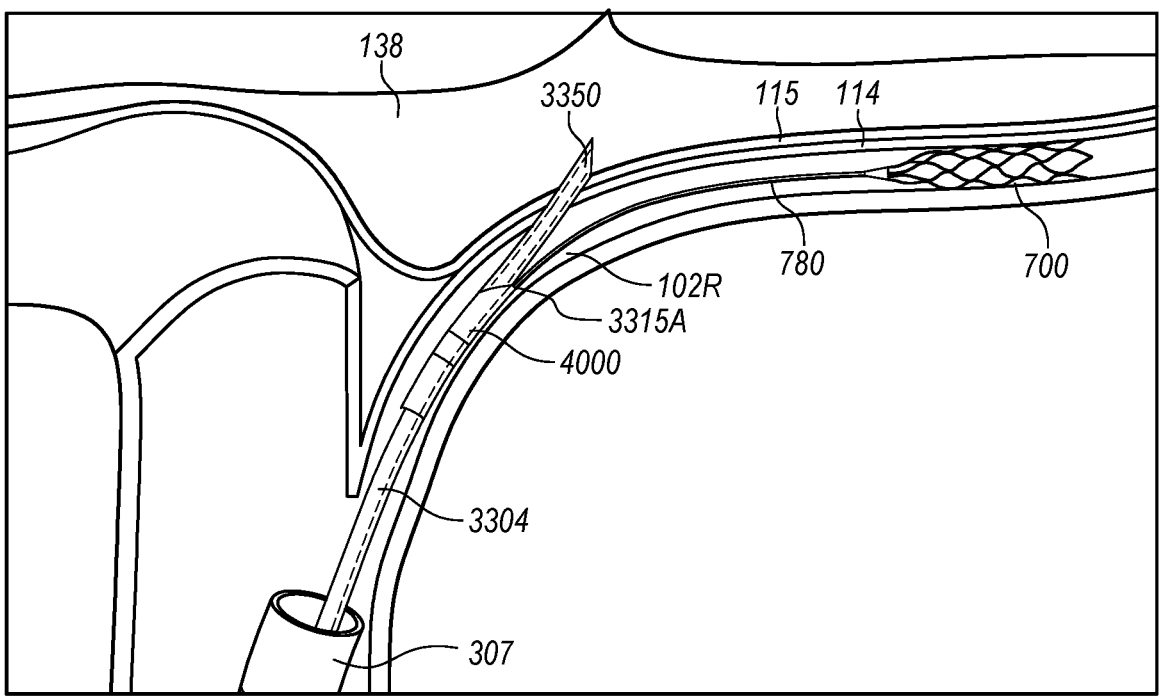
Figure 55J:
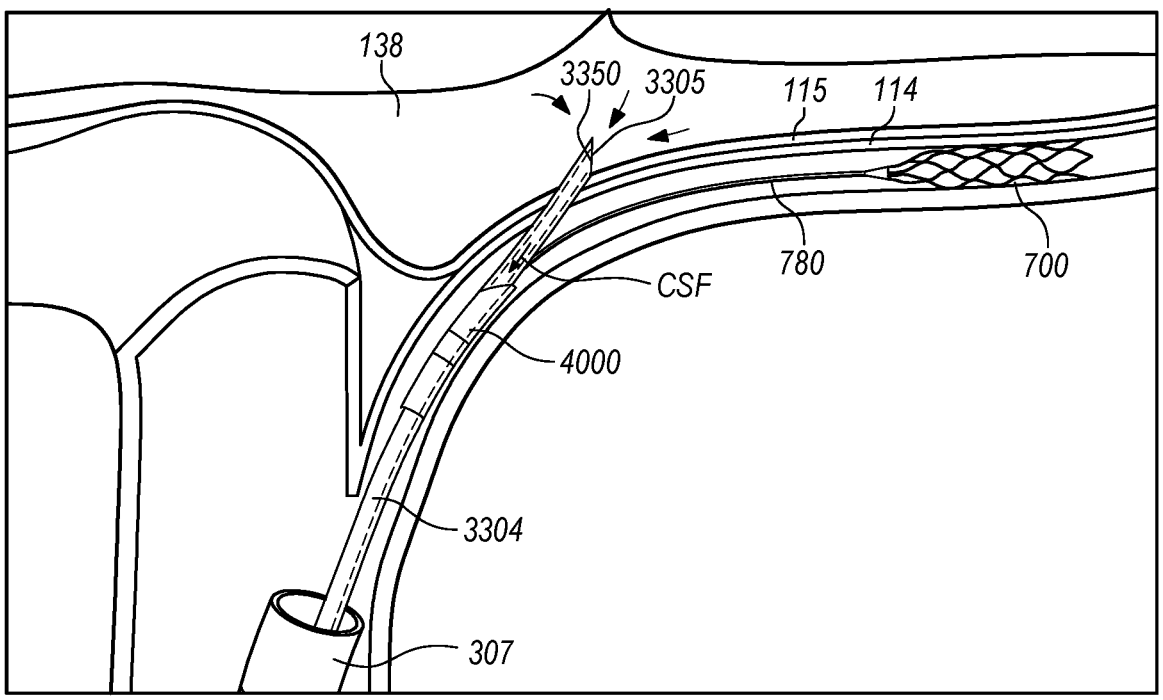
Figure 55K:
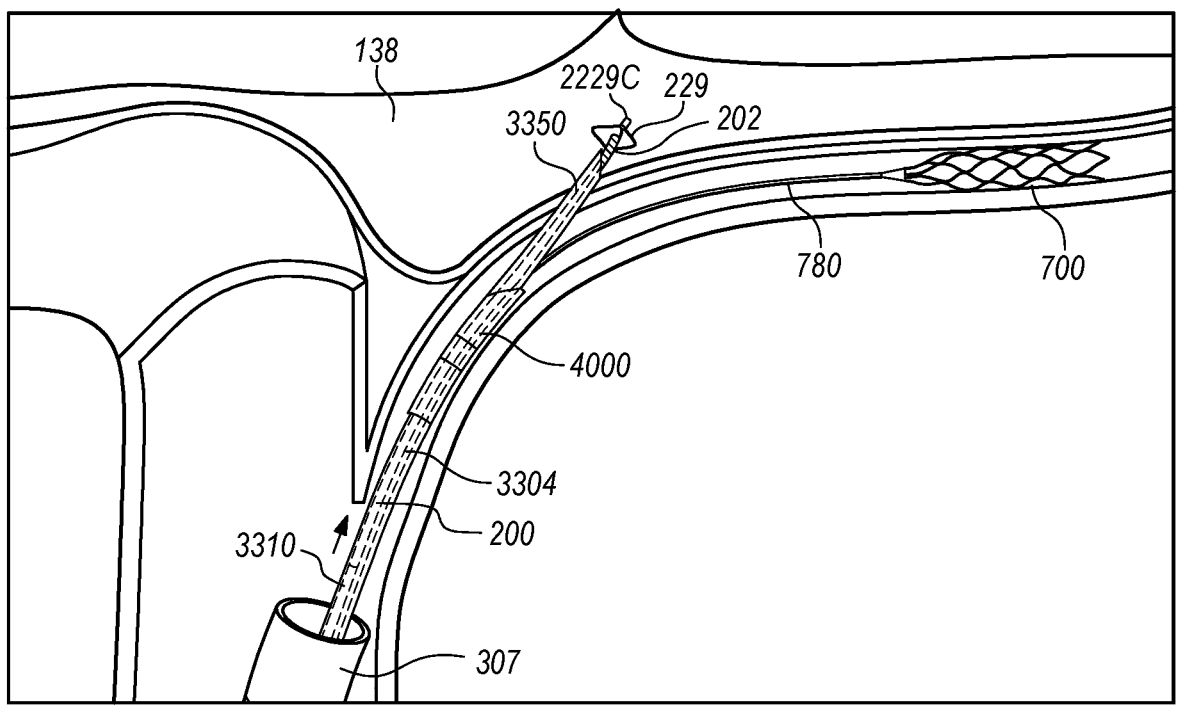
Figure 55L:
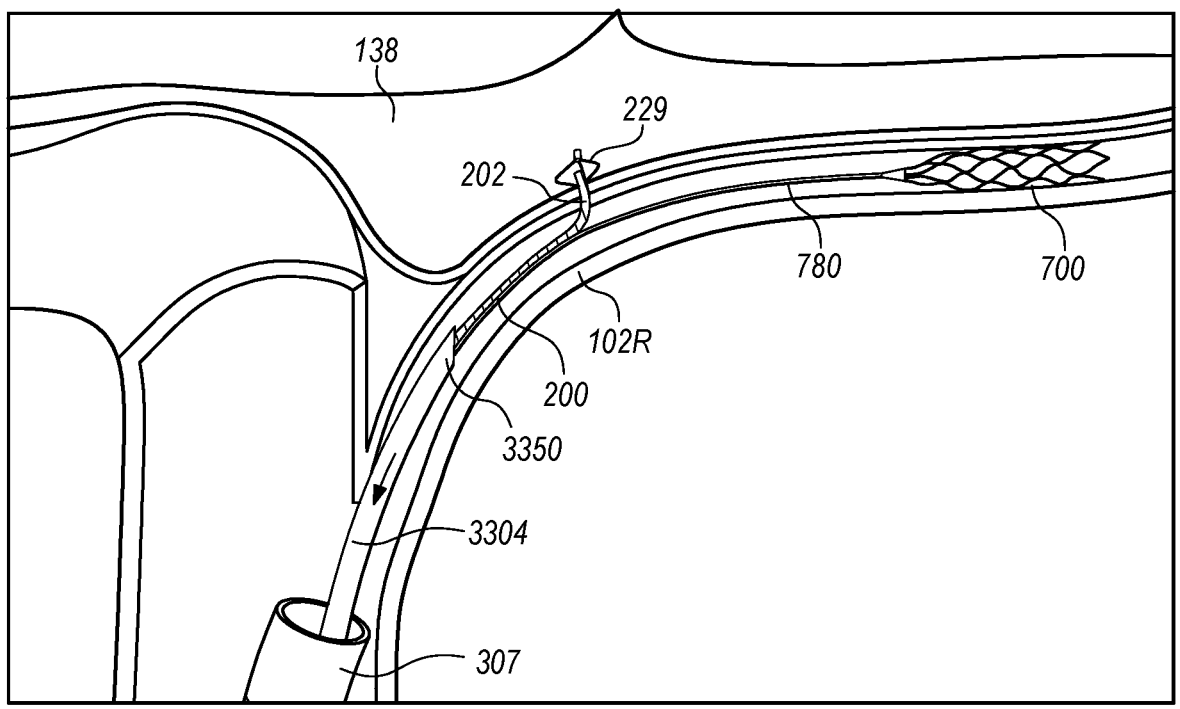
Figure 55M:
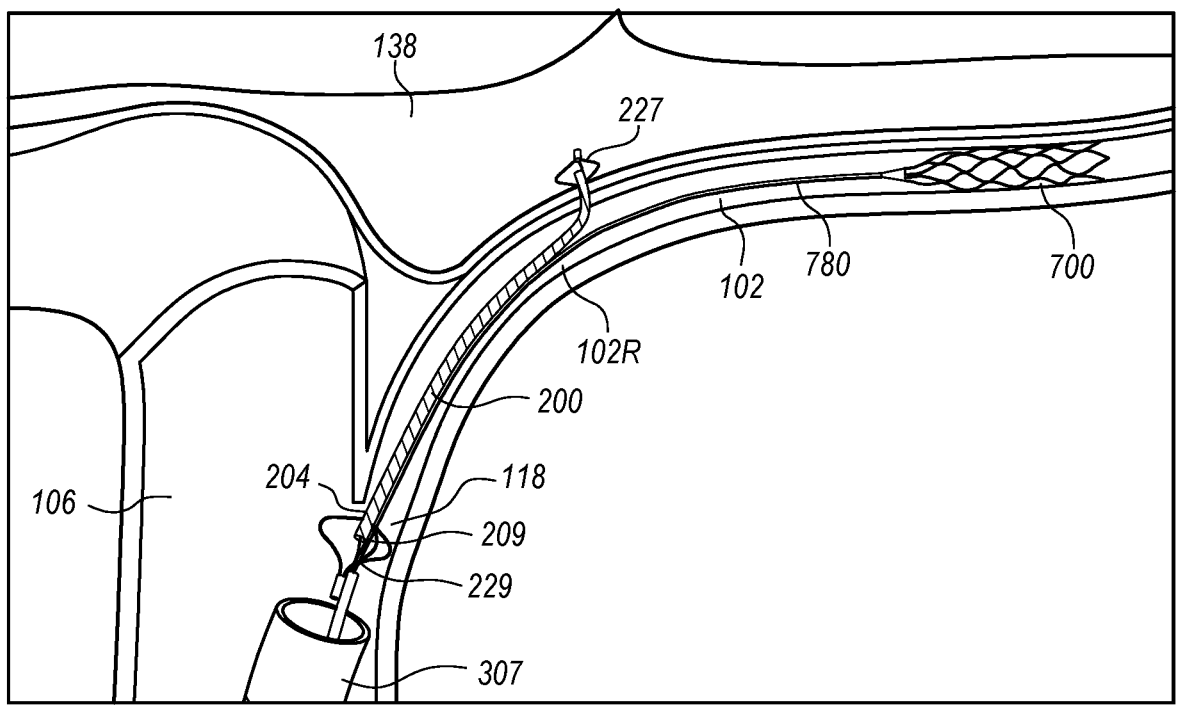
Figure 55N:
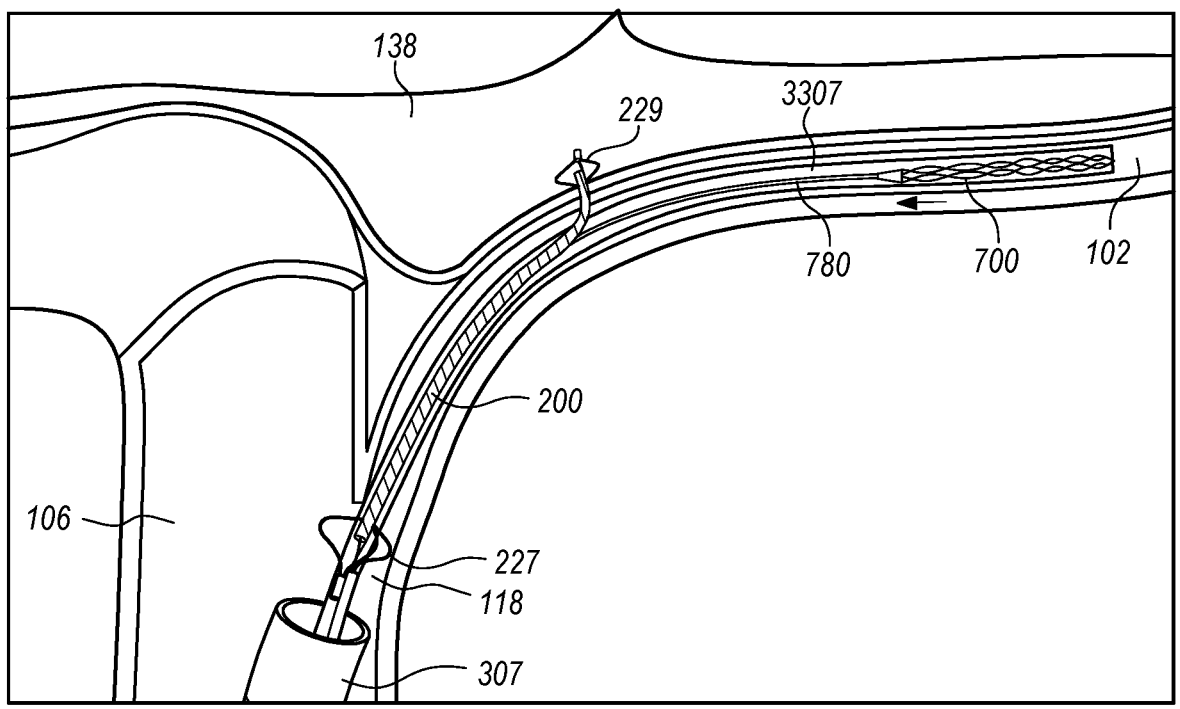
Figure 55O:
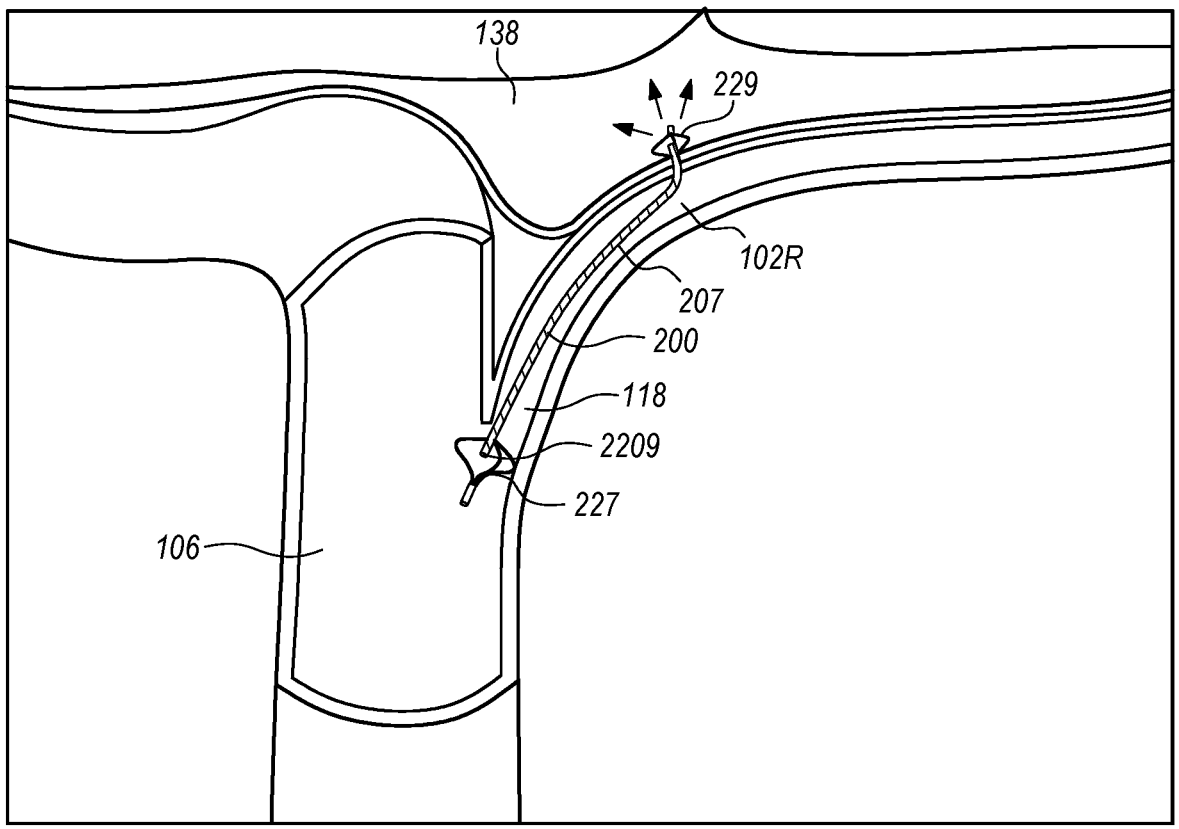
Figure 55P:
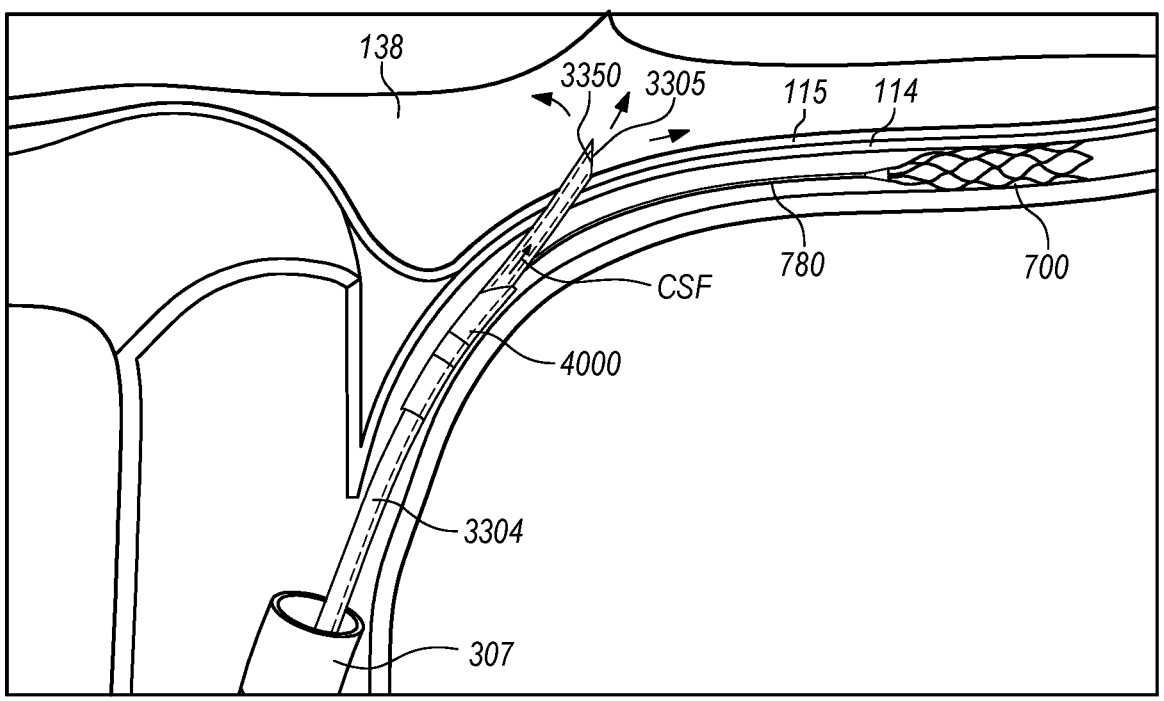

FIGS. 55A-P illustrate an exemplary procedure for administering a therapeutic agent and drug delivery device deployment procedure in a patient using embodiments of the imaging methods disclosed herein. FIGS. 55A-J further describe an exemplary endovascular drug delivery procedure including administration of a therapeutic agent from a delivery catheter into the intracranial SAS The clinician can obtain CT and/or MRI imaging (e.g., coronal, T2, thin cut MRI images with gadolinium contrast) studies of the patient's intracranial anatomy to ascertain the sizing and relative proximity between the patient's right IPS 102R and left IPS 102L, CP angle cistern 138, arterial structures (e.g., basilar artery), and surrounding bony anatomy; such imaging can also be used to assess the volume of unobstructed CSF space of CP angle cistern 138 surrounding the left and right IPS channels relative to a target penetration site 5000 in an IPS 102 where an anastomosis will be made during the drug delivery device implant procedure (or procedure to administer a therapeutic agent to the intracranial SAS). The clinician can use this pre-procedure imaging to select one or more preferred drug delivery device deployment locations along the first curved portion 102A and/or second curved portion 102B in the patient's right IPS 102R and/or left IPS 102L. To further illustrate the following exemplary procedure, the clinician selects the patient's right IPS 102R and a target penetration site 5000 along the first curve 102A of the IPS based on the pre-procedure MRI imaging study, as shown in FIG. 55A.

The clinician gains access to the patient's venous vasculature through the patient's right femoral vein using an introducer kit (e.g., Micropuncture Introducer Set from Cook Medical of Bloomington, Ind.) and the Seldinger technique. The clinician then navigates a guide wire (e.g., 0.035" guide wire such as an 0.035" GLIDEWIRE from Terumo Interventional Systems of Somerset, N.J.) and a guide catheter 307 (e.g., 6 Fr catheter such as 6Fr ENVOY Guiding Catheter from Codman Neuro of Raynham, Mass.) through the femoral vein access point, distally into the right jugular vein. The clinician can position the distal end of the guide catheter 307 about the JV-IPS junction 118 as shown in FIG. 55A, and in certain patient anatomies, the distal end of the guide catheter can access the proximal portion of the IPS 102. Optionally, a shuttle sheath (e.g., 7Fr Flexor Shuttle Guiding Sheath from Cook Medical of Bloomington, Ind.) may be advanced through the patient's venous vasculature, prior to advancing the guide catheter 307; the guide catheter 307 can then be advanced through the shuttle sheath lumen to the jugular vein or JV-IPS junction 118. The shuttle sheath can provide additional support to the guide catheter, other catheter and guide wire components navigated to IPS 102 during the drug delivery device procedure. If another venous access point, e.g., subclavian, cephalic, brachial, internal jugular, is used in the procedure, other, appropriately sized guide or intermediate guide catheters can be selected and advanced to the JV-IPS junction 118.

Then, the clinician accesses the right IPS 102R and/or cavernous sinus 104 with a micro catheter 3307 and micro wire 3333 (FIGS. 55B and 55C). The micro catheter 3307 (e.g., an 0.027" micro catheter such as any of the micro catheter embodiments disclosed in International Patent Application No. PCT/US18/20667 filed on Mar. 2, 2018, entitled "Catheter Systems and Methods for Medical Procedures Using Catheters," or commercially available micro catheters such as a Phenom 27 Catheter from Cathera, Inc. of Mountain View, Calif., an Excelsior SL-10 Micro catheter from Stryker Neurovascular of Fremont, Calif., or a Marksman Micro Catheter from Medtronic of Irvine, Calif.) advances through the guide catheter lumen, and the micro wire (e.g., an 0.010", 0.014", or 0.018" guide wire such as a Synchro2 Guidewire from Stryker Neurovascular of Fremont, Calif.) can pass through the micro catheter lumen. The clinician advances the micro wire 3333 and micro catheter 3307 through the JV-IPS junction 118 into the right IPS 102R (e.g., the micro wire 3333 may be advanced distally and incrementally, followed by the micro catheter 3307 advancing distally and incrementally over the micro wire 3333, repeating the wire and catheter advancement steps in serial fashion; the micro wire may be advanced to its distal location first with the micro catheter following thereafter in two separate advancements; or the micro wire and micro catheter can be advanced distally, simultaneously through the JV-IPS junction 118 and into the right IPS 102R). The clinician can position the distal end of the micro catheter 3307 at a location distal to the target penetration site 5000 in IPS wall 114 along first curve 102A of the right IPS 102R as shown in FIG. 55C. The clinician withdraws the micro wire 3333 from the micro catheter 3307, leaving the distal opening 3317 of the micro catheter 3307 distal to the target penetration site 5000 in IPS wall 114 along first curve 102A of the right IPS 102R, as shown in FIG. 55C.

The clinician or other operator can then complete the steps previously described herein to create a 3D volumetric reconstruction 130 comprising IPS wall 114 along first curve 102A of the right IPS 102R and CP angle cistern 138, select a target location 130A within the 3D reconstruction 130 and along IPS wall 114 where the operator intends to penetrate IPS wall and access CP angle cistern 138, crop a portion 130P of the reconstruction to pinpoint the target location along IPS wall 114 where the operator intends to penetrate the IPS and access CP angle cistern 138, and overlay portion 130P of the 3D reconstruction 130 with live fluoroscopy imaging 140 using a 3D road mapping technique to visually guide subsequent procedure steps. As will be described below, the clinician or other operator can selectively toggle the 3D roadmap of portion 130P on and off the fluoroscopy imaging 140 during the procedure.

The clinician then deploys an anchor 700 and guide member 780 in the distal portion of the right IPS 102R in step 5020 of the procedure, which results in the anchor 700 secured in IPS 102R, distal to the target penetration site along IPS wall 114 of the first curved portion 102A of the right IPS 102R as shown in FIG. 55E. The clinician can load the anchor 700 and elongate guide member 780 into the proximal opening (not show) of the micro catheter 3307. Using elongated pusher of FIGS. 13, 14A-E and by loading the proximal portion 784 of guide member 780 through the pusher lumen 3724 as previously disclosed, the clinician advances anchor 700 and guide member 780 distally through the micro catheter lumen until the anchor 700 reaches the distal opening 3317 of the micro catheter lumen as shown in FIG. 55D. The elongated guide member 780 may be disposed within the lumen 3724 of the elongated pusher 3710 (FIGS. 13, 14A-E) for delivering the anchor 700 into the IPS 102, while the proximal portion 784 of guide member 780 extends out the elongated pusher 3710 (e.g., out through the lumen opening 3726' of handle 3722), as previously described. A clinician can pinch or hold the proximal portion 784 of guide member 780 extending through the handle 3722 against the handle outer surface 3725 and then advance the handle 3722 and guide member 780 into a micro catheter to advance the anchor 700 distally. The clinician can then retract elongated pusher 3710 proximally over the proximal portion 784 of guide member 780 (i.e., by releasing the proximal portion 784 of guide member 780 pinched or held against the handle outer surface 3725), and thereafter repeat the advancing and retracting acts until the anchor 700 reaches a desired location (e.g., distal end of micro catheter lumen). The use of the elongated pusher 3710 facilitates the anchor 700 delivery and navigation by leveraging the column strength of guide member 780, as an alternative to having an anchor pusher member that extends at least the length of the micro catheter. FIG. 72 shows microcatheter 3307 tracked into the IPS lumen proximate to portion 130P overlaid on fluoroscopy imaging 140; anchor 700 is shown within the lumen of the micro catheter. Portion 130P provides a landmark for the clinician advancing endovascular componentry to a target site in the vasculature.

The clinician then positions the distal portion of the micro catheter 3307 (i.e., with anchor 700 and guide member 780 packed inside) about the location for anchor deployment, and withdraws the micro catheter 3307 proximally while holding the anchor 700 in place using guide member 780 and/or advances anchor 700 via guide member 780 distally through the distal opening 3317 of the micro catheter 3307 while holding the micro catheter 3307 in place until the anchor 700 emerges from the catheter lumen and expands against the walls of the sinus lumen. At this point of the procedure, a distal portion of guide member 780 such as joint 744 coupling the guide member and anchor 700, can be disposed in the sinus lumen; the remainder of guide member 780 remains within the micro catheter lumen. If the clinician is satisfied with the anchor deployment location, he then withdraws the micro catheter from the patient, leaving behind the deployed anchor 700 with guide member 780 that extends proximally from the proximal portion of anchor 700 through the first curved portion 102A and junction 118 as shown in FIG. 55E, through the patient's venous vasculature and out of the patient via the femoral vein access point. Alternatively, he can recapture the deployed anchor 700 and guide member 780 into the micro catheter lumen and redeploy the anchor in the sinus lumen one or more times until he is satisfied with the anchor deployment location. Optionally, the clinician can use elongated pusher 3710 with micro catheter 3307 to facilitate anchor 700 recapture and redeployment in the sinus lumen.

To continue the procedure, the clinician introduces delivery catheter 3304 into the patient's vasculature via the femoral vein access point and navigates the catheter 3304 distally through the JV-IPS junction 118 (as shown in FIG. 55F) to the target penetration site 5000 along IPS wall 114 of the first curved portion 102A of the right IPS 102R. The clinician can feed the proximal end of guide member 780 through the first lumen 3315 of delivery catheter 3304, via distal opening 3315a and proximal opening 3315b of the first lumen. The clinician then advances delivery catheter 3304 over guide member 780, through the femoral vein access point and tracks the delivery catheter 3304 distally, over the guide member 780 and through the patient's venous vasculature, until the distal portion 3344 of the delivery catheter 3304 is positioned about the target penetration site 5000 along IPS wall 114 of the first curved portion 102A of the right IPS 102R as shown in FIG. 55G. FIG. 73 depicts distal portion 3344 of the delivery catheter 3304 is positioned at the target penetration site 5000 along IPS wall 114 as represented by portion 130P. While tracking the delivery catheter 3304 distally, the clinician can hold the guide member 780 stationary or pull proximally on the proximal portion 784 of the guide member 780 to facilitate advancement of the delivery catheter 3304 through the patient's venous anatomy. In addition, the clinician can rotate the delivery catheter 3304 while tracking distally over the guide member 780 to overcome any resistance, e.g., resistance encountered while tracking the catheter through JV-IPS junction 118 and/or into right IPS 102R.

Figure 74:
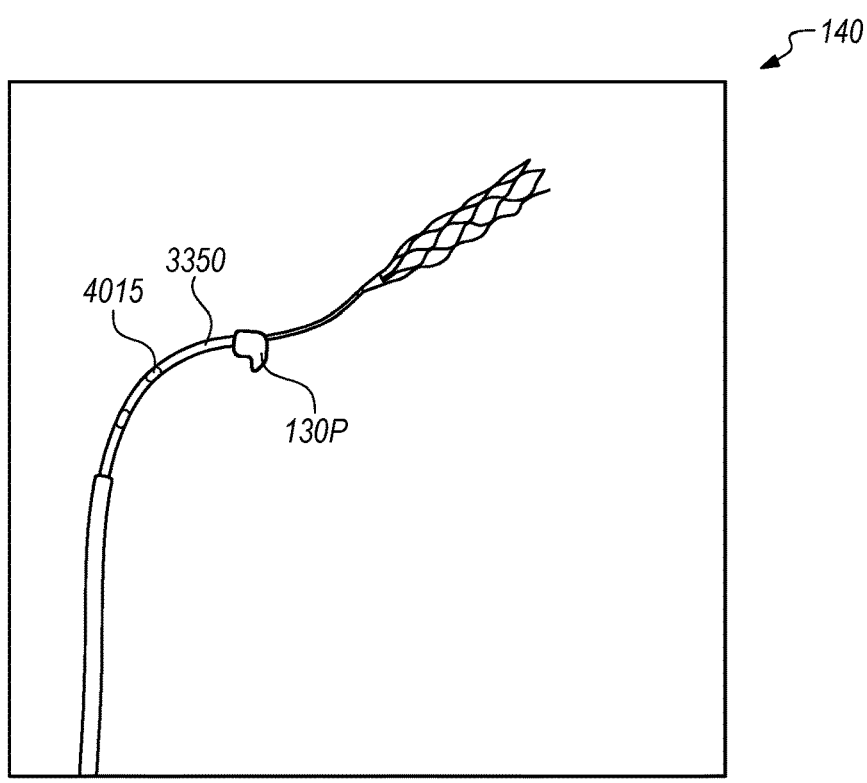
Figure 75:
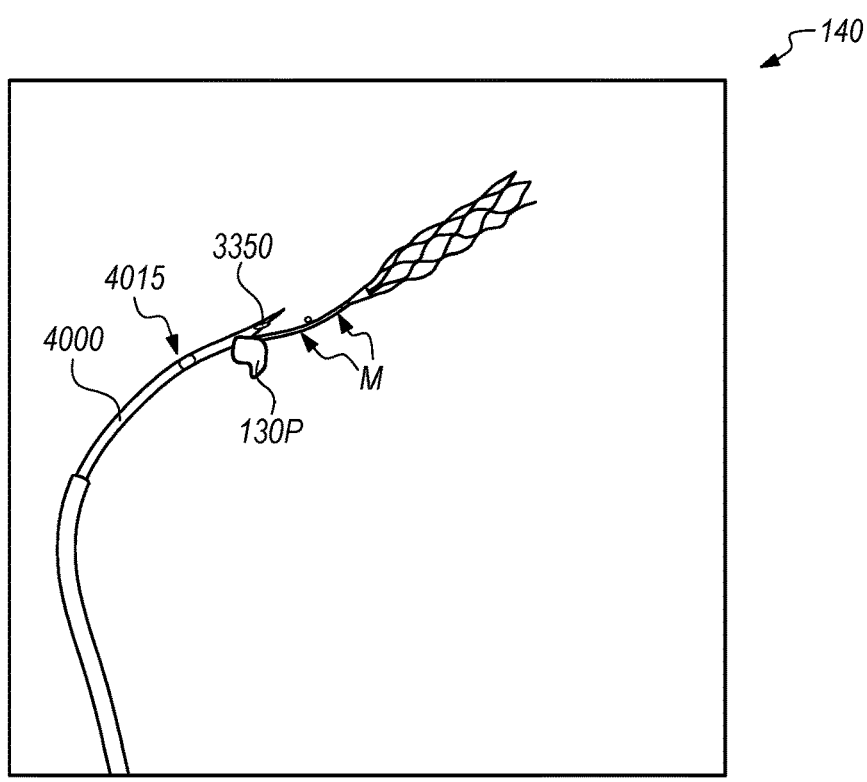

The clinician can confirm the orientation of the delivery catheter 3304 and the trajectory of penetrating element 3350 through IPS wall 114 into CP angle cistern 138 relative to the target penetration site 5000 using one or more of the previously disclosed imaging techniques. The clinician may use the distal 3354a and proximal 3354b markers located on the distal portion 3344 of the delivery catheter 3304 in this confirmation step. The markers will be visible under various imaging modalities used during the procedure (e.g., bi- or single-plane fluoroscopy). To the extent the clinician has created a 3D reconstruction of the patient's anatomy about the target penetration site 5000 (e.g., using 3D-rotational angiography or venography), the clinician can confirm the orientation and/or trajectory of the penetrating element 3350 by combining the fluoroscopy and 3D reconstruction using a 3D road mapping technique as depicted in FIGS. 73-75. Optionally, the clinician can use the 3D reconstruction data to create a window representing the target penetration site 5000; the 3D window or portion 130P and live fluoroscopy 140 can be overlaid with respect to each other to provide further guidance for the clinician to penetrate IPS wall 114 at target penetration site 5000.

Then, the clinician retracts the penetrating element guard or guard member 4000 to expose penetrating element 3350 in the IPS 102 at the target penetration site along IPS wall 114 of the first curved portion 102A of the right IPS 102R as shown in FIG. 55H. The clinician retracts the guard member 4000 by pulling proximally on pull wire 4010 while holding the remainder of delivery catheter 3304 in place. While retracting guard 4000 and using the previously disclosed imaging techniques, the clinician will observe marker 4015 in guard 4000 transition proximally towards and/or until it abuts or overlaps with distal marker 3354a located on the distal portion 3344 of delivery catheter 3304. Again, the clinician can confirm the trajectory of penetrating element 3350 through the IPS wall 114 into CP angle cistern 138 using one or more of the previously disclosed imaging techniques before penetrating IPS wall 114. If the clinician is unsatisfied with the trajectory of the penetrating element 3350 or perceived penetration site 5000 on IPS wall 114, the clinician can adjust the location of the distal portion 3344 of delivery catheter 3304 until the clinician is satisfied that penetrating element 3350 will penetrate the IPS wall 114 at the target location along the first curved portion 102A of the right IPS 102R. When adjusting the location of the distal portion 3344 of delivery catheter 3304 the clinician can re-sheath penetrating element 3350 by advancing the penetrating element guard 4000 distally via pull wire 4010 and then unsheath penetrating element by retracting guard 4000 proximally before penetrating IPS wall 114; this re-sheathing step can prevent inadvertent penetration or injury to the IPS walls that could occur if the penetrating element 3350 were uncovered or unprotected while the clinician repositioned delivery catheter 3304 in the IPS 102.

With the penetrating element 3350 oriented along a desired trajectory at the target penetration along IPS wall 114, the clinician advances delivery catheter 3304 distally so that penetrating element 3350 passes through the dura of IPS wall 114, arachnoid layer 115, and into the CSF-filled subarachnoid space of CP angle cistern 138 as shown in FIG. 55I. Embodiments of the disclosed inventions allow the clinician to visualize the penetrating element 3350 pass through IPS wall 114 and into CP angle cistern; FIG. 75 shows penetrating element 3350 extended through portion 130P and providing visual confirmation that the penetrating element has travelled to an extra-vascular location or through IPS wall 114 and into CP angle cistern 138. The clinician can pull proximally on the proximal portion of guide member 780 or hold the guide member 780 in place while advancing delivery catheter 3304 distally to cause the penetrating element 3350 to penetrate the IPS wall 114; these techniques allow the portion of delivery catheter 3304, distal of the lumen opening 3315a to track along the target trajectory and off-axis from the path of guide member 780 through the first curved portion 102A of the right IPS 102R. The clinician stops advancing delivery catheter 3304 distally when the clinician is satisfied that penetrating element 3350 and second lumen 3305 of delivery catheter 3304 have accessed CSF of the CP angle cistern 138; this can be confirmed via one or more of the previously disclosed imaging techniques, e.g., by 3D road mapping.

As an alternative method of confirming access to CP angle cistern 138, the clinician can aspirate CSF through the penetrating element 3350 and second lumen 3305 of delivery catheter 3304 to confirm that the penetrating element 3350 passed through IPS wall 114 and arachnoid layer 115 to access CSF within CP angle cistern 138 (e.g., aspirated CSF denoted by arrow-head lines in FIG. 55J). The clinician can use a syringe on the distal portion of handle (e.g., 10 cc syringe) to aspirate CSF proximally, through delivery catheter 3304. The presence of clear CSF in the syringe can confirm a successful penetration through the IPS into the CP angle cistern 138. If the clinician observes blood in the syringe, this can indicate that the penetrating element 3350 did not completely pass through IPS wall 114 or remained entirely within right IPS 102R. If the clinician did not penetrate IPS wall 114, the clinician can re-attempt to penetrate IPS wall 114 at the target site, attempt to penetrate IPS wall 114 at another target penetration site along the first curved portion 102A of right IPS 102R, attempt to penetrate IPS wall 114 along the second curved portion 102B of right IPS 102R as will be further described below, or abort the procedure.

In drug delivery procedures where one or more therapeutic agents are intended to be delivered to the intracranial SAS from the delivery catheter 3304, the clinician can deliver such agent(s) from the catheter via one or more second lumens 3305 of the delivery catheter. A syringe or other fluid delivery or flushing means can couple with the proximal end opening 217 of second lumen(s) 3305 to deliver (e.g., translate, flush, flow, or the like, denoted by the arrow-head lines in FIG. 55P) a therapeutic agent into CP angle cistern 138 (or other targeted location of the intracranial SAS). After delivering the therapeutic agent, the clinician can continue the procedure as described below regarding removal of delivery catheter 2204 in step 5060 and removal of anchor 700 in step 5070.

Referring back to the exemplary drug delivery device deployment procedure, after confirming that the penetrating element 3350 passed through IPS wall 114 and arachnoid layer 115 to access CSF within CP angle cistern 138, the clinician advances pusher member 3310 distally to advance drug delivery device 200 distally from the lumen 3305 of delivery catheter 3304 until the distal anchoring mechanism 229 of the drug delivery device 200 deploys in CP angle cistern 138 in step 5050 of the procedure as shown in FIG. 55K. The clinician can confirm that the distal anchoring mechanism 229 of the drug delivery device 200 deployed in the cistern by observing a radiopaque marking(s) (e.g., as denoted by the "M" reference in FIG. 75) on a distal portion of the drug delivery device 200 as it emerges from the catheter into the subarachnoid space, using one the previously disclosed imaging techniques (e.g., by using live fluoroscopy to observe the RO makings in the distal portion of the drug delivery device 200 transition from a delivery configuration to a deployed configuration as described in connection with FIG. 55C and/or by confirming that a distal portion of the drug delivery device 200 deploys within or proximate a 3D reconstruction that pinpoints a target penetration or device deployment site). By pulling drug delivery device pusher 3310 proximally (and, optionally, simultaneously pulling delivery catheter 3304 proximally), the clinician fully expands the distal anchoring mechanism 229 against arachnoid layer 115 in CP angle cistern 138.

The clinician continues deploying drug delivery device 200 across the penetration tract in IPS wall 114 and in the right IPS 102R in step 5055 of the procedure as shown in FIG. 55L. By holding drug delivery device pusher member 3310 in place while withdrawing delivery catheter 3304 proximally, drug delivery device 200 emerges from the delivery catheter lumen 3305 and deploys in the lumen of IPS 102R. At this point in the procedure, the proximal portion of drug delivery device 200 and, if included on the particular embodiment of drug delivery device 200 being deployed, proximal anchoring mechanism 227 on the drug delivery device remain inside lumen 3305 of delivery catheter 3304; the remainder of the drug delivery device is deployed in the CP angle cistern and right IPS 102R.

The clinician finishes deploying drug delivery device 200 in step 5060 of the procedure by further withdrawing delivery catheter 3304 proximally and holding drug delivery device pusher member 3310 in place (or advancing it distally), until drug delivery device 200 completely emerges from the delivery catheter lumen 3305 and deploys in the jugular vein 106 as illustrated in FIG. 55M. The clinician can then withdraw delivery catheter 3304 from the patient via the femoral vein access point.

The clinician recaptures anchor 700 into the micro catheter and removes the anchor from the patient via the femoral vein access point in step 5070 of the procedure. By feeding the proximal portion of guide member 780 through the micro catheter lumen, the clinician can track the micro catheter distally over the guide member, around proximal anchoring mechanism 227 (if present) of the drug delivery device 200 deployed in the jugular vein 106 or JV-IPS junction 118, until the distal end of the micro catheter reaches the joint 744 between the guide member and anchor.

He can then further advance the micro catheter distally and/or hold the catheter stationary and/or pull guide member 780 proximally to transition the anchor from its deployed or expanded configuration in the sinus lumen to its compressed configuration within the micro catheter lumen as shown in FIG. 55N. With the anchor compressed in the micro catheter lumen, the clinician withdraws the micro catheter and anchor from the patient proximally, through the venous vasculature and out of the femoral vein access point. Thereafter, he withdraws the guide catheter from the patient.

The deployed drug delivery device 200 (shown in FIG. 55O) can deliver one or more therapeutic agents to CP angle cistern 138 as described herein. The arrows in FIG. 55O depict the direction of therapeutic agent flow from the deployed drug delivery device 200 into CP angle cistern 138.

If in steps 5040 or 5045 of the procedure the clinician is unsuccessful at penetrating IPS wall 114 at the target penetration site along the first curved portion 102A, he can continue the procedure by attempting to penetrate IPS wall 114 along the second curved portion 102B of right IPS 102R (e.g., as shown in FIG. 2C). For example, in certain patient anatomies, an overhang of the petrous bone can prevent penetrating element 3350 from passing through IPS wall 114 into CP angle cistern 138. The presence of this bony overhang can be confirmed during the drug delivery procedure by using one or more of the previously disclosed imaging modalities. The clinician can then continue the procedure by re-sheathing penetrating element 3350 with penetrating element guard 4000, and advancing delivery catheter 3304 distally over guide member 780 until the distal portion of delivery catheter 3304 is positioned at a target penetration site along the second curved portion 102B of right IPS 102R. Optionally, the clinician can rotate delivery catheter 3304 from about 45 to 180 degrees while tracking distally from the first curved portion 102A toward the second curved portion 102B in IPS 102R; by rotating the delivery catheter, the clinician can orient penetrating element 3350 such that further distal advancement of delivery catheter 3304 will advance penetrating element 3350 through IPS wall 114 at a target penetration along the second curved portion 102B of right IPS 102R. The clinician can continue the procedure and deploy drug delivery device 200 through IPS wall 114 along the second curved portion 102B of right IPS 102R as previously described in steps 5030-5070 of the procedure and/or deliver a therapeutic agent to the intracranial SAS from delivery catheter 3304.

Embodiments of drug delivery device 200, 2200 that have been deployed in IPS 102 or other venous sinus location can be retrieved using a minimally invasive retrieval procedure guided by one or more of the imaging methods previously disclosed. The clinician can advance a guide catheter through the patient's vasculature (e.g., from a femoral or other venous access point in the patient) to the JV-IPS junction 118. The guide catheter can be advanced until the proximal end of the catheter is proximate to the proximal end of drug delivery device 200 deployed in the JV or further advanced until the proximal portion of the drug delivery device 200 is contained within the distal portion of the guide catheter lumen. The clinician can then navigate a micro catheter (e.g., any of the 0.027" micro catheter embodiments previously disclosed) through the guide catheter until the distal opening 3317 of the micro catheter is proximate to the proximal end of the deployed drug delivery device 200. An anchor 700 with elongate guide member 780 is then translated through the micro catheter, for example, using the elongated pusher 3710 and corresponding method of use as previously disclosed. The clinician can deploy anchor 700 from the distal opening 3317 of micro catheter 3307 and adjust the location of the expanded anchor 700 within the JV (and/or guide catheter lumen) until the proximal portion of the drug delivery device is contained within the lumen of anchor 700 and/or the proximal portion of the drug delivery device 200 has passed through one of the cells of anchor 700. The clinician then re-sheaths the anchor 700 into the micro catheter 3307, thereby compressing the proximal portion of drug delivery device 200 within anchor 700 inside the micro catheter. The clinician can then withdraw the micro catheter proximally until the distal anchoring mechanism 229 of the drug delivery device in CP angle cistern 138 collapses and passes through IPS wall 114. The clinician can further withdraw the micro catheter into the guide catheter lumen and continue withdrawing the micro catheter from the patient to complete the drug delivery device retrieval procedure. The retrieval procedure can also be completed using commercially available thrombectomy devices or embodiments of encapsulating shroud 7016 in addition to the anchor 700 as described above. After drug delivery device retrieval, for example, to prevent bleeding into the CP angle cistern 138 through the penetration tract in IPS wall 114, the clinician can temporarily deploy a balloon in the IPS to stop bleeding, deploy a covered stent in the IPS at the penetration site, or embolize that portion of the IPS using commercially available embolization devices (e.g., coils, particles, foam, adhesives).

FIGS. 56A-E illustrate an alternate embodiment of drug delivery device 2200. Drug delivery device 2200 includes a distal anchoring mechanism 2229 (i.e., malelcot), as well as a retaining element 2230 comprising a radiopaque material, which element will be further described below. Distal anchoring mechanism 2229 includes arms or tines 2229*a* comprising a hinge, living joint, or the like 2229*b*, as previously described herein. The drug delivery device 2200 further comprises a drug delivery device body 2203, drug delivery lumen 2207, and a proximal end opening 2217 for connection to an access port 27.

Figure 56A:
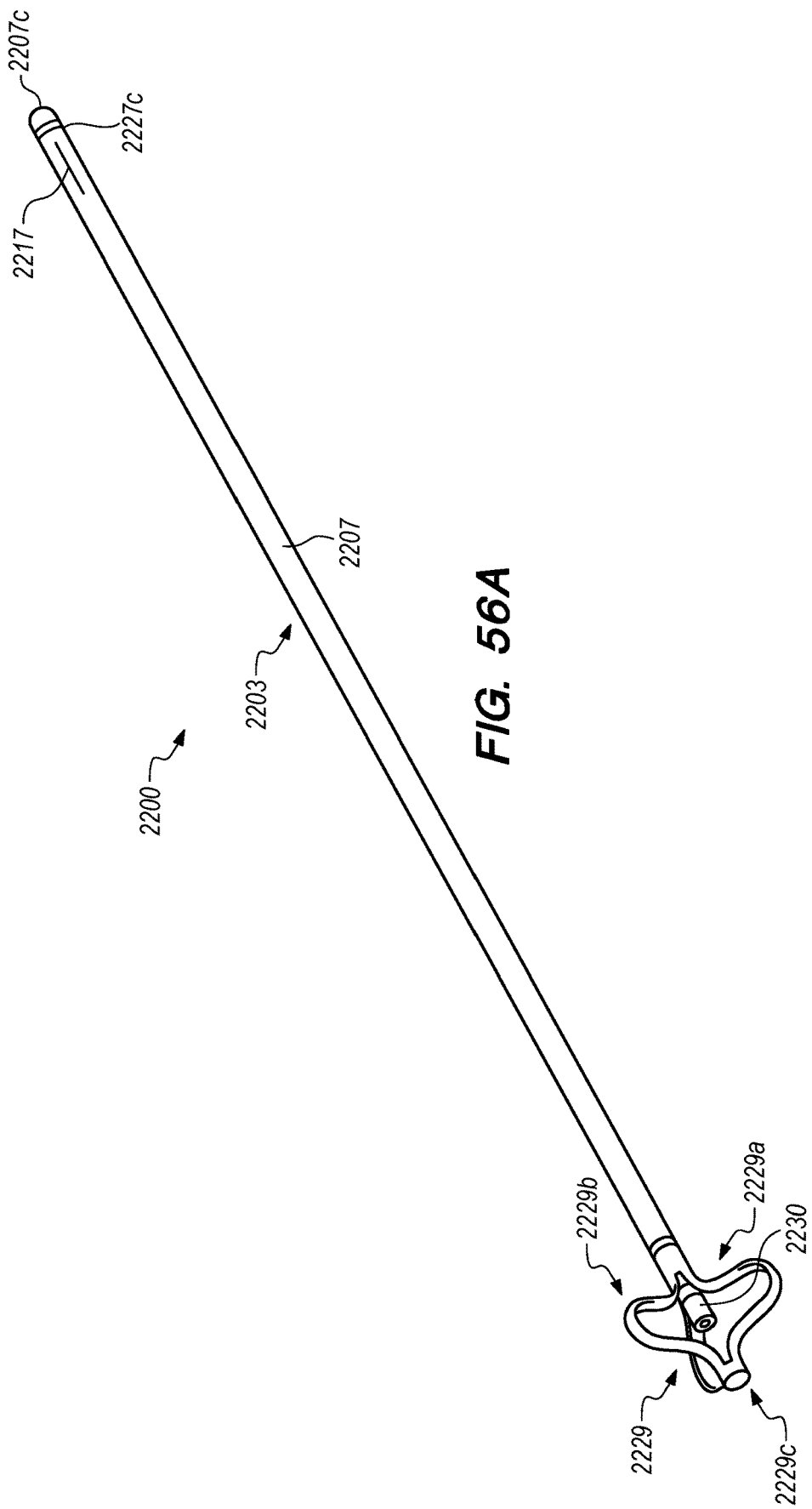

The drug delivery device body 2203 can have an elongate cylindrical configuration as depicted in FIG. 56A and extend between the distal 2219 and proximal 2227 portions of the drug delivery device. Drug delivery device body 2203 comprises drug delivery lumen 2207, e.g., as illustrated in the cross-section views of FIGS. 56C-D. Drug delivery device body 2203 can include an elastomeric polymer(s) suitable for implant applications including, but not limited to, silicone, polyurethane, polycarbonate urethane, thermoplastic polyurethane, aromatic or aliphatic polycarbonate thermoplastic polyurethane, silicone/polyurethane blends (e.g., thermoplastic silicone polycarbonate polyurethane comprising 20% silicone copolymer), or polyurethane silicone blends (e.g., polyurethane silicone copolymer). The durometer of the elastomer drug delivery device body 2203 can range from about 15 A to about 80 A; for a silicone-based drug delivery device body, the durometer can range from about 15 A to about 80 A, and for a urethane-based drug delivery device body, the durometer can range from about 55 A to about 80 A. A drug delivery device body 2203 comprised of an elastomeric polymer(s) advantageously resists thrombus formation on the portions of the implanted drug delivery device in the blood flow of the venous. Optionally, drug delivery device 2200 can include an anti-thrombotic coating to prevent thrombus formation including, but not limited to, heparin-based or phosphorylcholine-based anti-thrombotic coatings. To further prevent thrombus formation, the length of drug delivery device body 2203 can be configured such that the proximal portion 2227 is located proximal to the IPS-JV junction 118 (e.g., by 0.25" or more) when implanted in the patient's vasculature; junction 118, a location where the IPS and JV blood flows intersect, can experience more turbulent blood flow and have a higher risk for thrombus formation on a drug delivery device 2200 placed in the junction as compared to a location where the proximal portion of the drug delivery device is placed more proximally in the jugular vein or other venous location, away from junction 118.

FIG. 56C illustrates a cross section of drug delivery device 2200. The cross section of drug delivery device body 2203 includes a drug delivery device body wall thickness "W" in FIG. 56C. The wall thickness of an elastomer drug delivery device body 2203 can range from about 0.001 inch to about 0.010 inch or more. The diameter of the drug delivery lumen 2207 of drug delivery device 2200 can range from about 0.010 inch to about 0.020 inch or more. The outer diameter of drug delivery device body 2203 can range from about 0.006 inch to about 0.040 inch or more. The length of drug delivery device body 2203 can range from about 0.25" to 3.0" (6.35 mm 76.2 mm) or more (e.g., having sufficient length and extending from a distal anchoring mechanism 2229 in the intracranial SAS to the location of an access port 27).

Figure 56D:
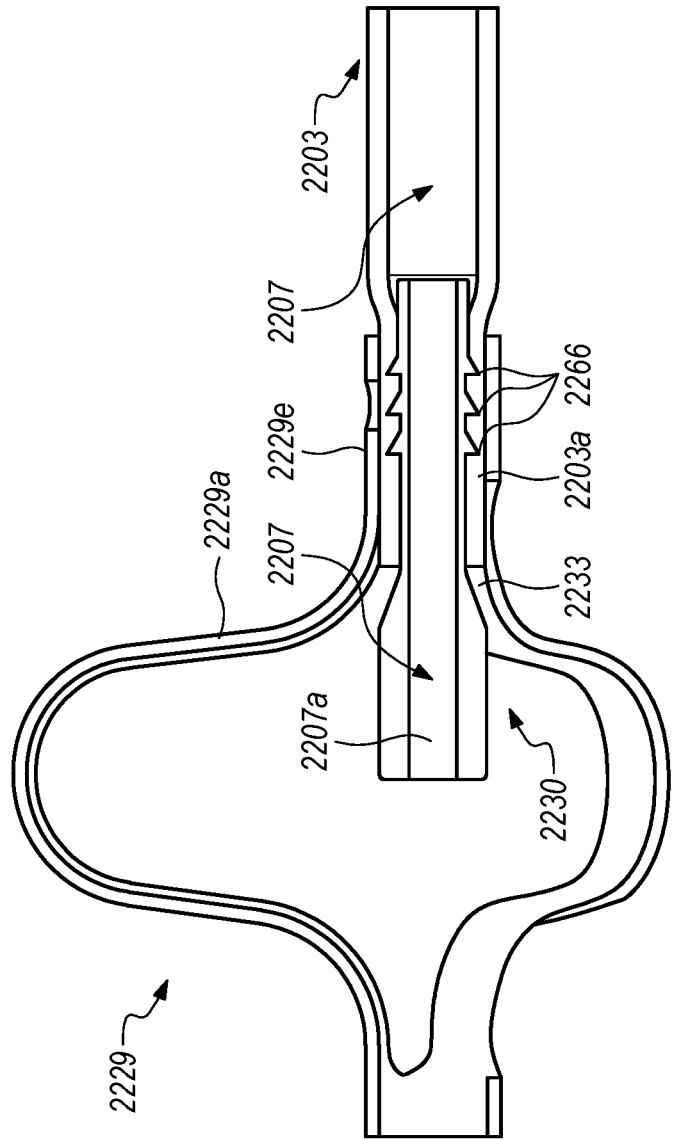
Figure 58A:
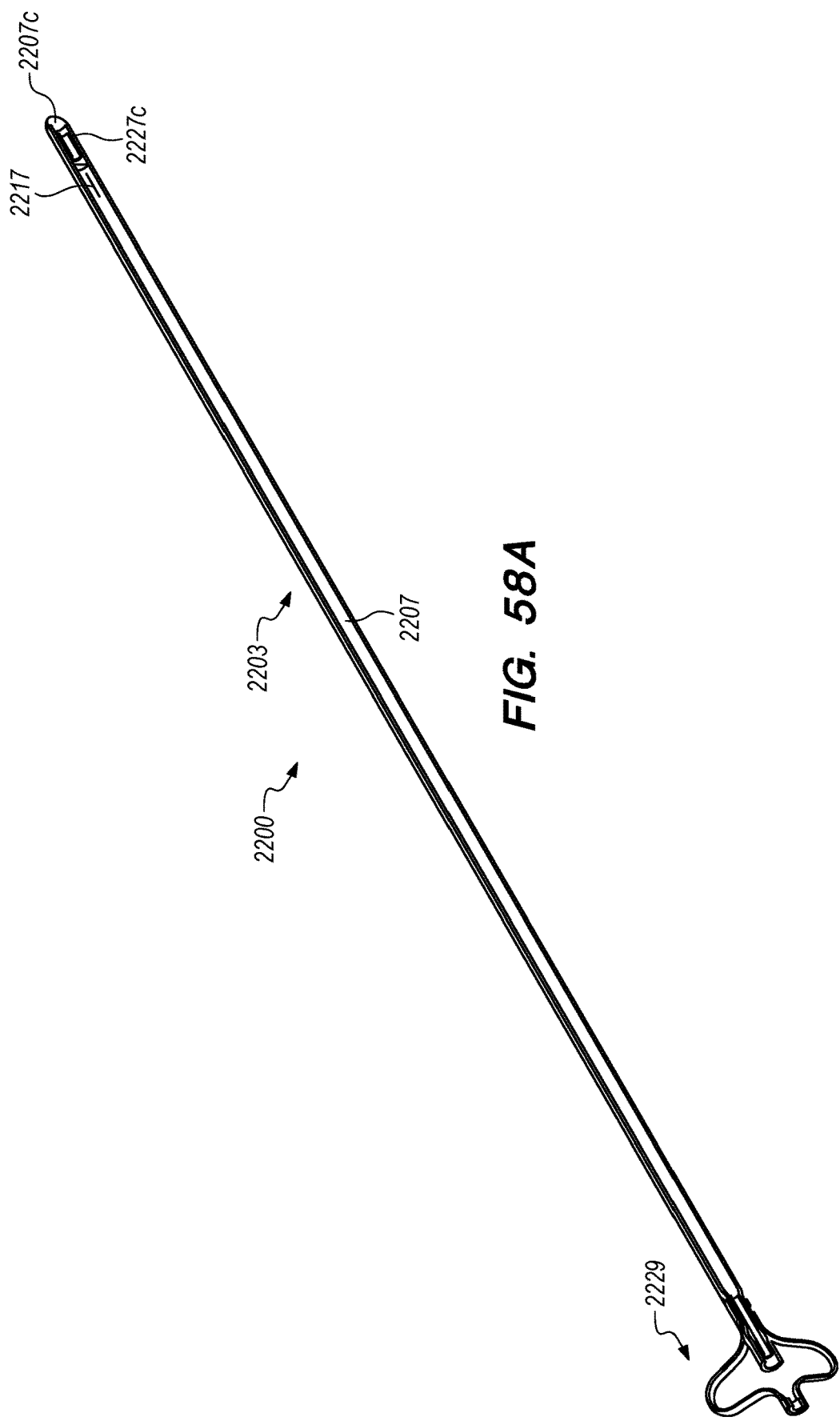
Figure 62A:
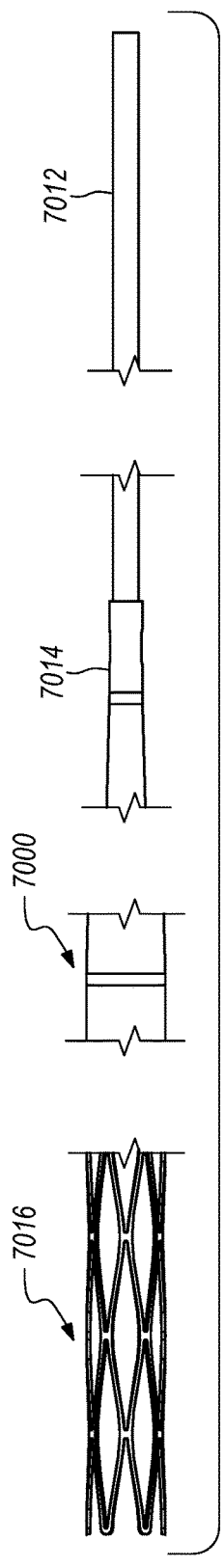
Figure 62B:
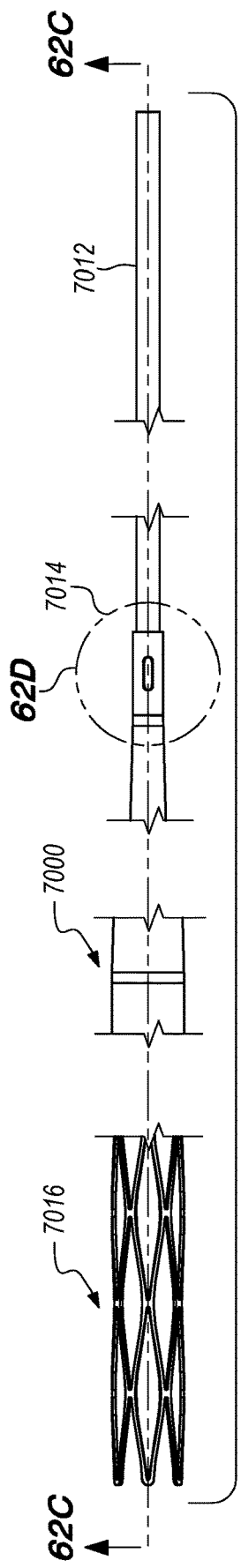
Figure 62C:
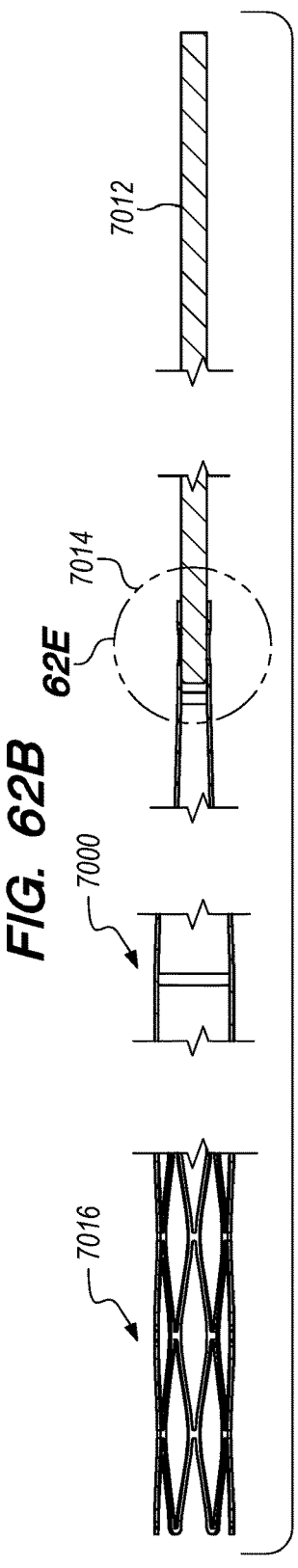
Figure 62D:
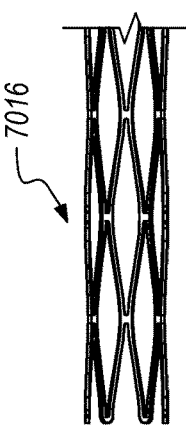
Figure 62E:
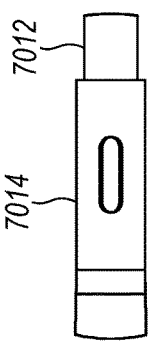

FIGS. 56B-D illustrate distal portion 2202 of drug delivery device 2200. With reference to FIG. 56B, retaining element 2230 comprises a radiopaque material (e.g., gold or other radiopaque material disclosed herein) and the distal portion of drug delivery lumen 2207 (further described herein). Anchoring mechanism 2229 can include a radiopaque marker located in the distal collar 2229c. When drug delivery device 2200 is deployed from a delivery catheter, anchoring mechanism 2229 transitions (e.g., self-expands) from a compressed configuration within the delivery catheter (e.g., denoted by the dotted line portion "C" marked on FIG. 56B) to its open or deployed configuration shown in FIG. 56B, during deployment, the clinician can observe the marker of distal collar 2229c move toward the radiopaque retaining element 2230 to confirm that the distal anchoring mechanism 2229 has properly transitioned to its deployed state in CP angle cistern 138.

FIGS. 56C-D illustrate cross sections of the distal portion 2202 of drug delivery device 2200 and the connection between distal anchoring mechanism 2229 and drug delivery device body 2203 using one embodiment of a retaining element 2230. Retaining element 2230 includes a lumen that forms the distal end opening 2207a (or 2239 in some embodiments) of drug delivery lumen 2207 of the drug delivery device and embodiments can have the same range of internal diameters as described above for drug delivery lumen 2207 of drug delivery device body 2203. Retaining element 2230 further includes a tapered portion 2233 to accommodate a curved portion of distal anchoring mechanism arms 2229a when the distal anchoring mechanism 2229 is in a compressed or delivery configuration; tapered portion 2233 also prevents retaining element 2230 from slipping proximally through the proximal portion 2229e of distal anchoring mechanism 2229 (e.g., during assembly).

The distal portion 2203a of drug delivery device body 2203 is secured within the distal anchoring mechanism 2229. As shown in FIGS. 56C-D, distal portion 2203a of drug delivery device body 2203 is compressed between the outer surface of retaining element 2203 and inner surface of the proximal portion 2229e of distal anchoring mechanism 2229. For example, distal portion 2229e of distal anchoring mechanism 2229 can be compressed (e.g., crimped, swaged) over the distal portion 2203a of the drug delivery device body and retaining element 2230. Further, retaining element 2230 can include retaining features 2266 (e.g., circumferential threads as shown in FIGS. 60C-D, barbs, tines, hooks, or the like) to secure the distal portion 2203a of drug delivery device body 2203 over retaining element 2230 and within the proximal portion 2229e of distal anchoring mechanism 2229.

FIGS. 57A-D illustrate the connection between distal anchoring mechanism 2229 and drug delivery device body 2203 with an alternate embodiment of retaining element 2230. For ease in illustration and disclosure, the features, functions, and configurations of the drug delivery device that are the same as in the drug delivery device of the present disclosure (e.g., FIGS. 56A-D) are incorporated by reference herewith; the differences will be described in further detail below. Retaining element of FIG. 57A comprises a cylindrical element that forms the distal end opening 2217 of drug delivery lumen 2207 of drug delivery device 2200, as illustrated in the cross-section views of FIGS. 57C-D. Retaining element 2230 can comprise titanium, stainless steel, Nitinol, or other super-elastic alloys. Retaining element 2230 can be connected to the proximal portion 2229e of distal anchoring mechanism 2229 (e.g., weld or adhesive placed through one or more openings 2229d in the distal anchoring mechanism 2229). A cylindrical marker band 2240 can be swaged over the distal portion 2203a of drug delivery device body 2203 and retaining element 2230 to secure the connection between the drug delivery device body and distal anchoring mechanism. The distal collar 2229c of anchoring mechanism 2229 can include a radiopaque marker (not shown in FIG. 57A-D). When drug delivery device 2200 is deployed from a delivery catheter, anchoring mechanism 2229 transitions (e.g., self-expands) from a compressed configuration within the delivery catheter (e.g., denoted by the dotted line portion "C" marked on FIG. 57C) to its open or deployed configuration shown in FIG. 57B; during deployment, the clinician can observe the marker of distal collar 2229c move toward the radiopaque marker band 2240 to confirm that the distal anchoring mechanism 2229 has properly transitioned to its deployed state.

Drug delivery devices comprising an elastomeric body 2203 (e.g., drug delivery device 2200 of FIGS. 56A-58F) can advantageously compress and elongate to facilitate translation through a delivery catheter lumen in a deployment procedure. For example, drug delivery device body 2203 can compress radially up to about 80% (e.g., such that compressed drug delivery device diameter is about 20% of its resting diameter). Further, drug delivery device body 2203 can extend, stretch, or elongate longitudinally up to about 400% of its resting length. The compression and elongation features of drug delivery device body 2203 can be leveraged to maintain a relatively smaller profile (e.g., outer diameter) of a delivery catheter and facilitate delivery catheter access and navigation, and drug delivery device deployment through narrow and/or tortuous vasculature.

FIGS. 58A-F illustrate an embodiment of drug delivery device 2200 that includes the connection between distal anchoring mechanism 2229 and drug delivery device body 2203 with a retaining element 2230 illustrated in FIG. 57A-D. FIGS. 58A-F further include the marker 227c and proximal plug 2207c of FIG. 57A-D. As shown in FIGS. 58C-F, the distal collar 2229c of distal anchoring mechanism 2229 includes a radiopaque marker band 2240 to confirm that the distal anchoring mechanism 2229 has properly transitioned from a compressed configuration in the delivery catheter lumen to a deployed configuration in CP angle cistern 138.

FIGS. 59-63B illustrates an embodiment of a delivery shuttle 7000 for translating and deploying a drug delivery device 2200 (e.g., embodiments of drug delivery device 2200 illustrated in FIGS. 56A-58F) through the second lumen 3305 of a delivery catheter 3304 (e.g., any of the delivery catheter embodiments disclosed herein including the delivery catheter illustrated in FIG. 64A-E). The delivery shuttle 7000 includes a distal shuttle portion 7016 (e.g., mesh, braid, shroud, stent-like, funnel-like, tubular body, or other configurations), coupled to an elongate proximal pusher 7012 (e.g., wire or elongated pushing member) via a junction 7014. The distal shuttle portion 7016 of the delivery shuttle 7000 comprises a proximal portion 7016*a* and a distal portion 7016*b*, having a lumen 7018 extending therebetween. The distal shuttle portion 7016 of the delivery shuttle 7000 is configured to receive, retain, push and/or shuttle the drug delivery device 2200, for example, through second lumen 3305 of a delivery catheter 3304. As illustrated in FIGS. 59A, 61A, 62A-C and 63C, the proximal portion 7016*a* of the distal shuttle portion 7016 tapers toward junction 7014.

The distal shuttle portion 7016 of the delivery shuttle 7000 can comprise a self-expanding braid, and is shown in an expanded configuration in FIG. 59. The distal shuttle portion 7016 is configured to receive drug delivery device 2200 (e.g., within the lumen 7018) and is configured to compress and elongate (e.g., FIG. 63A-B) suitable for translation within the second lumen 3305 of the delivery catheter for translating the drug delivery device 2200 through the catheter, into the implantation site of a patient. With a lined lumen (e.g., PTFE-lined second lumen of delivery catheter 3304), the distal shuttle portion 7016 of the delivery shuttle 7000 facilitates smooth transition of an elastomeric drug delivery device 2200 through the delivery catheter. The expanded or resting diameter of distal shuttle portion 7016 of delivery shuttle 7000 can range from about 0.5 mm to about 6 mm or more. The compressed length of the delivery shuttle 7000 (e.g., when compressed in a delivery catheter lumen) can range from about 0.25" to 3.0" (6.35 mm 76.2 mm) or more.

The distal shuttle portion 7016 of the delivery shuttle 7000 includes multiple filaments 7020 that are weaved to form the braid structure, as illustrated by the inset of FIG. 59A. Filaments can comprise Nitinol (e.g., heat-set), stainless steel, or a polymer (e.g., PTFE, HDPE, PET, PEEK, Kevlar). Embodiments of the distal shuttle portion 7016 of the delivery shuttle 7000 can include 8 to 144 filaments. Filaments 7020 of the distal shuttle portion 7016 can have round or non-round cross-sections; round cross-section filaments can have a diameter from about 0.0002 inch to about 0.005 inch. Filaments 7020 can be cut in the distal portion 7016*b* of the distal shuttle portion 7016 (e.g., as illustrated in FIG. 59), rounded, or braided back proximally toward the distal shuttle portion 7016 midsection to create a more atraumatic profile for the distal portion 7016*b* of the distal shuttle portion 7016.

The elongate proximal pusher 7012 can have a round or non-round cross-sectional profile. Embodiments of elongate proximal pusher 7012 with a round cross section can have a diameter of about 0.0006 to about 0.030 inch or more. The elongate proximal pusher 7012 can be solid or include a lumen to accommodate other delivery assembly components. Nitinol, stainless steel, or other like materials can be used for elongate proximal pusher 7012, provided the overall design provides sufficient column strength to deliver a drug delivery device 2200 in the delivery shuttle 7000 through a delivery catheter lumen and into a target implant site. The distal portion of the elongate proximal pusher 7012 can include a tapered grind or other features (e.g., cuts, slots, kerfs or the like) to increase the flexibility of such distal portion, which can facilitate drug delivery device translation through the delivery catheter when the catheter is being used in tortuous anatomy. Junction 7014 can be formed by gathering the proximal ends of the filaments 4320 of the distal shuttle portion 7016 of the delivery shuttle 7000 over the distal portion of the elongate proximal pusher 7012 and using a heat shrink material over the filaments and wire, by using a direct connection (e.g., by adhesive or welding, e.g., gathering the filaments over the wire and under a radiopaque marker band), or using any of the interlock configurations disclosed herein disclosed in the related applications.

Alternate embodiments of delivery shuttle 7000 can include any of the anchor 700 configurations disclosed herein as a substitute for the distal shuttle portion 7016 of the delivery shuttle 7000 for translating drug delivery device 2200 through delivery catheter 3304. For example, as shown in FIGS. 60A-63C, the delivery shuttle 7000 can be formed from a hypo tube with a wall thickness from about 0.0005 inch to about 0.004 inch or more. The strut width of the delivery shuttle 7000 can range from about 0.0002 inch to about 0.003 inch or more; the strut width can vary along the length of the delivery shuttle 7000 (e.g., creating a stiffer proximal portion of the delivery shuttle 7000 to facilitate translation of the drug delivery device 2200 through the delivery catheter lumen and a more flexible distal portion of the delivery shuttle 7000 radially capture drug delivery device 2200). FIGS. 62A-62E illustrate alternative junction 7014 between the distal shuttle portion 7016 of delivery shuttle 7000 and the elongate proximal pusher 7012, the junction 7014 uses any suitable coupling mechanism or technique.

Figure 63A:
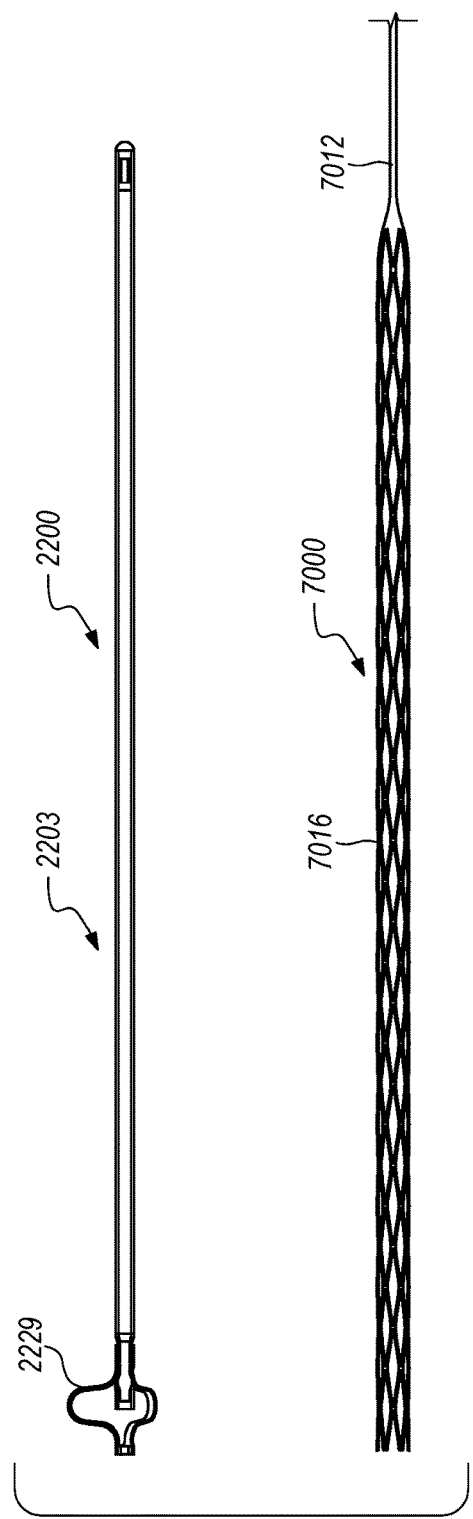
FIGS. 63A-C are perspective views of a drug delivery device and a drug delivery device delivery shuttle interface according to embodiments of the disclosed inventions.
Figure 63B:
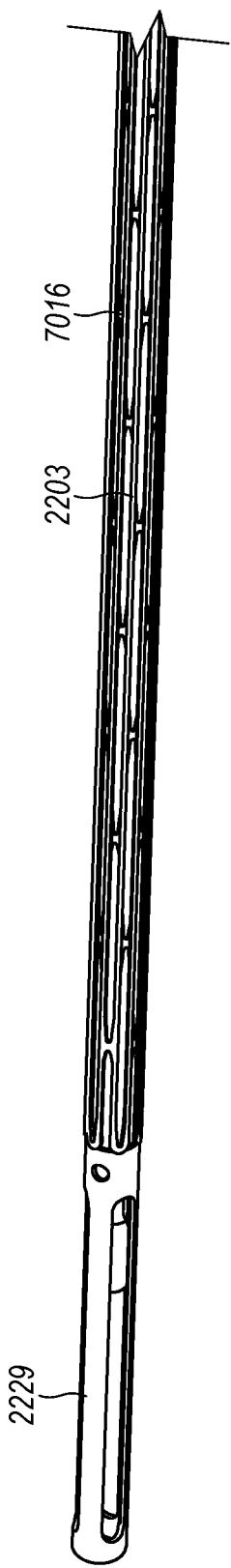
Figure 63C:
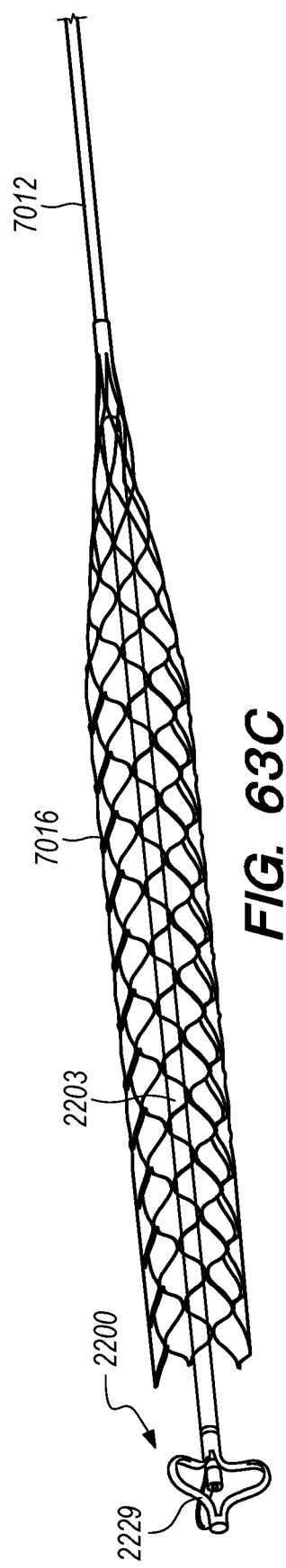

FIGS. 63A-C illustrate the drug delivery device 2200 and the delivery shuttle according to the embodiments of the invention. FIG. 63A shows the drug delivery device 2200 and the delivery shuttle 7000 separately, while FIGS. 63B and 63C show the interface between the drug delivery device 2200 and the delivery shuttle 7000. The delivery shuttle 7000 is configured to be at least partially positioned within the lumen of, and movable relative to, the delivery catheter. The distal shuttle portion 7016 of the delivery shuttle 7000 is configured to collapse around the elongate drug delivery device body 2203 (FIG. 63B) to thereby transport the drug delivery device body 2203 through the delivery catheter lumen, wherein the distal shuttle portion 7016 self-expands (FIG. 63C) to release the drug delivery device body 2203 when the distal shuttle portion 7000 is advanced out of the delivery catheter lumen through the opening of the tissue penetrating element 3350.

FIGS. 64A-E illustrate another embodiment of the delivery catheter 3304 embodiments described in connection with FIGS. 19A-I, 20, 21A-L, 30A-F. For ease in illustration and disclosure, the features, functions, and configurations of the delivery catheter that are the same as in the delivery catheter of the present disclosure (e.g., FIGS. 19A-I, 20, 21A-L, 30A-F) are incorporated by reference herewith; the differences will be described in further detail below. The delivery catheter illustrated in FIGS. 64A-E has received an elongate guide member 780 through first lumen 3315 of the penetrating element guard or guard member 4000 and delivery catheter 3304. Penetrating element guard 4000 is disposed over penetrating element 3350 to guard against inadvertent punctures in the vasculature while tracking the delivery catheter to the target penetration site in IPS wall 114 (or other target location in a venous sinus). As described in connection with FIGS. 20, 21, and 31, the penetrating element guard 4000 can translate proximally over the distal portion of the delivery catheter to expose the penetrating element 3350 at the target penetration site in the IPS.

Figure 64A:
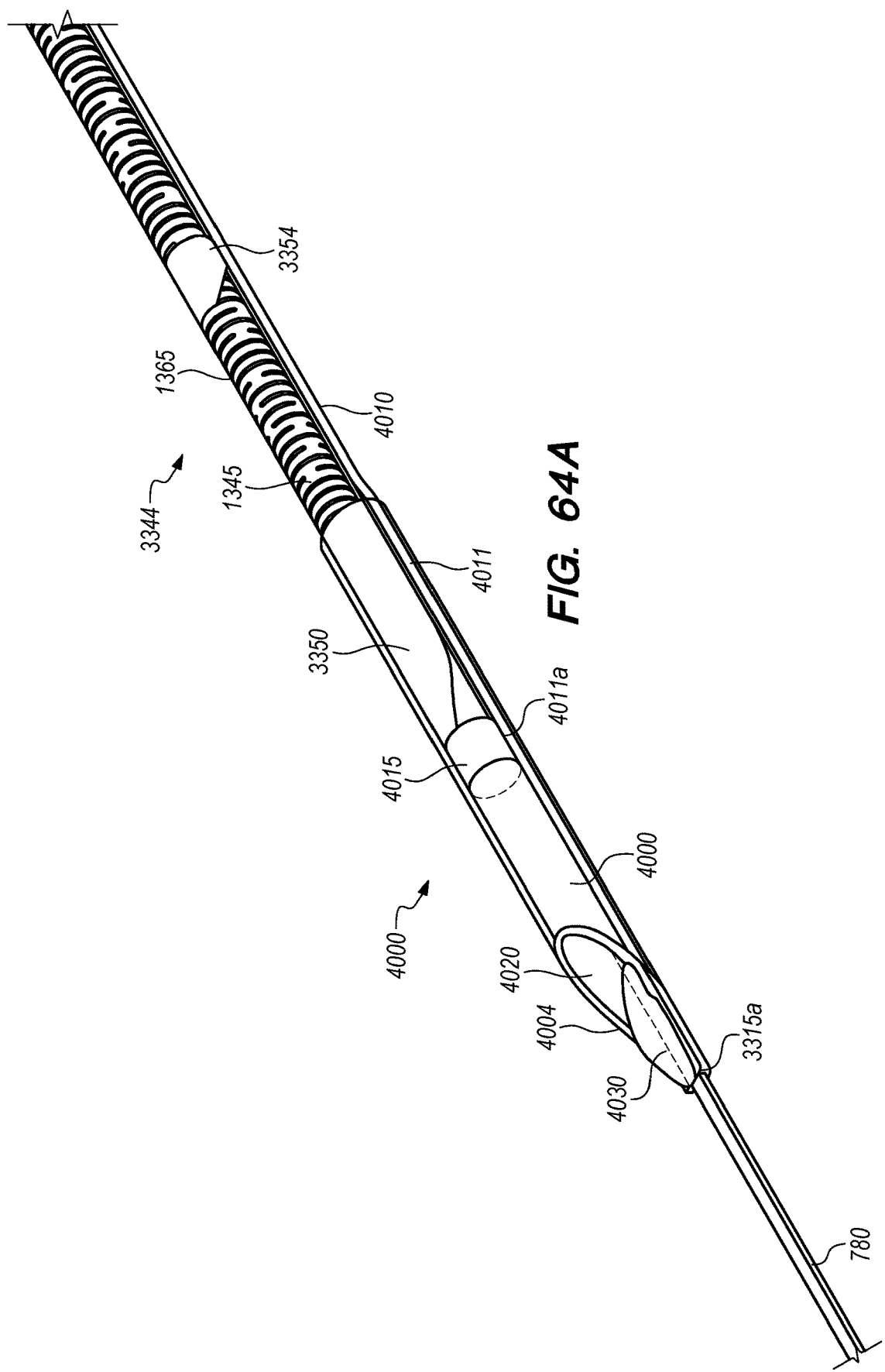
Figure 64B:
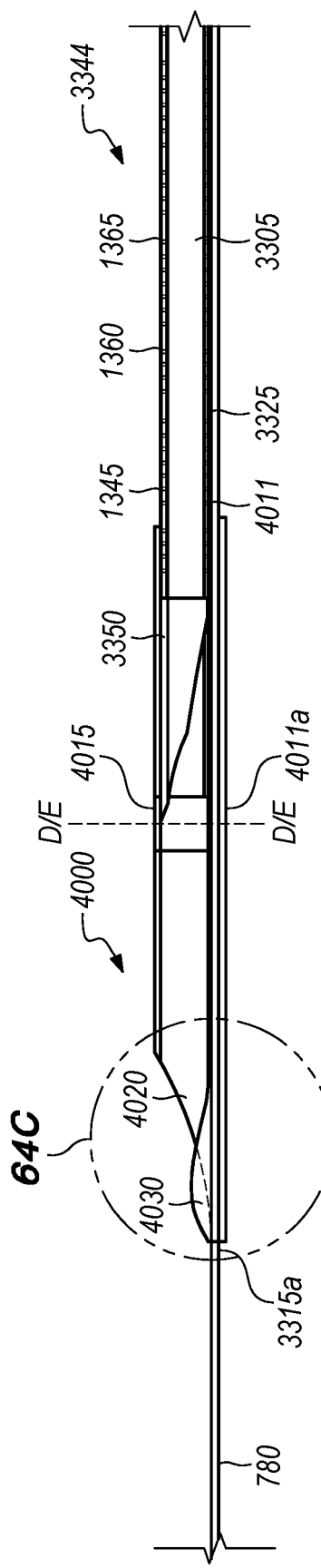
Figure 64C:
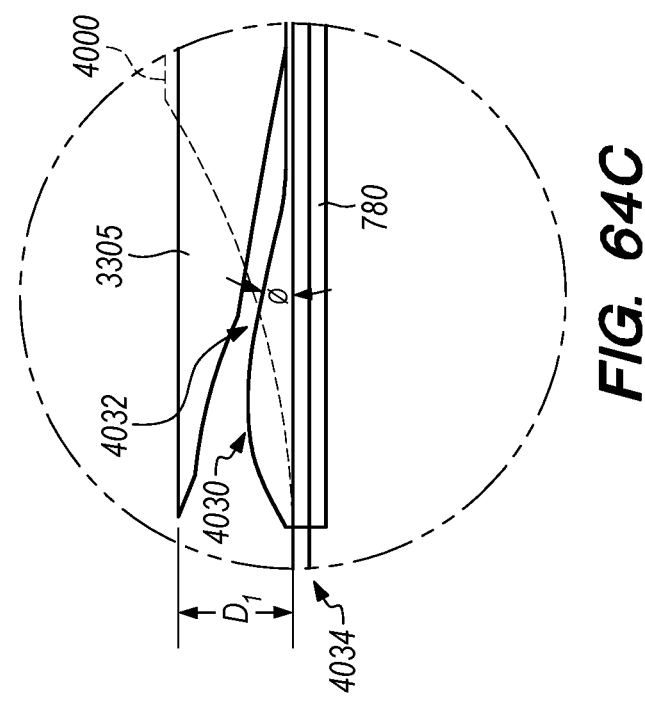

Penetrating element guard 4000 illustrated in FIGS. 64A-E includes a deflecting element 4030 to deflect penetrating element 3350 away from the elongate guide member 780 and towards a target penetration site in the patient's vasculature. FIG. 64B illustrates a cross-section of a distal portion of the delivery catheter including penetrating element guard 4000 and deflecting element 4030. FIG. 64C illustrates further details of the deflecting element 4030 illustrated in FIGS. 64A-B. Deflecting element 4030 includes proximal 4032 and distal 4034 portions. Distal portion 4034 can facilitate delivery catheter access into narrow or tortuous vasculature.

In use, penetrating element guard 4000 is retracted proximally over the delivery catheter to expose penetrating element 3350 at the target penetration site; as the guard 4000 retracts proximally, the proximal portion 4032 of deflecting element 4032 contacts the bevel of penetrating element 3350. As the clinician further retracts penetrating element guard 4000 proximally, deflecting element 4030 (e.g., proximal portion 4032) deflects penetrating element away from elongate guide member 780. To achieve this deflection for penetrating element 3350, the angle of the proximal portion 4032 of deflecting element 4030 relative to the longitudinal axis of elongate guide member 780, as illustrated by angle "Φ" in FIG. 64C, can range from about five degrees to about 30 degrees, or more. Deflecting element 4030, by increasing the angle of the penetrating element relative to the plane of the elongate guide member 780, increases the distance or separation between the penetrating element tip and guide member 780 (e.g., illustrated as D1 in FIG. 64C). Deflecting element 4030 facilitates tissue puncture in challenging patient anatomies, e.g., in a portion of the IPS 102, CS 104, or other venous that runs relatively parallel to CP angle cistern 138 or corresponding location within the intracranial SAS. For example, if the patient has a significant petrous bone overhang that prevents penetration through IPS wall 114 at the first turn 102A of IPS 102 (see FIGS. 2A-B), the clinician can use a delivery catheter and shuttle embodiment as illustrated in FIGS. 64A-E to penetrate IPS wall 114 beyond the petrous bone overhang, for example, between the first 102A and second 102B turns of IPS 102.

Deflecting element 4030 can be added to penetrating element guard 4000 using an ultraviolet light-cured adhesive or epoxy material. Alternatively, penetrating element guard 4000 and deflecting element 4030 can be molded as a single part. Materials for molded embodiments of the penetrating element guard and deflecting element can include Nylon, Pebax, polyurethane, or any other polymeric material disclosed herein for use with guard 4000 or delivery catheter 3304.

FIGS. 64D-E illustrate cross-section views of the delivery catheter 3304 shown in FIGS. 64A-C at reference line "D/E" of FIG. 64B (e.g., through marker band 4015 embedded in guard 4000). As shown in FIGS. 64D-E, delivery catheter 3304 includes a second penetrating element guard pull wire 4012. Pull wire 4012 includes a distal portion 4013 and connection point 4013a, which are illustrated in FIGS. 64D-E. Delivery catheter 3304 includes a fourth lumen 3335 (not shown) configured to receive the second pull wire 4012. A dual pull wire configuration of delivery catheter 3304 can provide smoother penetrating element guard 4000 retraction proximally over penetrating element and provide smoother distal retraction of guard 4000 to re-cover penetrating element 3350 compared to single pull wire embodiments.

Figure 65A:
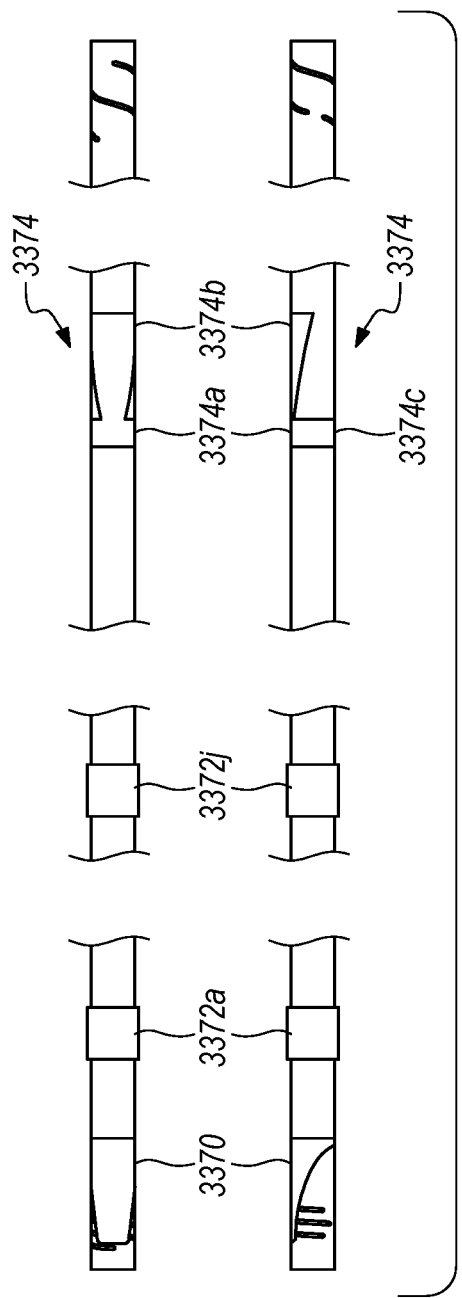
Figure 65B:
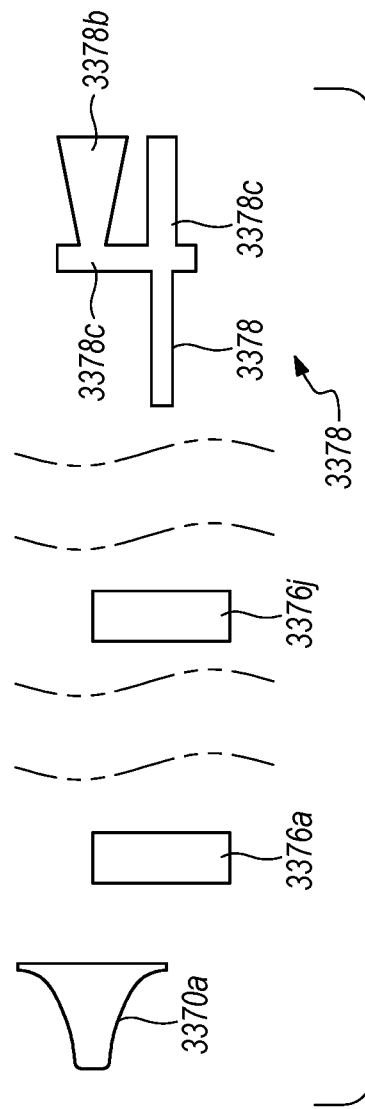

FIGS. 65A-C illustrate embodiments of radiopaque markers that enable a clinician to discern delivery catheter 3304 and penetrating element 3350 orientation in the patient's vasculature under flouroscopy. FIG. 65A illustrates marker bands 3370, 3372, and 3374 applied to reinforcing member 1345 of a delivery catheter 3304. FIG. 65B illustrates the patterns used to apply the marker bands shown in FIG. 65A; pattern 3370a of FIG. 65B corresponds to marker 3370 of FIG. 65A, patterns 3376a through 3376j of FIG. 65B corresponds to markers 3372a through 3372j of FIG. 65A, and pattern 3378 of FIG. 65B corresponds to marker 3374 of FIG. 65A. FIG. 65A illustrates catheter assembly alignment features 3374a-c of marker band 3374.

The markers illustrated in FIG. 65A can comprise gold plating (or other radiopaque materials) applied in the patterns reflected in FIG. 65B to reinforcing member 1345. The plating can range in thickness from about 0.0002 inch to about 0.002 inch or more. Distal marker band 3370 includes orienting features illustrated in FIGS. 65A-B and can be aligned axially with the bevel of penetrating element 3350 to help the clinician discern penetrating element orientation in vivo (e.g., under flouroscopy when deliver catheter 3304 has advanced into IPS 102). Additional dimensions of marker band 3370 and pattern 3370a used to form marker band 3370 are included in FIGS. 65A-B. Markers 3372a through 3372j comprise a series of marker bands placed with equal spacing between each band (e.g., 1 cm spacing between marker bands as illustrated in FIG. 65A) to provide the clinician with a reference point and measurement tool when delivery catheter has navigated to IPS 102. Each marker band 3372a through 3372j is approximately 1 mm wide, although other widths are possible. While FIG. 65A illustrates ten marker bands at equal 1 cm spacing between each band as the bands extend proximally from marker band 3372a, other configurations and spacing are possible. Orienting feature 3374b of marker band 3374 can also be aligned axially with the bevel of penetrating element 3350 to help the clinician discern penetrating element orientation in vivo. Orienting feature 3374c provides a reference point during manufacturing to ensure proper assembly and function of delivery catheter 3304. For example, elongate guide member 780 and first lumen 3315 of the delivery catheter can be axially aligned to orienting feature 3374c. In addition, one or more penetrating element guard pull wires (e.g., pull wire 4010, pull wire 4012) and the corresponding pull wire lumens (e.g., third lumen 3325, fourth lumen 3335) can be axially aligned to orienting feature 3374c. Additional dimensions and features of marker 3374 are included in FIGS. 65A-B.

FIG. 66 illustrates an embodiment of a handle assembly 6000 for use with a delivery catheter 3304. Handle assembly 6000 includes three main components: a needle hub 6002, a double hemostasis valve "Y" connector 6004, and a vented male Luer cap 6018. The proximal end of delivery catheter 3304 extends through needle hub 6002 into the distal hub of Y connector 6004 as illustrated in FIG. 66. The elongate proximal pusher 7012 of delivery shuttle 7000 extends proximally from the delivery catheter 3304 through a first hemostasis valve 6010 in Y connector 6004 as illustrated in FIG. 66. In alternate embodiments, first hemostasis valve 6010 in Y connector 6004 can be connected to a syringe or other fluid delivery means to deliver a therapeutic agent into proximal end opening 2217 of lumen 3305 for delivering the therapeutic agent into the intracranial SAS. Penetrating element guard pull wires 4010 and 4012 extend proximally from their respective lumens in delivery catheter 3304 through a second hemostasis valve 6020 in Y connector 6004. The proximal ends of pull wires 4010, 4012 extend through a female Luer lock and are fixed (e.g., welded, bonded with adhesive) to the underside of male Luer cap 6018. Hypotubes are used to provide additional support to pull wires 4010, 4012 in the second hemostasis valve portion 6020 of Y connector 6004: a smaller hypotube 6012, 6014 is placed over each of pull wires 4010 and 4012. The pull wire and smaller hypotubes are passed through a larger hypotube 6016 shown in FIG. 66. Hypotubes can have any suitable dimensions compatible with handle 6000 (e.g., standard hypotube gauging, dimensions, and materials can be ascertained from https://www.vitaneedle.com/hypodermic-tube-gauge-chart/). Dimensions and other details of hypotubes 6012, 6014, and 6014 are as follows: larger hypotube 6016 is 15 regular wall×1.89"; smaller hypotubes 6012, 6014 are 26 thin wall×2.05 inches. The hypotubes 6012, 6014, and 6014 subassembly in the second hemostasis valve 4020 portion of Y connector 6004 provides additional support and column strength for shuttle pull wires 4010, 4012 to enable smooth and consistent proximal and distal actuation of penetrating element guard 4000 via cap 6018.

Handle assembly 6000 can include a limit strap assembly 6024 that extends between a proximal connection point 6024P on the cap 6018 and a distal connection point 6024D on the "Y" connector 6004 as shown in FIG. 66. Connection points 6024P, 6024D can be a permanent connection at the cap 6018 and "Y" connector 6004 (e.g., through adhesive or other attachment means). As shown in FIG. 66, connection points 6024P, 6024D can further comprise a ring at either end of limit strap 6024 to further secure the limit strap connection points 6024P and 6024D around the cap 6018 and "Y" connector 6004, respectively. The length of limit strap 6024 is configured to limit the distance that a clinician can pull cap 6018 proximally, away from "Y" connector 6004, to prevent over retraction of guard 4000 over penetrating element 3350. Limit strap 6024 can comprise a urethane material (e.g., thermoplastic polyurethanes ranging in diameter from about 70 A to 100 A), poly ether block amide, low-density polyethylene other polymers, stainless steel wire or rope, or any other materials that would resist or prevent a clinician from over retracting cap 6018 away from "Y" connector 6004.

When handle assembly 6000 is in use with a delivery catheter 3304, unscrewing cap 6018 from Luer lock 6022 initiates proximal retraction of penetrating element guard 4000; after unscrewing cap 6018 from Luer lock 6022, the clinician can pull proximally on cap 6018 to further retract guard 4000 over penetrating element 3350. The clinician can then use delivery catheter 3304 to penetrate IPS wall. Handle assembly 6000 includes an aspiration/flush port 6006 that includes a lumen fluidically contiguous with second lumen 3305 of delivery catheter 3304; by attaching a syringe (e.g., 1 ml syringe) to the proximal end of port 6006, the operator can aspirate CSF from CP angle cistern 138, through penetrating element lumen 3355, delivery catheter lumen 3305, and port 6006 to observe CSF collecting in the syringe and confirm penetration through IPS wall into the subarachnoid space, and use lumen 3305 to deliver a therapeutic agent from the delivery catheter into the intracranial SAS. The delivery shuttle 7000 can be used to advance drug delivery device 2200 from delivery catheter lumen 3305 and penetrating element lumen 3355 until distal anchoring mechanism 2229 deploys in CP angle cistern 138. Port 6006 can also be used to flush saline or contrast through lumen 3305 and out of penetrating element lumen 3355 into the patient's vasculature at different points during the drug delivery device deployment procedure. By reversing the foregoing sequence described for cap 6018 (e.g., pushing distally on cap 6018 and screwing cap 6018 onto Luer lock 6022, the operator can advance guard 4000 distally clinician and re-cover penetrating element 3350 (e.g., after drug delivery device implantation and while withdrawing delivery catheter from the patient).

It should be appreciated that if the clinician inadvertently causes a tear in IPS wall 114, the clinician may elect to abort the procedure. If using an embodiment of anchor 700 that includes an outer polymeric layer that covers the cells of the anchor and a guide member 780 that can detach from anchor 700, he can, redeploy anchor 700 in the sinus lumen across the tear and leave the anchor 700 in the IPS 102 by detaching guide member 780; in this scenario, the anchor can prevent venous blood from leaving into the subarachnoid space and/or uncontrolled CSF leaking from the subarachnoid space into the venous system.

Figure 67A:
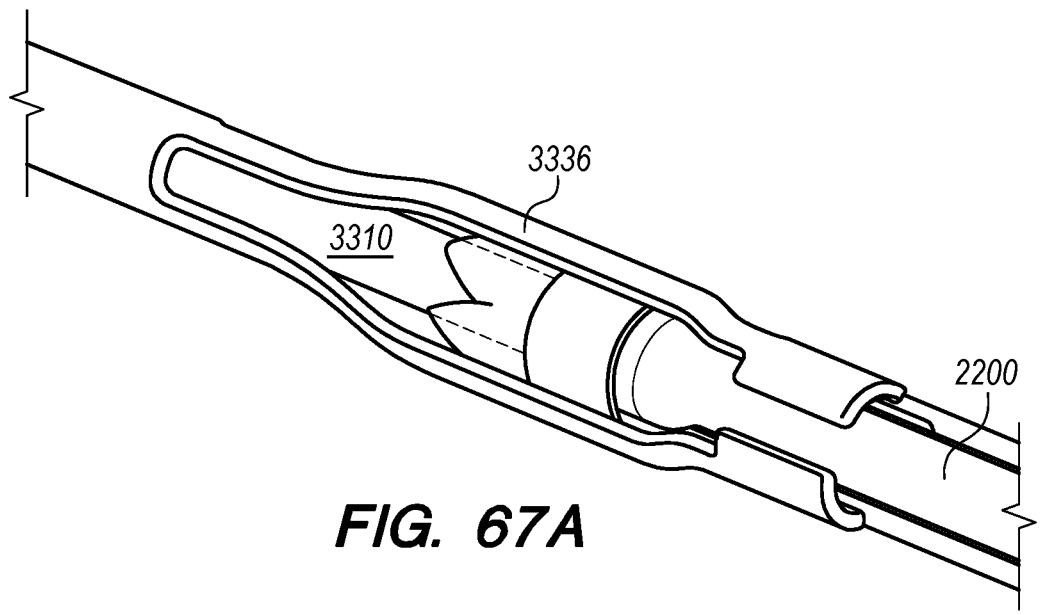
FIGS. 67A-I are side views of a drug delivery device pusher constructed according to embodiments of the disclosed inventions.

FIGS. 67A-H illustrates alternative delivery catheter, pusher member 3310 and drug delivery device 2200 interfaces, and respective interlocking members 3336, constructed according to embodiments of the disclosed inventions. As shown in FIG. 67A, the interlocking member 3336 of the pusher 3310 engages the outer surface of the drug delivery device 2200, which radially compresses without longitudinally stretching the drug delivery device 2200 and thereby reduces friction of the drug delivery device 2200 with the delivery catheter inner wall.

Figure 67B:
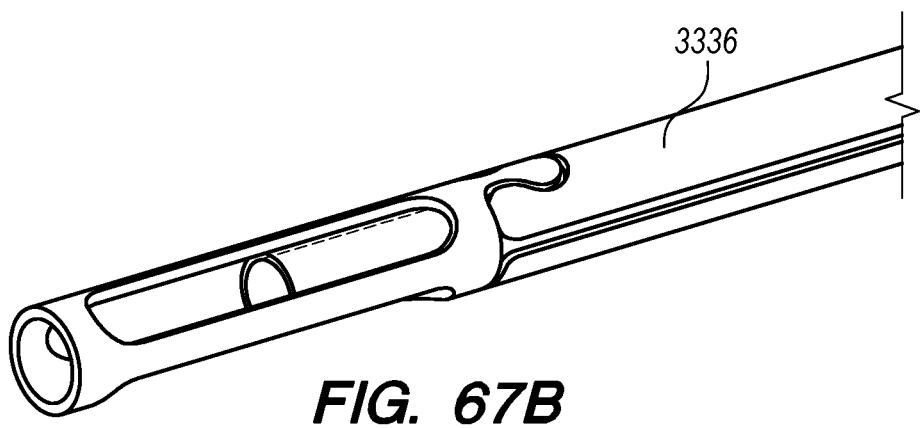
Figure 67C:
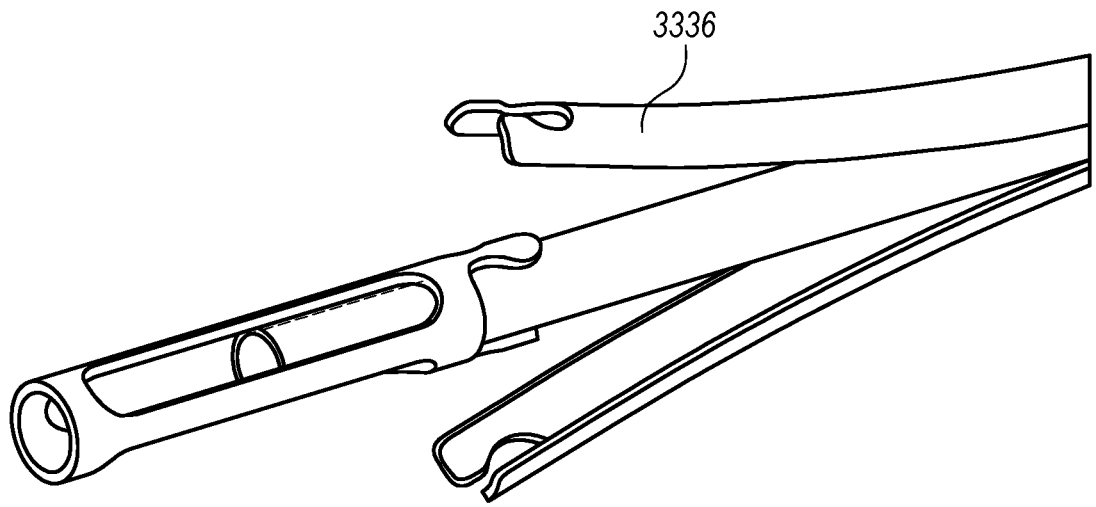

In FIGS. 67B-C, the interlocking member of the pusher 3310 engages the outer surface of the delivery catheter. In these embodiments, friction of the drug delivery device 2200 with the delivery catheter may be reduced, since the interlock member is mounted on the outer surface of the catheter. In alternative embodiments, the interlocking member 3336 of the pusher depicted in FIGS. 67B-C can be constrained within the lumen of a delivery catheter, as previously described in connection with other pusher embodiments disclosed herein.

Figure 67D:
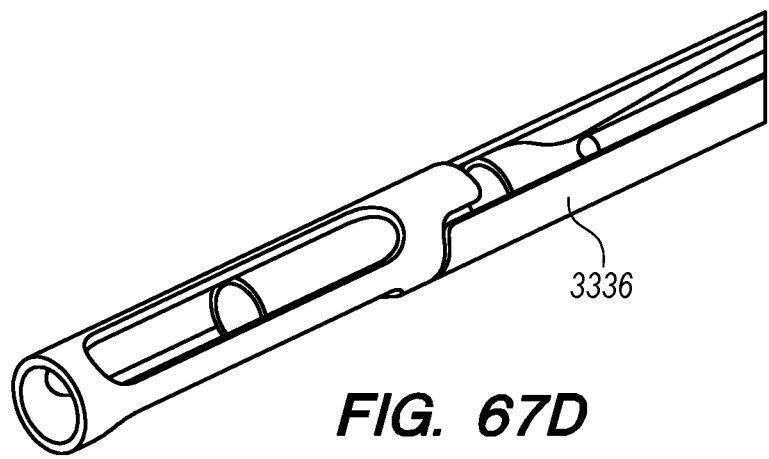
Figure 67E:
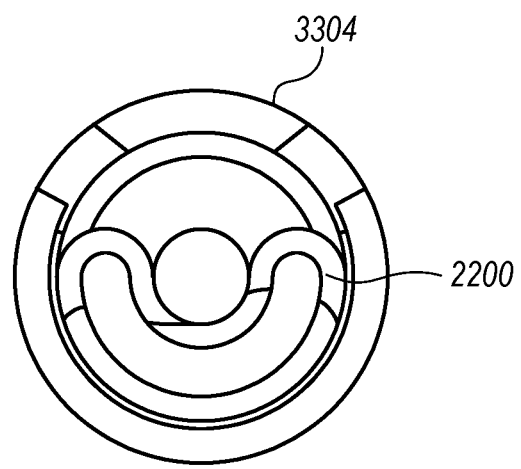

As shown in FIG. 67D-E, the drug delivery device 2200 may be further compressed (e.g., folded, bent, or the like) within the lumen 3305 of the delivery catheter 3304 for more efficient packing during delivery of the drug delivery device at the target site.

Figure 67F:
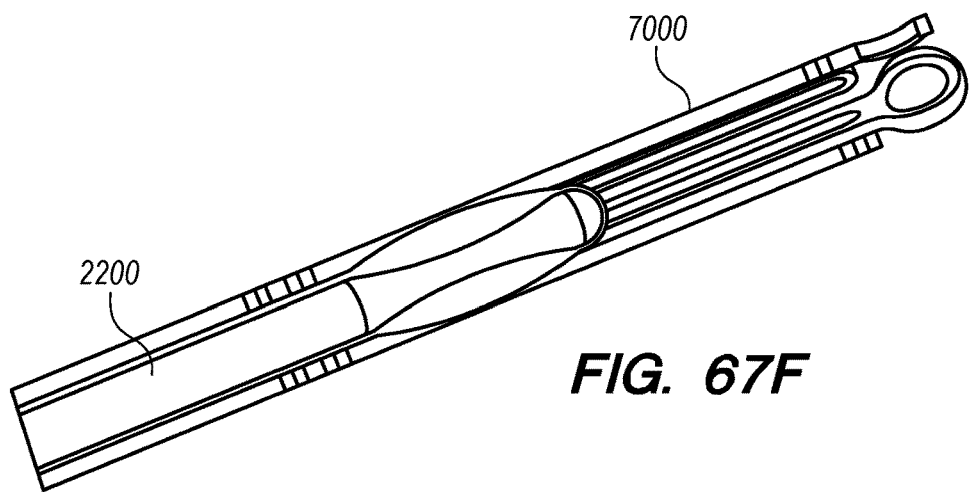
Figure 67G:
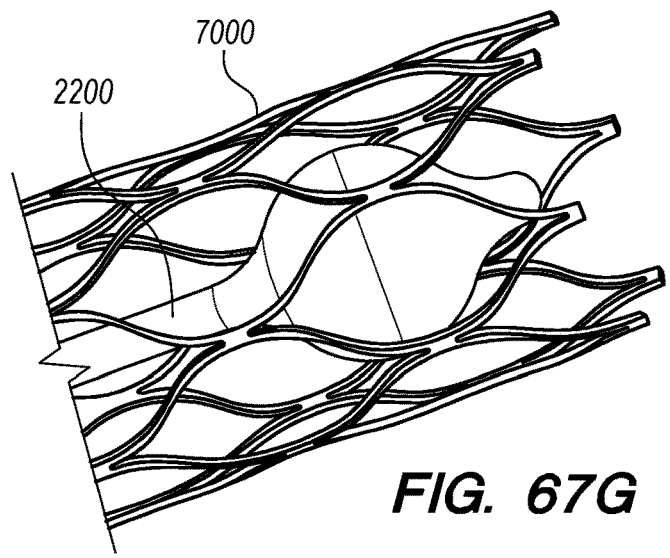

Alternatively or additionally, the drug delivery device 2200 may be compressed during delivery by the delivery shuttle 7000 having a stent-like structure, as shown in FIGS. 67F-G. In these embodiments, the drug delivery device comprises a polymeric body and anchoring mechanism (e.g., silicon) as it will be described in further detail below.

Figure 67H:
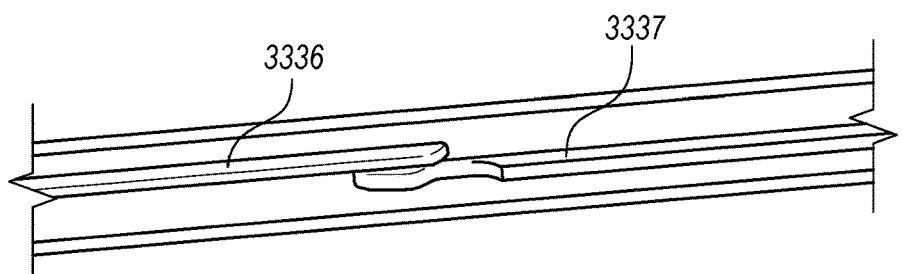
Figure 67I:
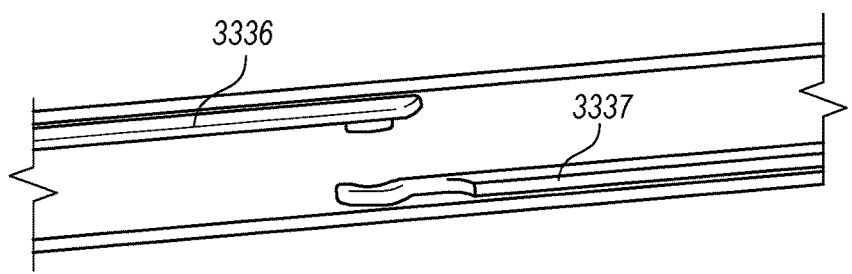

In yet another alternative embodiment, the interlocking members 3336 of the pusher and the interlocking members 3337 of the drug delivery device include mating elements, such as a protrusion and a slot, as shown in FIGS. 67H-I. The engagement of the interlocking members may be further assisted by a reduced inner diameter of the delivery catheter (not shown), magnetic elements, or the like.

FIGS. 76-81 illustrate an exemplary embodiment of a joint 744' between the elongate guide member 780 and the anchor 700, constructed according to the disclosed inventions. The anchor 700 and the elongate guide member 780 coupled to the proximal portion 740 of the anchor 700 can be manufactured from the same piece of material (e.g., a super-elastic alloy such as Nitinol®), or may comprise separate parts joined at a joint 744' between anchor 700 and the elongate guide member 780. The elongate guide member 780 of FIG. 76-79 includes a flat, rectangular cross-sectional profile, as better appreciated in FIG. 77 and FIG. 78A. In some embodiments, the outer dimension (OD) of the distal portion 782 is smaller than the OD of a middle body portion 786 the of elongate guide member 780 (FIG. 76). In those embodiments, the elongate guide member 780 includes a tapered surface at the distal portion 782 (shown covered by a bond 741 in FIG. 77) at the joint 744' between the elongate guide member 780 and the anchor 700. Additionally, the proximal portion 784 of the elongate guide member 780 may also have a smaller OD than the middle body portion 786 (FIG. 76).

Figure 78A:
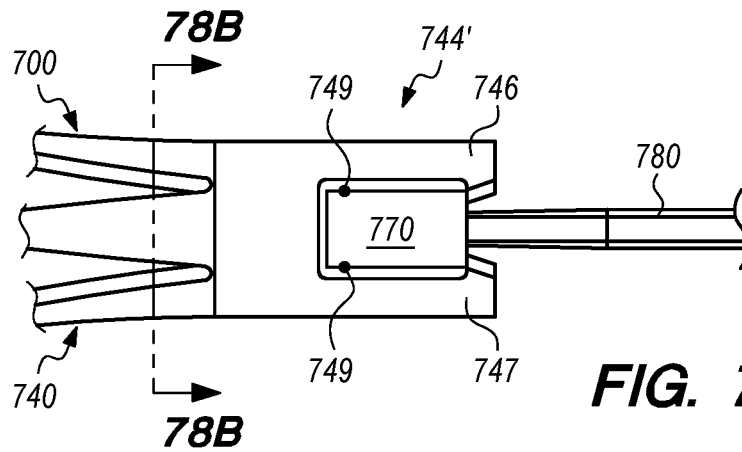
Figure 78B:
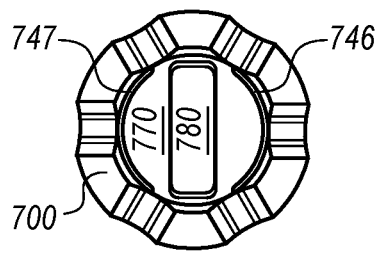
Figure 79:
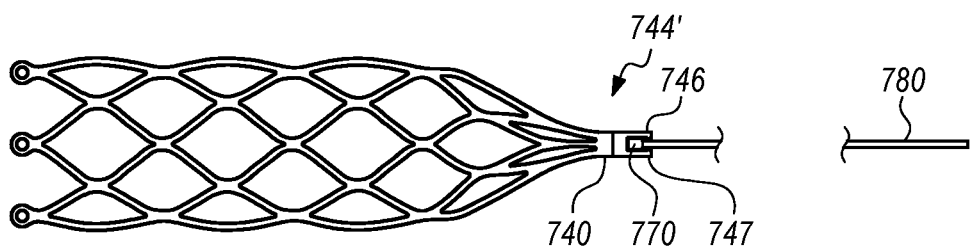
Figure 80A:
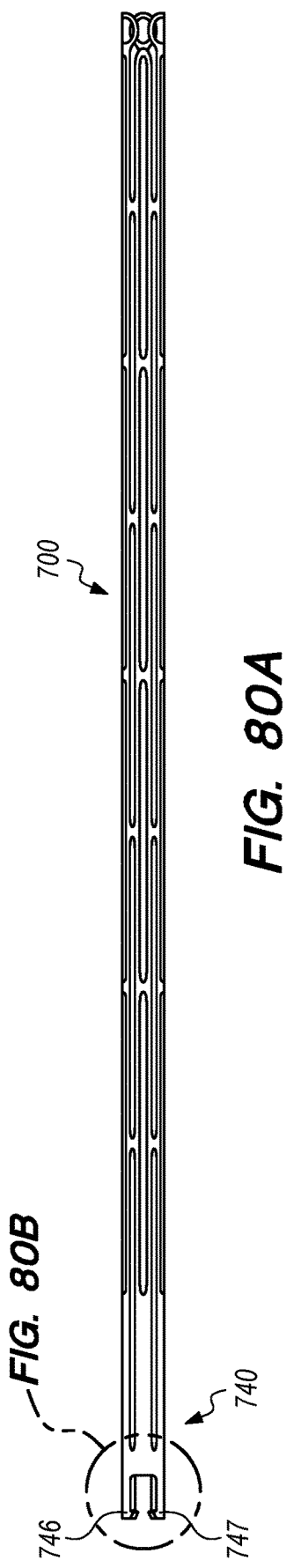

As shown in FIGS. 77-79, the elongate guide member 780 is coupled (e.g., directly or indirectly) to the proximal portion 740 of anchor 700 via joint 744'. The components of the joint 744', which will be described in further detail below, are further secured and/or covered by a bond 741 (e.g., suitable adhesive, ultraviolet light-cured adhesive, cyanoacrylate, epoxy, polymer, weld or any other suitable bond). The bond 741 is configured to create a tapered surface between the elongate guide member 780 and the anchor 700, as shown in FIG. 77.

Figure 81:
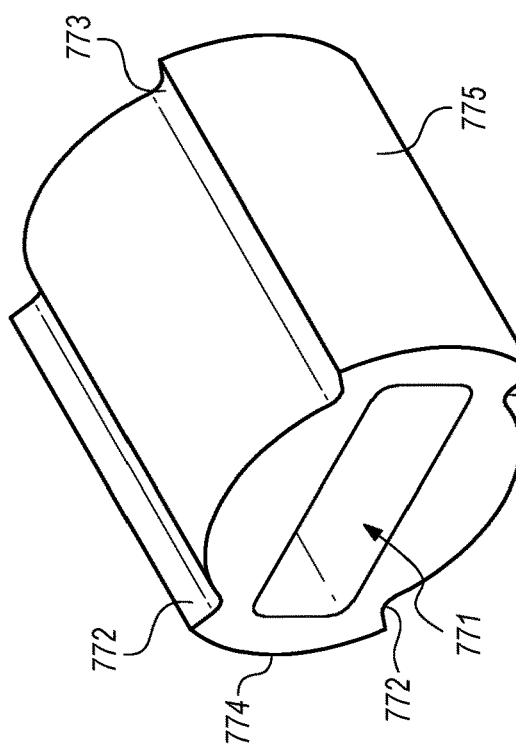
Figure 80B:
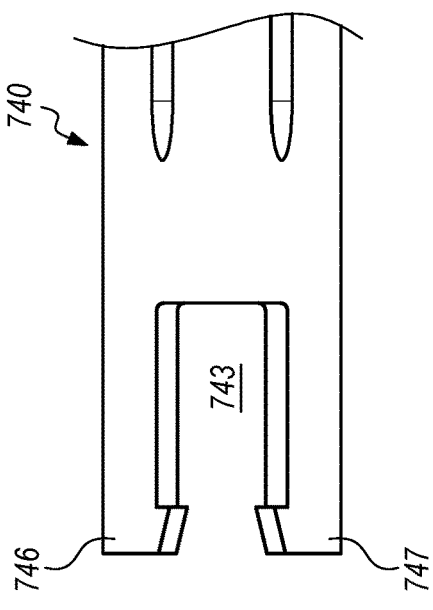

As better appreciated in FIG. 77, the joint 744' includes a marker 770 disposed between the proximal portion 740 of the anchor 700 and the distal portion 782 of the elongate guide member 780. The marker 770 is composed of suitable radio-opaque material for imaging purposes. As shown in FIG. 81, the marker 770 includes a quasi-tubular configuration having a pair of indentations 772 and 773, which forms respective fitting protrusions 774 and 775; the marker 770 further includes a lumen 771 configured to receive the distal portion 782 of the elongate guide member 780. As shown in FIGS. 78A-80B, the proximal portion 740 of the anchor 700 includes a pair of jaws 746 and 747 configured to slide through the respective pair of indentations 772 and 773 of the marker 770 until the marker 770 is disposed within a lumen 743 (FIG. 80B) of the proximal portion 740, and the jaws 746 and 747 are disposed proximately to the marker 770 (FIGS. 77-79).

The components of the joint 744' (e.g., jaws 746 and 747 of proximal portion 740 of the anchor 700, marker 770, and distal portion 782 of the elongate guide member 780) are configured to mate, press-fit and/or frictionally fit each other, as shown in FIGS. 77-79). In one embodiment, the distal portion 782 of the elongate guide member 780 is disposed within the marker 770 lumen 771; additional welding may be applied to secure the marker 770 to the guide member 780. Further, the marker 770 is advanced/pushed into the lumen 743 of the proximal portion 740 of the anchor 700 while the jaws 746 and 747 ride/slide through the respective pair of indentations 772 and 773 of the marker 770, until the jaws 746 and 747 are disposed proximately to the marker 770 (FIGS. 77-79). Additionally, welding 749 may be applied to the marker 770 proximately to the jaws 746 and 747, as exemplary shown in FIG. 78A. Although the welding 749 are shown as points in FIG. 78A, it should be appreciated that the welding 749 are continuous weld along the perimeter of the junctions between the marker 770 and the respective jaws 746 and 747. The continuous weld 749 at the joint 744' is configured to minimize or prevent bending of the proximal portion 740 of the anchor 700 at the welds 749, since if the anchor 700 (composed of Nitinol®) bends, Nitinol® tends to become brittle and creates undesirable micro cracks that extends into the anchor 700. Therefore, the welds 749 are disposed distally at the junction between the marker 770 the proximal portion 740 of the anchor, as shown in FIG. 78A. During delivery of the anchor 700 at the target site, as previously described, the elongate guide member 780 is expected to bend, so the proximal portion 782 of the elongate guide member 780 may bend at the joint 744' (e.g., closer to the jaws) without risk or with minimal risk of creating micro cracks in the anchor 700 since the weld 749 are distally disposed (FIG. 78A) such that only compression and/or tension forces are applied to the anchor 700 by the elongate guide member 780 (no bending forces). The welds 749 and their location are configured to act as a strain relief at the joint 744' between the elongate guide member 780 and the anchor 700.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

The invention claimed is:

1. A for accessing an intracranial subarachnoid space (ISAS) through a blood vessel wall of a patient to administer a therapeutic agent, the method comprising:
    acquiring a 3D volumetric reconstruction of the vessel wall;
    identifying a target location in the 3D reconstruction for accessing the ISAS through the vessel wall with a delivery catheter;
    overlaying a portion of the 3D reconstruction including the target location on a fluoroscopy imaging display of the patient's anatomy including the vessel wall;
    using the overlaid portion of the 3D reconstruction and fluoroscopy imaging display to visually track movement of the delivery catheter within the vessel to the target location;
    penetrating the vessel wall at the target location to create an anastomosis between the vessel and the ISAS;
    accessing the ISAS through the anastomosis with the delivery catheter; and
    administering a therapeutic agent from the delivery catheter into the ISAS.

2. A method for accessing an intracranial subarachnoid space (ISAS) through a blood vessel wall of a patient to deploy a drug delivery device, the method comprising:
    acquiring a 3D volumetric reconstruction of the vessel wall;
    identifying a target location in the 3D reconstruction for accessing the ISAS through the vessel wall with a delivery catheter;
    overlaying a portion of the 3D reconstruction including the target location on a fluoroscopy imaging display of the patient's anatomy including the vessel wall; and
    using the overlaid portion of the 3D reconstruction and fluoroscopy imaging display to visually track movement of the delivery catheter within the vessel to the target location;
    penetrating the vessel wall at the target location to create an anastomosis between the vessel and the ISAS; and
    deploying the drug delivery device in the anastomosis via the delivery catheter.

3. The method of claim 2, wherein the drug delivery device is connected to an access port.

4. The method of claim 3, further comprising administering a therapeutic agent through the access port, the drug delivery device, and into the ISAS, respectively.

5. The method of claim 2, further comprising administering a therapeutic agent into the ISAS from a reservoir of the drug delivery device.

6. The method of claim 2, further comprising overlaying an MR imaging data set of the patient's anatomy including the vessel wall onto the respective portion of the 3D reconstruction and fluoroscopy imaging display.

7. The method of claim 2, wherein the 3D volumetric reconstruction of the vessel wall is acquired by 3D-rotational venography or angiography.

8. &method for accessing an intracranial subarachnoid space (ISAS) through a blood vessel wall of a patient to administer a therapeutic agent, the method comprising:
   acquiring a 3D volumetric reconstruction of the vessel wall;
   identifying a target location in the 3D reconstruction for accessing the ISAS through the vessel wall with a delivery catheter;
   navigating the delivery catheter within the vessel to the target location;
   penetrating the vessel wall at the target location to create an anastomosis between the vessel and the ISAS;
   accessing the ISAS through the anastomosis with the delivery catheter; and
   administering a therapeutic agent from the delivery catheter into the ISAS.

9. The method of claim 8, wherein the 3D volumetric reconstruction of the vessel wall is acquired by 3D-rotational venography or angiography.

10. A method for accessing an intracranial subarachnoid space (ISAS) through a blood vessel wall of a patient to deploy a drug delivery device, the method comprising:
    acquiring a 3D volumetric reconstruction of the vessel wall;
    identifying a target location in the 3D reconstruction for accessing the ISAS through the vessel wall with a delivery catheter;
    navigating the delivery catheter within the vessel to the target location;
    penetrating the vessel wall at the target location to create an anastomosis between the vessel and the ISAS; and
    deploying the drug delivery device in the anastomosis via the delivery catheter.

11. The method of claim 10, wherein the drug delivery device is connected to an access port.

12. The method of claim 11, further comprising administering a therapeutic agent through the access port, the drug delivery device, and into the ISAS, respectively.

13. The method of claim 10, further comprising administering a therapeutic agent into the ISAS from a reservoir of the drug delivery device.

14. The method of claim 10, further comprising overlaying an MR imaging data set of the patient's anatomy including the vessel wall onto the 3D reconstruction.

15. The method of claim 10, wherein the 3D volumetric reconstruction of the vessel wall is acquired by 3D-rotational venography or angiography.

\* \* \* \* \*